(12) United States Patent
Baldwin et al.

(10) Patent No.: US 7,858,624 B2
(45) Date of Patent: Dec. 28, 2010

(54) PIPERIDINE AND MORPHOLINE RENIN INHIBITORS

(75) Inventors: John J. Baldwin, Gwynedd Valley, PA (US); David A. Claremon, Maple Glen, PA (US); Colin M. Tice, Ambler, PA (US); Salvacion Cacatian, Blue Bell, PA (US); Lawrence W. Dillard, Yardley, PA (US); Alexey V. Ishchenko, Somerville, MA (US); Jing Yuan, Lansdale, PA (US); Zhenrong Xu, Horsham, PA (US); Gerard McGeehan, Garnet Valley, PA (US); Wei Zhao, Eagleville, PA (US); Robert D. Simpson, Wilmington, DE (US); Suresh B. Singh, Kendall Park, NJ (US)

(73) Assignee: Vitae Pharmaceuticals, Inc., Fort Washington, PA (US)

( * ) Notice: Subject to any disclaimer, the term of this patent is extended or adjusted under 35 U.S.C. 154(b) by 0 days.

(21) Appl. No.: 12/225,986

(22) PCT Filed: Apr. 5, 2007

(86) PCT No.: PCT/US2007/008521

§ 371 (c)(1),
(2), (4) Date: Jan. 29, 2009

(87) PCT Pub. No.: WO2007/117560

PCT Pub. Date: Oct. 18, 2007

(65) Prior Publication Data

US 2009/0264432 A1 Oct. 22, 2009

Related U.S. Application Data

(60) Provisional application No. 60/789,723, filed on Apr. 5, 2006.

(51) Int. Cl.
| | |
|---|---|
| *A61K 31/5355* | (2006.01) |
| *A61K 31/4402* | (2006.01) |
| *A61K 31/4525* | (2006.01) |
| *A61K 31/445* | (2006.01) |
| *C07D 411/12* | (2006.01) |
| *C07D 213/30* | (2006.01) |
| *C07D 403/12* | (2006.01) |
| *C07D 405/12* | (2006.01) |
| *C07D 401/12* | (2006.01) |
| *C07D 211/22* | (2006.01) |

(52) U.S. Cl. ............ 514/237.2; 514/318; 514/326; 514/330; 544/129; 546/194; 546/208; 546/210; 546/214; 546/226

(58) Field of Classification Search ............... None
See application file for complete search history.

(56) References Cited

FOREIGN PATENT DOCUMENTS

WO   WO 2006/042150   *   4/2006

OTHER PUBLICATIONS

Dorwald F. A. Side Reactions in Organic Synthesis, 2005, Wiley: VCH, Weinheim. Preface and Chap. 1 included.*
Kubinyi, ed. 3D QSAR in Drug Design: Ligand-Protein Interactions and Molecular Similarity, vol. 2-3, Springer, 1998, 800 pages (relevant portions included).*

* cited by examiner

*Primary Examiner*—Kamal A Saeed
*Assistant Examiner*—Alicia L Otton
(74) *Attorney, Agent, or Firm*—Hamilton, Brook, Smith & Reynolds, P.C.

(57) ABSTRACT

Described are compounds which are orally active and bind to renin to inhibit its activity. They are useful in the treatment or amelioration of diseases associated with renin activity. Also described are methods of use of these compounds for treating or ameliorating a renin mediated disorder in a subject.

4 Claims, No Drawings

PIPERIDINE AND MORPHOLINE RENIN INHIBITORS

RELATED APPLICATIONS

This application claims the benefit of U.S. Provisional Application No. 60/789,723, filed Apr. 5, 2006, the entire teachings of which are incorporated herein by reference.

BACKGROUND OF THE INVENTION

In the renin-angiotensin-aldosterone system (RAAS) the biologically active peptide angiotensin II (Ang II) is generated by a two-step mechanism. The highly specific aspartic protease renin cleaves angiotensinogen to angiotensin I (Ang I), which is then further processed to Ang II by the less specific angiotensin-converting enzyme (ACE). Ang II is known to work on at least two receptor subtypes called $AT_1$ and $AT_2$. Whereas $AT_1$ seems to transmit most of the known functions of Ang II, the role of $AT_2$ is still unknown.

Modulation of the RAAS represents a major advance in the treatment of cardiovascular diseases (Zaman, M. A. et al *Nature Reviews Drug Discovery* 2002, 1, 621-636). ACE inhibitors and $AT_1$ blockers have been accepted as treatments of hypertension (Waeber B. et al., "The renin-angiotensin system: role in experimental and human hypertension", in Berkenhager W. H., Reid J. L. (eds): *Hypertension*: Amsterdam, Elsevier Science Publishing Co, 1996, 489-519; Weber M. A., *Am. J. Hypertens.*, 1992, 5, 247S). In addition, ACE inhibitors are used for renal protection (Rosenberg M. E. et al., *Kidney international*, 1994, 45, 403; Breyer J. A. et al., *Kidney International*, 1994, 45, S156), in the prevention of congestive heart failure (Vaughan D. E. et al., *Cardiovasc. Res.*, 1994, 28, 159; Fouad-Tarazi F. et al., *Am. J. Med.*, 1988, 84 (Suppl. 3A), 83) and myocardial infarction (Pfeffer M. A. et al., *N Engl. J. Med*, 1992, 327, 669).

Interest in the development of renin inhibitors stems from the specificity of renin (Kleinert H. D., *Cardiovasc. Drugs*, 1995, 9, 645). The only substrate known for renin is angiotensinogen, which can only be processed (under physiological conditions) by renin. In contrast, ACE can also cleave bradykinin besides Ang I and can be bypassed by chymase, a serine protease (Husain A., *J. Hypertens.*, 1993, 11, 1155). In patients, inhibition of ACE thus leads to bradykinin accumulation causing cough (5-20%) and potentially life-threatening angioneurotic edema (0.1-0.2%) (Israili Z. H. et al., *Annals of Internal Medicine*, 1992, 117, 234). Chymase is not inhibited by ACE inhibitors. Therefore, the formation of Ang II is still possible in patients treated with ACE inhibitors. Blockade of the ATI receptor (e.g., by losartan) on the other hand overexposes other AT-receptor subtypes to Ang II, whose concentration is dramatically increased by the blockade of ATI receptors. In summary, renin inhibitors are not only expected to be superior to ACE inhibitors and $AT_1$ blockers with regard to safety, but more importantly also with regard to their efficacy in blocking the RAAS.

Only limited clinical experience (Azizi M. et al., *J. Hypertens.*, 1994, 12, 419; Neutel J. M. et al., *Am. Heart*, 1991, 122, 1094) has been generated with renin inhibitors because their peptidomimetic character imparts insufficient oral activity (Kleinert H. D., *Cardiovasc. Drugs*, 1995, 9, 645). The clinical development of several compounds has been stopped because of this problem together with the high cost of goods. It appears that only one compound has entered clinical trials (Rahuel J. et al, *Chem. Biol.*, 2000, 7, 493; Mealy N. E., *Drugs of the Future*, 2001, 26, 1139). Thus, metabolically stable, orally bioavailable and sufficiently soluble renin inhibitors that can be prepared on a large scale are not available. Recently, the first non-peptide renin inhibitors were described which show high in vitro activity (Oefner C. et al., *Chem. Biol.*, 1999, 6, 127; Patent Application WO 97/09311; Maerki H. P. et al., *Il Farmaco*, 2001, 56, 21). The present invention relates to the unexpected identification of renin inhibitors of a non-peptidic nature and of low molecular weight. Orally active renin inhibitors of long duration of action which are active in indications beyond blood pressure regulation where the tissular reninchymase system may be activated leading to pathophysiologically altered local functions such as renal, cardiac and vascular remodeling, atherosclerosis, and possibly restenosis, are described.

SUMMARY OF THE INVENTION

Compounds of Formula I have now been found which are orally active and bind to renin to inhibit its activity. They are useful in the treatment or amelioration of diseases associated with renin activity.

In one embodiment the present invention is directed to a compound represented by Formula I

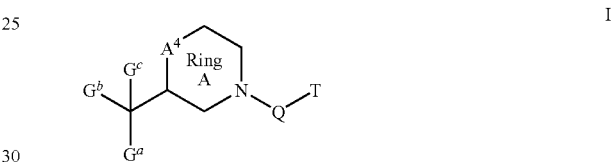

or an enantiomer, diastereomer or salt thereof.

$G^a$ is a) $(C_1-C_9)$alkyl, $(C_3-C_7)$cycloalkyl, $(C_4-C_9)$cycloalkylalkyl, halo$(C_1-C_9)$alkyl, halo$(C_3-C_7)$cycloalkyl, halo$(C_4-C_9)$cycloalkylalkyl, saturated heterocyclyl optionally substituted with 1 to 3 groups independently selected from fluorine, $(C_1-C_3)$alkyl, halo$(C_1-C_3)$alkyl, and oxo; or b) phenyl, napthyl, heteroaryl, or bicyclic heteroaryl each optionally substituted with 1 to 3 groups independently selected from the groups consisting of:

1) fluorine, chlorine, bromine, cyano, nitro, $(C_1-C_6)$alkyl, $(C_3-C_6)$cycloalkyl, $(C_4-C_7)$cycloalkylalkyl, $(C_2-C_6)$alkenyl, $(C_5-C_6)$cycloalkenyl, $(C_5-C_8)$cycloalkylalkenyl, $(C_2-C_6)$alkynyl, $(C_3-C_6)$cycloalkylethynyl, halo$(C_1-C_6)$alkyl, halo$(C_3-C_6)$cycloalkyl, halo$(C_4-C_7)$-cycloalkylalkyl, halo$(C_2-C_6)$alkenyl, halo$(C_3-C_6)$alkynyl, halo$(C_3-C_6)$cycloalkylethynyl, $(C_1-C_6)$alkoxy, $(C_3-C_6)$cycloalkoxy, $(C_4-C_7)$cycloalkylalkoxy, halo$(C_1-C_6)$alkoxy, halo$(C_3-C_6)$cycloalkoxy, halo$(C_4-C_7)$cycloalkylalkoxy, $(C_3-C_6)$alkenyloxy and $(C_1-C_6)$alkanesulfonyl; or 2) phenyl, heteroaryl, phenoxy, heteroaryloxy, phenylthio, heteroarylthio, benzyl, heteroarylmethyl, benzyloxy and heteroaryloxy, each optionally substituted with 1 to 3 groups independently selected from the group consisting of fluorine, chlorine, cyano, $(C_1-C_3)$alkyl, halo$(C_1-C_3)$alkyl, $(C_1-C_3)$alkoxy, halo$(C_1-C_3)$alkoxy, and aminocarbonyl.

$G^b$ is hydrogen, $(C_1-C_8)$alkyl, $(C_4-C_8)$cycloalkylalkyl, fluoro$(C_1-C_8)$alkyl, fluoro$(C_4-C_8)$cycloalkylalkyl, $(C_1-C_8)$alkoxy, $(C_4-C_8)$cycloalkylalkoxy, fluoro$(C_1-C_8)$alkoxy, hydroxy$(C_1-C_8)$alkyl, $(C_1-C_5)$alkoxy$(C_1-C_5)$alkyl, halo$(C_1-C_5)$alkylamino$(C_1-C_5)$alkyl, $(C_1-C_5)$alkoxy$(C_1-C_5)$hydroxyalkyl, $(C_3-C_4)$cycloalkoxy$(C_1-C_5)$alkyl, fluoro$(C_1-C_5)$alkoxy$(C_1-C_5)$alkyl, fluoro$(C_3-C_4)$cycloalkoxy$(C_1-C_5)$alkyl, $(C_1-C_5)$alkylthio$(C_1-C_5)$alkyl, $(C_1-C_5)$alkoxy$(C_1-C_5)$alkoxy, hydroxy$(C_1-C_8)$alkoxy, $(C_3-C_4)$cycloalkoxy$(C_1-C_5)$alkoxy, fluoro($C_1$-$C_5$)alkoxy($C_1$-$C_5$)alkoxy, fluoro($C_3$-$C_4$)cycloalkoxy($C_1$-$C_5$)alkoxy, ($C_1$-$C_3$)alkoxy($C_1$-$C_3$)alkoxy($C_1$-$C_3$)alkyl, fluoro($C_1$-$C_3$)alkoxy($C_1$-$C_3$)alkoxy($C_1$-$C_3$)alkyl, aminocarbonylamino($C_1$-$C_8$)alkyl, aminocarbonylamino($C_1$-$C_8$)alkoxy, ($C_1$-$C_5$)alkanoylamino($C_1$-$C_5$)alkyl, ($C_1$-$C_5$)alkanoylamino($C_1$-$C_5$)alkoxy, fluoro($C_1$-$C_5$)alkanoylamino($C_1$-$C_5$)alkyl, fluoro($C_1$-$C_5$)alkanoylamino($C_1$-$C_5$)alkoxy, ($C_1$-$C_3$)alkoxy($C_1$-$C_5$)alkanoylamino($C_1$-$C_5$)alkyl, ($C_1$-$C_3$)alkoxy($C_1$-$C_5$)alkanoylamino($C_1$-$C_5$)alkoxy, ($C_3$-$C_4$)cycloalkanecarbonyllamino($C_1$-$C_5$)alkyl, ($C_3$-$C_4$)cycloalkanecarbonyllamino($C_1$-$C_5$)alkoxy, aminosulfonylamino($C_1$-$C_8$)alkyl, aminosulfonylamino($C_1$-$C_8$)alkoxy, ($C_1$-$C_5$)alkanesulfonyl-amino($C_1$-$C_5$)alkyl, ($C_1$-$C_5$)alkanesulfonylamino($C_1$-$C_8$)alkoxy, formylamino($C_1$-$C_5$)alkyl, formylamino($C_1$-$C_5$)alkoxy, ($C_1$-$C_5$)alkoxycarbonylamino($C_1$-$C_5$)alkyl, ($C_1$-$C_5$)alkoxycarbonylamino($C_1$-$C_5$)alkoxy, ($C_1$-$C_5$)alkylaminocarbonylamino($C_1$-$C_5$)alkyl, ($C_1$-$C_5$)alkylaminocarbonyl-amino($C_1$-$C_5$)alkyl, di($C_1$-$C_5$)alkylaminocarbonylamino($C_1$-$C_5$)alkoxy, aminocarbonyl($C_1$-$C_5$)alkyl, aminocarbonyl($C_1$-$C_5$)alkoxy, ($C_1$-$C_5$)alkylaminocarbonyl($C_1$-$C_5$)alkyl, ($C_1$-$C_5$)alkylaminocarbonyl-($C_1$-$C_5$)alkoxy, aminocarboxy($C_1$-$C_5$)alkyl, aminocarboxy($C_1$-$C_5$)alkoxy, ($C_1$-$C_5$)alkylaminocarboxy($C_1$-$C_5$)alkyl, ($C_1$-$C_5$)alkylaminocarboxy($C_1$-$C_5$)alkoxy, ($C_1$-$C_8$)alkoxycarbonylamino, ($C_1$-$C_3$)alkylaminocarbonylamino, ($C_1$-$C_8$)alkanoylamino, fluoro($C_1$-$C_8$)alkoxycarbonylamino, fluoro($C_1$-$C_8$)alkylaminocarbonylamino, or fluoro($C_1$-$C_8$)alkanoylamino.

$G^c$ is —H, halogen, OH, ($C_1$-$C_4$)alkanoylamino, or ($C_1$-$C_3$)alkoxy; provided that i) $G^b$ and $G^c$ are not both hydrogen and ii) when $G^c$ is OH or halogen, $G^b$ is not ($C_1$-$C_8$)alkoxy, ($C_4$-$C_8$)cycloalkylalkoxy, fluoro($C_1$-$C_8$)alkoxy, ($C_1$-$C_5$)alkoxy($C_1$-$C_5$)alkoxy, hydroxy($C_1$-$C_8$)alkoxy, ($C_3$-$C_4$)cycloalkoxy($C_1$-$C_8$)alkoxy, fluoro($C_1$-$C_5$)alkoxy($C_1$-$C_5$)alkoxy, fluoro($C_3$-$C_4$)cycloalkoxy($C_1$-$C_5$)alkoxy, aminocarbonylamino($C_1$-$C_8$)alkoxy, ($C_1$-$C_8$)alkanoylamino($C_1$-$C_5$)alkoxy, fluoro($C_1$-$C_5$)alkanoylamino($C_1$-$C_5$)alkoxy, ($C_1$-$C_3$)alkoxy($C_1$-$C_5$)alkanoyl-amino($C_1$-$C_5$)alkoxy, ($C_3$-$C_4$)cycloalkanecarbonyllamino($C_1$-$C_5$)alkoxy, aminosulfonylamino($C_1$-$C_8$)alkoxy, ($C_1$-$C_5$)alkanesulfonylamino($C_1$-$C_5$)alkoxy, formylamino($C_1$-$C_5$)alkoxy, ($C_1$-$C_5$)alkoxy-carbonylamino($C_1$-$C_5$)alkoxy, di($C_1$-$C_5$)alkylaminocarbonylamino($C_1$-$C_5$)alkoxy, aminocarbonyl($C_1$-$C_5$)alkoxy, ($C_1$-$C_5$)alkylaminocarbonyl($C_1$-$C_5$)alkoxy, aminocarboxy($C_1$-$C_5$)alkoxy, ($C_1$-$C_5$)alkylaminocarboxy($C_1$-$C_5$)alkoxy, ($C_1$-$C_8$)alkoxycarbonylamino, ($C_1$-$C_8$)alkylaminocarbonylamino, ($C_1$-$C_8$)alkanoylamino, fluoro($C_1$-$C_8$)alkoxycarbonylamino, fluoro($C_1$-$C_8$)alkylaminocarbonylamino, or fluoro($C_1$-$C_8$)alkanoylamino.

$A^4$ is $CH_2$ or O.

Q is a divalent radical selected from:

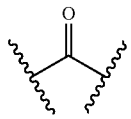
Q1

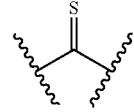
Q2

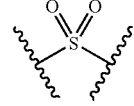
Q3

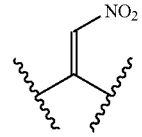
Q4

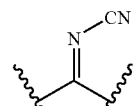
Q5

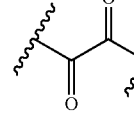
Q6

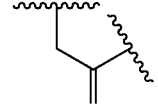
Q7

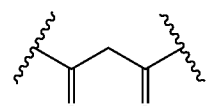
Q8

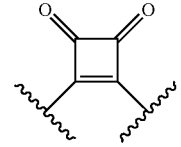
Q9

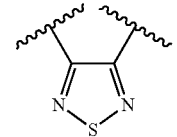
Q10

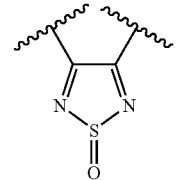
Q11

-continued

Q12

[chemical structure]

or

Q13

[chemical structure with Me]

wherein N and T are attached to the truncated bonds

T is a mimic of the Leu-Val cleavage site of angiotensinogen.

In another embodiment the present invention is directed to pharmaceutical compositions comprising a compound described herein or an enantiomer, diastereomer, or salt thereof and a pharmaceutically acceptable carrier or excipient.

In another embodiment the present invention is directed to method for treating or ameliorating an aspartic protease mediated disorder in a subject in need thereof comprising administering to said subject a therapeutically effective amount of a compound described herein or an enantiomer, diastereomer, or salt thereof.

In another embodiment the present invention is directed to a method for treating or ameliorating a renin mediated disorder in a subject in need thereof comprising administering to the subject an effective amount of a compound described herein or an enantiomer, diastereomer, or salt thereof.

In another embodiment the present invention is directed to a method for treating or ameliorating a renin mediated disorder in a subject in need thereof comprising administering to the subject a compound described herein in combination therapy with one or more additional agents said additional agent selected from the group consisting of α-blockers, β-blockers, calcium channel blockers, diuretics, angiotensin converting enzyme (ACE) inhibitors, dual ACE and neutral endopeptidase (NEP) inhibitors, angiotensin-receptor blockers (ARBs), aldosterone synthase inhibitors, aldosterone-receptor antagonists, and endothelin receptor antagonists.

DETAILED DESCRIPTION OF THE INVENTION

A description of preferred embodiments of the invention follows.

In a first embodiment, the invention provides compounds of Formula I

I

[chemical structure showing $G^b$, $G^c$, $G^a$, $A^4$, Ring A, N, Q, T]

wherein:
$G^a$ is a) $(C_1-C_9)$alkyl, $(C_3-C_7)$cycloalkyl, $(C_4-C_9)$cycloalkylalkyl, halo$(C_1-C_9)$alkyl, halo$(C_3-C_7)$cycloalkyl, halo$(C_4-C_8)$cycloalkylalkyl, saturated heterocyclyl optionally substituted with 1 to 3 groups independently selected from fluorine, $(C_1-C_3)$alkyl, halo$(C_1-C_3)$alkyl, and oxo;
or b) phenyl, napthyl, heteroaryl, or bicyclic heteroaryl each optionally substituted with 1 to 3 groups independently selected from:
1) fluorine, chlorine, bromine, cyano, nitro, $(C_1-C_6)$alkyl, $(C_3-C_6)$cycloalkyl, $(C_4-C_7)$cycloalkylalkyl, $(C_2-C_6)$alkenyl, $(C_5-C_6)$cycloalkenyl, $(C_5-C_8)$cycloalkylalkenyl, $(C_2-C_6)$alkynyl, $(C_3-C_6)$cycloalkylethynyl, halo$(C_1-C_6)$alkyl, halo$(C_3-C_6)$cycloalkyl, halo$(C_4-C_7)$-cycloalkylalkyl, halo$(C_2-C_6)$alkenyl, halo$(C_3-C_6)$alkynyl, halo$(C_3-C_6)$cycloalkylethynyl, $(C_1-C_6)$alkoxy, $(C_3-C_6)$cycloalkoxy, $(C_4-C_7)$cycloalkylalkoxy, halo$(C_1-C_6)$alkoxy, halo$(C_3-C_6)$cycloalkoxy, halo$(C_4-C_7)$cycloalkylalkoxy, $(C_3-C_6)$alkenyloxy and $(C_1-C_6)$alkanesulfonyl; or 2) phenyl, heteroaryl, phenoxy, heteroaryloxy, phenylthio, heteroarylthio, benzyl, heteroarylmethyl, benzyloxy and heteroaryloxy, each optionally substituted with 1 to 3 groups independently selected from:
fluorine, chlorine, cyano, $(C_1-C_3)$alkyl, halo$(C_1-C_3)$alkyl, $(C_1-C_3)$-alkoxy, halo$(C_1-C_3)$alkoxy, and aminocarbonyl;
$G^b$ is hydrogen, $(C_1-C_8)$alkyl, $(C_4-C_8)$cycloalkylalkyl, fluoro$(C_1-C_8)$alkyl, fluoro$(C_4-C_8)$cycloalkylalkyl, $(C_1-C_8)$alkoxy, $(C_4-C_8)$cycloalkylalkoxy, fluoro$(C_1-C_8)$alkoxy, hydroxy$(C_1-C_8)$alkyl, $(C_1-C_5)$alkoxy$(C_1-C_8)$alkyl, halo$(C_1-C_5)$alkylamino$(C_1-C_5)$alkyl, $(C_1-C_8)$alkoxy$(C_1-C_5)$hydroxyalkyl, $(C_3-C_4)$cycloalkoxy$(C_1-C_5)$alkyl, fluoro$(C_1-C_5)$alkoxy$(C_1-C_5)$alkyl, fluoro$(C_3-C_4)$cycloalkoxy$(C_1-C_8)$alkyl, $(C_1-C_5)$alkylthio$(C_1-C_8)$alkyl, $(C_1-C_8)$alkoxy$(C_1-C_5)$alkoxy, hydroxy$(C_1-C_8)$alkoxy, $(C_3-C_4)$cycloalkoxy$(C_1-C_5)$alkoxy, fluoro$(C_1-C_5)$alkoxy$(C_1-C_8)$alkoxy, fluoro$(C_3-C_4)$cycloalkoxy$(C_1-C_5)$alkoxy, $(C_1-C_3)$alkoxy$(C_1-C_3)$alkoxy$(C_1-C_3)$alkyl, fluoro$(C_1-C_3)$alkoxy$(C_1-C_3)$alkoxy$(C_1-C_3)$alkyl, aminocarbonylamino$(C_1-C_8)$alkyl, aminocarbonylamino$(C_1-C_8)$alkoxy, $(C_1-C_5)$alkanoylamino$(C_1-C_8)$alkyl, $(C_1-C_5)$alkanoylamino$(C_1-C_8)$alkoxy, fluoro$(C_1-C_5)$alkanoylamino$(C_1-C_5)$alkyl, fluoro$(C_1-C_5)$alkanoylamino$(C_1-C_5)$alkoxy, $(C_1-C_3)$alkoxy$(C_1-C_5)$alkanoylamino$(C_1-C_5)$alkyl, $(C_1-C_3)$alkoxy$(C_1-C_8)$alkanoylamino$(C_1-C_5)$alkoxy, $(C_3-C_4)$cycloalkanecarbonylamino$(C_1-C_5)$alkyl, $(C_3-C_4)$cycloalkanecarbonylamino$(C_1-C_5)$alkoxy, aminosulfonylamino$(C_1-C_8)$alkyl, aminosulfonylamino$(C_1-C_8)$alkoxy, $(C_1-C_5)$alkanesulfonyl-amino$(C_1-C_5)$alkyl, $(C_1-C_8)$alkanesulfonylamino$(C_1-C_5)$alkoxy, formylamino$(C_1-C_5)$alkyl, formylamino$(C_1-C_5)$alkoxy, $(C_1-C_5)$alkoxycarbonylamino$(C_1-C_5)$alkyl, $(C_1-C_5)$alkoxycarbonyl-amino$(C_1-C_5)$alkoxy, $(C_1-C_5)$alkylaminocarbonylamino$(C_1-C_5)$alkyl, $(C_1-C_5)$alkylaminocarbonyl-amino$(C_1-C_5)$alkyl, di$(C_1-C_5)$alkylaminocarbonylamino$(C_1-C_5)$alkoxy, aminocarbonyl$(C_1-C_5)$alkyl, aminocarbonyl$(C_1-C_5)$alkoxy, $(C_1-C_5)$alkylaminocarbonyl$(C_1-C_5)$alkyl, $(C_1-C_5)$alkylaminocarbonyl-$(C_1-C_5)$alkoxy, aminocarboxy$(C_1-C_5)$alkyl, aminocarboxy$(C_1-C_5)$alkoxy, $(C_1-C_5)$alkylaminocarboxy$(C_1-C_5)$alkyl, $(C_1-C_5)$alkylaminocarboxy$(C_1-C_8)$alkoxy, alkoxycarbonylamino, $(C_1-C_8)$alkylaminocarbonylamino, $(C_1-C_8)$alkanoylamino, fluoro$(C_1-C_8)$alkoxycarbonylamino, fluoro$(C_1-C_8)$alkylaminocarbonylamino, or fluoro$(C_1-C_8)$alkanoylamino;
$G^c$ is H, halogen, OH, $(C_1-C_4)$alkanoylamino, or $(C_1-C_3)$alkoxy;

provided that (i) $G^b$ and $G^c$ are not both hydrogen and (ii) when $G^c$ is OH or halogen, $G^b$ is not $(C_1-C_8)$alkoxy, $(C_4-C_8)$cycloalkylalkoxy, fluoro$(C_1-C_8)$alkoxy, $(C_1-C_5)$alkoxy$(C_1-C_8)$alkoxy, hydroxy$(C_1-C_8)$alkoxy, $(C_3-C_4)$cycloalkoxy$(C_1-C_5)$alkoxy, fluoro$(C_1-C_8)$alkoxy$(C_1-C_5)$alkoxy, fluoro$(C_3-C_4)$cycloalkoxy$(C_1-C_5)$alkoxy, aminocarbonylamino$(C_1-C_8)$alkoxy, $(C_1-C_5)$alkanoylamino$(C_1-C_5)$alkoxy, fluoro$(C_1-C_5)$alkanoylamino$(C_1-C_5)$alkoxy, $(C_1-C_3)$alkoxy$(C_1-C_5)$alkanoyl-amino$(C_1-C_5)$alkoxy, $(C_3-C_4)$cycloalkanecarbonylamino$(C_1-C_5)$alkoxy, aminosulfonylamino$(C_1-C_8)$alkoxy, $(C_1-C_5)$alkanesulfonyl amino$(C_1-C_5)$alkoxy, formylamino$(C_1-C_5)$alkoxy, $(C_1-C_8)$alkoxy-carbonylamino$(C_1-C_5)$alkoxy, di$(C_1-C_5)$alkylaminocarbonylamino$(C_1-C_5)$alkoxy, aminocarbonyl$(C_1-C_5)$alkoxy, $(C_1-C_5)$alkylaminocarbonyl$(C_1-C_5)$alkoxy, aminocarboxy$(C_1-C_5)$alkoxy, $(C_1-C_5)$alkylaminocarboxy$(C_1-C_5)$alkoxy, $(C_1-C_8)$alkoxycarbonylamino, $(C_1-C_8)$alkylaminocarbonylamino, $(C_1-C_8)$alkanoylamino, fluoro$(C_1-C_8)$alkoxycarbonylamino, fluoro$(C_1-C_8)$alkylaminocarbonylamino, or fluoro$(C_1-C_8)$alkanoylamino;

$A^4$ is $CH_2$ or O;

Q is a divalent radical selected from:

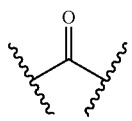
Q1

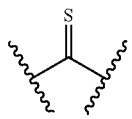
Q2

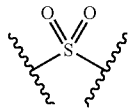
Q3

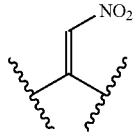
Q4

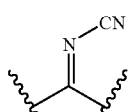
Q5

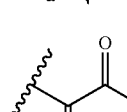
Q6

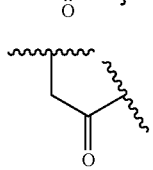
Q7

-continued

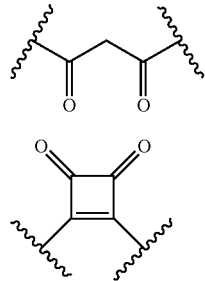
Q8

Q9

Q10

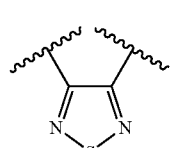
Q11

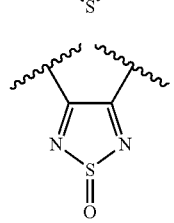
Q12

or

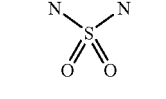
Q13 wherein N and T are attached to the truncated bonds

T is a mimic of the Leu-Val cleavage site of angiotensinogen. The term "mimic of the Leu-Val cleavage site of angiotensinogen" as used herein includes the substituents (T) disclosed in the following references:

Luly, et al., U.S. Pat. No. 4,645,759, issued Feb. 24, 1987, which is hereby incorporated by reference, discloses mimics of the Leu-Val cleavage site of angiotensinogen having the formula

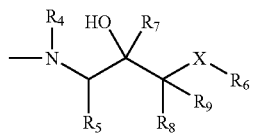

wherein $R_4$, $R_5$, $R_6$, $R_7$, $R_8$, $R_9$ and X are as defined therein;

Luly, et al., U.S. Pat. No. 4,652,551, issued Mar. 24, 1987, which is hereby incorporated by reference, discloses mimics of the Leu-Val cleavage site of angiotensinogen having the formula

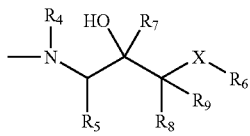

wherein $R_4$, $R_5$, $R_6$, $R_7$, $R_8$, $R_9$ and X are as defined therein;

Luly, et al., U.S. Pat. No. 4,680,284, issued Jul. 14, 1987, which is hereby incorporated by reference, discloses mimics of the Leu-Val cleavage site of angiotensinogen having the formula

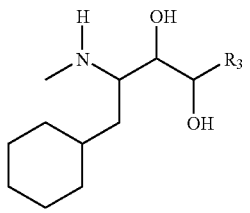

wherein $R_3$ is as defined therein;

Luly, et al., U.S. Pat. No. 4,725,584, issued Feb. 16, 1988, which is hereby incorporated by reference, discloses mimics of the Leu-Val cleavage site of angiotensinogen having the formula

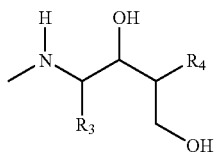

wherein $R_3$ and $R_4$ are as defined therein;

Luly, et al., U.S. Pat. No. 4,725,583, issued Feb. 16, 1988, which is hereby incorporated by reference, discloses mimics of the Leu-Val cleavage site of angiotensinogen having the formula

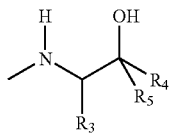

wherein $R_3$, $R_4$ and $R_5$ are as defined therein;

Rosenberg, et al., U.S. Pat. No. 4,837,204, issued Jun. 6, 1989, which is hereby incorporated by reference, discloses mimics of the Leu-Val cleavage site of angiotensinogen having the formula

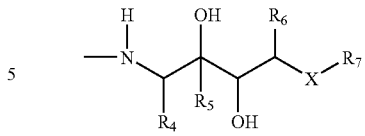

wherein $R_4$, $R_5$, $R_6$, $R_7$ and X are as defined therein;

Luly, et al., U.S. Pat. No. 4,845,079, issued Jul. 4, 1989, which is hereby incorporated by reference, discloses mimics of the Leu-Val cleavage site of angiotensinogen having the formula

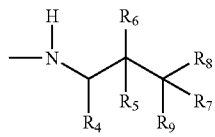

wherein $R_4$, $R_5$, $R_6$, $R_7$, $R_8$ and $R_9$ are as defined therein;

Sham, U.S. Pat. No. 4,826,958, issued May 2, 1989, which is hereby incorporated by reference, discloses mimics of the Leu-Val cleavage site of angiotensinogen having the formula

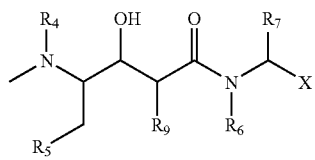

wherein $R_4$, $R_5$, $R_6$, $R_7$, $R_9$ and X are as defined therein;

Rosenberg et al., U.S. Pat. No. 4,857,507, issued Aug. 15, 1989, which is hereby incorporated by reference, discloses mimics of the Leu-Val cleavage site of angiotensinogen having the formula

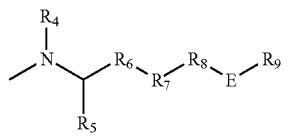

wherein $R_4$, $R_5$, $R_6$, $R_7$, $R_8$, $R_9$ and E are as defined therein;

Luly, et al., U.S. Pat. No. 4,826,815, issued May 2, 1989, which is hereby incorporated by reference, discloses mimics of the Leu-Val cleavage site of angiotensinogen having the formula

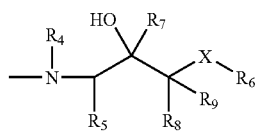

wherein $R_4$, $R_5$, $R_6$, $R_7$, $R_8$, $R_9$ and X are as defined therein;

Bender, et al., U.S. Pat. No. 4,818,748, issued Apr. 4, 1989, which is hereby incorporated by reference, discloses mimics of the Leu-Val cleavage site of angiotensinogen having the formula

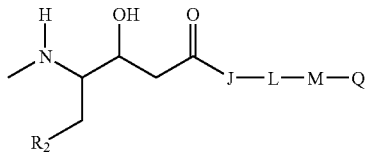

wherein $R_1$, J, L, M and Q are as defined therein;

Fuhrer, et al., U.S. Pat. No. 4,613,676, issued Sep. 23, 1986, which is hereby incorporated by reference, discloses mimics of the Leu-Val cleavage site of angiotensinogen having the formula

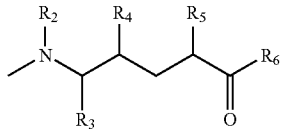

wherein $R_2$, $R_3$, $R_4$, $R_5$ and $R_6$ are as defined therein;

Riniker, et al., U.S. Pat. No. 4,595,677, issued Jun. 17, 1986, which is hereby incorporated by reference, discloses mimics of the Leu-Val cleavage site of angiotensinogen having the formula

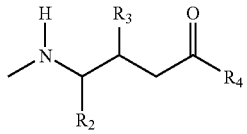

wherein $R_2$, $R_3$ and $R_4$ are as defined therein;

Buhlmayer, et al., U.S. Pat. No. 4,727,060, issued Feb. 23, 1988, which is hereby incorporated by reference, discloses mimics of the Leu-Val cleavage site of angiotensinogen having the formula

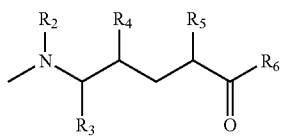

wherein $R_2$, $R_3$, $R_4$, $R_5$ and $R_6$ are as defined therein;

Buhlmayer, et al., U.S. Pat. No. 4,758,584, issued Jul. 19, 1988, which is hereby incorporated by reference, discloses mimics of the Leu-Val cleavage site of angiotensinogen having the formula

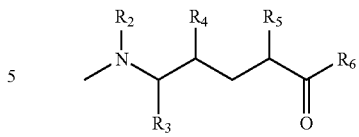

wherein $R_2$, $R_3$, $R_4$, $R_5$ and $R_6$ are as defined therein;

Szelke, et al., U.S. Pat. No. 4,609,643, issued Sep. 2, 1986, which is hereby incorporated by reference, discloses mimics of the Leu-Val cleavage site of angiotensinogen having the formula

-A-B—Z—W wherein A, B, Z and W are as defined therein;

Szelke, et al., U.S. Pat. No. 4,650,661, issued Mar. 17, 1987, which is hereby incorporated by reference, discloses mimics of the Leu-Val cleavage site of angiotensinogen having the formula

-A-B—Z—W wherein A, B, Z and W are as defined therein;

Szelke, et al., U.S. Pat. No. 4,713,445, issued Dec. 15, 1987, which is hereby incorporated by reference, discloses mimics of the Leu-Val cleavage site of angiotensinogen having the formula

-A-B—Z—W wherein A, B, Z and W are as defined therein;

Iizuka, et al., U.S. Pat. No. 4,656,269, issued Apr. 7, 1987, which is hereby incorporated by reference, discloses mimics of the Leu-Val cleavage site of angiotensinogen having the formula

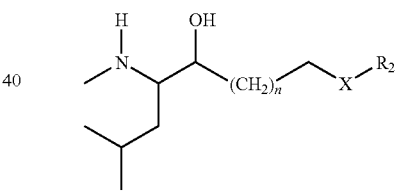

wherein n, X and $R_2$ are as defined therein;

Iizuka, et al., U.S. Pat. No. 4,711,958, issued Dec. 8, 1987, which is hereby incorporated by reference, discloses mimics of the Leu-Val cleavage site of angiotensinogen having the formula

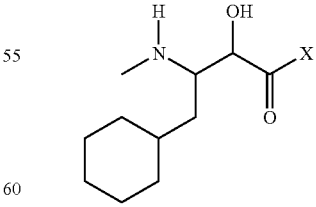

wherein X is as defined therein;

Kleinman, et al., U.S. Pat. No. 4,729,985, issued Mar. 8, 1988, which is hereby incorporated by reference, discloses mimics of the Leu-Val cleavage site of angiotensinogen having the formula

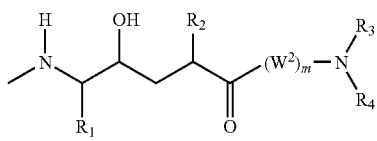

wherein $R_1$, $R_2$, m, $W^2$, $R_3$ and $R_4$ are as defined therein;

Hoover, U.S. Pat. No. 4,668,769, issued May 26, 1987, which is hereby incorporated by reference, discloses mimics of the Leu-Val cleavage site of angiotensinogen having the formula

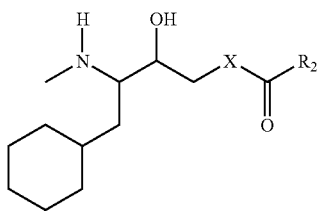

wherein X and $R_2$ are as defined therein;

Hoover, et al., U.S. Pat. No. 4,814,342, issued Mar. 21, 1989, which is hereby incorporated by reference, discloses mimics of the Leu-Val cleavage site of angiotensinogen having the formula

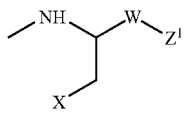

wherein X, W and $Z^1$ are as defined therein;

Bindra, et al., U.S. Pat. No. 4,749,687, issued Jun. 7, 1988, which is hereby incorporated by reference, discloses mimics of the Leu-Val cleavage site of angiotensinogen having the formula

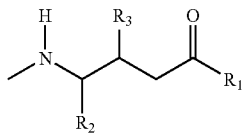

wherein $R_1$, $R_2$ and $R_3$ are as defined therein;

Hoover, et al., U.S. Pat. No. 4,814,342, issued Mar. 1, 1989, which is hereby incorporated by reference, discloses mimics of the Leu-Val cleavage site of angiotensinogen having the formula

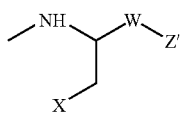

wherein X, W and $Z^1$ are as defined therein;

Matsueda, et al., U.S. Pat. No. 4,698,329, issued Oct. 6, 1987, which is hereby incorporated by reference, discloses mimics of the Leu-Val cleavage site of angiotensinogen having the formula

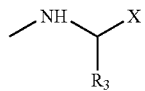

wherein $R_3$ and X are as defined therein;

Matsueda, et al., U.S. Pat. No. 4,548,926, issued Oct. 22, 1985, which is hereby incorporated by reference, discloses mimics of the Leu-Val cleavage site of angiotensinogen having the formula

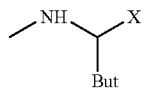

wherein But and X are as defined therein;

Wagnon, et al., U.S. Pat. No. 4,725,580, issued Feb. 16, 1988, which is hereby incorporated by reference, discloses mimics of the Leu-Val cleavage site of angiotensinogen having the formula

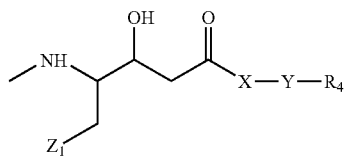

wherein $Z_1$, X, Y and $R_4$ are as defined therein;

Wagnon, et al., U.S. Pat. No. 4,746,648, issued May 24, 1988, which is hereby incorporated by reference, discloses mimics of the Leu-Val cleavage site of angiotensinogen having the formula

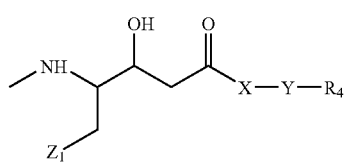

wherein $Z_1$, X, Y and $R_4$ are as defined therein;

Cazaubon, et al., U.S. Pat. No. 4,481,192, issued Nov. 6, 1984, which is hereby incorporated by reference, discloses mimics of the Leu-Val cleavage site of angiotensinogen having the formula

-Statyl$_1$-Ala-Statyl$_2$-R$^1$ wherein Statyl$_1$, Ala, Statyl$_2$ and R' are as defined therein;

Hansen, et al., U.S. Pat. No. 4,722,922, issued Feb. 2, 1988, which is hereby incorporated by reference, discloses mimics of the Leu-Val cleavage site of angiotensinogen having the formula

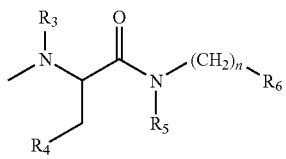

wherein $R_3$, $R_4$, $R_5$, n and $R_6$ are as defined therein;
Hansen, et al., U.S. Pat. No. 4,510,085, issued Apr. 9, 1985, which is hereby incorporated by reference, discloses mimics of the Leu-Val cleavage site of angiotensinogen having the formula

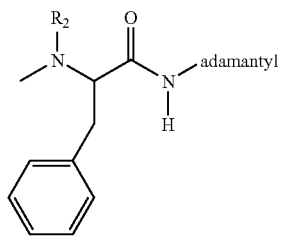

wherein $R_2$ is as defined therein;
Baran, et al., U.S. Pat. No. 4,657,931, issued Apr. 14, 1987, which is hereby incorporated by reference, discloses mimics of the Leu-Val cleavage site of angiotensinogen having the formula

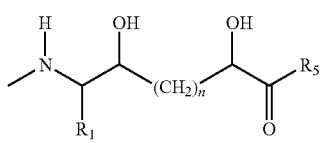

wherein $R_1$, n and $R_5$ are as defined therein;
Hansen, et al., U.S. Pat. No. 4,514,332 issued Apr. 30, 1985, which is hereby incorporated by reference, discloses mimics of the Leu-Val cleavage site of angiotensinogen having the formula

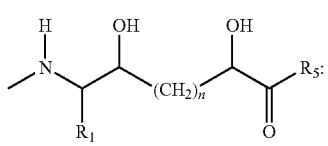

wherein $R_1$, n and $R_5$ are as defined therein;
Natarajan, et al., U.S. Pat. No. 4,757,050, issued Jul. 12, 1988, which is hereby incorporated by reference, discloses mimics of the Leu-Val cleavage site of angiotensinogen having the formula

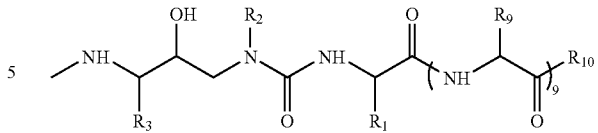

wherein $R_1$, $R_2$, $R_3$, q, $R_9$ and $R_{10}$ are as defined therein;
Gordon, U.S. Pat. No. 4,749,781, issued Jun. 7, 1988, which is hereby incorporated by reference, discloses mimics of the Leu-Val cleavage site of angiotensinogen having the formula

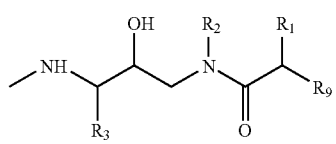

wherein $R_1$, $R_2$, $R_3$ and $R_9$ are as defined therein;
Ryono, et al., U.S. Pat. No. 4,665,193, issued May 12, 1987, which is hereby incorporated by reference, discloses mimics of the Leu-Val cleavage site of angiotensinogen having the formula

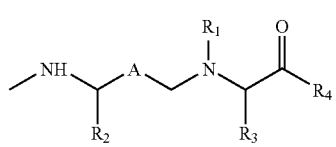

wherein $R_1$, $R_2$, $R_3$, $R_4$ and A are as defined therein;
Ryono, et al., U.S. Pat. No. 4,616,088, issued Oct. 1, 1986, which is hereby incorporated by reference, discloses mimics of the Leu-Val cleavage site of angiotensinogen having the formula

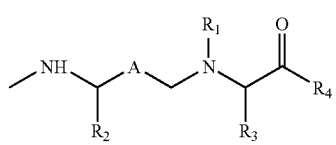

wherein $R_1$, $R_2$, $R_3$, $R_4$ and A are as defined therein;
Ryono, et al., U.S. Pat. No. 4,629,724, issued Dec. 16, 1986, which is hereby incorporated by reference, discloses mimics of the Leu-Val cleavage site of angiotensinogen having the formula

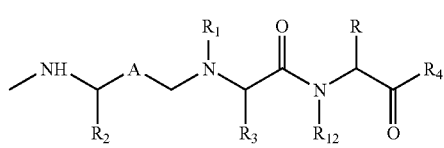

wherein $R_1$, $R_2$, $R_3$, $R_4$, R, $R_{12}$ and A are as defined therein;

Patel, U.S. Pat. No. 4,820,691, issued Apr. 11, 1989, which is hereby incorporated by reference, discloses mimics of the Leu-Val cleavage site of angiotensinogen having the formula

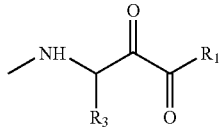

wherein $R_1$ and $R_3$ are as defined therein;

Thaisrivongs, U.S. Pat. No. 4,705,846, issued Nov. 10, 1987, which is hereby incorporated by reference, discloses mimics of the Leu-Val cleavage site of angiotensinogen having the formula $$-E_{10}-F_{11}-G_{12}-H_{13}-I_{14}-Z$$

wherein $E_{10}$, $F_{11}$, $G_{12}$, $H_{13}$, $I_{14}$ and Z are as defined therein;

Hudspeth, et al., U.S. Pat. No. 4,743,585, issued May 10, 1988, which is hereby incorporated by reference, discloses mimics of the Leu-Val cleavage site of angiotensinogen having the formula $$-T-(C)_n-W-(D)_n-V-(E)_n-U$$

wherein T, C, W, D, V, E, U and n are as defined therein;

Hudspeth, et al., U.S. Pat. No. 4,735,933, issued Apr. 5, 1988, which is hereby incorporated by reference, discloses mimics of the Leu-Val cleavage site of angiotensinogen having the formula $$-Y-W-U$$

wherein Y, W and U are as defined therein;

Kaltenbronn, et al., U.S. Pat. No. 4,804,743, issued Feb. 14, 1989, which is hereby incorporated by reference, discloses mimics of the Leu-Val cleavage site of angiotensinogen having the formula $$-T-U-V-W$$

wherein T, U, V and W are as defined therein;

Pinori, et al., U.S. Pat. No. 4,560,505, issued Dec. 24, 1985, which is hereby incorporated by reference, discloses mimics of the Leu-Val cleavage site of angiotensinogen having the formula

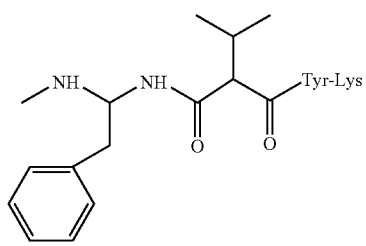

wherein Tyr and Lys are as defined therein;

Yamato, et al., U.S. Pat. No. 4,683,220, issued Jul. 28, 1987, which is hereby incorporated by reference, discloses mimics of the Leu-Val cleavage site of angiotensinogen having the formula

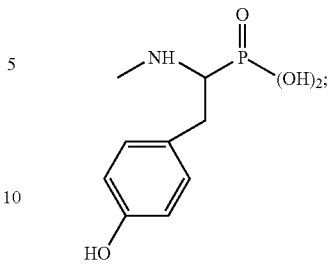

Boger, et al., U.S. Pat. No. 4,668,770, issued May 26, 1987, which is hereby incorporated by reference, discloses mimics of the Leu-Val cleavage site of angiotensinogen having the formula

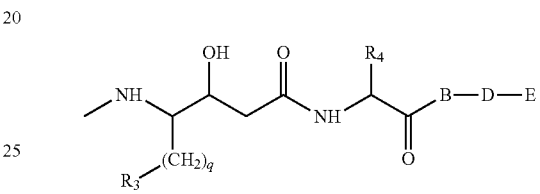

wherein $R_3$, $R_4$, q, B, D and E are as defined therein;

Boger, U.S. Pat. No. 4,668,663, issued May 26, 1987, which is hereby incorporated by reference, discloses mimics of the Leu-Val cleavage site of angiotensinogen having the formula

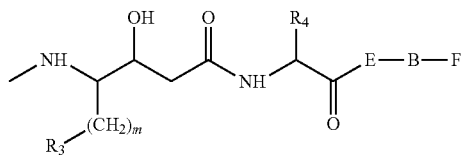

wherein $R_3$, $R_4$, m, E, B and F are as defined therein;

Bock, et al., U.S. Pat. No. 4,636,491, issued Jan. 3, 1987, which is hereby incorporated by reference, discloses mimics of the Leu-Val cleavage site of angiotensinogen having the formula

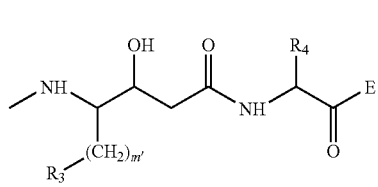

wherein $R_3$, $R_4$, m' and E are as defined therein;

Bock, et al., U.S. Pat. No. 4,663,310, issued May 5, 1987, which is hereby incorporated by reference, discloses mimics of the Leu-Val cleavage site of angiotensinogen having the formula

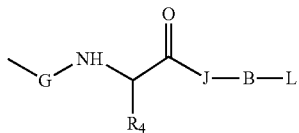

wherein G, R$_4$, J, B and L are as defined therein;
Boger, et al., U.S. Pat. No. 4,661,473, issued Apr. 28, 1987, which is hereby incorporated by reference, discloses mimics of the Leu-Val cleavage site of angiotensinogen having the formula

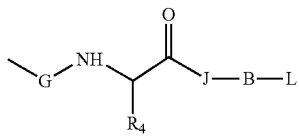

wherein G, R$_4$, J, B and L are as defined therein;
Veber, et al., U.S. Pat. No. 4,479,941, issued Oct. 30, 1984, which is hereby incorporated by reference, discloses mimics of the Leu-Val cleavage site of angiotensinogen having the formula

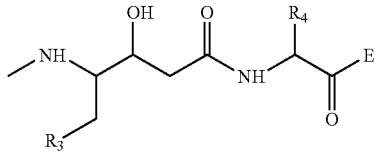

wherein R$_3$, R$_4$ and E are as defined therein;
Boger, et al., U.S. Pat. No. 4,470,971, issued Sep. 11, 1984, which is hereby incorporated by reference, discloses mimics of the Leu-Val cleavage site of angiotensinogen having the formula

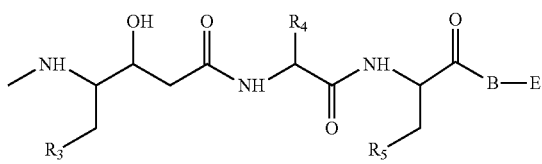

wherein R$_3$, R$_4$, R$_5$, B and E are as defined therein;
Veber, et al., U.S. Pat. No. 4,384,994, issued May 24, 1983, which is hereby incorporated by reference, discloses mimics of the Leu-Val cleavage site of angiotensinogen having the formula

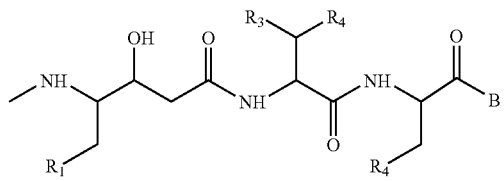

wherein R$_1$, R$_2$, R$_3$, R$_4$ and B are as defined therein;
Boger, et al., U.S. Pat. No. 4,812,442, issued Mar. 14, 1989, which is hereby incorporated by reference, discloses mimics of the Leu-Val cleavage site of angiotensinogen having the formula

-G-J wherein G and J are as defined therein;
Evans, U.S. Pat. No. 4,665,055, issued May 12, 1987, which is hereby incorporated by reference, discloses mimics of the Leu-Val cleavage site of angiotensinogen having the formula

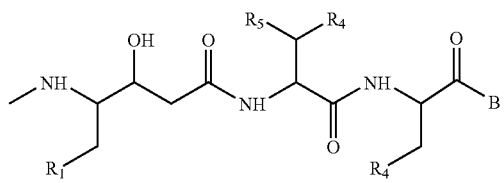

wherein R$_4$, R$_5$, B and C are as defined therein;
Evans, et al., U.S. Pat. No. 4,609,641, issued Sep. 2, 1986, which is hereby incorporated by reference, discloses mimics of the Leu-Val cleavage site of angiotensinogen having the formula

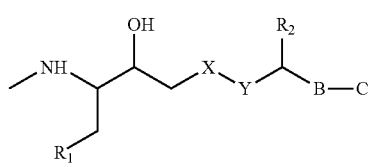

wherein R$_1$, R$_2$, X, Y, B and C are as defined therein;
Patchett, et al., U.S. Pat. No. 4,839,357, issued Jun. 13, 1989, which is hereby incorporated by reference, discloses mimics of the Leu-Val cleavage site of angiotensinogen having the formula

-G-J wherein G and J are as defined therein;
Boger, et al., U.S. Pat. No. 4,812,442, issued Mar. 14, 1989, which is hereby incorporated by reference, discloses mimics of the Leu-Val cleavage site of angiotensinogen having the formula

-G-J wherein G and J are as defined therein;
Boger, U.S. Pat. No. 4,665,052, issued May 12, 1987, which is hereby incorporated by reference, discloses mimics of the Leu-Val cleavage site of angiotensinogen having the formula

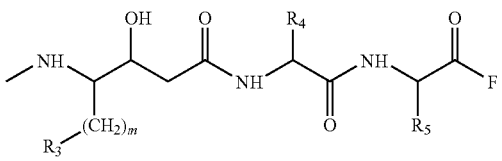

wherein $R_3$, $R_4$, $R_5$, m and F are as defined therein;

Veber, et al., U.S. Pat. No. 4,478,826, issued Oct. 23, 1984, which is hereby incorporated by reference, discloses mimics of the Leu-Val cleavage site of angiotensinogen having the formula

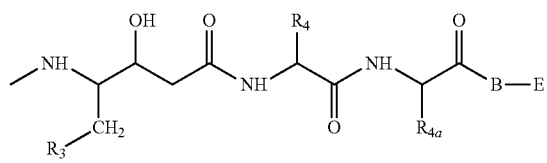

wherein $R_3$, $R_4$, $R_{4a}$, B and E are as defined therein;

Boger, et al., U.S. Pat. No. 4,485,099, issued Nov. 27, 1984, which is hereby incorporated by reference, discloses mimics of the Leu-Val cleavage site of angiotensinogen having the formula

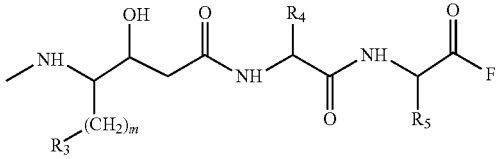

wherein $R_3$, $R_4$, $R_5$, m and F are as defined therein;

Boger, et al., U.S. Pat. No. 4,477,440 issued Oct. 16, 1984, which is hereby incorporated by reference, discloses mimics of the Leu-Val cleavage site of angiotensinogen having the formula

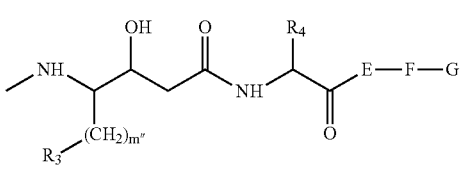

wherein $R_3$, $R_4$, m", E, F and G are as defined therein;

Raddatz, et al., U.S. Pat. No. 4,721,776, issued Jan. 26, 1988, which is hereby incorporated by reference, discloses mimics of the Leu-Val cleavage site of angiotensinogen having the formula

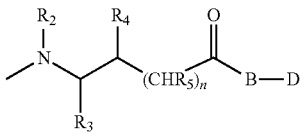

wherein $R_2$, $R_3$, $R_4$, $R_5$, n, B and D are as defined therein;

Holzemann, et al., U.S. Pat. No. 4,709,010, issued Nov. 24, 1987, which is hereby incorporated by reference, discloses mimics of the Leu-Val cleavage site of angiotensinogen having the formula

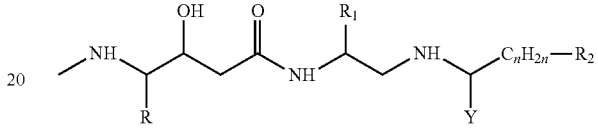

wherein R, $R_1$, $R_2$, n and Y are as defined therein;

Raddatz, et al., U.S. Pat. No. 4,812,555, issued Mar. 14, 1989, which is hereby incorporated by reference, discloses mimics of the Leu-Val cleavage site of angiotensinogen having the formula

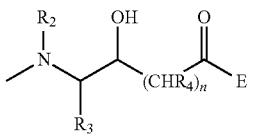

wherein $R_2$, $R_3$, $R_4$, n and E are as defined therein;

Raddatz, et al., U.S. Pat. No. 4,755,592, issued Jul. 5, 1988, which is hereby incorporated by reference, discloses mimics of the Leu-Val cleavage site of angiotensinogen having the formula

—W-E-W'—Y wherein W, E, W' and Y are as defined therein;

Raddatz, et al., U.S. Pat. No. 4,666,888, issued May 19, 1987, which is hereby incorporated by reference, discloses mimics of the Leu-Val cleavage site of angiotensinogen having the formula

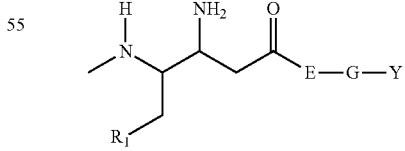

wherein $R_1$, E, G and Y are as defined therein;

Wagnon, et al., U.S. Pat. No. 4,840,935, issued Jun. 20, 1989, which is hereby incorporated by reference, discloses mimics of the Leu-Val cleavage site of angiotensinogen having the formula

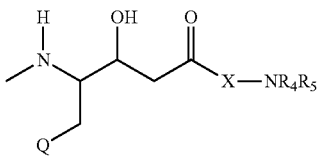

wherein $R_4$, $R_5$, Q and X are as defined therein;

Iizuka, et al., U.S. Pat. No. 4,841,067, issued Jun. 20, 1989, which is hereby incorporated by reference, discloses mimics of the Leu-Val cleavage site of angiotensinogen having the formula

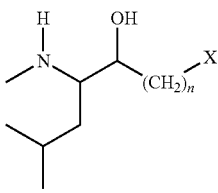

wherein n and X are as defined therein;

Raddatz, et al., U.S. Pat. No. 4,829,053, issued May 9, 1989, which is hereby incorporated by reference, discloses mimics of the Leu-Val cleavage site of angiotensinogen having the formula

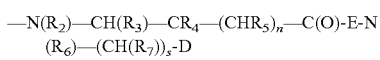

wherein n, s, $R_2$, $R_3$, $R_4$, $R_5$, $R_6$, $R_7$, E and D are as defined therein;

Biswanath et al., U.S. Pat. No. 5,164,388, issued Nov. 17, 1992, which is hereby incorporated by reference, discloses mimics of the Leu-Val cleavage site of angiotensinogen having the formula:

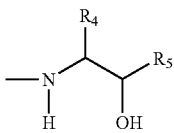

wherein $R_4$ and $R_5$ are as defined therein;

European Patent Application No. EP0264106, published Apr. 20, 1988, discloses mimics of the Leu-Val cleavage site of angiotensinogen having the formula

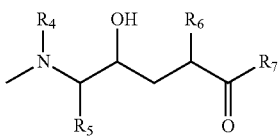

wherein $R_4$, $R_5$, $R_6$ and $R_7$ are as defined therein including $R_4$ is hydrogen or loweralkyl; $R_5$ is hydrogen, loweralkyl or an amino acid residue; $R_6$ is loweralkyl, cycloalkyl, cycloalkylalkyl or arylalkyl and $R_7$ is hydroxy, alkoxy, substituted alkoxy, amino, substituted amino or an N-heterocycle;

European Patent Application No. EP0272583, published Jun. 29, 1988, discloses mimics of the Leu-Val cleavage site of angiotensinogen having the formula

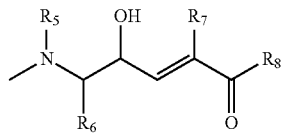

wherein $R_5$, $R_6$, $R_7$ and $R_8$ are as defined therein including $R_5$ is hydrogen or loweralkyl; $R_6$ is hydrogen, loweralkyl, cycloalkyl, cycloalkylalkyl, aryl, arylalkyl or an amino acid residue; and $R_7$ and $R_8$ are independently selected from hydrogen, loweralkyl, cycloalkyl, cycloalkylalkyl or arylalkyl;

European Patent Application No. EP0309766, published Apr. 5, 1989, discloses mimics of the Leu-Val cleavage site of angiotensinogen having the formula

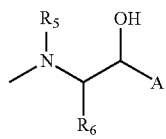

wherein $R_5$, $R_6$ and A are as defined therein including $R_5$ is hydrogen or loweralkyl; $R_6$ is hydrogen, loweralkyl, cycloalkyl, cycloalkylalkyl, aryl, aralkyl or heterocyclic; and A is —CH(OH)—(CH)$_q$—$R_7$ wherein q is 0-5 and $R_7$ is hydrogen, loweralkyl, cycloalkyl, cycloalkylalkyl, aryl, arylalkyl, heterocyclic, substituted thioalkyl, substituted sulfone, substituted sulfoxide, substituted amine, quaternized amine, heterocyclic, carboxyalkyl, alkoxycarbonylalkyl or amidoalkyl;

European Patent Application No. EP0300189, published Jan. 25, 1989, discloses mimics of the Leu-Val cleavage site of angiotensinogen having the formula

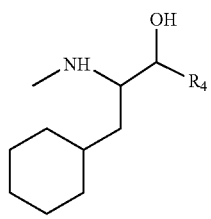

wherein $R_4$ is as defined therein including $R_4$ is loweralkyl;

European Patent Application No. EP0283970, published Sep. 28, 1988, discloses mimics of the Leu-Val cleavage site of angiotensinogen having the formula

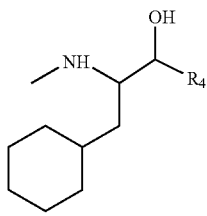

wherein R₄ is as defined therein including R₄ is loweralkyl;
European Patent Application No. EP0255082, published Feb. 3, 1988, discloses mimics of the Leu-Val cleavage site of angiotensinogen having the formula

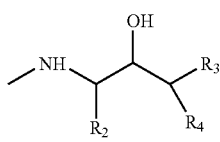

wherein $R_2$, $R_3$ and $R_4$ are as defined therein including $R_2$ is hydrogen, alkyl, cyclcoalkyl, cycloalkylalkyl, aryl or arylalkyl; $R_3$ is hydrogen, alkyl or arylalkyl; and $R_4$ is —X—(CH₂)ₙR₇ wherein X is absent, O or S, n' is 0-4 and R₇ is hydrogen, hydroxy, amino, heteroaryl or —CH(R₉)—(CH₂)ₚ—Y—(CH₂)_q—R₁₀ wherein p, q, Y and R₁₀ are as defined therein;
European Patent Application No. EP0230242, published Jul. 29, 1987, discloses mimics of the Leu-Val cleavage site of angiotensinogen having the formula

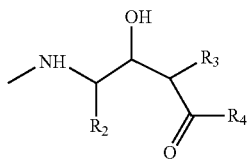

wherein $R_2$, $R_3$ and $R_4$ are as defined therein including $R_2$ is hydrogen, alkyl, cycloalkylalkyl, aryl or arylalkyl; $R_3$ is hydrogen, alkyl or alkenyl; and $R_4$ is —N(R₅)—CH(R₆)—(CH₂)ₙ—Ar or —N(R₅)—CH(R₆)—CH=CH—(CH₂)_m—Ar wherein n is 0-6, m is 0-4, R₅ is hydrogen or alkyl and R₆ is hydrogen, alkyl, hydroxyalkyl, alkoxyalkyl, thioalkoxyalkyl, carboxyalkyl, alkoxycarbonylalkyl, haloalkyl, alkylaminoalkyl, alkoxycarbonylaminoalkyl or arylalkoxycarbonylaminoalkyl;
European Patent Application No. EP0310015, published Apr. 5, 1989, discloses mimics of the Leu-Val cleavage site of angiotensinogen having the formula

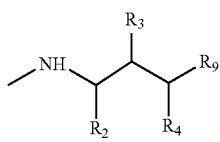

wherein $R_2$, $R_3$, $R_4$ and $R_9$ are as defined therein including $R_2$ is hydrogen, alkyl, cycloalkyl, cycloalkylalkyl, aryl or arylalkyl; $R_3$ is hydrogen, alkyl, aryl or arylalkyl; $R_9$ is hydroxy or fluoro; and $R_4$ is —(CH₂)ₚ—X—(CH₂)_q—R₇ wherein p is 0-4, q is 0-4, X is —CF₂—, —C(O)— or —CH(R₈)— wherein R₈ is alkyl, alkoxy, thioalkoxy, alkylamino, hydroxy, azido or halo and R₇ is hydrogen, hydroxy, amino, aryl or heteroaryl;
European Patent Application No. EP0315574, published May 10, 1989, discloses mimics of the Leu-Val cleavage site of angiotensinogen having the formula

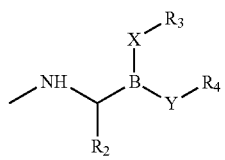

(B is a boron atom)

wherein $R_2$, X, Y, $R_3$ and $R_4$ are as defined therein including $R_2$ is hydrogen, alkyl, cycloalkyl, cycloalkylalkyl, aryl or heterocyclic; X and Y are independently selected from O or —N(R₁₃)— wherein R₁₃ is hydrogen, alkyl or substituted alkyl; and $R_3$ and $R_4$ are independently selected from hydrogen, alkyl or aryl; or the boron containing substituent is a boron containing cyclic group;
Japanese Patent Application No. J63275552, published Nov. 14, 1988 discloses mimics of the Leu-Val cleavage site of angiotensinogen having the formula

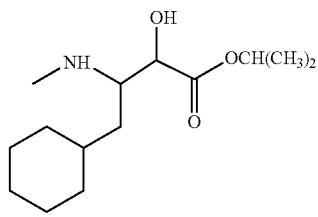

European Patent Application No. EP0252727, published Jan. 13, 1988, discloses mimics of the Leu-Val cleavage site of angiotensinogen having the formula

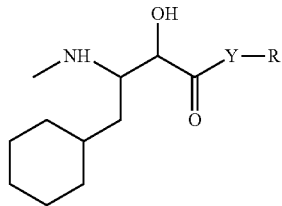

wherein Y and R are as defined therein including Y is O or NH and R is alkyl, cycloalkyl or halogenated alkyl;
European Patent Application No. EP0244083, published Nov. 4, 1987, discloses mimics of the Leu-Val cleavage site of angiotensinogen having the formula

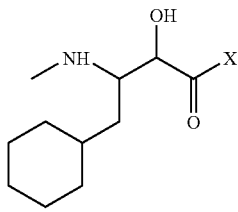

wherein X is as defined therein including X is alkoxy, alkyalamino, cycloalkyloxy, morpholino and haloalkoxy.

European Patent Application No. EP0216539, published Apr. 1, 1987, discloses mimics of the Leu-Val cleavage site of angiotensinogen having the formula

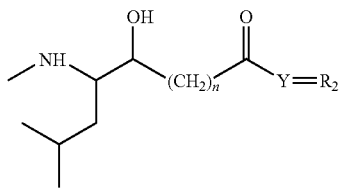

wherein n, Y and $R_2$ are as defined therein including n is 0-1, Y is O or NH and $R_2$ is alkyl;

European Patent Application No. EP0206807, published Dec. 30, 1986, discloses mimics of the Leu-Val cleavage site of angiotensinogen having the formula

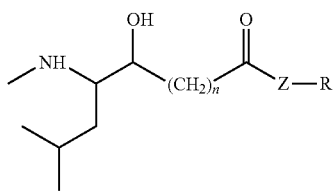

wherein n, Z and R are as defined therein including n is 0-1, Z is O or NH and R is alkyl;

European Patent Application No. EP0190891, published Aug. 13, 1986, discloses mimics of the Leu-Val cleavage site of angiotensinogen having the formula

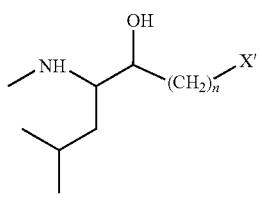

wherein n and X' are as defined therein including n is 0-1 and X' is alkoxycarbonyl, aralkoxycarbonyl, or —C(O)$NR_1R_2$ wherein $R_1$ is hydrogen, alkyl or aralkyl and $R_2$ is alkyl or —$CH_2$—Y—R wherein Y is O or NH and R is alkyl or aralkyl;

European Patent Application No. EP0181110, published May 14, 1986, discloses mimics of the Leu-Val cleavage site of angiotensinogen having the formula

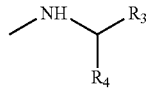

wherein $R_3$ and $R_4$ are as defined therein including $R_3$ is —CHO or —$CH_2$OH and $R_4$ is isobutyl or benzyl;

European Patent Application No. EP0297816, published Jan. 4, 1989, discloses mimics of the Leu-Val cleavage site of angiotensinogen having the formula

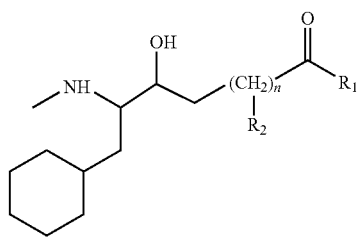

wherein n, $R_1$ and $R_2$ are as defined therein including n is 0-1, $R_1$ is —$NH_2$, alkylamino, alkoxy, or 2-alkoxycarbonylpyrrolidin-1-yl and $R_2$ is alkyl, alkenyl, haloalkenyl or azide substituted alkenyl;

European Patent Application No. EP0297815, published Jan. 4, 1989, discloses mimics of the Leu-Val cleavage site of angiotensinogen having the formula

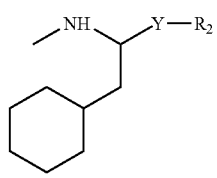

wherein Y and $R_2$ are as defined therein including Y is —CH(OH)— or —C(O)— and $R_2$ is —$CF_2$C(O)$NHCH_3$, —$CF_3$ or —$CF_2CH(CH_2CH(CH_3)_2)CO_2C_2H_5$;

European Patent Application No. EP0212903, published Mar. 4, 1987, discloses mimics of the Leu-Val cleavage site of angiotensinogen having the formula

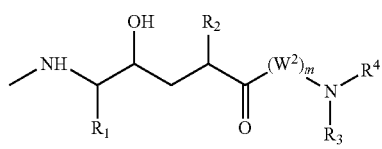

wherein m, $R_1$, $R_2$, $R_3$, $R_4$ and $W^2$ are as defined therein including m is 0-1, $R_1$ and $R_2$ are independently selected from hydrogen, alkyl, alkenyl, phenyl, naphthyl, cycloalkyl, cycloalkenyl, phenylalkyl, naphthylalkyl, cycloalkylalkyl and cycloalkenylalkyl, $R_3$ and $R_4$ are independently selected from alkyl, phenyl, naphthyl, cycloalkyl, adamantyl, phenylalkyl, naphthylalkyl, cycloalkylalkyl and adamantylalkyl; or $R_3$ is hydrogen and $R_4$ is —CH($R_7$)($CH_2$)$_p$(Q)$_r$CH($R_8$)($CH_2$)$_q$—Y wherein p and q are independently selected from 0,1,2,3,4,5 and 6, r is 0-1, Q is —$CH_2$—, —CH═CH—, —O—, —NH—, —CH(OH)— or —(O)—, Y is methyl, phenyl, —C(O)OR$_9$, C(O)NR$_9$R$_{10}$, —C(O)NHC(O) OCH$_2$C$_6$H$_5$, —NH$_2$, —NHC(O)CH$_2$C$_6$H$_5$, —NHCH (CH$_2$C$_6$H$_5$)C(O)OR$_9$ or —NHCH(CH$_2$C$_6$H$_5$)C(O)NR$_9$R$_{10}$ wherein R$_9$ and R$_{10}$ are independently selected from hydrogen, alkyl, phenyl, cycloalkyl, phenylalkyl, cycloalkylalkyl or adamantyl, and R$_7$ and R$_8$ are independently selected from hydrogen, alkyl, phenyl, cycloalkyl, phenylalkyl, cycloalkylalkyl or adamantyl; or R$_3$ and R$_4$ taken together with the nitrogen to which they are attached form a pyrrole, indoline, isoindoline, piperidine, 1,2,3,4-tetrahydroquinoline, 1,2,3,4-tetrahydroisoquinoline, perhydroazepine or morpholine ring; and W$^2$ is —NHCH((CH$_2$)$_3$R$_6$) —C(O)— wherein R$_6$ is —NH$_2$, —NHC(=NH)NH$_2$ or —CH$_2$NH$_2$; PCT Patent Application No. WO 88/03022, published May 5; 1988, discloses mimics of the Leu-Val cleavage site of angiotensinogen having the formula

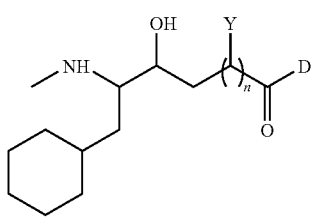

wherein n, Y and U are as defined therein including n is 0-1, Y is isobutyl, allyl or benzyl and D is 2-carboxypyrrolidin-1-yl or —ZR wherein Z is O or NH and R is alkyl, phenyl or substituted alkyl or substituted phenyl;

German Patent Application No. DE3725137, published Aug. 6, 1986, discloses mimics of the Leu-Val cleavage site of angiotensinogen having the formula

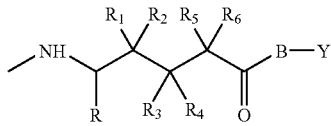

wherein R, R$_1$, R$_2$, R$_3$, R$_4$, R$_5$, R$_6$, B and Y are as defined therein including R is hydrogen, alkyl, cycloalkyl, cycloalkylalkyl, aryl, arylalkyl, heteroaryl or heteroarylalkyl, R$_1$ is hydroxy, alkoxy or aryloxy, R$_2$ is hydrogen or R$_1$ and R$_2$ taken together is oxo (=O), R$_3$, R$_4$, R$_5$ and R$_6$ are independently selected from hydrogen, fluoro, chloro, alkyl, cycloalkyl, cycloalkylalkyl, aryl, arylalkyl, heteroaryl and heteroarylalkyl, B is a peptide chain containing from 1 to 10 amino acid residues and Y is hydroxy or a protecting group for the peptide carboxy group;

British Patent Application No. GB2203740, published Oct. 26, 1988, discloses mimics of the Leu-Val cleavage site of angiotensinogen having the formula

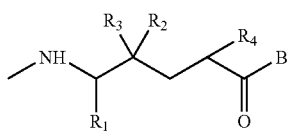

wherein R$_1$, R$_2$, R$_3$, R$_4$ and B are as defined therein including R$_1$ is a hydrophobic or hydrophilic side chain, R$_2$ is hydroxy or amino, R$_3$ is hydrogen or R$_2$ and R$_3$ taken together is oxo (=O), R$_4$ is a hydrophobic or hydrophilic side chain and B is —NHCH(R$_6$)C(R$_7$)(R$_8$)C(R$_9$)(R$_{10}$)CH$_2$C(O)NR$_{11}$R$_{12}$ wherein R$_6$ is R$_1$, R$_7$ and R$_8$ are the same as R$_2$ and R$_3$, R$_9$ and R$_{10}$ are independently selected from hydrogen and fluoro and R$_{11}$ and R$_{12}$ are independently selected from hydrogen, alkyl, arylalkyl, heteroarylalkyl and —CH(R$_{13}$)C(O)R$_{14}$ wherein R$_{13}$ is alkyl or hydroxyalkyl and R$_{14}$ is hydroxy, alkoxy, amino, alkylamino, aminomethylpyridyl or benzyl;

British Patent Application No. GB2200115, published Jul. 27, 1988, discloses mimics of the Leu-Val cleavage site of angiotensinogen having the formula

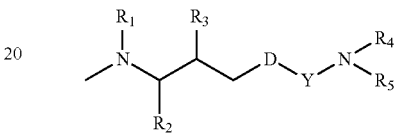

R$_1$, R$_2$, R$_3$, R$_4$, R$_5$, D and Y are as defined therein including R$_1$ is hydrogen or alkyl, R$_2$ is an amino acid side chain, R$_3$ is hydrogen, hydroxy, aryloxy or amino, R$_4$ and R$_5$ are independently selected from hydrogen, alkyl, arylalkyl, heteroarylalkyl and —CH(R$_{12}$)C(O)R$_{13}$ wherein R$_{12}$ is alkyl or hydroxyalkyl and R$_{13}$ is hydroxy, alkoxy, amino, alkylamino, aminomethylpyridyl or benzyl; or —NR$_4$R$_5$ represents pyrrolidinyl, piperidinyl, morpholinyl, piperazinyl or substituted piperazinyl; D is a bond, O, —N(R$_1$)— or —CH(R$_1$)— and Y is —C(O)—, —S(O)$_2$— or —P(O)—;

German Patent Application No. DE3830825, published Mar. 23, 1989, discloses mimics of the Leu-Val cleavage site of angiotensinogen having the formula

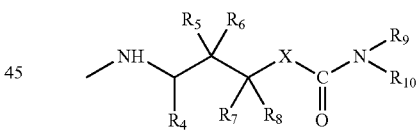

wherein R$_4$, R$_5$, R$_6$, R$_7$, R$_8$, R$_9$, R$_{10}$ and X are as defined therein including R$_4$ is a hydrophilic or hydrophobic amino acid side chain, R$_5$ is hydroxy or amino, R$^6$ is hydrogen or R$^5$ and R$^6$ taken together are oxo (=O), R$_7$ and R$_8$ are independently selected from hydrogen and fluoro, R$_9$ and R$_{10}$ are independently selected from hydrogen, alkyl and —CH(R$_{11}$)C(O)R$_{12}$ wherein R$_{11}$ is alkyl or hydroxyalkyl and R$_{12}$ is hydroxy, alkoxy, amino, alkylamino, aminomethylpyridyl, benzyl or —NH—(CH$_2$CH$_2$)$_m$—R1 wherein m is 1-20 and R$_1$ is as defined therein; and X is a bond or O, NH or —C(R$_{13}$)(R$_{14}$)— wherein R$_{13}$ and R$_{14}$ are independently selected from hydrogen, fluoro or R$_4$;

Japanese Patent Application No. J62246546, published Oct. 27, 1987, discloses mimics of the Leu-Val cleavage site of angiotensinogen having the formula

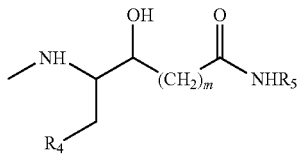

wherein m, $R_4$ and $R_5$ are as defined therein including m is 0-1, $R_4$ is alkyl, cycloalkyl or phenyl and $R_5$ is alkyl or substituted alkyl as defined therein;

European Patent Application No. EP0274259, published Jul. 13, 1988, discloses mimics of the Leu-Val cleavage site of angiotensinogen having the formula

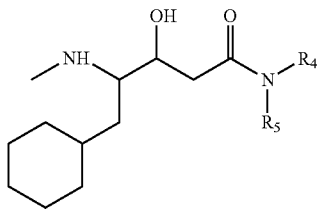

wherein $R_4$ and $R_5$ are as defined therein including $R_4$ is alkyl, hydroxyalkyl, (heterocyclic)alkyl, aminoalkyl, alkylaminoalkyl or dialkylaminoalkyl and $R_5$ is hydrogen or alkyl;

European Patent Application No. EP0228192, published Jul. 8, 1987, discloses mimics of the Leu-Val cleavage site of angiotensinogen having the formula

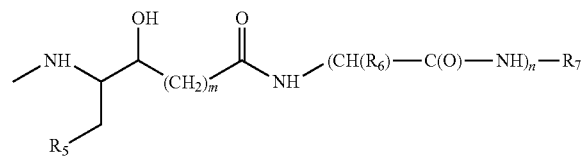

wherein m, n, $R_5$, $R_6$ and $R_7$ are as defined therein including m and n are independently selected from 0 and 1, $R_5$ is alkyl, cycloalkyl or phenyl, $R_6$ is alkyl and $R_7$ is alkyl or substituted alkyl as defined therein;

European Patent Application No. EP0273893, published Jul. 6, 1988, discloses mimics of the Leu-Val cleavage site of angiotensinogen having the formula

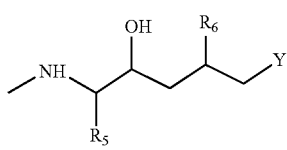

wherein $R_5$, $R_6$ and Y are as defined therein including $R_5$ is alkyl or cycloalkyl, $R_6$ is hydrogen or alkyl and Y is —SCH$(CH_3)_2$ or —S(O)$_2$CH$(CH_3)_2$;

European Patent Application No. EP0310070, published Apr. 5, 1989, discloses mimics of the Leu-Val cleavage site of angiotensinogen having the formula

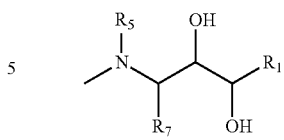

wherein $R_1$, $R_5$ and $R_7$ are as defined therein including $R_1$ is hydrogen, alkyl, haloalkyl, alkylcycloalkyl, alkylcycloalkenyl or alkoxycarbonyl, $R_5$ is hydrogen or alkyl and $R_7$ is cycloalkyl, phenyl, cycloalkylalkyl or phenylalkyl;

European Patent Application No. EP0310071, published Apr. 5, 1989, discloses mimics of the Leu-Val cleavage site of angiotensinogen having the formula

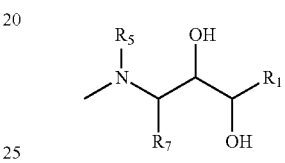

wherein $R_1$, $R_5$ and $R_7$ are as defined therein including $R_1$ is hydrogen, alkyl, haloalkyl, alkylcycloalkyl, alkylcycloalkenyl or alkoxycarbonyl, $R_5$ is hydrogen or alkyl and $R_7$ is cycloalkyl, phenyl, cycloalkylalkyl or phenylalkyl;

European Patent Application No. EP0310072, published Apr. 5, 1989, discloses mimics of the Leu-Val cleavage site of angiotensinogen having the formula

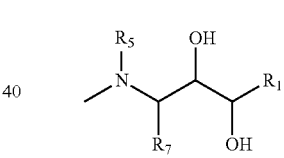

wherein $R_1$, $R_5$ and $R_7$ are as defined therein including $R_1$ is hydrogen, alkyl haloalkyl, alkylcycloalkyl, alkylcycloalkenyl or alkoxycarbonyl, $R_5$ is hydrogen or alkyl and $R_7$ is cycloalkyl, phenyl, cycloalkylalkyl or phenylalkyl;

European Patent Application No. EP0310073, published Apr. 5, 1989, discloses mimics of the Leu-Val cleavage site of angiotensinogen having the formulae

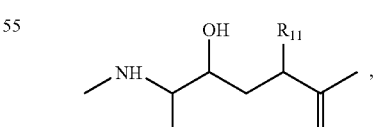

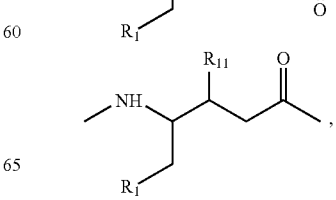

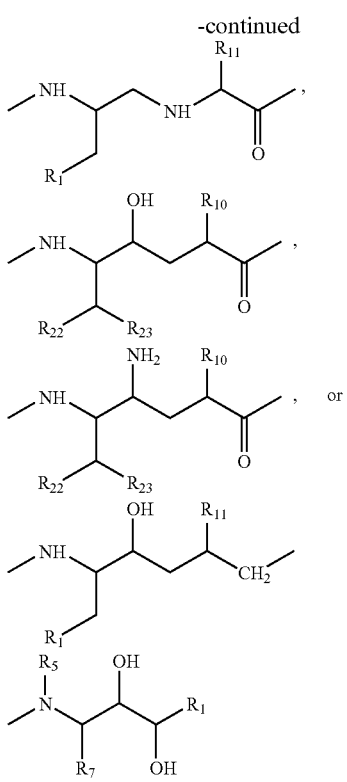

wherein $R_1$, $R_5$ and $R_7$ are as defined therein including $R_1$ is hydrogen, alkyl, haloalkyl, alkylcycloalkyl, alkylcycloalkenyl or alkoxycarbonyl, $R_5$ is hydrogen or alkyl and $R_7$ is cycloalkyl, phenyl, cycloalkylalkyl or phenylalkyl;

European Patent Application No. EP0313847, published May 3, 1989, discloses mimics of the Leu-Val cleavage site of angiotensinogen having the formula

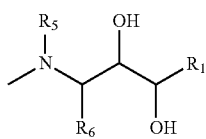

wherein $R_1$, $R_5$ and $R_6$ are as defined therein including $R_1$ is hydrogen, alkyl, haloalkyl, alkylcycloalkyl, alkylcycloalkenyl or alkoxycarbonyl, $R_5$ is hydrogen or alkyl and $R_6$ is cycloalkyl, phenyl, cycloalkylalkyl or phenylalkyl;

European Patent Application No. EP0296581, published Dec. 28, 1988, discloses mimics of the Leu-Val cleavage site of angiotensinogen having the formula

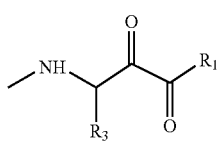

wherein $R_1$ and $R_3$ are as defined therein including $R_1$ is hydrogen, arylalkyl, aryl, (heterocyclic)alkyl or heterocyclic and $R_3$ is hydrogen, alkyl, haloalkyl, arylalkyl, (heterocyclic) alkyl, hydroxyalkyl, alkoxyalkyl, aminoalkyl, mercaptoalkyl, thioalkoxyalkyl, hydrorxyalkoxyalkyl, aminoalkoxyalkyl, hydroxythioalkoxyalkyl, carboxyalkyl, aminothioalkoxyalkyl, guanidinoalkyl, aminocarbonylalkyl or imidazolylalkyl;

European Patent Application No. EP0231919, published Aug. 12, 1987, discloses mimics of the Leu-Val cleavage site of angiotensinogen having the formula

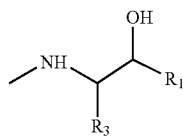

wherein $R_1$ and $R_3$ are as defined therein including $R_1$ is an N-heterocyclic ring and $R_3$ is hydrogen, alkyl, cycloalkylalkyl, haloalkyl, arylalkyl, (heterocyclic)alkyl, hydroxyalkyl, alkoxyalkyl, alkoxyalkyl, aminoalkyl, mercaptoalkyl, tioalkoxyalkyl, hydroxyalkoxyalkyl, aminoalkoxyalkyl, hydroxythioalkoxyalkyl, carboxyalkyl, aminothioalkoxyalkyl, guanidinoalkyl, aminocarbonylalkyl or imidazolylalkyl;

PCT Patent Application No. WO 87/05302, published May 3, 1989, discloses mimics of the Leu-Val cleavage site of angiotensinogen having the formula

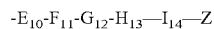

wherein $E_{10}$, $F_{11}$, $G_{12}$, $H_{13}$, $I_{14}$ and Z are as defined therein, including -$E_{10}$-$F_{11}$— is

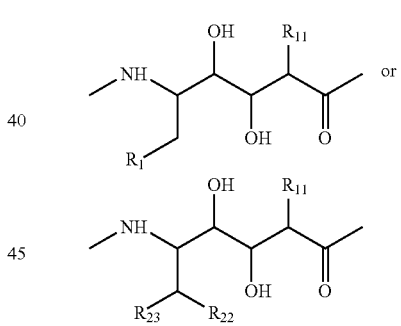

wherein $R_1$ is hydrogen, alkyl, aryl, cycloalkyl, heterocyclic, alkoxy or thioalkoxy, $R_{11}$ is hydrogen, alkyl, benzyl, cycloalkyl, hydroxyalkyl, cycloalkylalkyl, arylalkyl, (heterocyclic)alkyl, alkoxyalkyl or thioalkoxyalkyl, $R_{22}$ is hydrogen or alkyl and $R_{23}$ is hydroxyalkyl, aminoalkyl, aryl or alkyl, $G_{12}$ is absent or an amino acid residue, $H_{13}$ is absent or an amino acid residue, $I_{14}$ is absent or an amino acid residue and Z is hydroxy, substituted alkoxy, substituted amino or cyclic amino;

PCT Patent Application No. WO 87/02986, published May 21, 1987, discloses mimics of the Leu-Val cleavage site of angiotensinogen having the formula

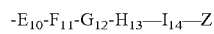

wherein $E_{10}$, $F_{11}$, $G_{12}$, $H_{13}$, $I_{14}$ and Z are as defined therein including -$E_{10}$-$F_{11}$— is

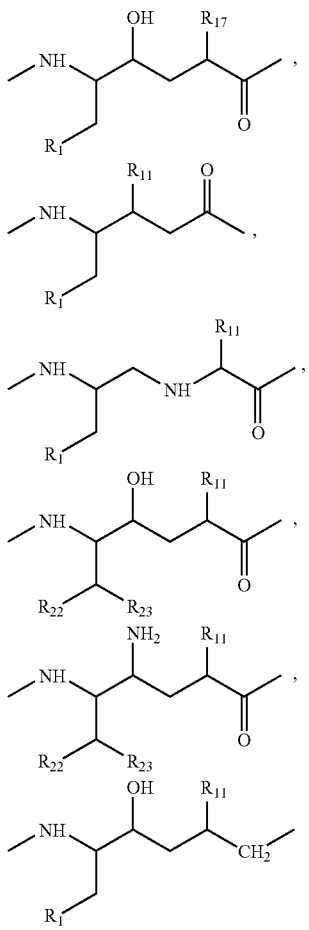

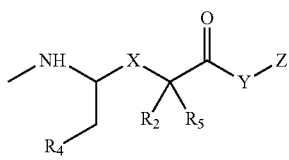

wherein $R_1$ is hydrogen, alkyl, aryl, cycloalkyl, heterocyclic, alkoxy or thioalkoxy, $R_1$ is hydrogen, alkyl, benzyl, cycloalkyl, hydroxyalkyl, cycloalkylalkyl, arylalkyl, (heterocyclic)alkyl, alkoxyalkyl or thioalkoxyalkyl, $R_{21}$ is hydroxy or amino, $R_{22}$ is hydrogen or alkyl and $R_{23}$ is hydroxy, amino, hydroxyalkyl, aminoalkyl, aryl or alkyl, $G_{12}$ is absent or an amino acid residue, $H_{13}$ is absent or an amino acid residue, $I_{14}$ is absent or an amino acid residue and Z is hydroxy, substituted alkoxy, substituted amino or cyclic amino;

PCT Patent Application No. WO 89/00161, published Jan. 12, 1989, discloses mimics of the Leu-Val cleavage site of angiotensinogen having the formula

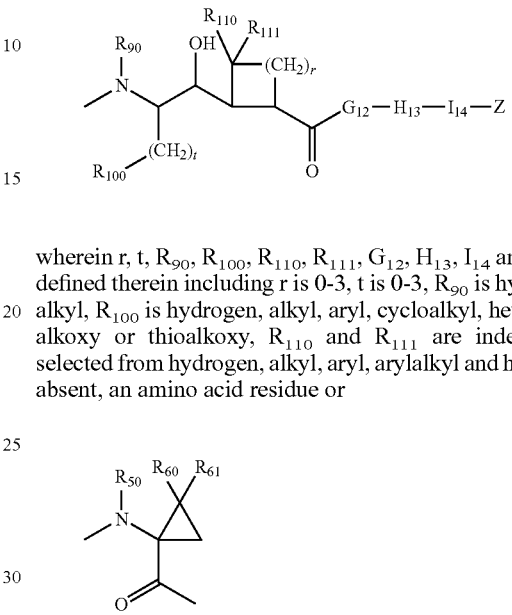

wherein $R_2$, $R_4$, $R_5$, X, Y and Z are as defined therein including $R_2$ is hydrogen or alkyl, $R_4$ is hydrogen, alkyl, cycloalkyl, aryl, heterocyclic, hydroxyalkyl or aminoalkyl, $R_5$ is hydrogen, alkyl, arylalkyl, (heterocyclic)alkyl or cycloalkyl, X is —CH(OH)—, —CH(NH$_2$)—, —C(O)—, —CH(OH)CH(OH)—, —CH(OH)CH$_2$—, —CH(NH$_2$)CH$_2$—, —C(O)—CH$_2$—, —CH$_2$—NH—, —CH$_2$—O— or —P(O)(A)B— wherein A is hydroxy or amino and B is absent, O, NH or CH$_2$, Y is absent or —NHCH(R$_5$)C(O)— and Z is hydroxy, substituted alkoxy, substituted amino or N-heterocyclic;

PCT Patent Application No. WO 88/07053, published Sep. 22, 1988, discloses mimics of the Leu-Val cleavage site of angiotensinogen having the formula

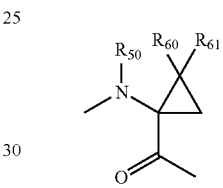

wherein r, t, $R_{90}$, $R_{100}$, $R_{110}$, $R_{111}$, $G_{12}$, $H_{13}$, $I_{14}$ and Z are as defined therein including r is 0-3, t is 0-3, $R_{90}$ is hydrogen or alkyl, $R_{100}$ is hydrogen, alkyl, aryl, cycloalkyl, heterocyclic, alkoxy or thioalkoxy, $R_{110}$ and $R_{111}$ are independently selected from hydrogen, alkyl, aryl, arylalkyl and halo, $G_{12}$ is absent, an amino acid residue or

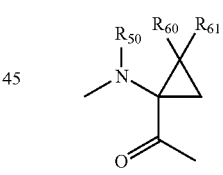

wherein $R_{50}$ is hydrogen, alkyl, arylalkyl, (heterocyclic)alkyl, cycloalkylalkyl or adamantyl, and $R_{60}$ and $R_{61}$ are independently selected from hydrogen, alkyl, aryl, arylalkyl, heterocyclic, (heterocyclic)alkyl, cycloalkyl, cycloalkylalkyl and adamantyl; or $R_{60}$ and $R_{61}$ taken together form a carbocyclic or heterocyclic spirocycle, $H_{13}$ is absent an amino acid residue or

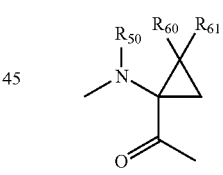

wherein $R_{50}$ is hydrogen, alkyl, arylalkyl, (heterocyclic)alkyl, cycloalkylalkyl or adamantyl, and $R_{60}$ and $R_{61}$ are independently selected from hydrogen, alkyl, aryl, arylalkyl, heterocyclic, (heterocyclic)alkyl, cycloalkyl, cycloalkylalkyl and adamantyl; or $R_{60}$ and $R_{61}$ taken together form a carbocyclic or heterocyclic spirocycle, $I_{14}$ is absent an amino acid residue or

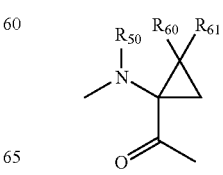

wherein $R_{50}$ is hydrogen, alkyl, arylalkyl, (heterocyclic) alkyl, cycloalkylalkyl or adamantyl, and $R_{60}$ and $R_{61}$ are independently selected from hydrogen, alkyl, aryl, arylalkyl, heterocyclic, (heterocyclic)alkyl, cycloalkyl, cycloalkylalkyl and adamantyl; or $R_{60}$ and $R_{61}$ taken together form a carbocyclic or heterocyclic spirocycle and Z is hydroxy, alkoxy, substituted alkoxy, amino, substituted amino or cyclic amino;

PCT Patent Application No. WO 88/02374, published Apr. 7, 1988, discloses mimics of the Leu-Val cleavage site of angiotensinogen having the formulae

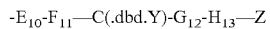 a)

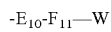 b)

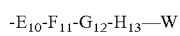 c)

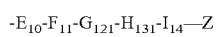 d)

wherein $E_{10}$, $F_{11}$, $G_{12}$, $H_{13}$, $G_{121}$, $H_{131}$, $I_{14}$, W, Y and Z are as defined therein including -$E_{10}$-$F_{11}$— is

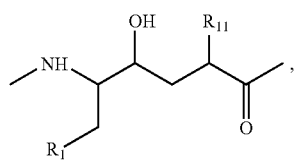

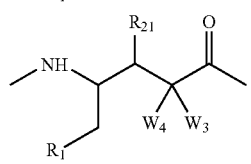

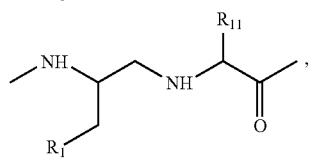

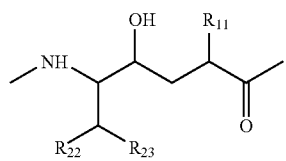

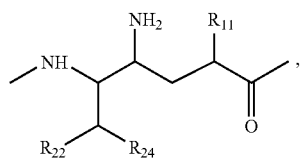

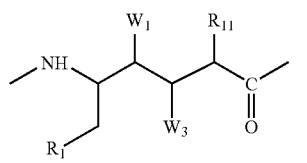

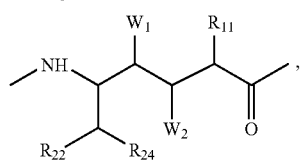

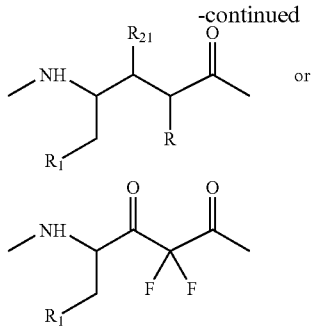

wherein R and $R_1$ are independently selected from alkyl, cycloalkyl, aryl, substituted alkyl as defined therein, alkoxy or thioalkoxy, $R_{11}$ is alkyl, cycloalkyl, aryl, substituted alkyl as defined therein, alkoxy, thioalkoxy, hydrogen, hydroxyalkyl, cycloalkylalkyl, arylalkyl, (heterocyclic)alkyl, alkoxyalkyl and thioalkoxyalkyl, $R_{22}$ is hydrogen or alkyl, $R_{23}$ is hydroxy, hydroxyalkyl, amino, aminoalkyl, aryl or alkyl, $R_{24}$ is aryl, amino, alkylamino, dialkylamino, trialkylamino, heterocyclic, hydroxy, alkoxy, alkanoyloxy, mercapto, carboxy, alkoxycarbonyl, dialkylaminoalkoxycarbonyl, aminocarbonyl, alkylaminocarbonyl, dialkylaminocarbonyl, cyclicamino, cycloalkylamino, guanidinyl, cyano, N-cyanoguanidinyl, cyanoamino, hydroxyalkylamino, di(hydroxyalkyl)amino, arylalkyl, aminoalkyl, alkylaminoalkyl, dialkylaminoalkyl, trialkyl aminoalkyl, heterocyclicalkyl, hydroxyalkyl, alkoxyalkyl, alkanoyloxyalkyl, mercaptoalkyl, carboxyalkyl, alkoxycarbonylalkyl, dialkylaminoalkoxycarbonylalkyl, aminocarbonylalkyl, alkylaminocarbonylalkyl, dialkylaminocarbonylalkyl, cyclicaminoalkyl, cycloalkylaminoalkyl, guanidinylalkyl, cyanoalkyl, N-cyanoguanidinylalkyl, cyanoaminoalkyl, hydroxyalkylaminoalkyl or di(hydroxyalkyl)aminoalkyl, $W_1$ and $W_2$ are independently selected from hydroxy and amino, $W_3$ and $W_4$ are independently selected from hydrogen and fluoro, W is as defined therein, Y is O, S, NH or —N(alkyl)-, Z is as defined therein, $G_{12}$ is absent or an amino acid residue, $H_{13}$ is absent or an amino acid residue, $G_{121}$ is absent or an amino acid residue, $H_{131}$ is absent or an amino acid residue and $I_{14}$ is absent or an amino acid residue;

PCT Patent Application No. WO 86/06379, published Apr. 5, 1989, discloses mimics of the Leu-Val cleavage site of angiotensinogen having the formula

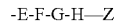

wherein E, F, G, H and Z are as defined therein including -E-F— is

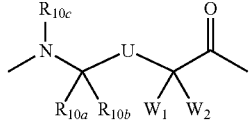

wherein $R_{10a}$ is hydrogen or alkyl, $R_{10b}$ is alkyl, cycloalkyl, cycloalkylalkyl, arylalkyl, (heterocyclic)alkyl, cycloalkenyl or cycloalkenylalkyl, R10c is hydrogen or alkyl, U is —C(O)—, —CH(OH)— or —CH($NH_2$)— and $W_1$ and $W_2$ are independently selected from hydrogen, fluoro, chloro and bromo, G is absent or an amino acid residue, H is absent or an amino acid residue and Z is hydroxy, thiol, amino, substituted alkoxy, substituted thioalkoxy, substituted alkylamino, Lys-OH, Lys-NH$_2$, Ser-OH or Ser-NH$_2$;

European Patent Application No. EP0271862, published Jun. 22, 1988, discloses mimics of the Leu-Val cleavage site of angiotensinogen having the formula

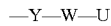

wherein Y, W and U are as defined therein including Y is Sta, Cysta or PhSta, W is Leu, Ile, N-MeLeu, Val or absent and U is —NHCH$_2$CH(CH$_3$)CH$_2$CH$_3$, —NHCH$_2$Ph, —NHCH(CH$_2$OH)CH(CH$_3$)CH$_2$CH$_3$, —NHCH$_2$CH(OH)CH$_2$SCH(CH$_3$)$_2$, —NHCH$_2$CH(OH)CH$_2$S(O)CH(CH$_3$)$_2$, —NHCH$_2$CH(OH)CH$_2$S(O)$_2$CH(CH$_3$)$_2$, —NHCH$_2$CH$_2$Ph, —NHCH$_2$(pyrid-2-yl), —NH$_2$, —NHCH$_2$CH=CH$_2$, —OEt,

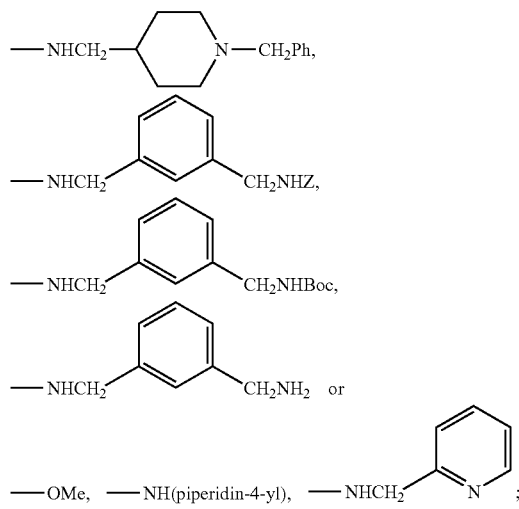

European Patent Application No. EP0275480, published Jul. 27, 1988, discloses mimics of the Leu-Val cleavage site of angiotensinogen having the formula

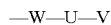

wherein W, U and V are as defined therein including W is Sta, PhSta or Cysta, U is absent, Leu, Ile, Val, N-MeLeu or N-MeIle and V is —NHCH$_2$Ph, —NHCH$_2$cyclohexyl, —NH(piperidin-4-yl), —NHCH$_2$(pyrid-2-yl), —NHCH$_2$CH(CH$_3$)CH$_2$CH$_3$, —OMe, —OEt, —NHCH(CH$_2$OH)CH(CH$_3$)CH$_2$CH$_3$, —NHCH$_2$CH$_2$(morpholin-1-yl),

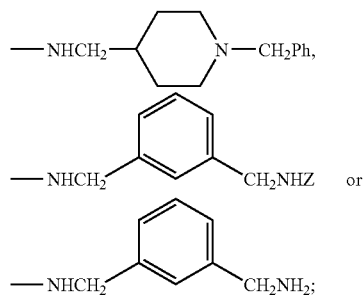

PCT Patent Application No. WO 88/03927, published Jun. 2, 1988, discloses mimics of the Leu-Val cleavage site of angiotensinogen having the formula

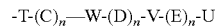

wherein T, C, W, D, V, E, U and n are as defined therein including n is 0-1, T is Sta, PhSta, Cysta, Leu, CyclohexylAla or Phe, W is absent, Leu, Gly or Ile, V is absent, Leu or Ile, C is —CH$_2$NH—, —H(OH)CH$_2$— or —CH(OH)—CH=CH—C(O)—, D is —CH$_2$NH—, E is CH$_2$NH— or —CH$_2$N(Cbz)- and U is —NHCH$_2$Ph, —NHCH$_2$cyclohexyl, —NH$_2$, —NH(piperidin-4-yl), —NHCH$_2$ (pyrid-2-yl), —NHCH$_2$CH(CH$_3$)CH$_2$CH$_3$, —OMe, —OEt,

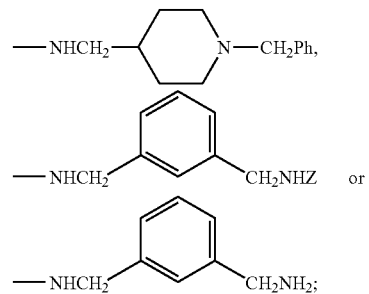

European Patent Application No. EP0314060, published May 3, 1989, discloses mimics of the Leu-Val cleavage site of angiotensinogen having the formula

wherein W and U are as defined therein including W is Sta, Cysta, PhSta, ChSta, DFKSta, DFKCys, DFKChs, ASta or ACys and U is —NHCH$_2$CH$_2$(morpholin-1-yl), —NHCH$_2$CH(CH$_3$)CH$_2$ CH$_3$, —NHCH(CH$_2$OH)CH(CH$_3$) CH$_2$CH$_3$, -LeuNHCH$_2$Ph, -LeuNHCH$_2$cyclohexyl, -LeuNH(piperidin-4-yl), -LeuNHCH$_2$ (pyrid-2-yl) or

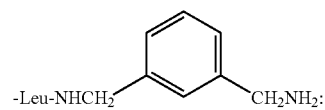

European Patent Application No. EP0310918, published Apr. 12, 1989, discloses mimics of the Leu-Val cleavage site of angiotensinogen having the formula

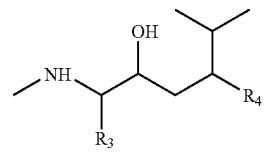

wherein R$_3$ and R$_4$ are as defined therein including R$_3$ is isobutyl, cyclohexylmethyl or benzyl and R$_4$ is phenyl, furyl, vinyl, ethyl or 1,2-dihydroxyethyl;

French Patent Application No. FR8700560, published Jul. 2, 1988, discloses mimics of the Leu-Val cleavage site of angiotensinogen having the formula

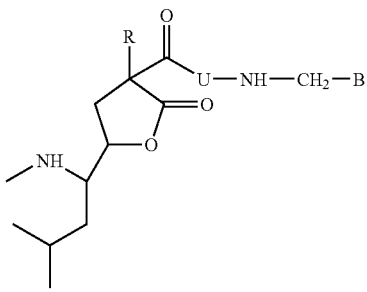

wherein R, U and B are as defined therein including R is hydrogen or hydroxyalkyl, U is Leu, Ala, Val or Ile and B is pyridyl;

European Patent Application No. EP0236948, published Sep. 16, 1987, discloses mimics of the Leu-Val cleavage site of angiotensinogen having the formula

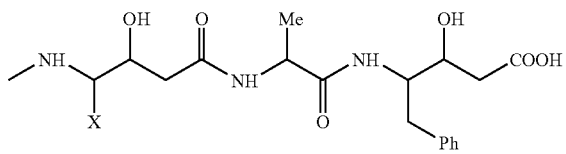

wherein X is as defined therein including X is isobutyl or benzyl;

European Patent Application No. EP0281316, published Sep. 7, 1988, discloses mimics of the Leu-Val cleavage site of angiotensinogen having the formula

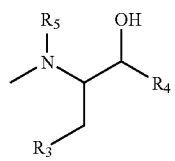

wherein $R_3$, $R_4$ and $R_5$ are as defined therein including $R_3$ is allyl, cyclohexyl or phenyl, $R_4$ is nitromethyl, alkoxycarbonyl or —CH$_2$S(O)$_n$—R$^d$ wherein n is 0-2 and R$^d$ is heterocyclic and $R_5$ is hydrogen or alkyl;

German Patent Application No. DE3825242, published Feb. 9, 1989, discloses mimics of the Leu-Val cleavage site of angiotensinogen having the formula

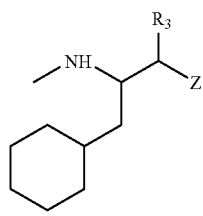

wherein $R_3$ and Z are as defined therein including $R_3$ is hydroxy or amino and Z is substituted carbonyl, substituted thiocarbonyl, substituted iminocarbonyl or unsubstituted or substituted phosphono, aminomethyl, thiomethyl, sulfinylmethyl, sulfonylmethyl or phosphonomethyl;

European Patent Application No. EP0275101, published Jul. 20, 1988, discloses mimics of the Leu-Val cleavage site of angiotensinogen having the formula

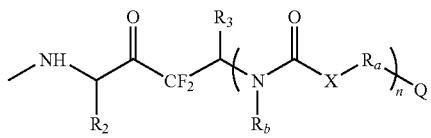

wherein $R_2$, $R_3$, $R_a$, $R_b$, n, X and Q are as defined therein including $R_2$ is an amino acid side chain, $R_3$ is hydrogen, alkyl, cyclohexyl, cyclohexylmethyl, phenyl, benzyl, 2-pyridylmethyl or an amino acid side chain, R.sub.a is an amino acid side chain, R.sub.b is hydrogen or alkyl or R.sub.a and R.sub.b taken together are —CH$_2$—CH$_2$—, n is 1-10, X is hydrogen, CH$_2$, alkoxy, substituted alkoxy, alkyl, phenyl, benzyl, cyclohexyl, cyclohexylmethyl or 2-pyridylmethyl and Q is hydrogen, alkyl, arylakyl, alkoxycarbonyl or an amino acid residue;

PCT Patent Application No. WO 89/01488, published Feb. 23, 1989, discloses mimics of the Leu-Val cleavage site of angiotensinogen having the formula

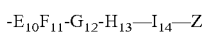

wherein $E_{10}$, $F_{11}$, $G_{12}$, $H_{13}$, $I_{14}$ and Z are as defined therein including -$E_{10}$-$F_{11}$— is

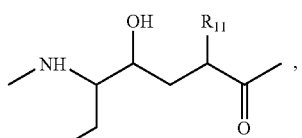

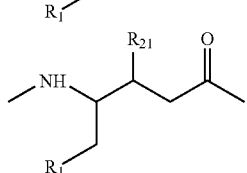

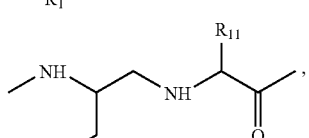

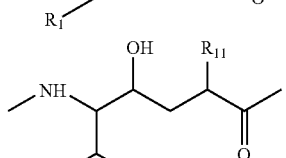

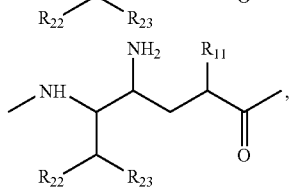

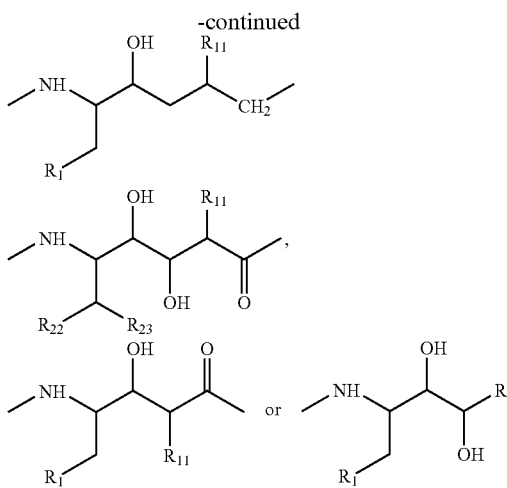

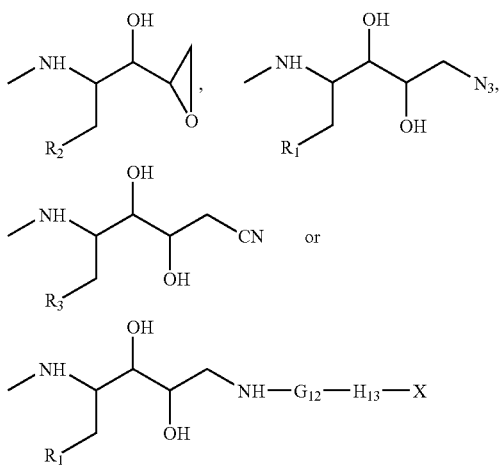

wherein $R_1$ is hydrogen, alkyl, aryl, cycloalkyl, heterocyclic, alkoxy or thioalkoxy, $R_{11}$ is hydrogen, alkyl, benzyl, cycloalkyl, hydroxyalkyl, cycloalkylalkyl, arylalkyl, (heterocyclic)alkyl, alkoxyalkyl or thioalkoxyalkyl, $R_{21}$ is hydroxy or amino, $R_{22}$ is hydrogen or alkyl and $R_{23}$ is hydroxy, amino, hydroxyalkyl, aminoalkyl, aryl or alkyl, $R_{24}$ is $R_1$ hydroxy, amino, hydroxyalkyl or aminoalkyl, $G_{12}$ is absent or an amino acid residue, $H_{13}$ is absent or an amino acid residue, $I_{14}$ is absent or an amino acid residue and Z is hydroxy, substituted alkoxy, substituted amino or cyclic amino;

European Patent Application No. EP0275101, published Jul. 20, 1988, discloses mimics of the Leu-Val cleavage site of angiotensinogen having the formulae wherein $R_1$, $G_{12}$, $H_{13}$ and X are as defined therein including $R_1$ is hydrogen, alkyl, aryl, cycloalkyl, heterocyclic, alkoxy or thioalkoxy, $G_{12}$ is absent, an amino acid residue or an amino acid residue wherein the alpha-amino group has been replaced by O, $H_{13}$ is absent, an amino acid residue or an amino acid residue wherein the alpha-amino group has been replaced by 0 and X is hydrogen, alkyl or substituted alkyl as defined therein;

European Patent Application No. EP0312291, published Apr. 19, 1989, discloses mimics of the Leu-Val cleavage site of angiotensinogen having the formula

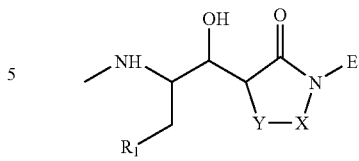

wherein $R_1$, Y, X and E are as defined therein including $R_1$ is hydrogen, alkyl, aryl, cycloalkyl, 1,3-dithiolan-2-yl or 1,3-dithian-2-yl, X is —$CH_2$—$C(R_{13})(R_{14})$ wherein $R_{13}$ and $R_{14}$ are independently selected from hydrogen, alkyl, alkenyl, carboxy, aminocarbonyl, substituted aminocarbonyl, substituted alkyl, alkanoyloxy, substituted aminocarbonyloxy, substituted carbonyl amino, substituted aminocarbonylamino, substituted sulfinyl, substituted sulfonyl, substituted sulfide, amino, alkylamino, dialkylamino or heterocyclic, Y is $CH_2$, O, S, SO or $SO_2$ or X and Y taken together is —$(CH_2)_4$— and E is hydrogen, aryl, heterocyclic, alkyl, cycloalkyl or substituted alkyl;

European Patent Application No. EP0312283, published Apr. 19, 1989, discloses mimics of the Leu-Val cleavage site of angiotensinogen having the formula

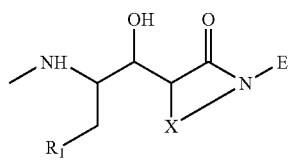

wherein $R_1$, X and E are as defined therein including $R_1$ is hydrogen, alkyl, aryl, cycloalkyl, 1,3-dithiolan-2-yl or 1,3-dithian-2-yl, X is —$CH_2$—$C(R_{13})(R_{14})$— wherein $R_{13}$ and $R_{14}$ are independently selected from hydrogen, alkyl, alkenyl, carboxy, aminocarbonyl, substituted aminocarbonyl, substituted alkyl, alkanoyloxy, substituted aminocarbonyloxy, substituted carbonylamino, substituted aminocarbonylamino, substituted sulfinyl, substituted sulfonyl, substituted sulfide, amino, alkylamino, dialkylamino or heterocyclic and E is hydrogen, aryl, heterocyclic, alkyl, cycloalkyl or substituted alkyl;

European Patent Application No. EP0312158, published Apr. 19, 1989, discloses mimics of the Leu-Val cleavage site of angiotensinogen having the formula

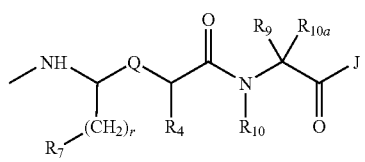

wherein r, $R_7$, $R_4$, $R_{10}$, $R_9$, $R_{10a}$, Q and J are as defined therein including r is 1-4, $R_7$ is alkyl, aryl or cycloalkyl, $R_4$ is hydrogen, alkyl, alkenyl, cycloalkyl, aryl or substituted alkyl, $R_{10}$ and $R_{10a}$ are independently selected from hydrogen and alkyl, $R_9$ is —$(CH_2)_s$—$NR_{11}R_{12}$ wherein s is 1-2 and $R_{11}$ and $R_{12}$ are independently selected from hydrogen, heterocyclic, aryl, cycloalkyl, alkyl, arylalkyl, (heterocyclic)alkyl, aminoalkyl, hydroxyalkyl, alkylaminoalkyl, dialkylaminoalkyl, carboxy, alkyl substituted by —SO$_3$H, aminocarbonylalkyl, alkylaminocarbonylalkyl or dialkylaminocarbonylalkyl, Q is —CH(OH)—, —CH(N(R$_8$))—, —CH(OH)CH$_2$— or —CH(N(R$_8$))CH$_2$— wherein R$_8$ is hydrogen, alkyl, formyl, alkanoyl, aroyl, alkoxycarbonyl, aryloxycarbonyl or araylalkoxycarbonyl and J is substituted alkylamino or substituted alkoxy;

European Patent Application No. EP0312157, published Apr. 19, 1989, discloses mimics of the Leu-Val cleavage site of angiotensinogen having the formula

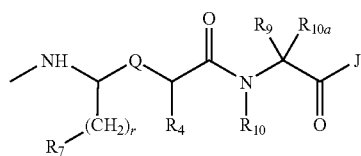

wherein r, R$_7$, R$_4$, R$_{10}$, R$_9$, R$_{10a}$, Q and J are as defined therein including r is 1-4, R$_7$ is alkyl, aryl or cycloalkyl, R$_4$ is hydrogen, alkyl, alkenyl, cycloalkyl, aryl or substituted alkyl, R$_{10}$ and R$_{10a}$ are independently selected from hydrogen and alkyl, R$_9$ is —(CH$_2$)$_s$—NR$_{11}$R$_{12}$ wherein s is 1-2 and R$_{11}$ and R$_{12}$ are independently selected from hydrogen, heterocyclic, aryl, cycloalkyl, alkyl, arylalkyl, (heterocyclic)alkyl, aminoalkyl, hydroxyalkyl, alkylaminoalkyl, dialkylaminoalkyl, carboxy, alkyl substituted by —SO$_3$H, aminocarbonylalkyl, alkylaminocarbonylalkyl or dialkylaminocarbonylalkyl, Q is —CH(OH)—, —CH(N(R$_8$))—, —CH(OH)CH$_2$— or —CH(N(R8))CH$_2$— wherein R$_8$ is hydrogen, alkyl, formyl, alkanoyl, aroyl, alkoxycarbonyl, aryloxycarbonyl or araylalkoxycarbonyl and J is substituted alkylamino, substituted alkoxy, heterocyclic, heterocyclicamino or substitute guanidino;

European Patent Application No. EP0314239, published May 3, 1989, discloses mimics of the Leu-Val cleavage site of angiotensinogen having the formula

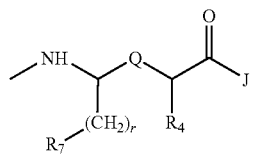

wherein r, R$_7$, R$_4$, Q and J are as defined therein including r is 1-4, R$_7$ is alkyl, aryl or cycloalkyl, R$_4$ is hydrogen, alkyl, alkenyl, cycloalkyl, aryl or substituted alkyl, Q is —CH(OH)—, —CH(N(R$_8$))—, —CH(OH)CH$_2$— or —CH(N(R$_8$))CH$_2$— wherein R$_8$ is hydrogen, alkyl, formyl, alkanoyl, aroyl, alkoxycarbonyl, aryloxycarbonyl or araylalkoxycarbonyl and J is amino, hydroxy, substituted alkylamino or substituted alkoxy;

South African Patent Application No. 866642, published Feb. 24, 1987, discloses mimics of the Leu-Val cleavage site of angiotensinogen having the formula

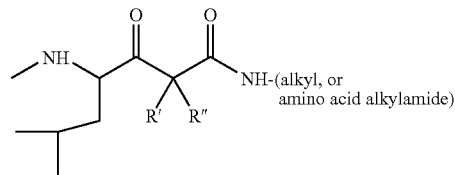

wherein R' and R" are as defined therein including R' is fluoro and R" is hydrogen or fluoro;

European Patent Application No. EP0273696, published Jul. 6, 1988, discloses mimics of the Leu-Val cleavage site of angiotensinogen having the formula

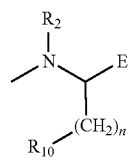

wherein n, R$_2$, R$_{10}$ and E are as defined therein including n is 0-5, R$_2$ is hydrogen or alkyl, R$_{10}$ is alkyl, cycloalkyl, cycloalkylalkyl, arylalkyl, (heterocyclic)alkyl, alkoxyalkyl, thioalkoxyalkyl, hydroxyalkyl or aminoalkyl and E is —CH(W)-G wherein W is hydroxy, amino, alkanoyloxy or alkanoyloxyalkyloxy and G is -Q-C(O)-T-U—V wherein Q is a bond or —CH(R$_{13}$)— wherein R$_{13}$ is hydrogen, aryl, alkyl, cycloalkyl or substituted alkyl, T and U are independently absent or selected from an amino acid residue and V is hydroxy, substituted alkoxy, amino or substituted amino;

European Patent Application No. EP0278158, published Aug. 17, 1988, discloses mimics of the Leu-Val cleavage site of angiotensinogen having the formula

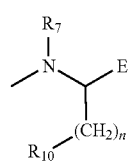

wherein n, R$_7$, R$_{10}$ and E are as defined therein including n is 0-3, R$_7$ is alkyl or substituted alkyl, R$_{10}$ is alkyl, cycloalkyl, cycloalkylalkyl, arylalkyl, (heterocyclic)alkyl, alkoxyalkyl, thioalkoxyalkyl, hydroxyalkyl or aminoalkyl and E is —CH(W)-G wherein W is hydroxy, amino, alkanoyloxy or alkanoyloxyalkyloxy and G is -Q-C(O)-T-U—V wherein Q is a bond or —CH(R$_{13}$)— wherein R$_{13}$ is hydrogen, aryl, alkyl, cycloalkyl or substituted alkyl, T and U are independently absent or selected from an amino acid residue and V is hydroxy, substituted alkoxy, amino or substituted amino;

German Patent Application No. DE3721855, published Sep. 22, 1988, discloses mimics of the Leu-Val cleavage site of angiotensinogen having the formula

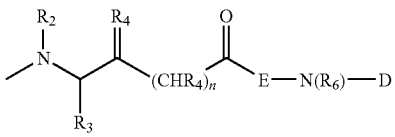

wherein n, $R_2$, $R_3$, $R_4$, $R_5$, $R_6$, E and D are as defined therein including n is 1-2, $R_2$ is hydrogen or alkyl, $R_3$ is hydrogen, alkyl, aryl, arylalkyl, (heterocyclic)alkyl, cycloalkyl, alkoxy or cycloalkylalkyl, $R_4$ is (H,OH), (H,NH$_2$) or 0, $R_5$ is hydrogen or alkyl, $R_6$ is hydrogen or alkyl, E is 0-2 amino acid residues and D is —CH$_2$CHOHCH$_2$OH, substituted sulfonyl, substituted sulfonylalkyl, substituted carbonyl, substituted phosphonyl, phenyl, phenylalkyl, furyl, furylalkyl, thienyl, thienylalkyl, pyridyl, pyridylalkyl or other (heterocyclic) alkyl;

European Patent Application No. EP0309841, published Apr. 5, 1989, discloses mimics of the Leu-Val cleavage site of angiotensinogen having the formula

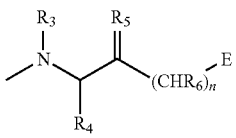

wherein n, $R_3$, $R_4$, $R_5$, $R_6$ and E are as defined therein including n is 1-2, $R_3$ is hydrogen or alkyl, $R_4$ is hydrogen, alkyl, aryl, arylalkyl, heterocyclic, (heterocyclic)alkyl, cycloalkyl, alkoxy or cycloalkylalkyl, $R_5$ is (H,OH), (H,NH$_2$) or O, $R_6$ is hydrogen, alkyl or alkenyl and E is —SR$_7$, —SOR$_7$, —SO$_2$R$_7$, O$_{20}$R$_7$ or —SO$_2$NR$_7$R$_8$ wherein $R_7$ and $R_8$ are independently selected from $R_4$;

European Patent Application No. EP0292800, published Nov. 30, 1988, discloses mimics of the Leu-Val cleavage site of angiotensinogen having the formula

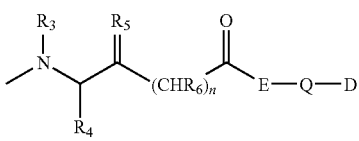

wherein n, $R_3$, $R_4$, $R_5$, $R_6$, E, Q and Y are as defined therein including n is 1-2, $R_3$ is hydrogen or alkyl, $R_4$ is hydrogen, alkyl, aryl, arylalkyl, heterocyclic, (heterocyclic)alkyl, cycloalkyl, cycloalkylalkyl or alkoxy, $R_5$ is (H,OH), (H,NH$_2$), or O, $R_6$ is hydrogen or alkyl, E is 0-2 amino acid residues, Q is O or NH and Y is H or substituted alkyl;

European Patent Application No. EP0249096, published Dec. 16, 1987, discloses mimics of the Leu-Val cleavage site of angiotensinogen having the formula

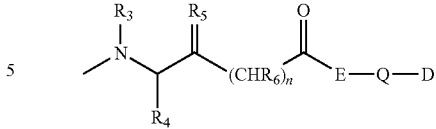

wherein n, $R_3$, $R_4$, $R_5$, $R_6$, E, Q and Y are as defined therein including n is 1-2, $R_3$ is hydrogen or alkyl, $R_4$ is hydrogen, alkyl, aryl, arylalkyl, heterocyclic, (heterocyclic)alkyl, cycloalkyl, cycloalkylalkyl or alkoxy, $R_5$ is (H,OR$_{12}$), (H,NR$_{12}$R$_{13}$), or O wherein $R_{12}$ and $R_{13}$ are independently selected from hydrogen and alkyl, $R_6$ is hydrogen or alkyl, E is 0-2 amino acid residues, Q is O or NH and Y is H or substituted alkyl; and European Patent Application No. EP0264795, published Apr. 27, 1988, discloses mimics of the Leu-Val cleavage site of angiotensinogen having the formula

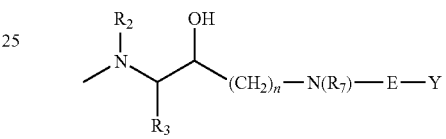

wherein n, $R_2$, $R_3$, $R_4$, E and Y are as defined therein including n is 1-2, $R_2$ is hydrogen or alkyl, $R_3$ is hydrogen, alkyl, aryl, arylalkyl, heterocyclic, (heterocyclic)alkyl, cycloalkyl, cycloalkylalkyl or alkoxy, $R_4$ is hydrogen or alkyl, E is —C(O)NH—, —C(S)NH—, —C(O)O—, —SO$_2$—, —SO$_2$NH—, or —PO(OA)O— wherein A is hydrogen or alkyl and Y is carboxy, carboxyalkyl, substituted carboxyalkyl, alkoxycarbonyl, alkoxycarbonylalkyl, substituted alkoxycarbonylalkyl, aminocarbonyl, substituted aminocarbonyl, aminocarbonylalkyl, substituted aminocarbonylalkyl, hydrogen, alkyl, aryl, arylalkyl, cycloalkyl or cycloalkylalkyl; or E-Y is pyrrolidinocarbonyl, piperidinocarbonyl, morpholinocarbonyl, pyrrolidinosulfonyl, piperidinosulfonyl or morpholinosulfonyl.

Ocain and Delninger, U.S. Pat. No. 5,023,338, issued Jun. 11, 1999, which is hereby incorporated by reference, discloses mimics of the Leu-Val cleavage site of angiotensinogen having the formula:

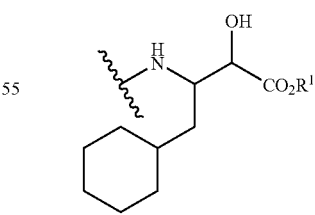

wherein $R^1$ is as defined therein.

Albright et. al., U.S. Pat. No. 5,104,869, issued Apr. 14, 1992, which is hereby incorporated by reference, discloses mimics of the Leu-Val cleavage site of angiotensinogen having the formula:

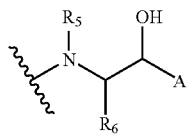

wherein $R^5$, $R^6$ and A are as defined therein

Albright et. al., U.S. Pat. No. 5,106,835, issued Apr. 21, 1992, which is hereby incorporated by reference, discloses mimics of the Leu-Val cleavage site of angiotensinogen having the formula:

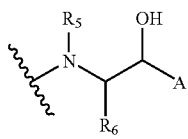

wherein $R^5$, $R^6$ and A are as defined therein

Ashton et. al., U.S. Pat. No. 5,114,925, issued May 19, 1992, which is hereby incorporated by reference, discloses mimics of the Leu-Val cleavage site of angiotensinogen having the formula:

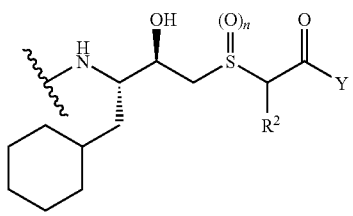

wherein $R^2$, Y and n are as defined therein.

Ruger et. al., U.S. Pat. No. 5,185,324, issued Feb. 9, 1993, which is hereby incorporated by reference, discloses mimics of the Leu-Val cleavage site of angiotensinogen having the formula:

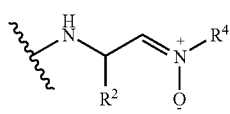

wherein $R^2$ and $R^4$ are as defined therein.

Doherty and Sircar, U.S. Pat. No. 5,071,837, issued Dec. 10, 1991, which is hereby incorporated by reference, discloses mimics of the Leu-Val cleavage site of angiotensinogen having the formulae:

-DFKCYS-AEM

-DFCYS-AEM wherein DFKCYS, DFCYS and AEM are as defined therein

Raddatz et. al., U.S. Pat. No. 5,147,857, issued Sep. 15, 1992, which is hereby incorporated by reference, discloses mimics of the Leu-Val cleavage site of angiotensinogen having the formula:

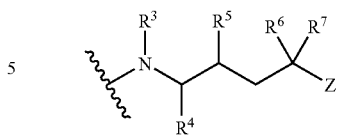

wherein $R^3$, $R^4$, $R^5$, $R^6$, $R^7$ and Z are as defined therein;

Almquist et. al., U.S. Pat. No. 5,268,361, issued Dec. 7, 1993, which is hereby incorporated by reference, discloses mimics of the Leu-Val cleavage site of angiotensinogen having the formula:

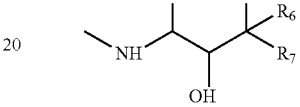

wherein $R^5$, $R^6$ and $R^7$ are as defined therein;

Toyoda et. al., U.S. Pat. No. 5,272,268, issued Dec. 21, 1993, which is hereby incorporated by reference, discloses mimics of the Leu-Val cleavage site of angiotensinogen having the formula:

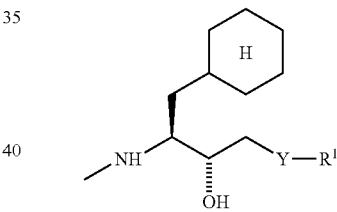

wherein Y and $R^1$ are as defined therein;

Hanson et. al., U.S. Pat. No. 5,330,996, issued Jul. 19, 1994, which is hereby incorporated by reference, discloses mimics of the Leu-Val cleavage site of angiotensinogen having the formula:

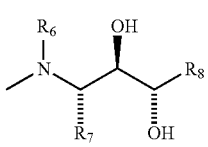

wherein $R^6$, $R^7$ and $R^8$ are as defined therein;

Henning et. al., U.S. Pat. No. 5,360,791, issued Nov. 1, 1994, which is hereby incorporated by reference, discloses mimics of the Leu-Val cleavage site of angiotensinogen having the formula:

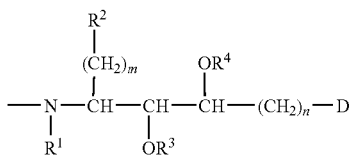

wherein $R^1$, $R^2$, $R^3$, $R^4$, m, n and D are as defined therein;

Morisawa et. al., U.S. Pat. No. 5,378,689, issued Jan. 3, 1995, which is hereby incorporated by reference, discloses mimics of the Leu-Val cleavage site of angiotensinogen having the formula:

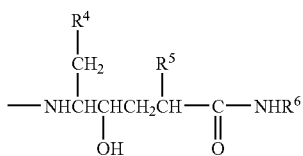

wherein $R^4$, $R^5$ and $R^6$ are as defined therein;

Morishima et. al., U.S. Pat. No. 5,424,309, issued Jun. 13, 1995, which is hereby incorporated by reference, discloses mimics of the Leu-Val cleavage site of angiotensinogen having the formula:

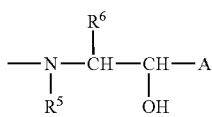

wherein $R^5$, $R^6$ and A are as defined therein;

Albright et al., U.S. Pat. No. 5,459,131, issued Oct. 17, 1995, which is hereby incorporated by reference, discloses mimics of the Leu-Val cleavage site of angiotensinogen having the formula:

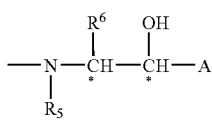

wherein $R^5$, $R^6$ and A are as defined therein;

Branca et al., U.S. Pat. No. 5,688,946, issued Nov. 18, 1997, which is hereby incorporated by reference, discloses mimics of the Leu-Val cleavage site of angiotensinogen having the formula:

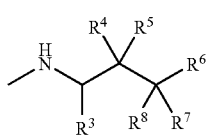

wherein $R^3$, $R^4$, $R^5$, $R^6$, $R^7$ and $R^8$ are as defined therein

Shibat et. al., U.S. Pat. No. 5,750,696, issued May 12, 1998, which is hereby incorporated by reference, discloses mimics of the Leu-Val cleavage site of angiotensinogen having the formula:

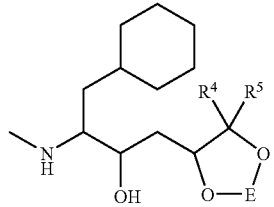

wherein $R^4$, $R^5$ and E are as defined therein;

Hamby et. al., U.S. Pat. No. 5,198,426, issued Mar. 30, 1993, which is hereby incorporated by reference, discloses mimics of the Leu-Val cleavage site of angiotensinogen having the formula:

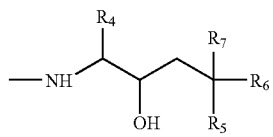

wherein $R^4$, $R^5$, $R^6$ and $R^7$ are as defined therein;

Rosenberg., U.S. Pat. No. 5,258,368, issued Nov. 2, 1993, which is hereby incorporated by reference, discloses mimics of the Leu-Val cleavage site of angiotensinogen having the formula:

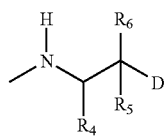

wherein $R^4$, $R^5$, $R^6$ and D are as defined therein;

European Patent Application No. EP0353211, published Jan. 31, 1990, which is hereby incorporated by reference, discloses mimics of the Leu-Val cleavage site of angiotensinogen having the formula

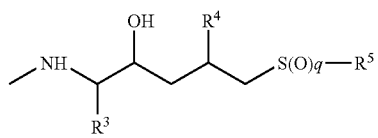

wherein $R^3$, $R^4$, $R^5$ and q are as defined therein;

European Patent Application No. EP0362002, published Apr. 4, 1990, which is hereby incorporated by reference, discloses mimics of the Leu-Val cleavage site of angiotensinogen having the formula

—NHCHR$^2$C(=O)CF$_2$CHR$^3$NHC(=O)X' wherein $R^2$, $R^3$ and X' are as defined therein;

European Patent Application No. EP0369065, published Nov. 7, 1990, which is hereby incorporated by reference, discloses mimics of the Leu-Val cleavage site of angiotensinogen having the formula

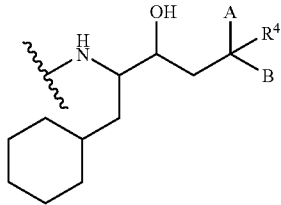

wherein A, B and $R^4$ are as defined therein;

European Patent Application No. EP0416393, published Mar. 13, 1991, which is hereby incorporated by reference, discloses mimics of the Leu-Val cleavage site of angiotensinogen having the formula

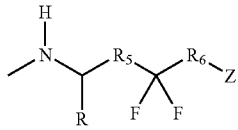

wherein $R^4$, $R^5$, $R^6$ and Z are as defined therein;

European Patent Application No. EP0438233, published Jul. 24, 1991, which is hereby incorporated by reference, discloses mimics of the Leu-Val cleavage site of angiotensinogen having the formula

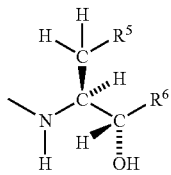

wherein $R^5$ and $R^6$ are as defined therein;

European Patent Application No. EP0438311, published Jul. 24, 1991, which is hereby incorporated by reference, discloses mimics of the Leu-Val cleavage site of angiotensinogen having the formula

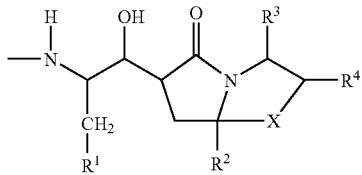

wherein $R^1$, $R^2$, $R^3$, $R^4$ and X are as defined therein;

European Patent Application No. EP0483271, published May 6, 1992, which is hereby incorporated by reference, discloses mimics of the Leu-Val cleavage site of angiotensinogen having the formula:

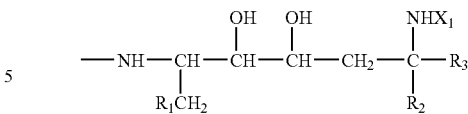

wherein $R_1$, $R_2$, $R_3$ and $X_1$ are as defined therein;

European Patent Application No. EP0501280, published Sep. 2, 1992, which is hereby incorporated by reference, discloses mimics of the Leu-Val cleavage site of angiotensinogen having the formula:

$$-NR^2-CHR^3-R^4-CH_2-CR^5R^6-Y$$

wherein $R^2$, $R^3$, $R^4$, $R^5$, $R^6$ and Y are as defined therein;

The teachings of all documents cited above are incorporated by herein by reference in their entirety.

All documents cited herein are incorporated by reference.

A second embodiment of the invention is a compound of Formula I wherein:

$G^a$ is a) $(C_3-C_7)$cycloalkyl; or b) phenyl, heteroaryl, or bicyclic heteroaryl optionally substituted with 1 to 3 groups independently selected from:

1) fluorine, chlorine, bromine, cyano, nitro, $(C_1-C_6)$alkyl, $(C_3-C_6)$cycloalkyl, $(C_4-C_7)$cycloalkylalkyl, $(C_2-C_6)$alkenyl, $(C_5-C_6)$cycloalkenyl, $(C_5-C_8)$cycloalkylalkenyl, $(C_2-C_6)$alkynyl, $(C_3-C_6)$cycloalkylethynyl, halo$(C_1-C_6)$alkyl, halo$(C_3-C_6)$cycloalkyl, halo$(C_4-C_7)$-Cycloalkylalkyl, halo$(C_2-C_6)$alkenyl, halo$(C_3-C_6)$alkynyl, halo$(C_3-C_6)$cycloalkylethynyl, $(C_1-C_6)$alkoxy, $(C_3-C_6)$cycloalkoxy, $(C_4-C_7)$cycloalkylalkoxy, halo$(C_1-C_6)$alkoxy, halo$(C_3-C_6)$cycloalkoxy, halo$(C_4-C_7)$Cycloalkylalkoxy, $(C_3-C_6)$alkenyloxy and $(C_1-C_6)$alkanesulfonyl; or 2) phenyl, heteroaryl, phenoxy, heteroaryloxy, phenylthio, heteroarylthio, benzyl, heteroarylmethyl, benzyloxy and heteroaryloxy, each optionally substituted with 1 to 3 groups independently selected from:

fluorine, chlorine, cyano, $(C_1-C_3)$alkyl, halo$(C_1-C_3)$alkyl, $(C_1-C_3)$-alkoxy, halo$(C_1-C_3)$alkoxy, and aminocarbonyl;

$G^b$ is $(C_1-C_8)$alkyl, $(C_4-C_8)$cycloalkylalkyl, fluoro$(C_1-C_8)$alkyl, fluoro$(C_4-C_8)$cycloalkylalkyl, $(C_1-C_8)$alkoxy, $(C_4-C_8)$cycloalkylalkoxy, fluoro$(C_1-C_8)$alkoxy, hydroxy$(C_1-C_8)$alkyl, $(C_1-C_5)$alkoxy$(C_1-C_5)$alkyl, halo$(C_1-C_5)$alkylamino$(C_1-C_5)$alkyl, $(C_1-C_5)$alkoxy$(C_1-C_5)$hydroxyalkyl, $(C_3-C_4)$cycloalkoxy$(C_1-C_5)$alkyl, fluoro$(C_1-C_5)$alkoxy$(C_1-C_5)$alkyl, fluoro$(C_3-C_4)$cycloalkoxy$(C_1-C_5)$alkyl, $(C_1-C_5)$alkylthio$(C_1-C_5)$alkyl, $(C_1-C_5)$alkoxy$(C_1-C_5)$alkoxy, hydroxy$(C_1-C_8)$alkoxy, $(C_3-C_4)$cycloalkoxy$(C_1-C_5)$alkoxy, fluoro$(C_1-C_5)$alkoxy$(C_1-C_8)$alkoxy, fluoro$(C_3-C_4)$cycloalkoxy$(C_1-C_5)$alkoxy, $(C_1-C_3)$alkoxy$(C_1-C_3)$alkoxy$(C_1-C_3)$alkyl, fluoro$(C_1-C_3)$alkoxy$(C_1-C_3)$alkoxy$(C_1-C_3)$alkyl, aminocarbonylamino$(C_1-C_8)$alkyl, aminocarbonylamino$(C_1-C_8)$alkoxy, $(C_1-C_5)$alkanoylamino$(C_1-C_5)$alkyl, $(C_1-C_5)$alkanoylamino$(C_1-C_5)$alkoxy, fluoro$(C_1-C_5)$alkanoylamino$(C_1-C_5)$alkyl, fluoro$(C_1-C_5)$alkanoylamino$(C_1-C_5)$alkoxy, $(C_1-C_3)$alkoxy$(C_1-C_5)$alkanoylamino$(C_1-C_5)$alkyl, $(C_1-C_3)$alkoxy$(C_1-C_5)$alkanoylamino$(C_1-C_5)$alkoxy, $(C_3-C_4)$cycloalkanecarbonyllamino$(C_1-C_5)$alkyl, $(C_3-C_4)$cycloalkanecarbonyllamino$(C_1-C_5)$alkoxy, aminosulfonylamino$(C_1-C_8)$alkyl, aminosulfonylamino$(C_1-C_8)$alkoxy, $(C_1-C_5)$alkanesulfonyl-amino$(C_1-C_5)$alkyl, $(C_1-C_5)$alkanesulfonylamino$(C_1-C_5)$alkoxy, formylamino$(C_1-C_5)$alkyl, formylamino$(C_1-C_5)$alkoxy, $(C_1-C_5)$alkoxycarbonylamino$(C_1-C_5)$alkyl, $(C_1-C_5)$ alkoxycarbonyl-amino($C_1$-$C_5$)alkoxy, ($C_1$-$C_5$)alkylaminocarbonylamino($C_1$-$C_5$)alkyl, ($C_1$-$C_5$)alkylaminocarbonylamino($C_1$-$C_5$)alkyl, di($C_1$-$C_5$)alkylaminocarbonylamino($C_1$-$C_5$)alkoxy, aminocarbonyl($C_1$-$C_5$)alkyl, aminocarbonyl($C_1$-$C_5$)alkoxy, ($C_1$-$C_5$)alkylaminocarbonyl($C_1$-$C_5$)alkyl, ($C_1$-$C_5$)alkylaminocarbonyl-($C_1$-$C_5$)alkoxy, aminocarboxy($C_1$-$C_5$)alkyl, aminocarboxy($C_1$-$C_5$)alkoxy, ($C_1$-$C_5$)alkylaminocarboxy($C_1$-$C_5$)alkyl, ($C_1$-$C_5$)alkylaminocarboxy($C_1$-$C_5$)alkoxy, ($C_1$-$C_8$)alkoxycarbonylamino, ($C_1$-$C_8$)alkylaminocarbonylamino, ($C_1$-$C_8$)alkanoylamino, fluoro($C_1$-$C_8$)alkoxycarbonylamino, fluoro($C_1$-$C_8$)alkylaminocarbonylamino, or fluoro($C_1$-$C_8$)alkanoylamino;

$G^c$ is H, halogen, OH, ($C_1$-$C_4$)alkanoylamino, or ($C_1$-$C_3$)alkoxy;

provided that when $G^c$ is OH or halogen, then $G^b$ is not ($C_1$-$C_8$)alkoxy, ($C_4$-$C_8$)cycloalkylalkoxy, fluoro($C_1$-$C_8$)alkoxy, ($C_1$-$C_5$)alkoxy($C_1$-$C_5$)alkoxy, hydroxy($C_1$-$C_8$)alkoxy, ($C_3$-$C_4$)cycloalkoxy($C_1$-$C_5$)alkoxy, fluoro($C_1$-$C_5$)alkoxy($C_1$-$C_5$)alkoxy, fluoro($C_3$-$C_4$)cycloalkoxy($C_1$-$C_5$)alkoxy, aminocarbonylamino($C_1$-$C_8$)alkoxy, ($C_1$-$C_5$)alkanoylamino($C_1$-$C_5$)alkoxy, fluoro($C_1$-$C_5$)alkanoylamino($C_1$-$C_5$)alkoxy, ($C_1$-$C_3$)alkoxy($C_1$-$C_5$)alkanoylamino($C_1$-$C_5$)alkoxy, ($C_3$-$C_4$)cycloalkanecarbonyllamino($C_1$-$C_5$)alkoxy, aminosulfonylamino($C_1$-$C_8$)alkoxy, ($C_1$-$C_8$)alkanesulfonylamino($C_1$-$C_5$)alkoxy, formylamino($C_1$-$C_5$)alkoxy, ($C_1$-$C_5$)alkoxycarbonyl-amino($C_1$-$C_5$)alkoxy, ($C_1$-$C_5$)alkylaminocarbonylamino($C_1$-$C_5$)alkyl, ($C_1$-$C_8$)alkylaminocarbonylamino($C_1$-$C_5$)alkyl, aminocarbonyl($C_1$-$C_5$)alkyl, ($C_1$-$C_5$)alkylaminocarbonyl($C_1$-$C_5$)alkyl, aminocarboxy($C_1$-$C_5$)alkyl, ($C_1$-$C_5$)alkylamino-carboxy($C_1$-$C_8$)alkyl, $A^4$ is $CH_2$ or O;

Q is a divalent radical selected from: Q1, Q2, Q4, Q5, Q9, or Q10

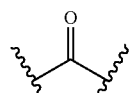

Q1

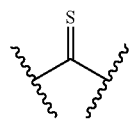

Q2

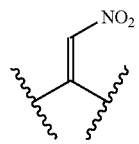

Q4

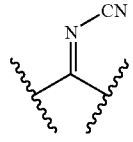

Q5

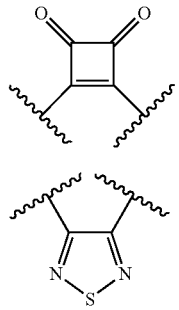

Q9

Q10 wherein N and T are attached to the truncated bonds

T is as described above.

A third embodiment of the invention is a compound of Formula I, wherein $G^a$ is a) cyclohexyl or trifluoromethyl; or b) phenyl, 2-thienyl, 3-thienyl, 2-pyridyl, 2-imidazolyl, 2-thiazolyl, 2-benzothienyl, 4-benzofuryl, 4-benzothienyl, 7-benzofuryl, 2,3-dihydro-7-benzofuryl, 7-benzothienyl, 1,3-benzodioxol-4-yl, 7-indazolyl, or 8-quinolinyl optionally substituted with 1 to 3 substituents independently selected from:

fluorine, chlorine, bromine, cyano, methyl, ethyl, isopropyl, t-butyl, isobutyl, trifluoromethyl, allyl, cyclohexyl, cyclohexen-1-yl, cyclopropylethynyl, methoxy, trifluoromethoxy, neopentyloxy, methylthio, allyloxy, cyclopropylmethoxy, 2-(cyclopropyl)ethoxy, cyclopentyloxy, cyclopentylmethoxy, benzyloxy, hydroxyl, aminocarbonyl, methoxycarbonyl, phenyl, phenoxy, benzyloxy, and heteroaryloxy, wherein the phenyl phenoxy, benzyloxy and heteroaryloxy groups are optionally substituted with 1 to 3 substituents independently selected from fluorine, chlorine, cyano, methyl, ethyl, trifluoromethyl, and aminocarbonyl;

$G^b$ is methyl, ethyl, propyl, butyl, hexyl, 5-pentenyl, 3,3,3-trifluoropropyl, 4,4-difluoropentyl, 3-(cyclopropyl)propyl, 4-(cyclopropyl)butyl, 3-hydroxypropyl, 4-hydroxybutyl, 4-hydroxypentyl, 4-hydroxyhexyl, 3-ethoxypropyl, 4-methoxybutyl, 4-ethoxybutyl, 2-(ethoxy)ethoxy, 3-methoxypropoxy, 3-ethoxypropoxy, 3-propoxypropoxy, 2-cyclopropylethoxy, 3-(2,2,2-trifluoroethylamino)propyl, 3-(formylamino)propyl, 3-(acetylamino)propyl, 3-(propionylamino)propyl, 3-(butanoylamino)propyl, 3-((2-methoxypropionyl)amino)propyl, 3-(cyclopropanecarbonylamino)propyl, 3-(trifluoroacetylamino)propyl, 3-(methoxycarbonylamino)propyl, 3-(ethoxycarbonylamino)propyl, 2-(methoxycarbonylamino)ethoxy, 2-(ethoxycarbonylamino)ethoxy, 3-(methylaminocarbonylamino)propyl, 3-(dimethylaminocarbonylamino)propyl, 2-(acetylamino)ethoxy, aminocarbonylmethoxy, (methylamino)carbonylmethoxy or 3-(aminosulfonylamino)propyl;

$G^c$ is H, F, OH, methoxy, ethoxy, 3-hydroxypropoxy, acetylamino, propionylamino, (2-methylpropionyl)amino, or butanoylamino, provided that when $G^c$ is F or OH, $G^b$ is not 2-(ethoxy)ethoxy, 3-methoxypropoxy, 3-ethoxypropoxy, 3-propoxypropoxy, 2-cyclopropylethoxy, 2-(methoxycarbonylamino)ethoxy, 2-(ethoxycarbonylamino)ethoxy, 2-(acetylamino)ethoxy, aminocarbonylmethoxy, (methylamino)carbonylmethoxy or 3-(aminosulfonylamino)propyl;

$A^4$ is $CH_2$ or O;

Q is Q1

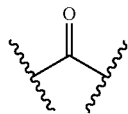

wherein N and T are attached to the truncated bonds

T is selected from 1) T1-T9 wherein $G^d$ is $(C_1-C_8)$alkyl, $(C_3-C_7)$cycloalkyl or $(C_3-C_7)$cycloalkyl$(C_1-C_2)$alkyl;

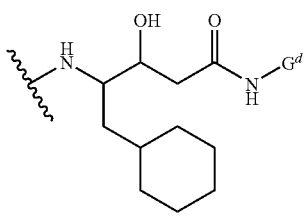

T1

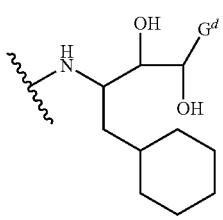

T2

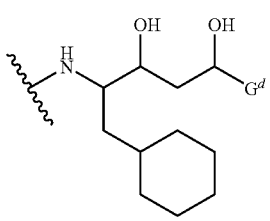

T3

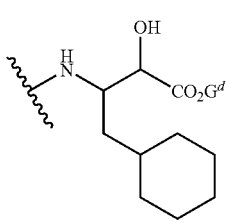

T4

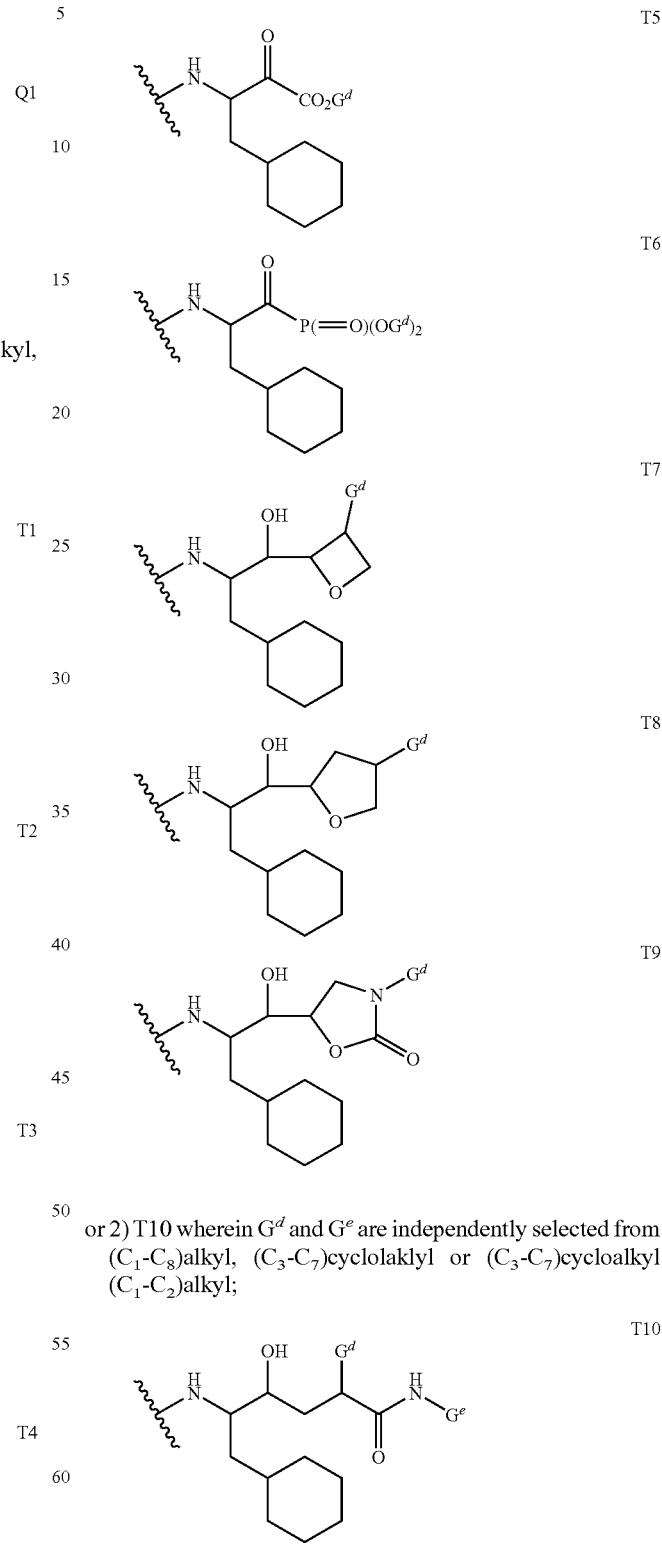

or 2) T10 wherein $G^d$ and $G^e$ are independently selected from $(C_1-C_8)$alkyl, $(C_3-C_7)$cyclolaklyl or $(C_3-C_7)$cycloalkyl $(C_1-C_2)$alkyl;

or 3) T11-T14 wherein $G^f$ is a heteroaryl or heterocyclyl group, preferably $G^f$ is 2-pyridyl, 1-piperidinyl or 4-morpholinyl;

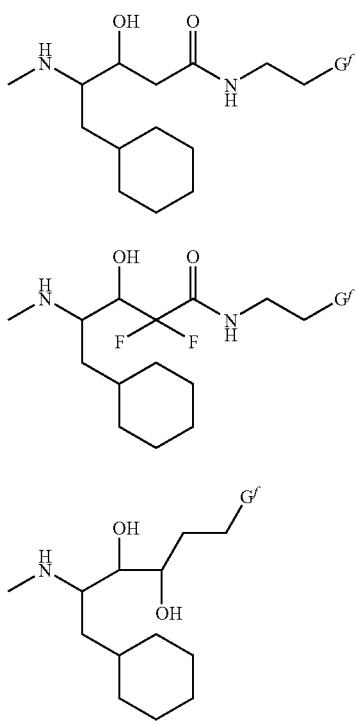
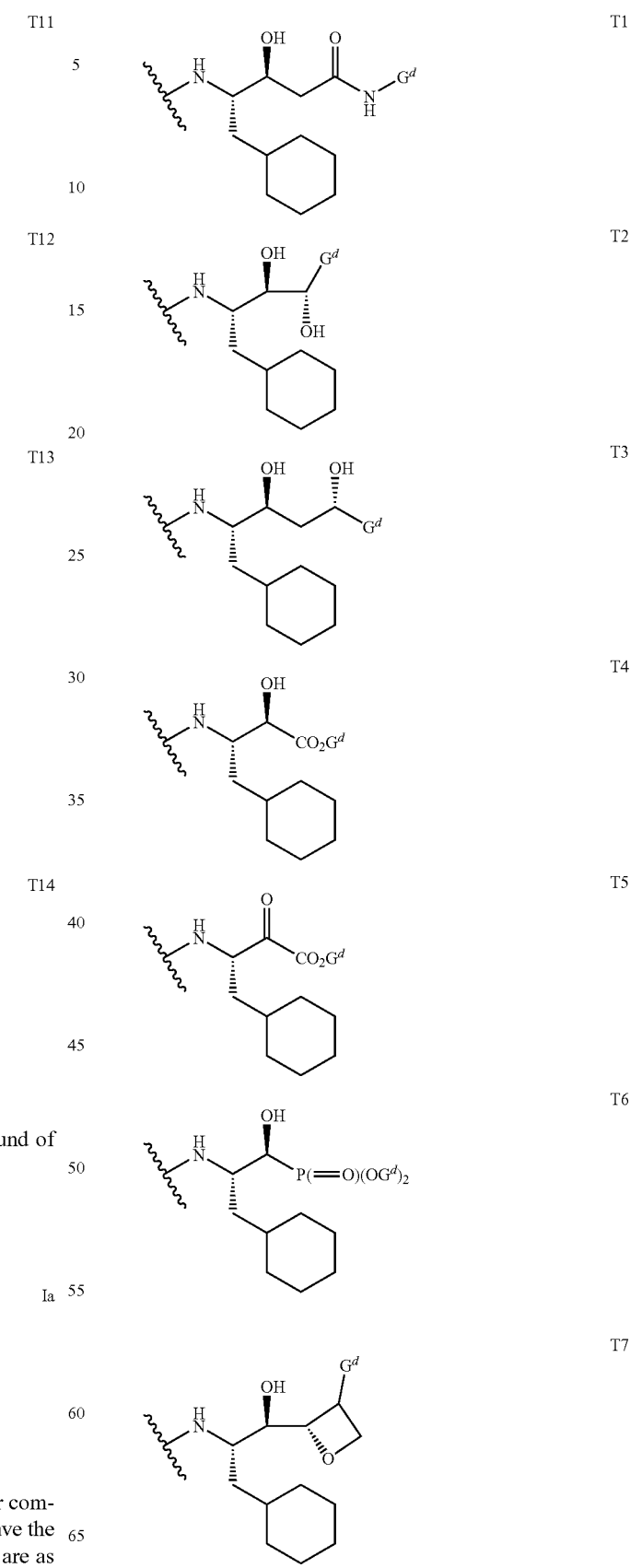
or 4) T15 wherein $G^g$ is a heteroaryl group
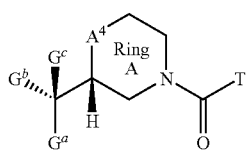
A fourth embodiment of the invention is a compound of Formula I defined by Formula Ia:
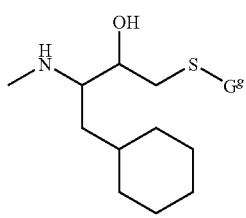
Ia
wherein $G^a$, $G^b$, $G^c$, $A^4$ and T are as defined above for compounds of Formula I. Preferably the groups T1-T14 have the stereochemistry shown below and $G^d$, $G^e$, $G^f$ and $G^g$ are as defined above for Formula I:

-continued

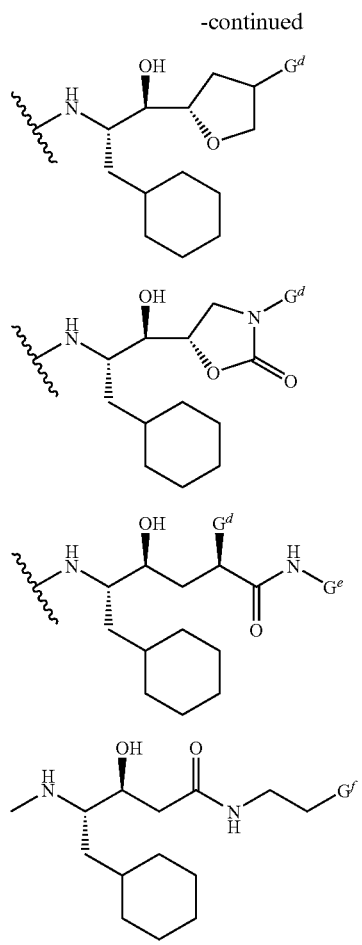

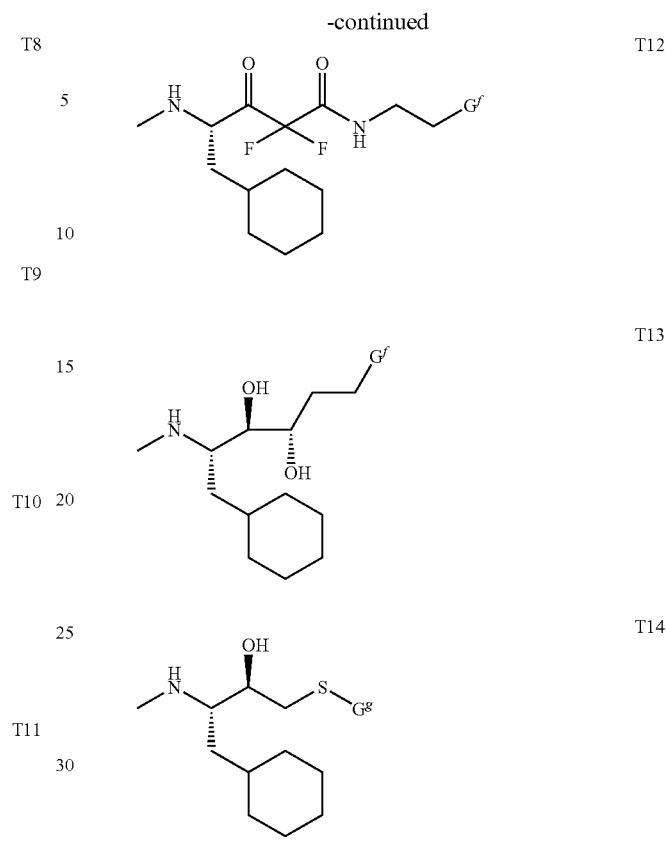

Another embodiment of the invention is each of the following compounds and their enantiomers, diastereomers, and salts:

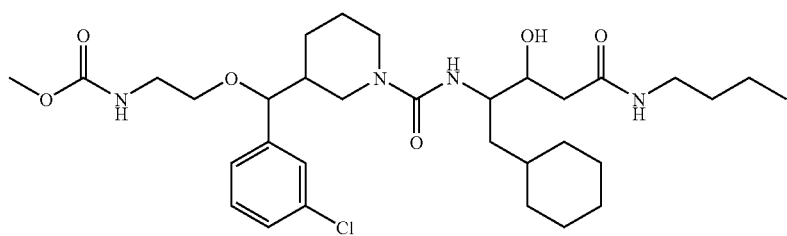

methyl 2-((1-(5-(butylamino)-1-cyclohexyl-3-hydroxy-5-oxopentan-2-ylcarbamoyl)piperidin-3-yl)(3-chlorophenyl)methoxy)ethylcarbamate

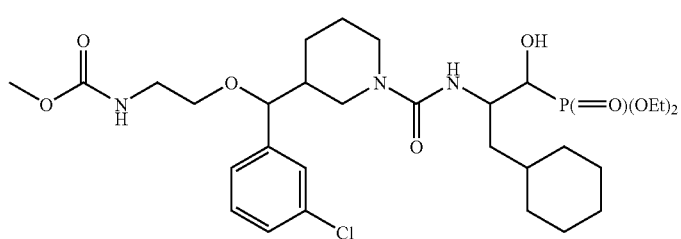

methyl 2-((3-chlorophenyl)(1-(3-cyclohexyl-1-(diethoxyphosphoryl)-1-hydroxypropan-2-ylcarbamoyl)piperidin-3-yl)methoxy)ethylcarbamate

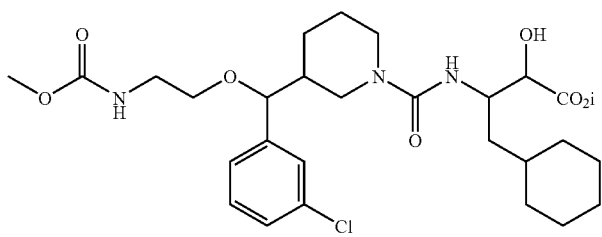

isopropyl 3-(3-((3-chlorophenyl)(2-methoxycarbonylamino)ethoxy)methyl)piperidine-1-carboxamido)-4-cyclohexyl-2-hydroxybutanoate

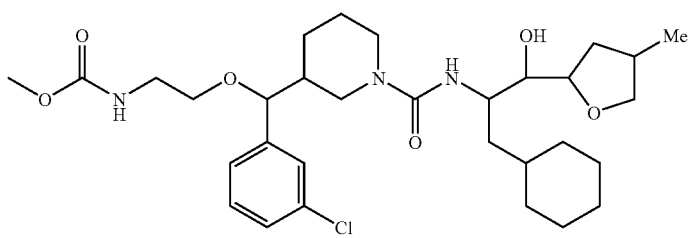

methyl 2-((3-chlorophenyl)(1-(3-cyclohexyl-1-(4-methyltetrahydrofuran-2-yl)-1-hydroxypropan-2-ylcarbamoyl)piperidin-3-yl)methoxy)ethylcarbamate

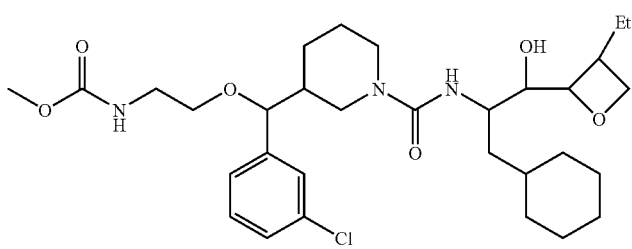

methyl 2-((3-chlorophenyl)(1-(3-cyclohexyl-1-(3-ethyloxetan-2-yl)-1-hydroxypropan-2-ylcarbamoyl)piperidin-3-yl)methoxy)ethylcarbamate

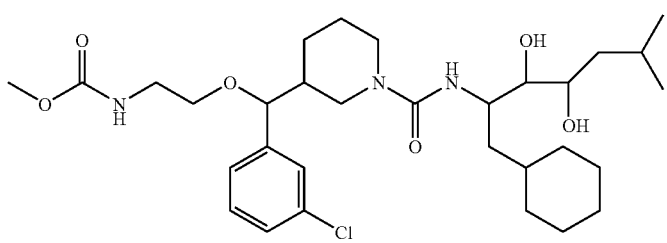

methyl 2-((3-chlorophenyl)(1-(1-cyclohexyl-3,4-dihydroxy-6-methylheptan-2-ylcarbamoyl)piperidin-3-yl)methoxy)ethylcarbamate

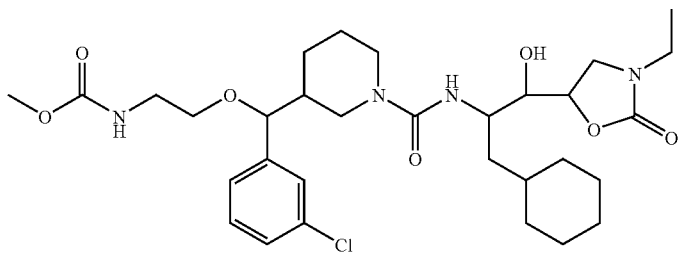

methyl 2-((3-chlorophenyl)(1-(3-cyclohexyl-1-(3-ethyl-2-oxooxazolidin-5-yl)-1-hydroxypropan-2-ylcarbamoyl)piperidin-3-yl)methoxy)ethylcarbamate

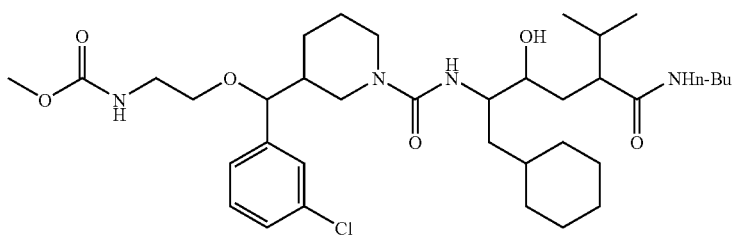

methyl 2-((1-5-(butylcarbamoyl)-1-cyclohexyl-3-
hydroxy-6-methylheptan-2-ylcarbamoyl)piperidin-
3-yl)(3-chlorophenyl)methoxy)ethylcarbamate

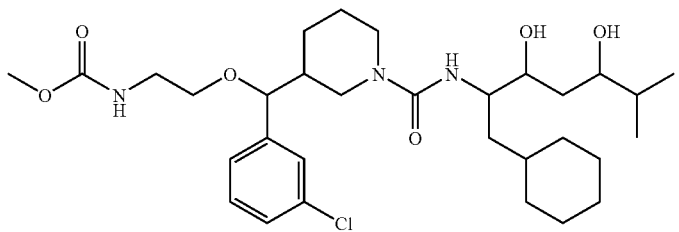

methyl 2-((3-chlorophenyl)(1-(1-cyclohexyl-
3,5-dihydroxy-6-methylheptan-2-ylcarbamoyl)
piperidin-3-yl)methoxy)ethylcarbamate

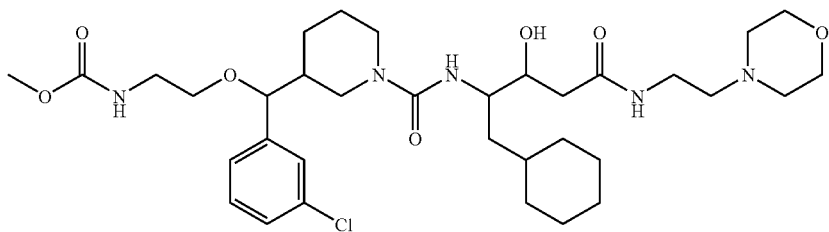

methyl 2-((3-chlorophenyl)(1-(1-cyclohexyl-3-hydroxy-5-
(2-morpholinoethylamino)-5-oxopentan-2-
ylcarbamoyl)piperidin-3-yl)methoxy)ethylcarbamate

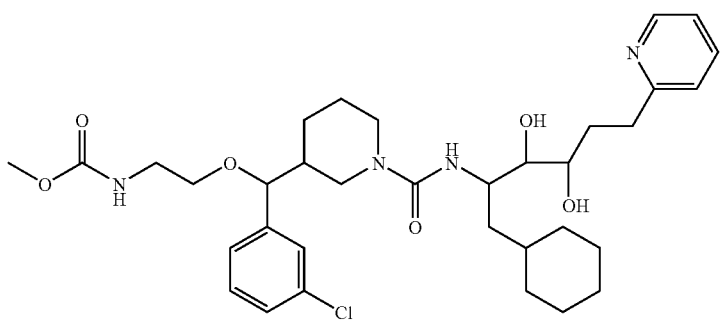

methyl 2-((3-chlorophenyl)(1-(1-cyclohexyl-3,4-
dihydroxy-6-(pyridin-2-yl)hexan-2-ylcarbamoyl)piperidin-
3-yl)methoxy)ethylcarbamate

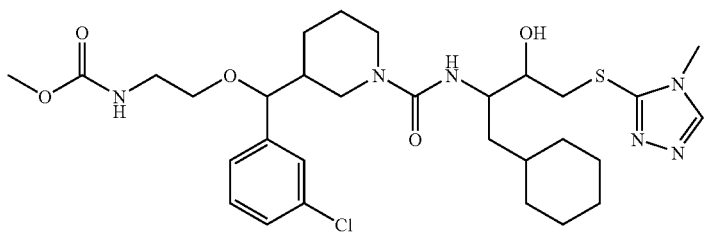

methyl 2-((3-chlorophenyl)(1-(1-cyclohexyl-3-hydroxy-4-
(4-methyl-4H-1,2,4-triazol-3-ylthio)butan-2-
ylcarbamoyl)piperidin-3-yl)methoxy)ethylcarbamate

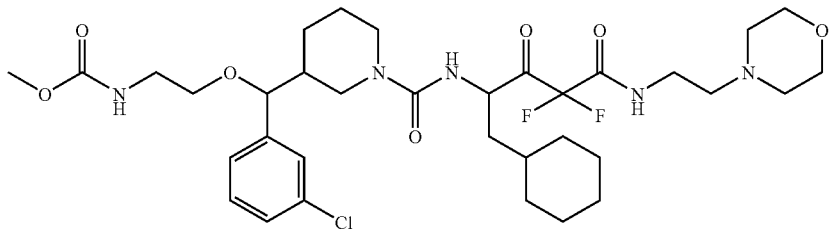

methyl 2-((3-chlorophenyl)(1-(1-cyclohexyl-4,4-difluoro-
5-(2-morpholinoethylamino)-3,5-dioxopentan-2-ylcarbamoyl)
piperidin-3-yl)methoxy)ethylcarbamate

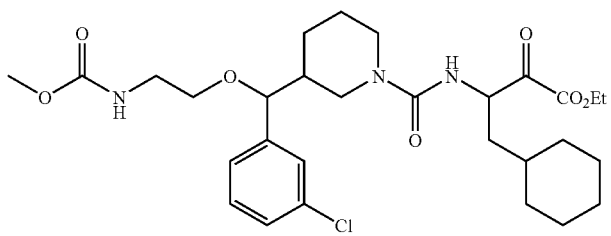

ethyl 3-(3-((3-chlorophenyl)(2-(methoxycarbonylamino)
ethoxy)methyl)piperidine-1-carboxamido)-4-
cyclohexyl-2-oxobutanoate Another embodiment of the invention is each of the compounds listed below and their salts, especially their pharmaceutically acceptable salts:

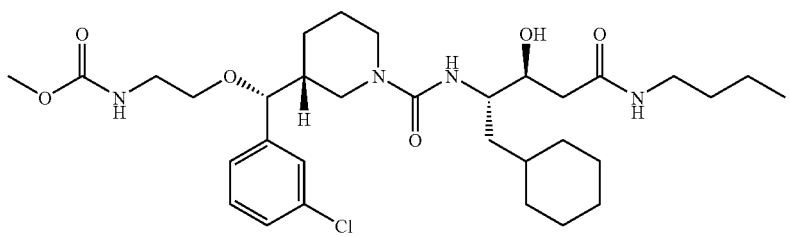

methyl-2-((R)-((R)-1-((2S,3S)-5-(butylamino)-1-cyclohexyl-3-
hydroxy-5-oxopentan-2-ylcarbamoyl)piperidin-3-yl)(3-
chlorophenyl)methoxy)ethylcarbamate

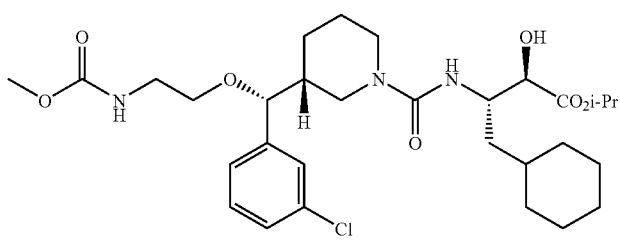

(2R,3S)-isopropyl 3-((R)-3-((R)-(3-chlorophenyl)(2-
(methoxycarbonylamino)ethoxy)methyl)piperidine-
1-carboxamido)-4-cyclohexyl-2-hydroxybutanoate

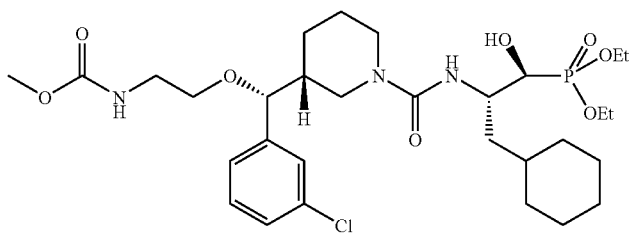

methyl 2-((R)-(3-chlorphenyl)((R)-1-((1S,2S)-3-cyclohexyl-1-(diethoxyphosphoryl)-1-hydroxypropan-2-ylcarbamoyl)piperidin-3-yl)methoxy)ethylcarbamate

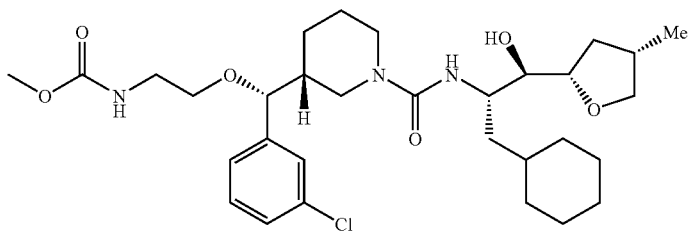

methyl 2-((R)-(3-chlorophenyl)((R)-1-((1R,2S)-3-cyclohexyl-1-hydroxy-1-((2S,4S)-4-methyltetrahydrofuran-2-yl)propan-2-ylcarbamoyl)piperidin-3-yl)methoxy)ethylcarbamate

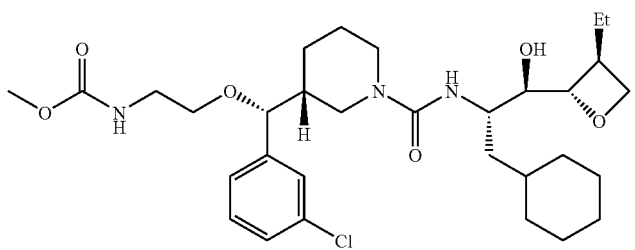

methyl 2-((R)-(3-chlorophenyl)((R)-1-((1R,2S)-3-cyclohexyl-1-((2S,3S)-3-ethyloxetan-2-yl)-1-hydroxypropan-2-ylcarbamoyl)piperidin-3-yl)methoxy)ethylcarbamate

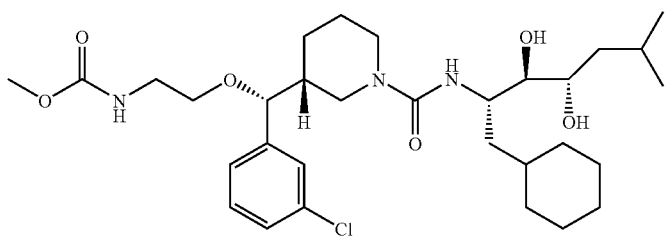

methyl 2-((R)-(3-chlorophenyl)((R)-1-((2S,3R,4S)-1-cyclohexyl-3,4-dihydroxy-6-methylheptan-2-ylcarbamoyl)piperidin-3-yl)methoxy)ethylcarbamate

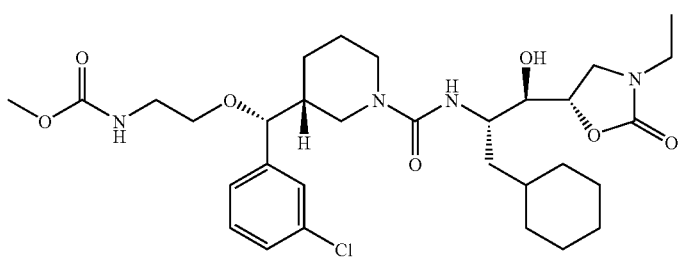

methyl 2-((R)-(3-chlorophenyl)((R)-1-((1R,2S)-3-cyclohexyl-1-((S)-3-ethyl-2-oxooxazolidin-5-yl)-1-hydroxypropan-2-ylcarbamoyl)piperidin-3-yl)methoxy)ethylcarbamate -continued

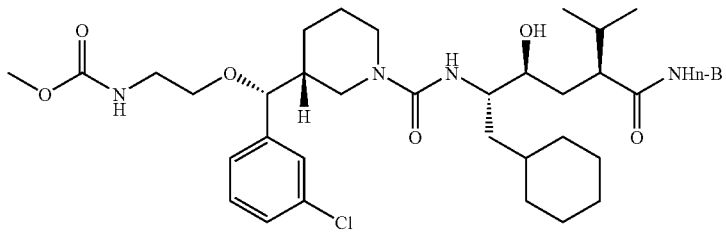

methyl 2-((R)-((R)-1-(2S,3S,5S)-5-(butylcarbamoyl)-1-cyclohexyl-3-hydroxy-6-methylheptan-2-ylcarbamoyl)piperidin-3-yl)(3-chlorophenyl)methoxy)ethylcarbamate

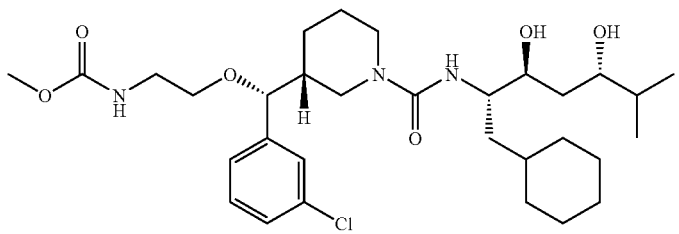

methyl 2-((R)-(3-chlorophenyl)((R)-1-((2S,3S,5S)-1-cyclohexyl-3,5-dihydroxy-6-methylheptan-2-ylcarbamoyl)piperidin-3-yl)methoxy)ethylcarbamate

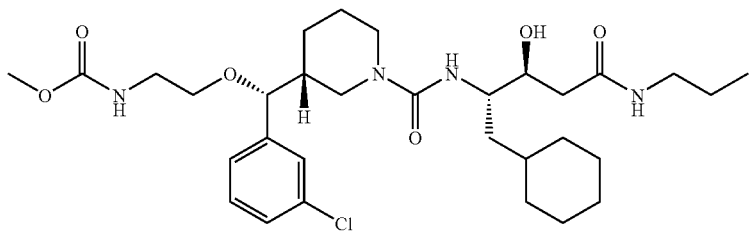

methyl 2-((R)-(3-chlorophenyl)((R)-1-((2S,3S)-1-cyclohexyl-3-hydroxy-5-(2-morpholinoethylamino)-5-oxopentan-2-ylcarbamoyl)piperidin-3-yl)methoxy)ethylcarbamate

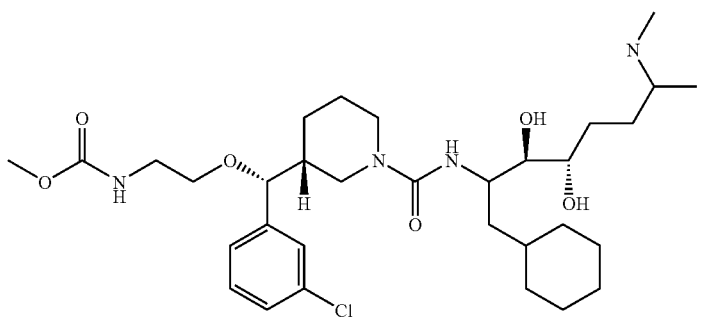

methyl 2-((R)-(3-chlorophenyl)((R)-1-((2S,3R,4S)-1-cyclohexyl-3,4-dihydroxy-6-(pyridin-2-yl)hexan-2-ylcarbamoyl)piperidin-3-yl)methoxy)ethylcarbamate

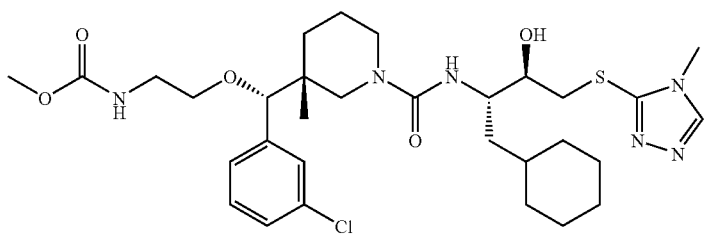

methyl 2-((R)-(3-chlorophenyl)((R)-1-((2S,3R)-1-cyclohexyl-3-hydroxy-4-(1-methyl-1H-tetrazol-5-ylthio)butan-2-ylcarbamoyl)piperidin-3-yl)methoxy)ethylcarbamate -continued

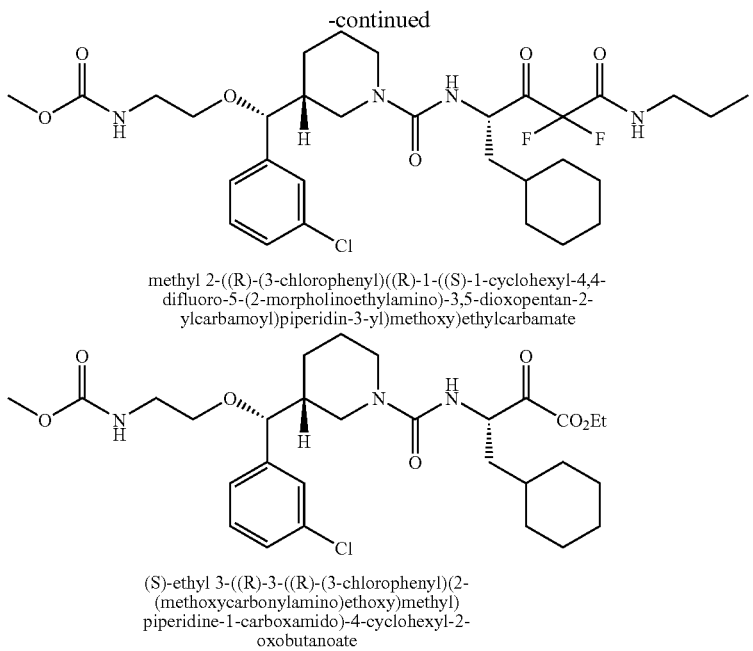

methyl 2-((R)-(3-chlorophenyl)((R)-1-((S)-1-cyclohexyl-4,4-difluoro-5-(2-morpholinoethylamino)-3,5-dioxopentan-2-ylcarbamoyl)piperidin-3-yl)methoxy)ethylcarbamate (S)-ethyl 3-((R)-3-((R)-(3-chlorophenyl)(2-(methoxycarbonylamino)ethoxy)methyl)piperidine-1-carboxamido)-4-cyclohexyl-2-oxobutanoate When any variable (e.g., aryl, heterocyclyl, $R_1$, $R_2$, etc.) occurs more than once in a compound, its definition on each occurrence is independent of any other occurrence.

"Alkyl" means a saturated aliphatic branched or straight-chain mono- or divalent hydrocarbon radical having the specified number of carbon atoms. Thus, "$(C_1-C_8)$alkyl" means a radical having from 1-8 carbon atoms in a linear or branched arrangement. "$(C_1-C_6)$alkyl" includes methyl, ethyl, propyl, butyl, pentyl, and hexyl.

"Cycloalkyl" means a saturated aliphatic cyclic hydrocarbon radical having the specified number of carbon atoms. Thus, $(C_3-C_7)$cycloalkyl means a radical having from 3-8 carbon atoms arranged in a ring. $(C_3-C_7)$cycloalkyl includes cyclopropyl, cyclobutyl, cyclopentyl, cyclohexyl, and cycloheptyl.

Haloalkyl and halocycloalkyl include mono, poly, and perhaloalkyl groups where the halogens are independently selected from fluorine, chlorine, and bromine Saturated heterocyclic rings are 4-, 5-, 6-, and 7-membered heterocyclic rings containing 1 to 4 heteroatoms independently selected from N, O, and S, and include pyrrolidine, piperidine, tetrahydrofuran, tetrahydropyran, tetrahydrothiophene, tetrahydrothiopyran, isoxazolidine, 1,3-dioxolane, 1,3-dithiolane, 1,3-dioxane, 1,4-dioxane, 1,3-dithiane, 1,4-dithiane, morpholine, thiomorpholine, thiomorpholine 1,1-dioxide, tetrahydro-2H-1,2-thiazine 1,1-dioxide, and isothiazolidine 1,1-dioxide. Oxo substituted saturated heterocyclic rings include tetrahydrothiophene 1-oxide, tetrahydrothiophene 1,1-dioxide, thiomorpholine 1-oxide, thiomorpholine 1,1-dioxide, tetrahydro-2H-1,2-thiazine 1,1-dioxide, and isothiazolidine 1,1-dioxide, pyrrolidin-2-one, piperidin-2-one, piperazin-2-one, and morpholin-2-one.

"Heteroaryl" means a monovalent heteroaromatic monocyclic and polycylic ring radical containing 1 to 4 heteroatoms independently selected from N, O, and S. Heteroaryl rings include furyl, thienyl, thiophenyl, pyrrolyl, oxazolyl, thiazolyl, imidazolyl, pyrazolyl, isoxazolyl, isothiazolyl, oxadiazolyl, triazolyl, thiadiazolyl, pyridinyl, pyridinyl-N-oxide, pyridazinyl, pyrimidinyl, pyrazinyl, indolizinyl, indolyl, isoindolyl, benzo[b]furyl, benzo[b]thienyl, indazolyl, benzimidazolyl, benzthiazolyl, purinyl, 4H-quinolizinyl, quinolinyl, isoquinolinyl, cinnolinyl, phthalzinyl, quinazolinyl, quinoxalinyl, 1,8-naphthyridinyl, 1,2,3-triazolyl, 1,2,4-triazolyl, 1,3,4-oxadiazolyl, 1,2,5-thiadiazolyl, 1,2,5-thiadiazolyl-1-oxide, 1,2,5-thiadiazolyl-1,1-dioxide, 1,3,4-thiadiazolyl, 1,2,4-triazinyl, 1,3,5-triazinyl, tetrazolyl, and pteridinyl.

Bicyclic heteroaryl rings are bicyclo[4.4.0] and bicyclo[4,3.0] fused ring systems of which at least one ring is aromatic containing 1 to 4 heteroatoms independently selected from N, O, and S, and include indole, quinoline, isoquinoline, quinazoline, benzothiophene, benzofuran, 2,3-dihydrobenzofuran, benzodioxole, benzimidazole, indazole, benzisoxazole, benzoxazole, and benzothiazole.

Bicycloalkyl rings are fused, bridged and spiro ring systems and include bicyclo[1.1.0]butane, bicyclo[1.2.0]pentane, bicyclo[2.2.0]hexane, bicyclo[3.2.0]heptane, bicyclo[3.3.0]octane, bicyclo[4.2.0]octane, bicyclo[2.2.1]heptane, bicyclo[2.2.2]octane, bicyclo[3.2.1]octane, bicyclo[3.2.2]nonane, bicyclo[3.3.1]nonane, bicyclo[3.3.2]decane and bicyclo[3.3.3]undecane, spiro[2.2]pentane, spiro[2.3]hexane, spiro[3.3]heptane, spiro[2.4]heptane, spiro[3.4]octane and spiro[2.5]octane.

Tricycloalkyl rings are fused, bridged and spiro ring systems and include tricyclo[3.3.1.0$^{3,7}$]nonane (noradamantane) and tricyclo[3.3.1.1$^{3,7}$]decane (adamantane).

"Alkoxy" means an alkyl radical attached through an oxygen linking atom. "$(C_1-C_4)$-alkoxy" includes the methoxy, ethoxy, propoxy, and butoxy.

"Aromatic" means an unsaturated cycloalkyl ring system.

"Aryl" means an aromatic monocyclic or polycyclic ring system. Aryl systems include phenyl, naphthalenyl, fluorenyl, indenyl, azulenyl, and anthracenyl.

"Hetero" refers to the replacement of at least one carbon atom member in a ring system with at least one heteroatom selected from N, S, and O. A hetero ring may have 1, 2, 3, or 4 carbon atom members replaced by a heteroatom.

"Oxo" refers to =O. When an oxo group is a substituent on a carbon atom, they form a carbonyl group (—C(O)—). When one oxo group is a substituent on a sulfur atom, they form a sulfinyl (sulfoxide —S(O)—) group. When two oxo groups are a substituent on a sulfur atom, they form a sulfonyl (sulfone —S(O)$_2$—) group.

In certain instances herein when describing functional groups, "alkane", "cycloalkane" and the like are used interchangeably with "alkyl" and "cycloalkyl", respectively. Thus, by way of example, "alkanesulfonyl" means an alkyl group attached to a sulfonyl moiety, and "cycloalkanesulfonyl" refers to a cycloalkyl group attached to a sulfonyl moiety.

Enantiomers, Diastereomers, and Salts

Certain compounds of Formula I may exist in various stereoisomeric or tautomeric forms. The invention encompasses all such forms, including active compounds in the form of essentially pure enantiomers, racemic mixtures, and tautomers, and including forms not depicted structurally.

The compounds of the invention may be present in the form of pharmaceutically acceptable salts. For use in medicines, the salts of the compounds of the invention refer to non-toxic "pharmaceutically acceptable salts." Pharmaceutically acceptable salt forms include pharmaceutically acceptable acidic/anionic or basic/cationic salts.

Pharmaceutically acceptable acidic/anionic salts include, the acetate, benzenesulfonate, benzoate, bicarbonate, bitartrate, bromide, calcium edetate, camsylate, carbonate, chloride, citrate, dihydrochloride, edetate, edisylate, estolate, esylate, fumarate, glyceptate, gluconate, glutamate, glycollylarsanilate, hexylresorcinate, hydrobromide, hydrochloride, hydroxynaphthoate, iodide, isethionate, lactate, lactobionate, malate, maleate, mandelate, mesylate, methylsulfate, mucate, napsylate, nitrate, pamoate, pantothenate, phosphate/diphospate, polygalacturonate, salicylate, stearate, subacetate, succinate, sulfate, tannate, tartrate, teoclate, tosylate, and triethiodide salts.

The compounds of the invention include pharmaceutically acceptable anionic salt forms, wherein the anionic salts include the acetate, benzenesulfonate, benzoate, bicarbonate, bitartrate, bromide, calcium edetate, camsylate, carbonate, chloride, citrate, dihydrochloride, edetate, edisylate, estolate, esylate, fumarate, glyceptate, gluconate, glutamate, glycollylarsanilate, hexylresorcinate, hydrobromide, hydrochloride, hydroxynaphthoate, iodide, isethionate, lactate, lactobionate, malate, maleate, mandelate, mesylate, methylsulfate, mucate, napsylate, nitrate, pamoate, pantothenate, phosphate/diphospate, polygalacturonate, salicylate, stearate, subacetate, succinate, sulfate, tannate, tartrate, teoclate, tosylate, and triethiodide salts.

The anionic salt form of a compound of the invention includes the acetate, bromide, camsylate, chloride, edisylate, fumarate, hydrobromide, hydrochloride, iodide, isethionate, lactate, mesylate, maleate, napsylate, salicylate, sulfate, and tosylate salts.

When a disclosed compound or its pharmaceutically acceptable salt is named or depicted by structure, it is to be understood that solvates or hydrates of the compound or its pharmaceutically acceptable salts are also included. "Solvates" refer to crystalline forms wherein solvent molecules are incorporated into the crystal lattice during crystallization. Solvate may include water or nonaqueous solvents such as ethanol, isopropanol, DMSO, acetic acid, ethanolamine, and EtOAc. Solvates, wherein water is the solvent molecule incorporated into the crystal lattice, are typically referred to as "hydrates." Hydrates include stoichiometric hydrates as well as compositions containing variable amounts of water.

When a disclosed compound or its pharmaceutically acceptable salt is named or depicted by structure, it is to be understood that the compound, including solvates thereof, may exist in crystalline forms, non-crystalline forms or a mixture thereof. The compound or its pharmaceutically acceptable salts or solvates may also exhibit polymorphism (i.e. the capacity to occur in different crystalline forms). These different crystalline forms are typically known as "polymorphs." It is to be understood that when named or depicted by structure, the disclosed compound and its pharmaceutically acceptable salts, solvates or hydrates also include all polymorphs thereof. Polymorphs have the same chemical composition but differ in packing, geometrical arrangement, and other descriptive properties of the crystalline solid state. Polymorphs, therefore, may have different physical properties such as shape, density, hardness, deformability, stability, and dissolution properties. Polymorphs typically exhibit different melting points, IR spectra, and X-ray powder diffraction patterns, which may be used for identification. One of ordinary skill in the art will appreciate that different polymorphs may be produced, for example, by changing or adjusting the conditions used in solidifying the compound. For example, changes in temperature, pressure, or solvent may result in different polymorphs. In addition, one polymorph may spontaneously convert to another polymorph under certain conditions.

It may be necessary and/or desirable during synthesis to protect sensitive or reactive groups on any of the molecules concerned. Representative conventional protecting groups are described in T. W. Greene and P. G. M. Wuts "Protective Groups in Organic Synthesis" John Wiley & Sons, Inc., New York 1999. Protecting groups may be added and removed using methods well known in the art.

The invention also includes various isomers and mixtures thereof. "Isomer" refers to compounds that have the same composition and molecular weight but differ in physical and/or chemical properties. The structural difference may be in constitution (geometric isomers) or in the ability to rotate the plane of polarized light (stereoisomers).

Certain of the disclosed aspartic protease inhibitors may exist in various stereoisomeric forms. Stereoisomers are compounds which differ only in their spatial arrangement. Enantiomers are pairs of stereoisomers whose mirror images are not superimposable, most commonly because they contain an asymmetrically substituted carbon atom that acts as a chiral center. "Enantiomer" means one of a pair of molecules that are mirror images of each other and are not superimposable. Diastereomers are stereoisomers that are not related as mirror images, most commonly because they contain two or more asymmetrically substituted carbon atoms. The symbol "*" in a structural formula represents the presence of a chiral carbon center. "R" and "S" represent the configuration of substituents around one or more chiral carbon atoms. Thus, "R*" and "S*" denote the relative configurations of substituents around one or more chiral carbon atoms. When a chiral center is not defined as R or S, a mixture of both configurations is present.

"Racemate" or "racemic mixture" means a compound of equimolar quantities of two enantiomers, wherein such mixtures exhibit no optical activity; i.e., they do not rotate the plane of polarized light.

"Geometric isomer" means isomers that differ in the orientation of substituent atoms in relationship to a carbon-carbon double bond, to a cycloalkyl ring, or to a bridged bicyclic system. Atoms (other than H) on each side of a carbon-carbon double bond may be in an E (substituents are on opposite sides of the carbon-carbon double bond) or Z (substituents are oriented on the same side) configuration.

Atoms (other than H) attached to a carbocyclic ring may be in a cis or trans configuration. In the "cis" configuration, the substituents are on the same side in relationship to the plane of the ring; in the "trans" configuration, the substituents are on opposite sides in relationship to the plane of the ring. A mixture of "cis" and "trans" species is designated "cis/trans".

"R," "S," "S*," "R*," "E," "Z," "cis," and "trans," indicate configurations relative to the core molecule.

The point at which a group or moiety is attached to the remainder of the compound or another group or moiety can be indicated by "∿∿"which represents "⋯∎", "━∎"or "-".

The compounds of the invention may be prepared as individual isomers by either isomer-specific synthesis or resolved from an isomeric mixture. Conventional resolution techniques include forming the salt of a free base of each isomer of an isomeric pair using an optically active acid (followed by fractional crystallization and regeneration of the free base), forming the salt of the acid form of each isomer of an isomeric pair using an optically active amine (followed by fractional crystallization and regeneration of the free acid), forming an ester or amide of each of the isomers of an isomeric pair using an optically pure acid, amine or alcohol (followed by chromatographic separation and removal of the chiral auxiliary), or resolving an isomeric mixture of either a starting material or a final product using various well known chromatographic methods.

When the stereochemistry of a disclosed compound is named or depicted by structure, the named or depicted stereoisomer is at least 60%, 70%, 80%, 90%, 99% or 99.9% by weight pure relative to the other stereoisomers. When a single enantiomer is named or depicted by structure, the depicted or named enantiomer is at least 60%, 70%, 80%, 90%, 99% or 99.9% by weight optically pure. Percent optical purity by weight is the ratio of the weight of the enantiomer over the weight of the enantiomer plus the weight of its optical isomer.

When a disclosed compound is named or depicted by structure without indicating the stereochemistry, and the inhibitor has at least one chiral center, it is to be understood that the name or structure encompasses one enantiomer of inhibitor free from the corresponding optical isomer, a racemic mixture of the inhibitor and mixtures enriched in one enantiomer relative to its corresponding optical isomer.

When a disclosed aspartic protease inhibitor is named or depicted by structure without indicating the stereochemistry and has at least two chiral centers, it is to be understood that the name or structure encompasses a diastereomer free of other diastereomers, a pair of diastereomers free from other diastereomeric pairs, mixtures of diastereomers, mixtures of diastereomeric pairs, mixtures of diastereomers in which one diastereomer is enriched relative to the other diastereomer(s) and mixtures of diastereomeric pairs in which one diastereomeric pair is enriched relative to the other diastereomeric pair(s).

The compounds of the invention are useful for ameliorating or treating disorders or diseases in which decreasing the levels of aspartic protease products is effective in treating the disease state or in treating infections in which the infectious agent depends upon the activity of an aspartic protease. In hypertension elevated levels of angiotensin I, the product of renin catalyzed cleavage of angiotensinogen are present. Thus, the compounds of the invention can be used in the treatment of hypertension, heart failure such as (acute and chronic) congestive heart failure; left ventricular dysfunction; cardiac hypertrophy; cardiac fibrosis; cardiomyopathy (e.g., diabetic cardiac myopathy and post-infarction cardiac myopathy); supraventricular and ventricular arrhythmias; arial fibrillation; atrial flutter; detrimental vascular remodeling; myocardial infarction and its sequelae; atherosclerosis; angina (whether unstable or stable); renal failure conditions, such as diabetic nephropathy; glomerulonephritis; renal fibrosis; scleroderma; glomerular sclerosis; microvascular complications, for example, diabetic retinopathy; renal vascular hypertension; vasculopathy; neuropathy; complications resulting from diabetes, including nephropathy, vasculopathy, retinopathy and neuropathy, diseases of the coronary vessels, proteinuria, albumenuria, post-surgical hypertension, metabolic syndrome, obesity, restenosis following angioplasty, eye diseases and associated abnormalities including raised intra-ocular pressure, glaucoma, retinopathy, abnormal vascular growth and remodelling, angiogenesisrelated disorders, such as neovascular age related macular degeneration; hyperaldosteronism, anxiety states, and cognitive disorders (Fisher N. D.; Hollenberg N. K. *Expert Opin. Investig. Drugs*. 2001, 10, 417-26).

A pharmaceutical composition of the invention may, alternatively or in addition to a compound of Formula I, comprise a pharmaceutically acceptable salt of a compound of Formula I or a prodrug or pharmaceutically active metabolite of such a compound or salt and one or more pharmaceutically acceptable carriers therefor.

The compositions of the invention are renin inhibitors. Said compositions contain compounds having a mean inhibition constant ($IC_{50}$) against aspartic proteases of between about 5,000 nM to about 0.001 nM; preferably between about 50 nM to about 0.001 nM; and more preferably between about 5 nM to about 0.01 nM. The compositions of the invention reduce blood pressure.

The invention includes a therapeutic method for treating or ameliorating an aspartic protease mediated disorder in a subject in need thereof comprising administering to a subject in need thereof an effective amount of a compound of Formula I, or the enantiomers, diastereomers, or salts thereof or composition thereof.

Administration methods include administering an effective amount (i.e., a therapeutically effective amount) of a compound or composition of the invention at different times during the course of therapy or concurrently in a combination form. The methods of the invention include all known therapeutic treatment regimens.

"Prodrug" means a pharmaceutically acceptable form of an effective derivative of a compound (or a salt thereof) of the invention, wherein the prodrug may be: 1) a relatively active precursor which converts in vivo to a compound of the invention; 2) a relatively inactive precursor which converts in vivo to a compound of the invention; or 3) a relatively less active component of the compound that contributes to therapeutic activity after becoming available in vivo (i.e., as a metabolite). See "Design of Prodrugs", ed. H. Bundgaard, Elsevier, 1985.

"Metabolite" means a pharmaceutically acceptable form of a metabolic derivative of a compound (or a salt thereof) of the invention, wherein the derivative is an active compound that contributes to therapeutic activity after becoming available in vivo.

"Effective amount" means that amount of active compound agent that elicits the desired biological response in a subject. Such response includes alleviation of the symptoms of the disease or disorder being treated. The effective amount of a compound of the invention in such a therapeutic method is from about 10 mg/kg/day to about 0.01 mg/kg/day, preferably from about 0.5 mg/kg/day to 5 mg/kg/day.

The invention includes the use of a compound of the invention for the preparation of a composition for treating or ameliorating an aspartic protease mediated chronic disorder or disease or infection in a subject in need thereof, wherein the composition comprises a mixture one or more compounds of the invention and an optional pharmaceutically acceptable carrier.

"Pharmaceutically acceptable carrier" means compounds and compositions that are of sufficient purity and quality for use in the formulation of a composition of the invention and that, when appropriately administered to an animal or human, do not produce an adverse reaction.

"Renin protease mediated disorder or disease" includes disorders or diseases associated with the elevated expression or overexpression of renin and conditions that accompany such diseases.

An embodiment of the invention includes administering a renin inhibiting compound of Formula I or composition thereof in a combination therapy (see U.S. Pat. Nos. 5,821,232, 6,716,875, 5,663,188, or Fossa, A. A.; DePasquale, M. J.; Ringer, L. J.; Winslow, R. L. "Synergistic effect on reduction in blood pressure with coadministration of a renin inhibitor or an angiotensin-converting enzyme inhibitor with an angiotensin II receptor antagonist" *Drug Development Research* 1994, 33(4), 422-8) with one or more additional agents for the treatment of hypertension including α-blockers, β-blockers, calcium channel blockers, diuretics, natriuretics, saluretics, centrally acting antihypertensives, angiotensin converting enzyme (ACE) inhibitors, dual ACE and neutral endopeptidase (NEP) inhibitors, angiotensin-receptor blockers (ARBs), aldosterone synthase inhibitors, aldosterone-receptor antagonists, or endothelin receptor antagonists.

α-Blockers include doxazosin, prazosin, tamsulosin, and terazosin.

β-Blockers for combination therapy are selected from atenolol, bisoprol, metoprolol, acetutolol, esmolol, celiprolol, taliprolol, acebutolol, oxprenolol, pindolol, propanolol, bupranolol, penbutolol, mepindolol, carteolol, nadolol, carvedilol, and their pharmaceutically acceptable salts.

Calcium channel blockers include dihydropyridines (DHPs) and non-DHPs. The preferred DHPs are amlodipine, felodipine, ryosidine, isradipine, lacidipine, nicardipine, nifedipine, nigulpidine, niludipine, nimodiphine, nisoldipine, nitrendipine, and nivaldipine, and their pharmaceutically acceptable salts. NonDHPs are flunarizine, prenylamine, diltiazem, fendiline, gallopamil, mibefradil, anipamil, tiapamil, and verampimil, and their pharmaceutically acceptable salts.

A diuretic is, for example, a thiazide derivative selected from amiloride, chlorothiazide, hydrochlorothiazide, methylchlorothiazide, and chlorothalidon.

Centrally acting antihypertensives include clonidine, guanabenz, guanfacine and methyldopa.

ACE inhibitors include alacepril, benazepril, benazaprilat, captopril, ceronapril, cilazapril, delapril, enalapril, enalaprilat, fosinopril, lisinopril, moexipiril, moveltopril, perindopril, quinapril, quinaprilat, ramipril, ramiprilat, spirapril, temocapril, trandolapril, and zofenopril. Preferred ACE inhibitors are benazepril, enalpril, lisinopril, and ramipril.

Dual ACE/NEP inhibitors are, for example, omapatrilat, fasidotril, and fasidotrilat.

Preferred ARBs include candesartan, eprosartan, irbesartan, losartan, olmesartan, tasosartan, telmisartan, and valsartan.

Preferred aldosterone synthase inhibitors are anastrozole, fadrozole, and exemestane.

Preferred aldosterone-receptor antagonists are spironolactone and eplerenone.

A preferred endothelin antagonist is, for example, bosentan, enrasentan, atrasentan, darusentan, sitaxsentan, and tezosentan, and their pharmaceutically acceptable salts.

An embodiment of the invention includes administering an HIV protease inhibiting compound of Formula I or composition thereof in a combination therapy with one or more additional agents for the treatment of AIDS including reverse transcriptase inhibitors, non-nucleoside reverse transcriptase inhibitors, other HIV protease inhibitors, HIV integrase inhibitors, entry inhibitors (including attachment, co-receptor and fusion inhibitors), antisense drugs, and immune stimulators.

Preferred reverse transcriptase inhibitors are zidovudine, didanosine, zalcitabine, stavudine, lamivudine, abacavir, tenofovir, and emtricitabine.

Preferred non-nucleoside reverse transcriptase inhibitors are nevirapine, delaviridine, and efavirenz.

Preferred HIV protease inhibitors are saquinavir, ritonavir, indinavir, nelfinavir, amprenavir, lopinavir, atazanavir, and fosamprenavir.

Preferred HIV integrase inhibitors are L-870,810 and S-1360.

Entry inhibitors include compounds that bind to the CD4 receptor, the CCR5 receptor or the CXCR4 receptor. Specific examples of entry inhibitors include enfuvirtide (a peptidomimetic of the HR2 domain in gp41) and sifurvitide.

A preferred attachment and fusion inhibitor is enfuvirtide.

An embodiment of the invention includes administering β-secretase inhibiting compound of Formula I or composition thereof in a combination therapy with one or more additional agents for the treatment of Alzheimer's disease including tacrine, donepezil, rivastigmine, galantamine, and memantine.

Combination therapy includes co-administration of the compound of the invention and said other agent, sequential administration of the compound and the other agent, administration of a composition containing the compound and the other agent, or simultaneous administration of separate compositions containing the compound and the other agent.

The invention further includes the process for making the composition comprising mixing one or more of the present compounds and an optional pharmaceutically acceptable carrier; and includes those compositions resulting from such a process, which process includes conventional pharmaceutical techniques.

The compositions of the invention include ocular, oral, nasal, transdermal, topical with or without occlusion, intravenous (both bolus and infusion), and injection (intraperitoneally, subcutaneously, intramuscularly, intratumorally, or parenterally). The composition may be in a dosage unit such as a tablet, pill, capsule, powder, granule, liposome, ion exchange resin, sterile ocular solution, or ocular delivery device (such as a contact lens and the like facilitating immediate release, timed release, or sustained release), parenteral solution or suspension, metered aerosol or liquid spray, drop, ampoule, auto-injector device, or suppository; for administration ocularly, orally, intranasally, sublingually, parenterally, or rectally, or by inhalation or insufflation.

Compositions of the invention suitable for oral administration include solid forms such as pills, tablets, caplets, capsules (each including immediate release, timed release, and sustained release formulations), granules and powders; and, liquid forms such as solutions, syrups, elixirs, emulsions, and suspensions. Forms useful for ocular administration include sterile solutions or ocular delivery devices. Forms useful for parenteral administration include sterile solutions, emulsions, and suspensions.

The compositions of the invention may be administered in a form suitable for once-weekly or once-monthly administration. For example, an insoluble salt of the active compound may be adapted to provide a depot preparation for intramuscular injection (e.g., a decanoate salt) or to provide a solution for ophthalmic administration.

The dosage form containing the composition of the invention contains a therapeutically effective amount of the active ingredient necessary to provide a therapeutic effect. The composition may contain from about 5,000 mg to about 0.5 mg (preferably, from about 1,000 mg to about 0.5 mg) of a compound of the invention or salt form thereof and may be constituted into any form suitable for the selected mode of administration. The composition may be administered about 1 to about 5 times per day. Daily administration or post-periodic dosing may be employed.

For oral administration, the composition is preferably in the form of a tablet or capsule containing, e.g., 500 to 0.5 milligrams of the active compound. Dosages will vary depending on factors associated with the particular patient being treated (e.g., age, weight, diet, and time of administration), the severity of the condition being treated, the compound being employed, the mode of administration, and the strength of the preparation.

The oral composition is preferably formulated as a homogeneous composition, wherein the active ingredient is dispersed evenly throughout the mixture, which may be readily subdivided into dosage units containing equal amounts of a compound of the invention. Preferably, the compositions are prepared by mixing a compound of the invention (or pharmaceutically acceptable salt thereof) with one or more optionally present pharmaceutical carriers (such as a starch, sugar, diluent, granulating agent, lubricant, glidant, binding agent, and disintegrating agent), one or more optionally present inert pharmaceutical excipients (such as water, glycols, oils, alcohols, flavoring agents, preservatives, coloring agents, and syrup), one or more optionally present conventional tableting ingredients (such as corn starch, lactose, sucrose, sorbitol, talc, stearic acid, magnesium stearate, dicalcium phosphate, and any of a variety of gums), and an optional diluent (such as water).

Binder agents include starch, gelatin, natural sugars (e.g., glucose and betalactose), corn sweeteners and natural and synthetic gums (e.g., acacia and tragacanth). Disintegrating agents include starch, methyl cellulose, agar, and bentonite.

Tablets and capsules represent an advantageous oral dosage unit form. Tablets may be sugarcoated or filmcoated using standard techniques. Tablets may also be coated or otherwise compounded to provide a prolonged, control-release therapeutic effect. The dosage form may comprise an inner dosage and an outer dosage component, wherein the outer component is in the form of an envelope over the inner component. The two components may further be separated by a layer which resists disintegration in the stomach (such as an enteric layer) and permits the inner component to pass intact into the duodenum or a layer which delays or sustains release. A variety of enteric and non-enteric layer or coating materials (such as polymeric acids, shellacs, acetyl alcohol, and cellulose acetate or combinations thereof) may be used.

Compounds of the invention may also be administered via a slow release composition; wherein the composition includes a compound of the invention and a biodegradable slow release carrier (e.g., a polymeric carrier) or a pharmaceutically acceptable non-biodegradable slow release carrier (e.g., an ion exchange carrier).

Biodegradable and non-biodegradable slow release carriers are well known in the art. Biodegradable carriers are used to form particles or matrices which retain an active agent(s) and which slowly degrade/dissolve in a suitable environment (e.g., aqueous, acidic, basic and the like) to release the agent. Such particles degrade/dissolve in body fluids to release the active compound(s) therein. The particles are preferably nanoparticles (e.g., in the range of about 1 to 500 nm in diameter, preferably about 50-200 nm in diameter, and most preferably about 100 nm in diameter). In a process for preparing a slow release composition, a slow release carrier and a compound of the invention are first dissolved or dispersed in an organic solvent. The resulting mixture is added into an aqueous solution containing an optional surface-active agent(s) to produce an emulsion. The organic solvent is then evaporated from the emulsion to provide a colloidal suspension of particles containing the slow release carrier and the compound of the invention.

The compound of Formula I may be incorporated for administration orally or by injection in a liquid form such as aqueous solutions, suitably flavored syrups, aqueous or oil suspensions, flavored emulsions with edible oils such as cottonseed oil, sesame oil, coconut oil or peanut oil and the like, or in elixirs or similar pharmaceutical vehicles. Suitable dispersing or suspending agents for aqueous suspensions, include synthetic and natural gums such as tragacanth, acacia, alginate, dextran, sodium carboxymethylcellulose, methylcellulose, polyvinyl-pyrrolidone, and gelatin. The liquid forms in suitably flavored suspending or dispersing agents may also include synthetic and natural gums. For parenteral administration, sterile suspensions and solutions are desired. Isotonic preparations, which generally contain suitable preservatives, are employed when intravenous administration is desired.

The compounds may be administered parenterally via injection. A parenteral formulation may consist of the active ingredient dissolved in or mixed with an appropriate inert liquid carrier. Acceptable liquid carriers usually comprise aqueous solvents and other optional ingredients for aiding solubility or preservation. Such aqueous solvents include sterile water, Ringer's solution, or an isotonic aqueous saline solution. Other optional ingredients include vegetable oils (such as peanut oil, cottonseed oil, and sesame oil), and organic solvents (such as solketal, glycerol, and formyl). A sterile, non-volatile oil may be employed as a solvent or suspending agent. The parenteral formulation is prepared by dissolving or suspending the active ingredient in the liquid carrier whereby the final dosage unit contains from 0.005 to 10% by weight of the active ingredient. Other additives include preservatives, isotonizers, solubilizers, stabilizers, and pain-soothing agents. Injectable suspensions may also be prepared, in which case appropriate liquid carriers, suspending agents and the like may be employed.

Compounds of the invention may be administered intranasally using a suitable intranasal vehicle.

Compounds of the invention may also be administered topically using a suitable topical transdermal vehicle or a transdermal patch.

For ocular administration, the composition is preferably in the form of an ophthalmic composition. The ophthalmic compositions are preferably formulated as eye-drop formulations and filled in appropriate containers to facilitate administration to the eye, for example a dropper fitted with a suitable pipette. Preferably, the compositions are sterile and aqueous based, using purified water. In addition to the compound of the invention, an ophthalmic composition may contain one or more of: a) a surfactant such as a polyoxyethylene fatty acid ester; b) a thickening agents such as cellulose, cellulose derivatives, carboxyvinyl polymers, polyvinyl polymers, and polyvinylpyrrolidones, typically at a concentration n the range of about 0.05 to about 5.0% (wt/vol); c) (as an alternative to or in addition to storing the composition in a container containing nitrogen and optionally including a free oxygen absorber such as Fe), an anti-oxidant such as butylated hydroxyanisol, ascorbic acid, sodium thiosulfate, or butylated hydroxytoluene at a concentration of about 0.00005 to about 0.1% (wt/vol); d) ethanol at a concentration of about 0.01 to 0.5% (wt/vol); and e) other excipients such as an isotonic agent, buffer, preservative, and/or pH-controlling agent. The pH of the ophthalmic composition is desirably within the range of 4 to 8.

Methods of Preparation

In the discussion below $G^a$, $G^b$, $G^c$, $A^4$, Q, T are defined as described above for compounds of Formulae I and Ia. In cases where the synthetic intermediates and final products of Formula I described below contain potentially reactive functional groups, for example amino, hydroxyl, thiol and carboxylic acid groups, that may interfere with the desired reaction, it may be advantageous to employ protected forms of the intermediate. Methods for the selection, introduction and subsequent removal of protecting groups are well known to those skilled in the art. (T. W. Greene and P. G. M. Wuts "Protective Groups in Organic Synthesis" John Wiley & Sons, Inc., New York 1999). Such protecting group manipulations are assumed in the discussion below and not described explicitly.

In the first process of the invention a compound of Formula I is prepared by reaction of an intermediate of formula II wherein $Z^1$ is a leaving group such as halide, 1-imidazolyl, aryloxide, or alkoxide with a group of formula III which contains one reactive primary or secondary amine:

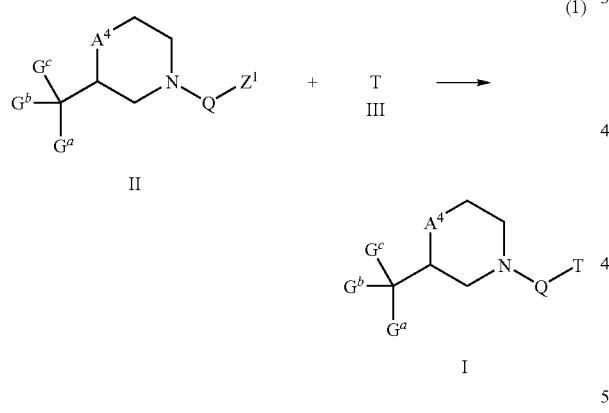

(1)

Intermediates of formula II are prepared by reaction of piperidine and morpholine intermediates of formula IV by reaction with intermediates of formula V wherein $Z^1$ and $Z^2$ are independently selected from halide, 1-imidazolyl, 3-methyl-1-imidazolium, alkylthio, arylthio, aryloxide and alkoxide:

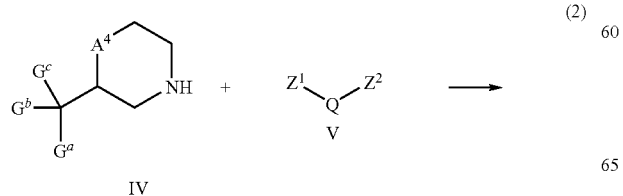

(2)

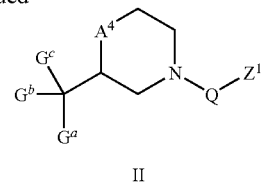

For example, when Q is Q1 (C=O) in II and V, $Z^1$ and $Z^2$ are both chloride or 1-imidazolyl. When Q is Q3 in II and V, $Z^1$ is 1-imidazolyl and $Z^2$ is 3-methyl-1-imidazolium. When Q is Q4 or Q6 in II and V, $Z^1$ and $Z^2$ are both SMe. When Q is Q6 or Q8 in II and V, $Z^1$ and $Z^2$ are both chloride. When Q is Q9, Q11, Q12 or Q13 in II and V, $Z^1$ and $Z^2$ are both MeO.

Intermediates of formula IV are prepared from intermediates of Formula VI:

(3)

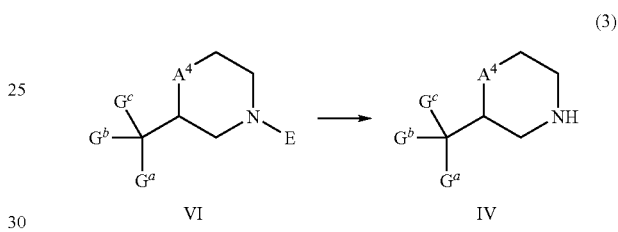

wherein E is an amine protecting group, including carbamate, amide, and sulfonamide protecting groups known in the art (T. W. Greene and P. G. M. Wuts "Protective Groups in Organic Synthesis" John Wiley & Sons, Inc., New York 1999).

Intermediates of Formula VI wherein $G^c$=OH are prepared from ketone intermediates of formula VII by addition of an organometallic reagent of formula VIII, wherein M is, for example, Li, MgCl, MgBr, or MgI:

(4)

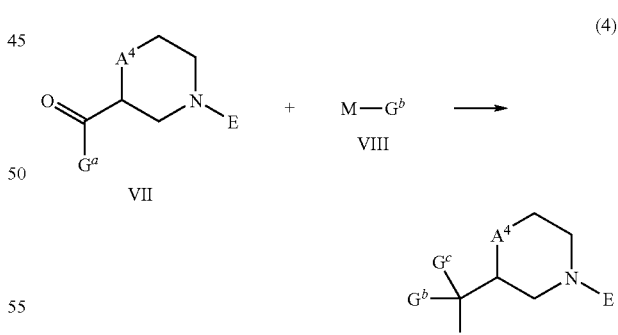

Intermediates of Formula VI wherein $G^b$ is a group $OG^{bb}$, attached through an ether linkage, are prepared by reaction of alcohol intermediates of formula IX with alkylating agents of formula X wherein $Z^3$ is a leaving group such as halide, alkanesulfonate, haloalkanesulfonate or arylsulfonate under basic conditions:

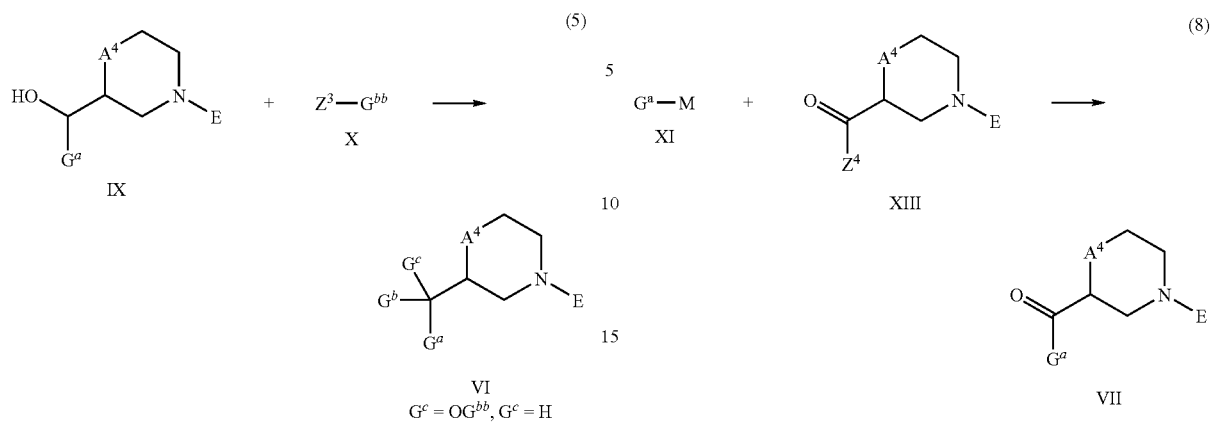

Alcohol Intermediates of formula IX are prepared by reduction of ketone intermediates of formula VII with, for example, a hydride reducing agent such NaBH$_4$, LiAlH$_4$, or diisobutylaluminum hydride:

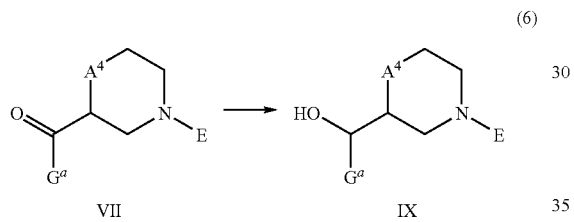

or by addition of an organometallic reagent of formula XI wherein M is, for example, Li, MgCl, MgBr, or MgI to an aldehyde of Formula XII:

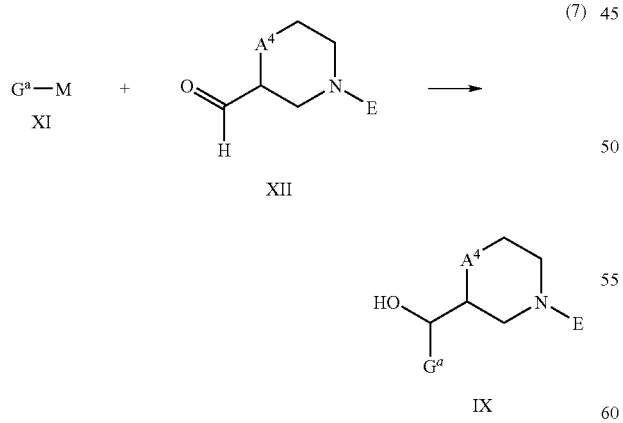

Ketone intermediates of formula VII are prepared by the addition of an organometallic reagent of formula XI to a carboxylic acid derivative of formula XII wherein $Z^4$ is an alkoxide, dialkylamino group, or an N-alkoxy-N-alkylamino group:

Organometallic reagents of formula XI are prepared by known processes including halogen-lithium exchange, ortho-lithiation, and treatment of halides $G^a$-Hal with magnesium or lithium metal.

Aldehyde intermediates of formula XII are prepared by reduction of carboxylic acid derivatives of formula XIII wherein $Z^4$ is an alkoxy or N-alkoxy-N-alkylamino group using, for example, a hydride reducing agent such as LiAlH$_4$ or diisobutylaluminum hydride:

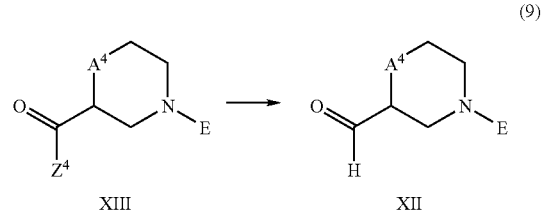

Ketone intermediates of formula VII are also prepared by oxidation of alcohol intermediates of formula IX:

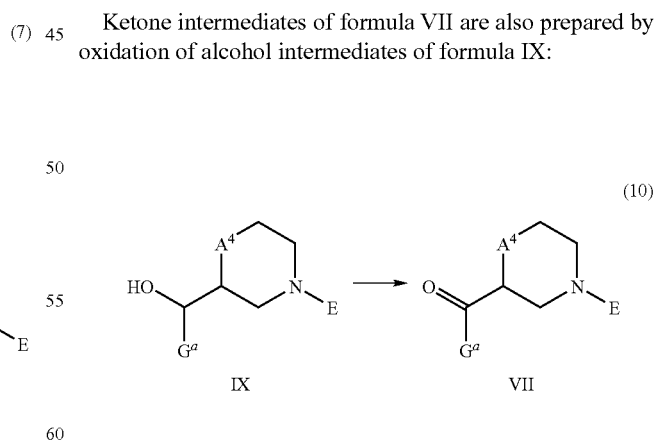

In the second process of the invention a compound of Formula I is prepared by reaction of a piperidine or morpholine intermediate of formula IV with an intermediate of Formula XIV wherein $Z^1$ is a leaving group such as halide, aryloxide, or alkoxide and Q is attached to a nitrogen atom that is part of T:

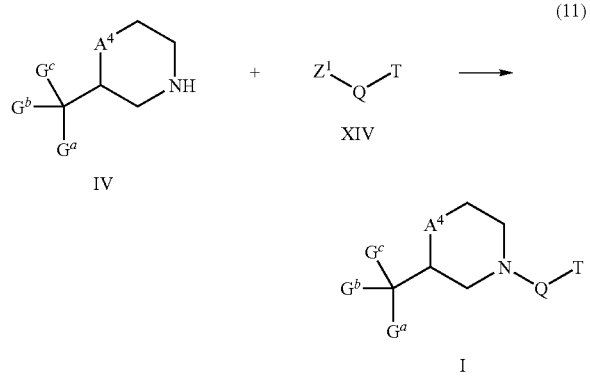

(11)

IV + XIV → I

Intermediates of Formula XIV are prepared by reaction of III by reaction with intermediates of formula V wherein $Z^1$ and $Z^2$ are independently selected from halide, 1-imidazolyl, 3-methyl-1-imidazolium, alkylthio, arylthio, aryloxide and alkoxide:

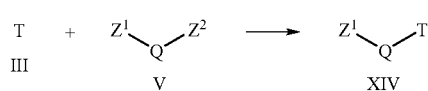

(12)

III + V → XIV

For example, when Q is Q1 (C=O) in V and XIV, $Z^1$ and $Z^2$ are both chloride or 1-imidazolyl. When Q is Q3 in V and XIV, $Z^1$ is 1-imidazolyl and $Z^2$ is 3-methyl-1-imidazolium. When Q is Q4 or Q6 in V and XIV, $Z^1$ and $Z^2$ are both SMe. When Q is Q6 or QS in V and XIV, $Z^1$ and $Z^2$ are both chloride. When Q is Q9, Q11, Q12 or Q13 in V and XIV, $Z^1$ and $Z^2$ are both MeO.

Preparation of Intermediates of Formula III is Described in the References cited above.

In the third process of the invention a compound of Formula I is prepared from another, optionally protected, compound of Formula I:

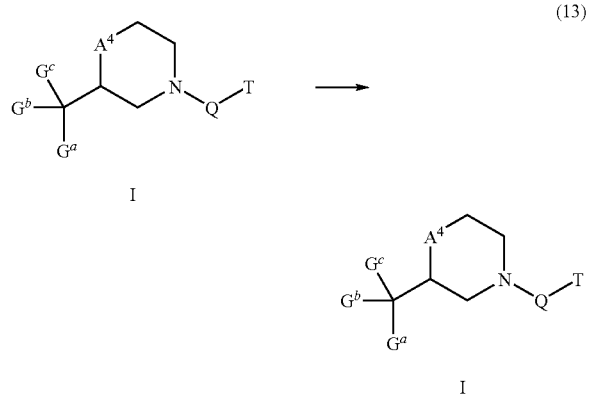

(13)

I → I

For example, when $G^a$ is a bromophenyl, iodophenyl or trifluoromethanesulfonyloxyphenyl group in a compound of Formula I, it may be transformed into compounds of formula I wherein $G^a$ is (i) a biphenyl group using a Suzuki coupling, (ii) an alkynylbenzene using a Sonogashira coupling, (iii) an allylbenzene using a Stille coupling, (iv) a cyanobenzene using CuCN, or (v) a methoxycarbonylbenzene using a palladium catalyzed carbonylation in the presence of methanol. A second example is the transformation of a compound of Formula I wherein $G^c$=OH to the analogous compound wherein $G^c$=H by dehydration followed by hydrogenation or in a single step by deoxygenation using Raney nickel. A third example is the deoxygenation of a compound of Formula I wherein Q=Q11 to a compound of Formula I where Q=Q10. A fourth example is the alkylkation of a compound of Formula I wherein $G^a$ is a hydroxyphenyl group to provide a compound of formula I wherein $G^a$ is an alkoxyphenyl, cycloalkoxyphenyl, cycloalkylalkoxyphenyl, or arylalkoxyphenyl group.

In a fourth process of the invention optionally protected compounds of Formula I wherein $G^c$=OH are prepared from optionally protected ketone compounds of formula XV by addition of an organometallic of formula VIII:

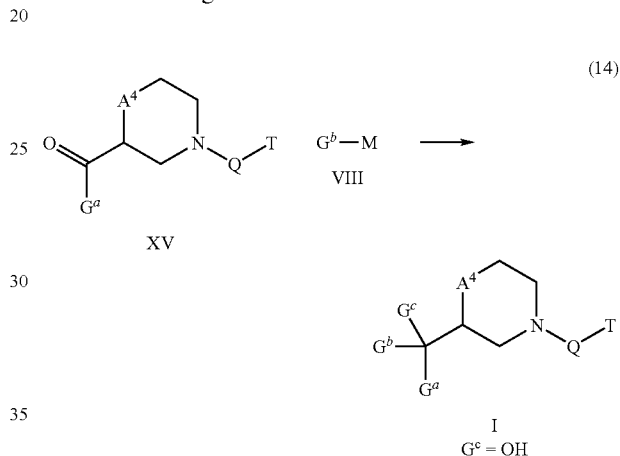

(14)

XV + VIII → I, $G^c$ = OH

The following abbreviations have the indicated meanings:

| Abbreviation | Meaning |
| --- | --- |
| Aq | aqueous |
| Boc | tert-butoxy carbonyl or t-butoxy carbonyl |
| (Boc)$_2$O | di-tert-butyl dicarbonate |
| Brine | saturated aqueous NaCl |
| Cbz | Benzyloxycarbonyl |
| CbzCl | Benzyl chloroformate |
| CDI | carbonyl diimidazole |
| CH$_2$Cl$_2$ | methylene chloride |
| CH$_3$CN or MeCN | acetonitrile |
| Cpd | compound |
| D | day |
| DAST | diethylaminosulfur trifluoride |
| DBU | 1,8-diazabicyclo[5.4.0]undec-7-ene |
| DCC | N,N'-dicyclohexylcarbodiimide |
| DCU | N,N'-dicyclohexylurea |
| DIAD | diisopropyl azodicarboxylate |
| DIEA | N,N-diisopropylethylamine |
| DMAP | 4-(dimethylamino)pyridine |
| DMF | N,N-dimethylformamide |
| DMPU | 1,3-dimethyl-3,4,5,6-tetrahydro-2(1H)-pyrimidinone |
| 2,4-DNP | 2,4-dinitrophenylhydrazine |
| EDC•HCl | 1-[3-(dimethylamino)propyl]-3-ethylcarbodiimide hydrochloride |
| Equiv | equivalents |
| Et | ethyl |
| Et$_2$O | ethyl ether |
| EtOAc | EtOAc |
| Fmoc | 1-[[(9H-fluoren-9-ylmethoxy)carbonyl]oxy]- |

| Abbreviation | Meaning |
|---|---|
| Fmoc-OSu | 1-[[(9H-fluoren-9-ylmethoxy)carbonyl]oxy]-2,5-pyrrolidinedione |
| h, hr | hour |
| HOBt | 1-hydroxybenzotriazole |
| HATU | 2-(7-Aza-1H-benzotriazole-1-yl)-1,1,3,3-tetramethyluronium hexafluorophosphate |
| HBTU | 2-(1H-Benzotriazole-1-yl)-1,1,3,3-tetramethyluronium hexafluorophosphate |
| KHMDS | potassium hexamethyldisilazane |
| LAH or LiAlH$_4$ | lithium aluminum hydride |
| LC-MS | liquid chromatography-mass spectroscopy |
| LHMDS | lithium hexamethyldisilazane |
| Me | methyl |
| MeCN | acetonitrile |
| MeOH | methanol |
| MsCl | methanesulfonyl chloride |
| Min | minute |
| MS | mass spectrum |
| NaH | sodium hydride |
| NaHCO$_3$ | sodium bicarbonate |
| NaN$_3$ | sodium azide |
| NaOH | sodium hydroxide |
| Na$_2$SO$_4$ | sodium sulfate |
| NMM | N-methylmorpholine |
| NMP | N-methylpyrrolidinone |
| Pd$_2$(dba)$_3$ | tris(dibenzylideneacetone)dipalladium(0) |
| PE | petroleum ether |
| Ph | phenyl |
| Quant | quantitative yield |
| Rt | room temperature |
| Satd | saturated |
| SOCl$_2$ | thionyl chloride |
| SPE | solid phase extraction |
| TBS | t-butyldimethylsilyl |
| TBSCl | t-butyldimethylsilyl chloride |
| TEA | triethylamine or Et$_3$N |
| TEMPO | 2,2,6,6-tetramethyl-1-piperidinyloxy free radical |
| Teoc | 1-[2-(trimethylsilyl)ethoxycarbonyloxy]- |
| Teoc-OSu | 1-[2-(trimethylsilyl)ethoxycarbonyloxy]pyrrolidin-2,5-dione |
| TFA | trifluoroacetic acid |
| THF | tetrahydrofuran |
| Tlc | thin layer chromatography |
| TMS | trimethylsilyl |
| TMSCl | chlorotrimethylsilane or trimethylsilyl chloride |
| t$_R$ | retention time |
| TsOH | p-toluenesulfonic acid |

Purification Methods

Prep HPLC refers to preparative reverse phase HPLC on a C-18 column eluted with a water/acetonitrile gradient containing 0.01% TFA run on a Gilson 215 system.

Analytical Methods

LC-MS (3 min)
Column: Chromolith SpeedRod, RP-18e, 50×4.6 mm; Mobil phase: A: 0.01% TFA/water, B: 0.01% TFA/CH$_3$CN; Flow rate: 1 mL/min; Gradient:

| Time (min) | A % | B % |
|---|---|---|
| 0.0 | 90 | 10 |
| 2.0 | 10 | 90 |
| 2.4 | 10 | 90 |
| 2.5 | 90 | 10 |
| 3.0 | 90 | 10 |

LC-MS (16 min)
Column: Chromolith SpeedRod, RP-18e, 50×4.6 mm; Mobil phase: A: 0.01% TFA/water, B: 0.01% TFA/CH$_3$CN; Flow rate: 1 mL/min; Gradient:

| Time (min) | A % | B % |
|---|---|---|
| 0.0 | 90 | 10 |
| 14.0 | 10 | 90 |
| 15.0 | 10 | 90 |
| 15.1 | 90 | 10 |
| 16.0 | 90 | 10 |

Preparations

Piperidine and morpholine compounds of formula IV wherein $G^a$, $G^b$, $G^c$ and $A^4$ have the meanings described above for compounds of formulae I and Ia are useful for the preparation of compounds of formula I and Ia. The following procedures describe the preparation of intermediates of formula IV.

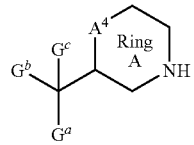

IV

Preparation 1

(R)-tert-butyl 3-(N-methoxy-N-methylcarbamoyl)piperidine-1-carboxylate

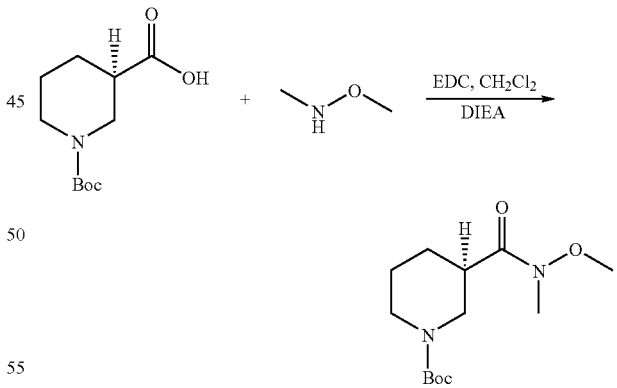

(R)-1-(tert-butoxycarbonyl)piperidine-3-carboxylic acid (25 g, 0.11 mol, 1.0 equiv), N,O-dimethylhydroxylamine hydrochloride, (10.5 g, 0.14 mol, 1.25 equiv), EDC.HCl (26.3 g, 0.14 mol, 1.25 equiv) and DIEA (48 mL, 0.28 mol, 2.5 equiv) were dissolved in CH$_2$Cl$_2$ (400 mL) and stirred overnight at rt. The reaction mixture was diluted with EtOAc, washed with 5% aq HCl (2×150 mL), satd aq NaHCO$_3$ (150 mL), brine (100 mL), and dried over Na$_2$SO$_4$. Concentration afforded (R)-tert-butyl 3-(N-methoxy-N-methylcarbamoyl)-piperidine 1-carboxylate (24.42 g, 82%) as a clear oil.

Preparation 2

(S)-1-(3-chlorophenyl)-5-methoxy-1-((R)-piperidin-3-yl)pentan-1-ol

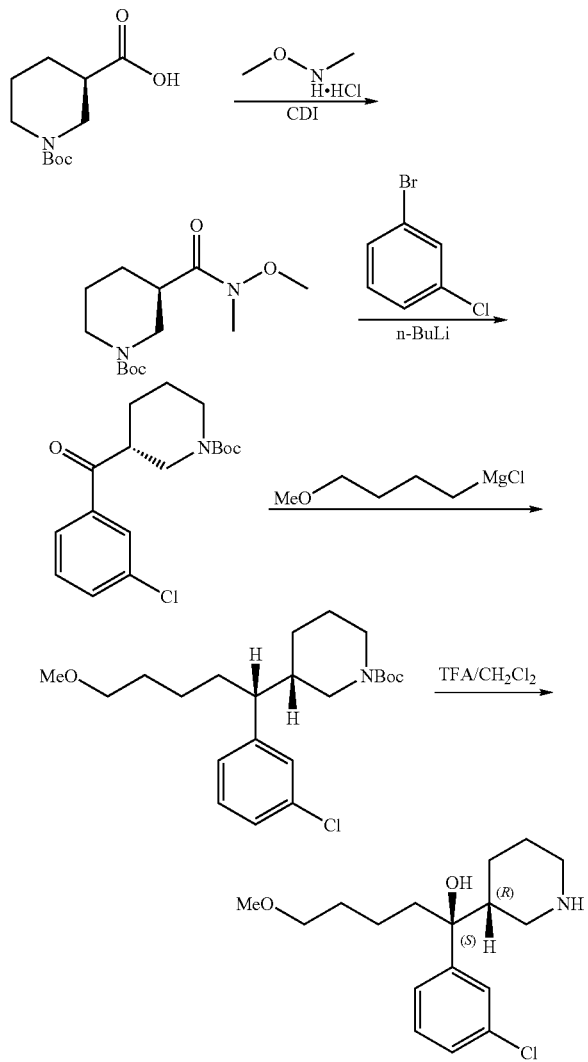

Step 1. (R)-tert-butyl 3-(methoxy(methyl)carbamoyl)piperidine-1-carboxylate

To a stirred solution of R-piperidine-1,3-dicarboxylic acid 1-tert-butyl ester (233 g, 1.2 mol) in THF (1.2 L) was added carbonyldiimidazole (230 g, 1.42 mol). The mixture was stirred for 1 h in an ice-water bath. A suspension of triethylamine (207 mL, 1.41 mol) and N,O-dimethylhydroxylamine hydrochloride (138 g, 1.42 mol) in THF (900 mL) was added. The reaction mixture was allowed to warm to rt and stirred overnight. After TLC showed the reaction was complete, solvent was evaporated to give a residue, which was dissolved in $CH_2Cl_2$ (1.2 L) and washed successively with 0.5 N aq HCl, sat'd aq $Na_2CO_3$ and brine, dried over anhydrous sodium sulfate and evaporated to give the crude compound (R)-tert-butyl 3-(methoxy(methyl)-carbamoyl)piperidine-1-carboxylate (250 g, 91%), which was used in the next step directly without purification. $^1$H NMR (400 MHz, $CDCl_3$): 1.44 (s, 9H), 1.60-1.78 (m, 2H), 1.90 (m, 1H), 2.65 (m, 1H), 2.75-2.85 (m, 2H), 3.16 (s, 3H), 3.71 (s, 3H), 4.05-4.19 (m, 2H). MS (E/Z): 273 (M+H$^+$).

Step 2. (R)-tert-butyl 3-(3-chlorobenzoyl)piperidine-1-carboxylate

To a solution of 1-bromo-3-chlorobenzene (15 g, 78.3 mmol) in anhydrous THF (150 mL) cooled to −78° C. was added dropwise a solution of 2.5 M n-BuLi in hexane (31.3 mL, 78.34 mmol). The reaction mixture was stirred at −78° C. for 1 h and a solution of (R)-tert-butyl 3-(methoxy(methyl)carbamoyl)piperidine-1-carboxylate (17.8 g, 65.3 mmol) in anhydrous THF (50 mL) was added dropwise. After addition, the mixture was allowed to warm to rt and stirred for 2 h. The mixture was quenched with saturated $NH_4Cl$ (250 mL) and extracted with EtOAc (3×150 mL). The combined organic layers were washed with brine, dried over $Na_2SO_4$ and concentrated in vacuo. The residue was purified by flash column chromatography (PE/EtOAc 5:95) to give (R)-tert-butyl 3-(3-chlorobenzoyl)piperidine-1-carboxylate (12.9 g, 51%). $^1$H NMR (400 MHz, $CDCl_3$): 1.45 (s, 9H), 1.54-1.73 (m, 2H), 1.75 (m, 1H), 2.00 (m, 1H), 2.71-2.78 (m, 1H), 2.93 (m, 2H), 3.30-3.35 (m, 1H), 4.22 (m, 1H), 7.39-7.42 (t, 1H), 7.52 (d, 1H), 7.89 (d, 1H), 7.90 (m, 1H). MS (E/Z): 324 (M+H$^+$).

Step 3. (R)-tert-butyl 3-((S)-1-(3-chlorophenyl)-1-hydroxy-5-methoxypentyl)piperidine-1-carboxylate A 250 mL three-necked flask was charged with magnesium turnings (2.88 g, 0.12 mol) and a small crystal of iodine in THF (20 mL). The flask was evacuated and refilled with $N_2$. A solution of 1-chloro-4-methoxybutane (15 g, 0.12 mol) in THF (40 mL) was added dropwise to the above mixture. After heating under reflux for 1 h, most of magnesium was consumed, the reaction mixture cooled to rt. Another 250 mL three-necked flask was charged with (R)-3-(3-chloro-benzoyl)piperidine-1-carboxylic acid tert-butyl ester (3.24 g, 10 mmol) and THF (50 mL), which was evacuated and refilled with $N_2$. The mixture was cooled with dry ice-acetone bath and the Grignard reagent derived from 1-chloro-4-methoxybutane (20 mL) was added dropwise. After addition, the mixture was allowed to warm slowly to rt and stirred for 2 h. The mixture was quenched with sat'd aq $NH_4Cl$ (100 mL), extracted with EtOAc (3×80 mL). The combined organic layers were washed with brine, dried over $Na_2SO_4$ and concentrated in vacuo. The residue was purified by flash column chromatography (EA/PE 10:90) to give (R)-tert-butyl 3-((S)-1-(3-chlorophenyl)-1-hydroxy-5-methoxypentyl)piperidine-1-carboxylate (3.0 g, 73%). $^1$H NMR (400 MHz, $CDCl_3$): 1.45 (s, 9H), 1.52-1.58 (m, 3H), 1.75 (m, 1H), 1.92 (m, 2H), 2.52 (m, 2H), 3.25 (s, 3H), 3.27 (m, 2H), 3.95 (m, 1H), 4.35 (m, 1H), 7.20-7.26 (m, 3H), 7.36 (m, 1H). MS (E/Z): 412 (M+H$^+$).

Step 4. (S)-1-(3-chlorophenyl)-5-methoxy-1-((R)-piperidin-3-yl)pentan-1-ol (R)-tert-butyl 3-((S)-1-(3-chlorophenyl)-1-hydroxy-5-methoxypentyl)piperidine-1-carboxylate (4.1 g, 0.01 mol) was dissolved in 20% TFA/$CH_2Cl_2$ (40 mL). The reaction mixture was stirred at rt for 2 h, tlc showed the reaction was complete. A solution of sat'd aq $Na_2CO_3$ was added dropwise to adjust the pH to 8~9 and the mixture was extracted with EtOAc (3×50 mL). The combined organic layers were washed with brine, dried over $Na_2SO_4$ and concentrated in vacuo to give crude (S)-1-(3-chlorophenyl)-5-methoxy-1-((R)piperidin-3-yl)pentan-1-ol (3.0 g, 97%), which was used without purification.

The compounds listed below were prepared following procedures analogous to those described above:

(S)-1-(3-fluoro-4-methylphenyl)-5-methoxy-1-((R)-piperidin-3-yl)pentan-1-ol using 3-fluoro-4-methylbromobenzene in Step 2

(S)-5-methoxy-1-((R)-piperidin-3-yl)-1-(2,3,5-trifluorophenyl)pentan-1-ol using 2,3,5-trifluorobromobenzene in Step 2.

(S)-5-ethoxy-1-((R)-piperidin-3-yl)-1-(2,3,5-trifluorophenyl)pentan-1-ol using 2,3,5-trifluorobromobenzene in Step 2 and 4-ethoxybutylmagnesium chloride in Step 3.

(S)-1-(3-fluoro-5-methylphenyl)-5-methoxy-1-((R)-piperidin-3-yl)pentan-1-ol using 3-fluoro-5-methylbromobenzene in Step 2

(S)-1-(2-fluorophenyl)-5-methoxy-1-((R)-piperidin-3-yl)pentan-1-ol using 2-fluorobromobenzene in Step 2.

(S)-1-(3,5-difluorophenyl)-5-methoxy-1-((R)-piperidin-3-yl)pentan-1-ol using 3,5-difluorobromobenzene in Step 2.

(S)-1-(2,3-difluorophenyl)-5-methoxy-1-((R)-piperidin-3-yl)pentan-1-ol using 2,3-difluorobromobenzene in Step 2.

(S)-1-(2-fluoro-3-methyl phenyl)-5-methoxy-1-((R)-piperidin-3-yl)pentan-1-ol using 2-fluoro-3-methyliododbenzene in Step 2.

(S)-1-(3-fluoro-2-methylphenyl)-5-methoxy-1-((R)-piperidin-3-yl)pentan-1-ol using 2-methyl-3-fluorobromobenzene in Step 2.

(S)-1-(2-fluoro-5-methylphenyl)-5-methoxy-1-((R)-piperidin-3-yl)pentan-1-ol using 2-fluoro-5-methylbromobenzene and n-BuLi in Step 2.

(S)-1-(5-fluoro-2-methylphenyl)-5-methoxy-1-((R)-piperidin-3-yl)pentan-1-ol using 2-methyl-5-fluorobromobenzene in Step 2.

(S)-1-(2-chlorophenyl)-5-methoxy-1-((R)-piperidin-3-yl)pentan-1-ol using 2-chlorobromobenzene in Step 2.

(S)-5-methoxy-1-((R)-piperidin-3-yl)-1-(2-(trifluoromethoxy)phenyl)pentan-1-ol using 2-(trifluoromethoxy)bromobenzene and n-BuLi in Step 2.

(S)-1-(3,5-dimethylphenyl)-5-methoxy-1-((R)-piperidin-3-yl)pentan-1-ol using 3,5-dimethylbromobenzene in Step 2.

(S)-5-methoxy-1-(3-(methylthio)phenyl)-1-((R)-piperidin-3-yl)pentan-1-ol using 3-(methylthio)bromobenzene and n-BuLi in Step 2.

(S)-1-(2-fluoro-6-methoxyphenyl)-5-methoxy-1-((R)-piperidin-3-yl)pentan-1-ol using 2-fluoro-6-methoxybromobenzene and n-BuLi in Step 2.

(S)-5-methoxy-1-((R)-piperidin-3-yl)-1-(2-(trifluoromethyl)phenyl)pentan-1-ol using 2-(trifluoromethyl)bromobenzene and n-BuLi in Step 2.

(S)-1-(5-fluoro-2-methoxyphenyl)-5-methoxy-1-((R)-piperidin-3-yl)pentan-1-ol using 2-methoxy-5-fluorobromobenzene and n-BuLi in Step 2.

(S)-5-methoxy-1-((R)-piperidin-3-yl)-1-(3-(trifluoromethoxy)phenyl)pentan-1-ol using 3-(trifluoromethoxy)bromobenzene and n-BuLi in Step 2.

(S)-1-(3-fluoro-5-methylphenyl)-5-methoxy-1-((R)-piperidin-3-yl)pentan-1-ol using 3-fluoro-5-methylbromobenzene and n-BuLi in Step 2.

(S)-1-(2,3-dimethylphenyl)-5-methoxy-1-((R)-piperidin-3-yl)pentan-1-ol using 2,3-dimethylbromobenzene and n-BuLi in Step 2.

(S)-1-(2,5-dimethylphenyl)-5-methoxy-1-((R)-piperidin-3-yl)pentan-1-ol using 2,5-dimethylbromobenzene and n-BuLi in Step 2.

(S)-5-methoxy-1-(3-methoxyphenyl)-1-((R)-piperidin-3-yl)pentan-1-ol using 3-methoxybromobenzene and n-BuLi in Step 2.

(S)-1-(2,3-difluorophenyl)-5-methoxy-1-((R)-piperidin-3-yl)pentan-1-ol using 2,3-difluorobromobenzene and n-BuLi in Step 2.

(S)-1-(3-chloro-2-methyl phenyl)-5-methoxy-1-((R)-piperidin-3-yl)pentan-1-ol using 3-chloro-2-methylbromobenzene and n-BuLi in Step 2.

(S)-1-(3-chloro-5-fluorophenyl)-5-methoxy-1-((R)-piperidin-3-yl)pentan-1-ol using 3-bromo-5-chloroiodobenzene and n-BuLi in Step 2.

(S)-1-(3-chloro-2,4-difluorophenyl)-5-methoxy-1-((R)-piperidin-3-yl)pentan-1-ol using 3-chloro-2,4-difluorobromobenzene in Step 2.

(S)-1-(2-(allyloxy)-3-bromophenyl)-5-methoxy-1-((R)-piperidin-3-yl)pentan-1-ol using 2-allyloxy-1,3-dibromobenzene and n-BuLi in Step 2.

1-(2-(allyloxy)-5-fluorophenyl)-5-ethoxy-1-((R)-piperidin-3-yl)pentan-1-ol using 2-allyloxy-5-fluorobromobenzene and n-BuLi in Step 2.

(S)-5-methoxy-1-((R)-piperidin-3-yl)-1-(2,3,5-trifluorophenyl)pentan-1-ol using 2,3,5-trifluorobromobenzene and n-BuLi in Step 2.

Preparation 3

(S)-1-(3-chloro-2-fluorophenyl)-5-methoxy-1-((R)-piperidin-3-yl)pentan-1-ol

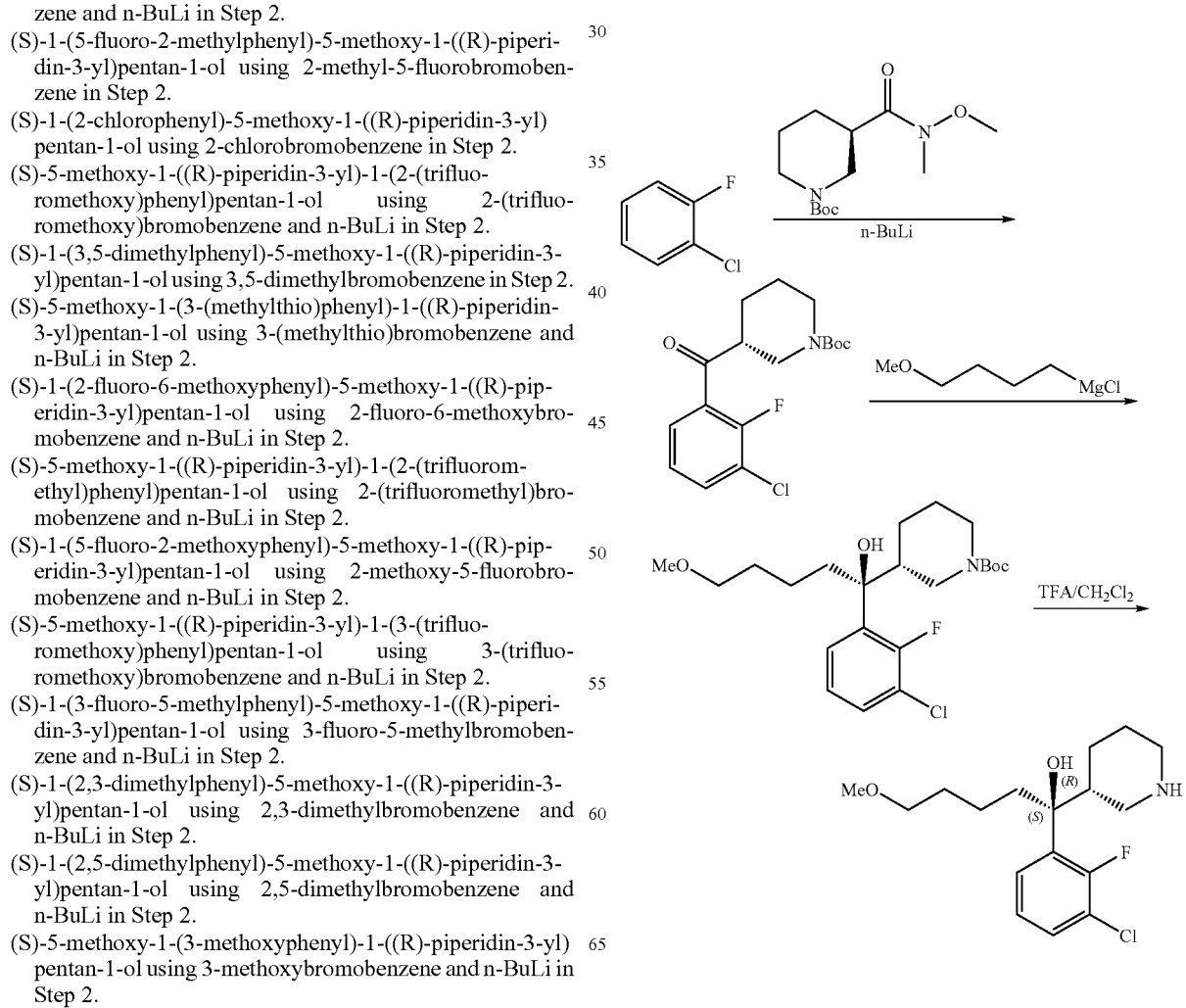

Step 1. (R)-tert-butyl 3-(3-chloro-2-fluorobenzoyl)piperidine-1-carboxylate

To a stirred solution of 1-chloro-2-fluoro-benzene (13.0 g, 0.1 mol) in THF (250 mL) at −75° C. was added dropwise 2.5 M BuLi in hexane (40 mL, 0.1 mol) during 45 min. After additional stirring for 30 min at −75° C., a solution of (R)-tert-butyl 3-(methoxy(methyl)-carbamoyl)piperidine-1-carboxylate (21.76 g, 0.08 mol) in THF (100 mL) was added dropwise over 30 min. The mixture was allowed to warm from −70° C. to 0° C. The mixture was quenched with sat'd aq NH$_4$Cl, extracted with EtOAc (3×) and the combined organic layers were dried over Na$_2$SO$_4$. Solvent removal and flash column chromatography, eluting with 5% EtOAc/PE afforded (R)-tert-butyl 3-(3-chloro-2-fluorobenzoyl)piperidine-1-carboxylate (19.2 g, 70%). $^1$H NMR (400 MHz, CDCl$_3$): 1.45 (s, 9H), 1.63 (m, 2H), 1.76 (m, 1 H), 2.06 (m, 1H), 2.87 (m, 1H), 3.15 (m, 1H), 3.25 (m, 1H), 3.9 (m, 1H), 4.2 (m, 1H), 7.18 (m, 1H), 7.60 (m, 2H). MS (E/Z): 342 (M+H$^+$).

Step 2. (R)-tert-butyl 3-((S)-1-(3-chloro-2-fluorophenyl)-1-hydroxy-5-methoxypentyl)piperidine-1-carboxylate A flame dried 250 mL three-necked flask was charged with magnesium turnings (7.02 g, 0.293 mol), a small crystal of iodine and THF (30 mL). The flask was evacuated and refilled with N$_2$. A solution of 1-chloro-4-methoxybutane (28.69 g, 0.234 mol) in THF (120 mL) was added dropwise slowly to the mixture. The reaction mixture was stirred under reflux for 2.5 h and most of magnesium was consumed. The resulting Grignard reagent was used as follows To another 100 mL three-necked flask was added (R)-tert-butyl 3-(3-chloro-2-fluorobenzoyl)piperidine-1-carboxylate (10 g, 0.0293 mol) and THF (100 mL). The flask was evacuated and refilled with N$_2$. The mixture was cooled with dry ice-acetone bath and the Grignard reagent (250 mL) was added. The reaction mixture was allowed to warm slowly to rt while stirring overnight. The mixture was quenched with satd aq NH$_4$Cl (50 mL), extracted with EtOAc (3×), and the combined organic layers were dried over Na$_2$SO$_4$. Evaporation of the solvent gave the crude product. The LC-MS analysis of the crude product indicated the presence of two isomers (95:5). Flash column chromatography, eluting with 10% EtOAc/PE afforded (R)-tert-butyl 3-((S)-1-(3-chloro-2-fluorophenyl)-1-hydroxy-5-methoxypentyl)piperidine-1-carboxylate (9.4 g, 75% yield). $^1$H NMR (400 MHz, DMSO): 0.68 (m, 1H), 1.50-1.01 (m, 7H), 1.37 (s, 9H), 1.75 (m, 2H), 2.01 (m, 1H), 3.11 (s, 3H), 3.17 (m, 2H), 3.85 (m, 1H), 7.2 (t, 1H), 7.45 (m, 2H). MS (E/Z): 430 (M+H$^+$).

Step 3. (S)-1-(3-chloro-2-fluorophenyl)-5-methoxy-1-((R)-piperidin-3-yl)pentan-1-ol A solution of (R)-tert-butyl 3-((S)-1-(3-chloro-2-fluorophenyl)-1-hydroxy-5-methoxypentyl)piperidine-1-carboxylate (100 mg) in 20% TFA/CH$_2$Cl$_2$ was stirred at 0° C. for 30 min. The mixture was neutralized by addition of sat'd aq NaHCO$_3$, extracted with CH$_2$Cl$_2$ (3×) and dried over Na$_2$SO$_4$. Evaporation of the solvent gave (S)-1-(3-chloro-2-fluorophenyl)-5-methoxy-1-((R)-piperidin-3-yl)pentan-1-ol (70 mg, 91%), which was used without further purification. $^1$H NMR (400 MHz, CDCl$_3$): 0.90 (m, 1H), 1.52-1.24 (m, 6 H), 1.78 (m, 1H), 1.83 (m, 1H), 1.93 (m, 1H), 2.21 (m, 1 H), 2.40 (m, 1 H), 2.83 (m, 1H), 3.00 (m, 1H), 3.12 (s, 3H), 3.31 (m, 2 H), 3.63 (m, 1H), 7.06 (m, 1H), 7.30 (m, 1H), 7.55 (t, 1H). MS (E/Z): 330 (M+H$^+$).

The compounds listed below were prepared following procedures analogous to those described above:

(S)-1-(2,3-dichlorophenyl)-5-methoxy-1-((R)-piperidin-3-yl)pentan-1-ol using 1,2-dichlorobenzene in Step 1.

(S)-5-methoxy-1-((R)-piperidin-3-yl)-1-(2,3,4-trifluorophenyl)pentan-1-ol using 1,2,3-trifluorobenzene in Step 1.

1-(3-chloro-2-fluorophenyl)-5-ethoxy-1-((R)-piperidin-3-yl)pentan-1-ol using 4-(ethoxy)butylmagnesium chloride in Step 2.

(S)-1-(2,3-dichlorophenyl)-5-ethoxy-1-((R)-piperidin-3-yl)pentan-1-ol using 1,2-dichlorobenzene in Step 1 and 4-(ethoxy)butylmagnesium chloride in Step 2.

Preparation 4

4-Cyclopropyl-1-phenyl-1-(piperidin-3-yl)butan-1-ols

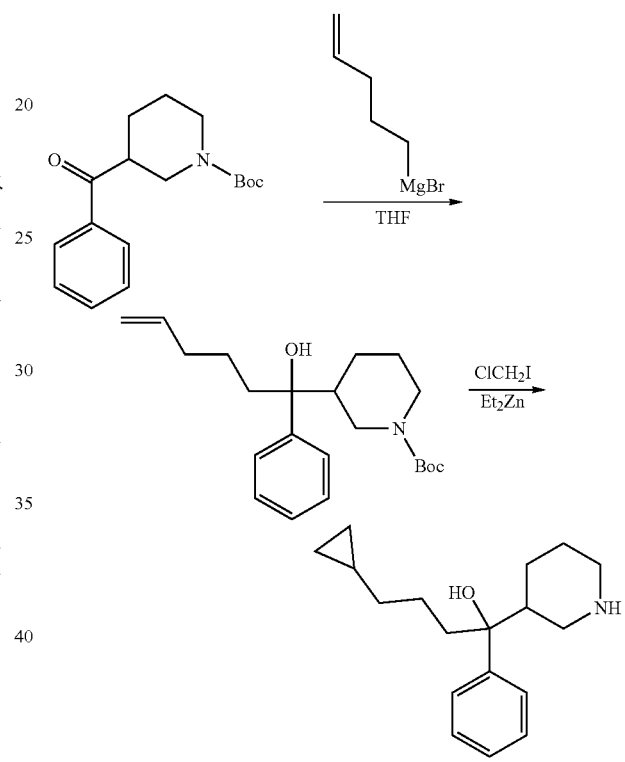

Step 1. tert-Butyl 3-((R)-1-hydroxy-1-phenylhex-5-enyl)piperidine-1-carboxylate

A stirred solution of tert-butyl 3-benzoylpiperidine-1-carboxylate (160 mg, 0.55 mmol) in dry THF (2 mL) was cooled to −70° C. and 4-pentenylmagnesium bromide in THF (1.8 mL of ~2.5 M, 2.8 mmol) was added dropwise. The mixture was stirred at −78° C. and allowed to warm to rt overnight. The reaction was quenched with satd aq ammonium chloride. The aqueous layer was extracted with Et$_2$O (3×). The combined organic layers were washed with brine, dried over Na$_2$SO$_4$, filtered and evaporated to dryness. The crude material was purified by flash chromatography on a prepacked silica cartridge eluted with an EtOAc/hexanes gradient. tert-Butyl 3-((R)-1-hydroxy-1-phenylhex-5-enyl)piperidine-1-carboxylate (174 mg, 88%) was isolated as an oil. MS ESI+ve m/z 382 (M+Na)$^+$.

Step 2. 4-Cyclopropyl-1-phenyl-1-(piperidin-3-yl)butan-1-ol

To a 0° C. solution of diethyl zinc (1.0 mL of 1M in hexane, 1 mmol) in dry dichloroethane (2 mL), chloroiodomethane (0.14 ml, 2.0 mmol) was added dropwise over five minutes. The reaction was removed from the ice bath and allowed to stir at rt for 40 min A dichloroethane solution (1 mL) of tert-butyl 3-((R)-1-hydroxy-1-phenylhex-5-enyl)piperidine-1-carboxylate (174 mg, 0.480 mmol) was added dropwise. The reaction was allowed to stir overnight. The reaction was quenched with satd ammonium chloride. The aqueous layer was extracted 3× with $CH_2Cl_2$. The combined organic layers were washed with brine, dried over $Na_2SO_4$, filtered, and evaporated to dryness. The crude material was purified via preparative HPLC (C-18 column, 10 to 90% $CH_3CN$ in $H_2O$ containing 0.01% $CF_3CO_2H$ over 10 min, 20 mL/min) to afford the trifluoroacetic acid salt of 4-cyclopropyl-1-phenyl-1-(piperidin-3-yl)butan-1-ol (32 mg, 24%). MS ESI+ve m/z 274 (M+1).

Preparation 5

Methyl (S)-4-(3-chlorophenyl)-4-hydroxy-4-((R)-piperidin-3-yl)butylcarbamate

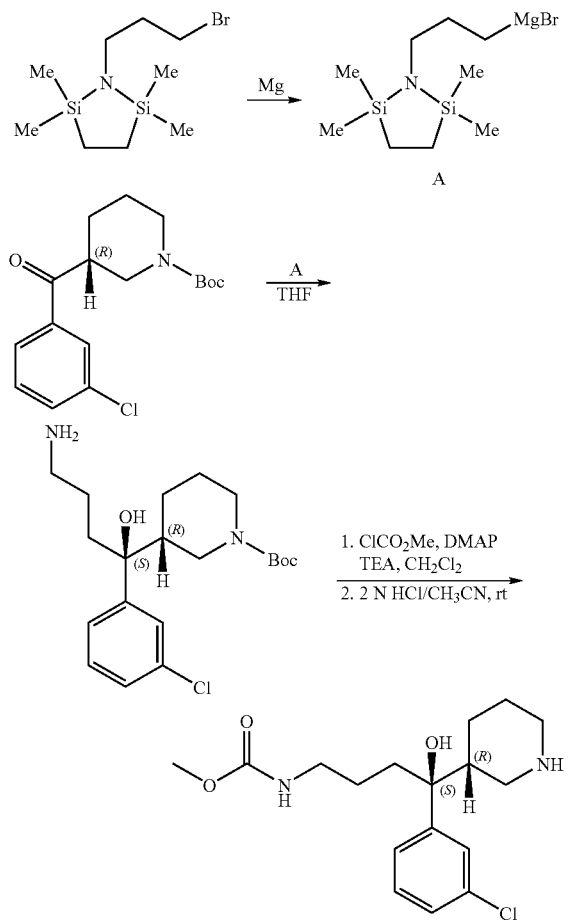

Step 1. [3-(2,2,5,5-tetramethyl-1-aza-2,5-disilacyclopent-1-yl)propyl]magnesium Bromide A 250 mL, round bottom flask was charged with magnesium turnings (0.528 g, 21.7 mmol, 1.16 equiv) and THF (10 mL). The flask was degassed and heated to 100° C. A small crystal of iodine was then added. A solution of 1-(3-bromopropyl)-2,2,5,5-tetramethyl-1-aza-2,5-disilacyclopentance (5.239 g, 18.7 mmol, 1.0 equiv) in THF (15 mL) was added dropwise to the boiling TI-IF mixture over 10 min. The reaction mixture was stirred and heated under reflux for 2.5 h and most of magnesium was consumed. The resulting Grignard reagent (A) was used in the next step.

Step 2. (R)-tert-butyl 3-((S)-4-amino-1-(3-chlorophenyl)-1-hydroxybutyl)piperidine-1-carboxylate To a 250 mL, round bottom flask were added (3-chlorophenyl)((R)—N-Bocpiperidin-3-yl)methanone (0.800 g, 2.47 mmol) and THF (10 mL). The flask was evacuated and refilled with $N_2$. The mixture was cooled with a dry ice-acetone bath and the [3-(2,2,5,5-tetramethyl-1-aza-2,5-disilacyclopent-1-yl)propyl]magnesium bromide solution (A), obtained in Step 1, was added via a cannula. The reaction mixture was allowed to slowly warm to −8° C. while stirring overnight. The mixture was quenched with 10% aq $Na_2CO_3$ (10 mL), stirred at rt for 3 h, extracted with $CH_2Cl_2$ (3×), and dried over $Na_2SO_4$. The crude product was purified by reversed-phase HPLC (Phenomenex® Luna 5μ C18(2) 100A, 250×21.20 mm, 5 micron, 10%→90% $CH_3CN/H_2O$, 0.1% $CF_3COOH$ over 13 min and then 90% $CH_3CN/H_2O$, 0.1% $CF_3COOH$ over 3.5 min, flow rate 25 mL/min) to give 0.883 g (72%) of TFA salt of (R)-tert-butyl 3-((S)-4-amino-1-(3-chlorophenyl)-1-hydroxybutyl)piperidine-1-carboxylate. LC-MS (3 min) $t_R$=1.30 min, m/z 383, 385 (MH$^+$), 327, 329; $^1$H NMR (400 MHz, $CD_3OD$) ☐ 7.36 (m, 1H), 7.27-7.13 (m, 3H), 4.26 (br s, 1H), 3.89 (d, J=12.9 Hz, 1H), 2.82-2.68 (m, 2H), 2.44 (br s, 1H), 2.36 (t, J=12.2 Hz, 1H), 1.97-1.79 (m, 2H), 1.64-1.08 (m, 16H), 1.34 (s); $^{13}$C NMR (100 MHz, $CD_3OD$) ☐ 156.69, 148.15, 135.39, 130.69, 127.74, 127.36, 125.41, 81.04, 78.10, 40.95, 28.69, 26.64, 26.51, 23.30.

Step 3. (R)-tert-butyl 3-((S)-4-(methoxycarbonylamino)-1-(3-chlorophenyl)-1-hydroxybutyl)-piperidine-1-carboxylate To a 100 mL round bottom flask were added the TFA salt of (R)-tert-butyl 3-((S)-4-amino-1-(3-chlorophenyl)-1-hydroxybutyl)piperidine-1-carboxylate (0.8164 g, 1.64 mmol, 1.0 equiv), DMAP (0.542 g), $CH_2Cl_2$ (40 mL) and triethylamine (6 mL). The mixture was cooled in an ice bath and a solution of methyl chloroformate (0.550 g, 5.82 mmol, 3.5 equiv) in $CH_2Cl_2$ (10 mL) was added. The reaction mixture was allowed to slowly warm to rt and stirred overnight. After the solvents were removed in vacuo, the residue was purified by reversed-phase HPLC (Phenomenex® Luna 5μ C18(2) 100A, 250×21.20 mm, 5 micron, 70%→90% $CH_3CN/H_2O$, 0.1% $CF_3COOH$ over 8 min and then 90% $CH_3CN/H_2O$, 0.1% $CF_3COOH$ over 1.5 min, flow rate 25 mL/min) to give 0.5020 g (69%) of (R)-tert-butyl 3-((S)-4-(methoxycarbonylamino)-1-(3-chlorophenyl)-1-hydroxybutyl)piperidine-1-carboxylate. LC-MS (3 min) $t_R$=1.91 min, m/z 463 (MNa$^+$), 441 (MH$^+$), 343 341; $^1$H NMR (400 MHz, $CDCl_3$) ☐ 7.37-7.36 (m, 1H), 7.28-7.17 (m, 3H), 4.90 (br s, 2H), 4.37 (d, J=12.0 Hz, 1H), 3.97 (d, J=12.3 Hz, 1H), 3.64 (s, 3H), 3.16-3.04 (m, 2H), 2.58-2.49 (m, 2H), 1.98-1.86 (m, 2H), 1.76-1.70 (m, 1H), 1.61-1.56 (m, 1H), 1.45 (s, 9H), 1.48-1.13 (m, 5H); $^{13}$C NMR (100 MHz, $CDCl_3$) ☐ 157.60, 155.31, 146.51, 134.31, 129.36, 126.72, 125.96, 123.76, 80.08, 77.65, 52.21, 46.45, 44.91, 44.56, 40.91, 35.97, 28.42, 25.33, 25.25, 24.34.

Step 4. Methyl (S)-4-(3-chlorophenyl)-4-hydroxy-4-((R)-piperidin-3-yl)butylcarbamate A mixture of (R)-tert-butyl 3-((S)-4-(methoxycarbonylamino)-1-(3-chlorophenyl)-1-hydroxybutyl)piperidine-1-carboxylate (0.0322 g, 0.073 mmol), obtained as described above, in $CH_3CN$ (30 mL) and 2 N aq HCl (25 mL) was vigorously stirred at rt for 24 h. The solvents were removed in vacuo to give the HCl salt of methyl (S)-4-(3-chlorophenyl)-4-hydroxy-4-((R)-piperidin-3-yl)butylcarbamate, which was used without further purification. LC-MS (3 min) $t_R$=0.98 min, m/z 343, 341 (M+H$^+$), 323.

Preparation 6

N—((S)-4-(3-chlorophenyl)-4-hydroxy-4-((R)-piperidin-3-yl)butyl)acetamide

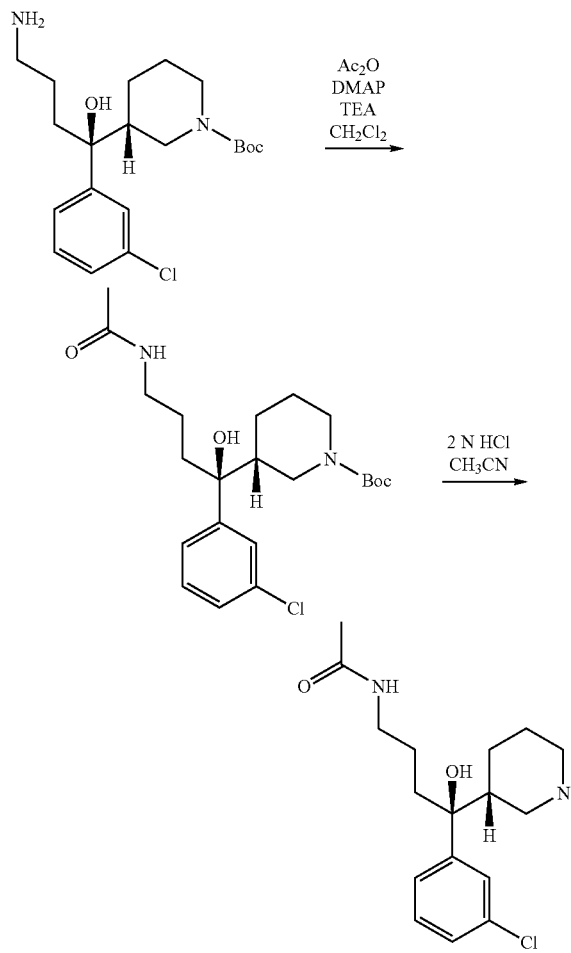

Step 1. (R)-tert-butyl 3-((S)-4-acetamido-1-(3-chlorophenyl)-1-hydroxybutyl)piperidine-1-carboxylate To a 100 mL, round bottom flask were added TFA salt of (R)-tert-butyl 3-((S)-4-amino-1-(3-chlorophenyl)-1-hydroxybutyl)piperidine-1-carboxylate (0.374 g, 0.75 mmol, 1.0 equiv), DMAP (0.1615 g), CH$_2$Cl$_2$ (10 mL), and triethylamine (3 mL). The mixture was cooled in an ice bath and a solution of acetic anhydride (0.280 g, 2.74 mmol, 3.6 equiv) in CH$_2$Cl$_2$ (10 mL) was added. The reaction mixture was allowed to slowly warm to rt while stirring overnight (16 h). After the solvents were removed in vacuo, the residue was purified by reversed-phase HPLC (Phenomenex® Luna 5μ C18(2) 100A, 250×21.20 mm, 5 micron, 70%→90% CH$_3$CN/H$_2$O, 0.1% CF$_3$COOH over 8 min and then 90% CH$_3$CN/H$_2$O, 0.1% CF$_3$COOH over 1.5 min, flow rate 25 mL/min) to give 0.2589 g (81%) of (R)-tert-butyl 3-((S)-4-acetamido-1-(3-chlorophenyl)-1-hydroxybutyl)-piperidine-1-carboxylate. LC-MS (3 min) $t_R$=1.72 min, m/z 447, 449 (MNa$^+$), 425 (MH$^+$), 325, 327; $^1$H NMR (400 MHz, CDCl$_3$) □ 7.38-7.37 (m, 1H), 7.28-7.18 (m, 3H), 6.06 (br s, 1H), 4.36-4.34 (m, 1H), 3.97-3.95 (m, 1H), 3.35-3.26 (m, 1H), 3.13-3.05 (m, 1H), 2.99 (br s, 2H), 2.55-2.49 (m, 2H), 1.97 (s, 3H), 1.44 (s, 9H), 1.95-1.15 (m, 6H); $^{13}$C NMR (100 MHz, CDCl$_3$) □ 171.41, 155.17, 146.75, 134.24, 129.33, 126.63, 126.01, 123.83, 79.68, 77.60, 46.34, 44.69, 39.71, 35.91, 28.43, 25.40, 25.23, 24.15, 22.99.

Step 2. N—((S)-4-(3-chlorophenyl)-4-hydroxy-4-((R)-piperidin-3-yl)butyl)acetamide A mixture of (R)-tert-butyl 3-((S)-4-acetamido-1-(3-chlorophenyl)-1-hydroxybutyl)-piperidine-1-carboxylate (0.1773 g, 0.4172 mmol) in CH$_3$CN (50 mL) and 2 N aq HCl (45 mL) was vigorously stirred at rt for 24 h. The solvents were removed in vacuo to give the HCl salt of N—((S)-4-(3-chlorophenyl)-4-hydroxy-4-((R)-piperidin-3-yl)butyl)acetamide, which was used in the next step without further purification. LC-MS (3 min) $t_R$=0.91 min, m/z 325, 327 (MH$^+$).

The following piperidines were prepared following procedures analogous to those described in Preparations 5 and 6:

N—((S)-4-(2-fluorophenyl)-4-hydroxy-4-((R)-piperidin-3-yl)butyl)acetamide using (2-fluorophenyl)((R)—N-Boc-piperidin-3-yl)methanone in Step 2 of Preparation 5.

N—((S)-4-(2-fluoro-5-methylphenyl)-4-hydroxy-4-((R)-piperidin-3-yl)butyl)acetamide using (2-fluoro-5-methylphenyl)((R)—N-Boc-piperidin-3-yl)methanone in Step 2 of Preparation 5.

N—((S)-4-(3-fluoro-5-methylphenyl)-4-hydroxy-4-((R)-piperidin-3-yl)butyl)acetamide using (3-fluoro-5-methylphenyl)((R)—N-Boc-piperidin-3-yl)methanone in Step 2 of Preparation 5.

N—((S)-4-(2,3-difluorophenyl)-4-hydroxy-4-((R)-piperidin-3-yl)butyl)acetamide using (2,3-difluorophenyl)((R)—N-Boc-piperidin-3-yl)methanone in Step 2 of Preparation 5.

N—((S)-4-(3,5-difluorophenyl)-4-hydroxy-4-((R)-piperidin-3-yl)butyl)acetamide using (3,5-difluorophenyl)((R)—N-Boc-piperidin-3-yl)methanone in Step 2 of Preparation 5.

N—((S)-4-(2-chloro-3-fluorophenyl)-4-hydroxy-4-((R)-piperidin-3-yl)butyl)acetamide using (2-chloro-3-fluorophenyl)((R)—N-Boc-piperidin-3-yl)methanone in Step 2 of Preparation 5.

N—((S)-4-(3-chloro-2-fluorophenyl)-4-hydroxy-4-((R)-piperidin-3-yl)butyl)acetamide using (3-chloro-2-fluorophenyl)((R)—N-Boc-piperidin-3-yl)methanone in Step 2 of Preparation 5.

N—((S)-4-(3-chloro-5-fluorophenyl)-4-hydroxy-4-((R)-piperidin-3-yl)butyl)acetamide using (3-chloro-5-fluorophenyl)((R)—N-Boc-piperidin-3-yl)methanone in Step 2 of Preparation 5.

N—((S)-4-(3-chlorophenyl)-4-hydroxy-4-((R)-piperidin-3-yl)butyl)-2,2,2-trifluoroacetamide using trifluoroacetic anhydride in Step 1 of Preparation 6.

N—((S)-4-(3-chlorophenyl)-4-hydroxy-4-((R)-piperidin-3-yl)butyl)butyramide using butyric anhydride in Step 3 of Preparation 6.

(R)—N—((S)-4-(3-chlorophenyl)-4-hydroxy-4-((R)-piperidin-3-yl)butyl)-2-methoxypropanamide using (R)-2-methoxypropanoic acid and EDC in place of acetic anhydride in Step 3 of Preparation 6.

(S)—N—((S)-4-(3-chlorophenyl)-4-hydroxy-4-((R)-piperidin-3-yl)butyl)-2-methoxypropanamide using (S)-2-methoxypropanoic acid and EDC in place of acetic anhydride in Step 3 of Preparation 6.

N—((S)-4-(3-chlorophenyl)-4-hydroxy-4-((R)-piperidin-3-yl)butyl)propionamide using propionic anhydride in Step 3 of Preparation 6.

N—((S)-4-(3-chlorophenyl)-4-hydroxy-4-((R)-piperidin-3-yl)butyl)cyclopropanecarboxamide using cyclopropanecarboxylic acid and EDC in place of the anhydride in Step 3 of Preparation 6.

Preparation 7

1-((S)-4-(3-Chlorophenyl)-4-hydroxy-4-((R)-piperidin-3-yl)butyl)-3-methylurea

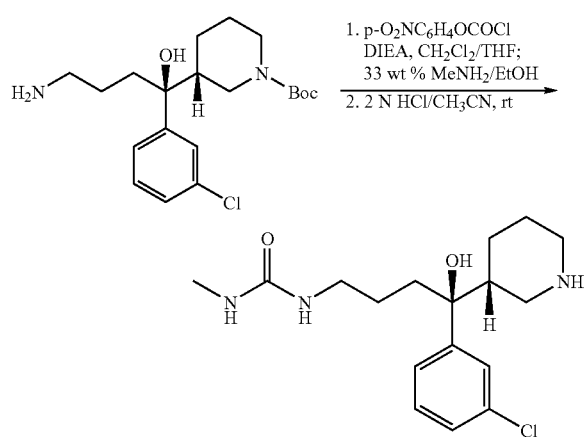

Step 1. (R)-tert-butyl 3-((S)-4-(methylaminocarbonylamino)-1-(3-chlorophenyl)-1-hydroxybutyl)-piperidine-1-carboxylate To a stirred mixture of the TFA salt of (R)-tert-butyl 3-((S)-4-amino-1-(3-chlorophenyl)-1-hydroxybutyl)piperidine-1-carboxylate (0.0388 g, 0.078 mmol, 1.0 equiv) in THF (5 mL) and $CH_2Cl_2$ (5 mL) at rt were added of DIEA (0.7 mL) and p-nitrophenyl chloroformate (0.0350 g, 0.17 mmol, 2.2 equiv). The mixture was stirred at rt for 3 h. One half of the resulting solution was withdrawn and 33 wt % $MeNH_2$ in EtOH (1.5 mL) was added. The resulting mixture was stirred at rt for 1 h. The solvents were removed in vacuo and the residue was purified by reversed-phase preparative HPLC (Phenomenex® Luna 5µ C18(2) 100A, 250×21.20 mm, 5 micron, 70%→90% $CH_3CN/H_2O$, 0.1% $CF_3COOH$ over 8 min and then 90% $CH_3CN/H_2O$, 0.1% $CF_3COOH$ over 7 min, flow rate 25 mL/min) to give (R)-tert-butyl 3-((S)-4-(methylamino-carbonylamino)-1-(3-chlorophenyl)-1-hydroxybutyl)piperidine-1-carboxylate (0.0043 g). LC-MS (3 min) $t_R$=1.71 min, m/z 442, 440 (M+H$^+$), 340.

Step 2. 1-((S)-4-(3-chlorophenyl)-4-hydroxy-4-((R)-piperidin-3-yl)butyl)-3-methylurea A mixture of (R)-tert-butyl 3-((S)-4-(methylaminocarbonylamino)-1-(3-chlorophenyl)-1-hydroxybutyl)piperidine-1-carboxylate, $CH_3CN$ (20 mL) and 2 N aq HCl (15 mL) was vigorously stirred at rt for 2 d. The solvents were removed in vacuo to give the HCl salt of 1-((S)-4-(3-chlorophenyl)-4-hydroxy-4-((R)-piperidin-3-yl)butyl)-3-methylurea, which was used without further purification. LC-MS (3 min) $t_R$=0.93 min, m/z 342, 340 (M+H$^+$).

3-((S)-4-(3-chlorophenyl)-4-hydroxy-4-((R)-piperidin-3-yl)butyl)-1,1-dimethylurea was prepared using procedures analogous to those above, using dimethylamine in Step 1.

Preparation 8

(S)-4-(Aminosulfonylamino)-1-(3-chlorophenyl)-1-((R)-piperidin-3-yl)butan-1-ol

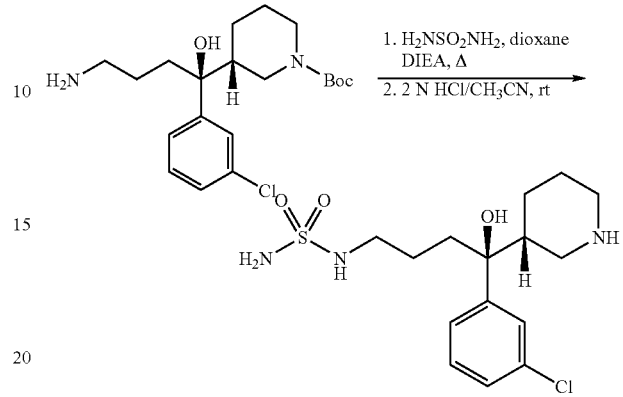

Step 1. (R)-tert-butyl 3-((S)-4-(aminosulfonylamino)-1-(3-chlorophenyl)-1-hydroxybutyl)-piperidine-1-carboxylate To a 50 mL round bottom flask were added the TFA salt of (R)-tert-butyl 3-((S)-4-amino-1-(3-chlorophenyl)-1-hydroxybutyl)piperidine-1-carboxylate (0.0803 g, 0.16 mmol, 1.0 equiv), sulfamide (0.2368 g, 2.46 mmol, 15 equiv), 1,4-dioxane (5 mL) and DIEA (1 mL). The resulting mixture was heated at 110° C. for 2 h. After the solvents were removed in vacuo, the residue was purified by reversed-phase HPLC (Phenomenex® Luna 5µ C18(2) 100A, 250×21.20 mm, 5 micron, 70%→90% $CH_3CN/H_2O$, 0.1% $CF_3COOH$ over 8 min and then 90% $CH_3CN/H_2O$, 0.1% $CF_3COOH$ over 1.5 min, flow rate 25 mL/min) to give 0.0438 g (59%) of (R)-tert-butyl 3-((S)-4-(aminosulfonylamino)-1-(3-chlorophenyl)-1-hydroxybutyl)piperidine-1-carboxylate. LC-MS (3 min) $t_R$=1.74 min, m/z 486, 484 (MNa$^+$), 362.

Step 2. (S)-4-(aminosulfonylamino)-1-(3-chlorophenyl)-1-((R)-piperidin-3-yl)butan-1-ol A mixture of (R)-tert-butyl 3-((S)-4-(aminosulfonylamino)-1-(3-chlorophenyl)-1-hydroxybutyl)piperidine-1-carboxylate (0.0438 g, 0.095 mmol), $CH_3CN$ (35 mL) and 2 N aq HCl (30 mL) was vigorously stirred at rt for 24 h. The solvents were removed in vacuo to give the HCl salt of (S)-4-(aminosulfonylamino)-1-(3-chlorophenyl)-1-((R)-piperidin-3-yl)butan-1-ol, which was used without further purification. LC-MS (3 min) $t_R$=0.93 min, m/z 364, 362 (MH$^+$), 285, 283.

Preparation 9

1,1,1-trifluoro-6-methoxy-2-(piperidin-3-yl)hexan-2-ol

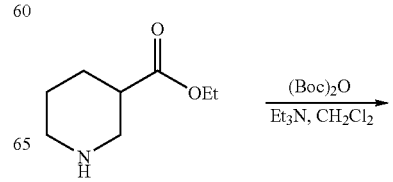

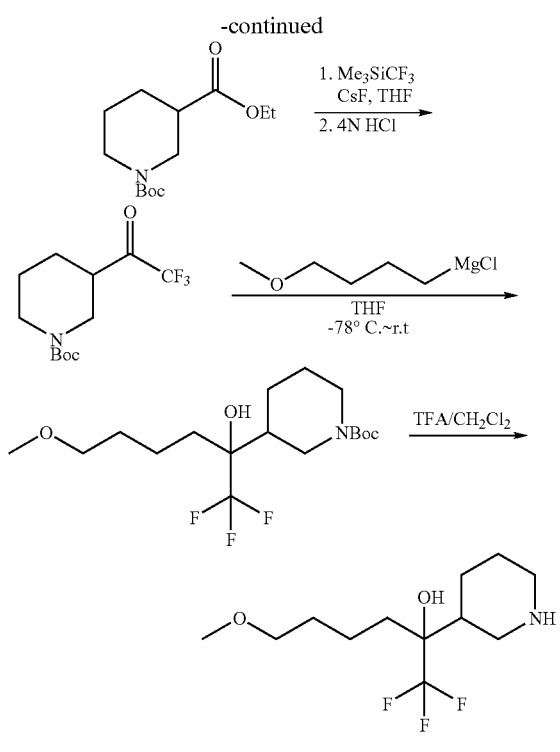

Step 1. 1-tert-butyl 3-ethyl piperidine-1,3-dicarboxylate

Ethyl nipecotate (1.55 mL, 10 mmol), (Boc)$_2$O (2.4 g, 1.1 equiv), triethylamine (2.8 mL, 2.1 equiv) and dichloromethane (70 mL) were mixed and stirred overnight at rt. The reaction mixture was diluted with EtOAc (200 mL), washed with 5% aq HCl (2×25 mL), sat'd aq NaHCO$_3$ (30 mL) and brine (20 mL), and dried over Na$_2$SO$_4$. After concentration, the crude product was purified by chromatography on a 40-g silica cartridge eluted with a 0-30% EtOAc in hexanes gradient to afford 1-tert-butyl 3-ethyl piperidine-1,3-dicarboxylate (2.61 g, 100%) as a clear oil.

Step 2. tert-butyl 3-(2,2,2-trifluoroacetyl)piperidine-1-carboxylate 1-tert-butyl 3-ethyl piperidine-1,3-dicarboxylate (424 mg, 1.65 mmol) and CsF (ca 10 mg) were combined in a vial under N$_2$. Dry THF (3 mL) was added, followed by Me$_3$SiCF$_3$ (256 μL, 1.05 equiv). After stirring for 3 h, 4N aq HCl (4 mL) was added to the vial and the mixture was stirred for 1 h. The mixture was extracted with diethyl ether (2×15 mL). The combined organic layers were washed with brine (8 mL), dried over Na$_2$SO$_4$, and concentrated to afford tert-butyl 3-(2,2,2-trifluoroacetyl)piperidine-1-carboxylate (173 mg. 37%)

Step 3. tert-butyl 3-(1,1,1-trifluoro-2-hydroxy-6-methoxyhexan-2-yl)piperidine-1-carboxylate Under protection of N$_2$ gas, tert-butyl 3-(2,2,2-trifluoroacetyl)piperidine-1-carboxylate (102 mg, 0.363 mmol) was dissolved dry THF (8 mL) and cooled to −78° C. (dry ice/acetone bath). 1.22 M methoxybutylmagnesium chloride in THF (600 μL, 2 equiv) solution was added slowly. After 10 min, the reaction was allowed to warm up to rt slowly. After 2 h, satd aq NH$_4$Cl (15 mL) solution was added to the reaction mixture. The mixture was diluted with diethyl ether and the layers were separated. The aqueous layer was extracted with diethyl ether (3×10 mL). The combined organic layers were washed with brine (10 mL) and dried over Na$_2$SO$_4$. After concentration, the crude product was purified by prep HPLC to afford tert-butyl 3-(1,1,1-trifluoro-2-hydroxy-6-methoxyhexan-2-yl)piperidine-1-carboxylate (20 mg, 15%).

Step 4. 1,1,1-trifluoro-6-methoxy-2-(piperidin-3-yl)hexan-2-ol

Tert-butyl 3-(1,1,1-trifluoro-2-hydroxy-6-methoxyhexan-2-yl)piperidine-1-carboxylate (20 mg) was dissolved in 1:1 TFA/dichloromethane (4 mL). The mixture was stirred for 30 min. The mixture was concentrated to afford 1,1,1-trifluoro-6-methoxy-2-(piperidin-3-yl)hexan-2-ol which was used without purification.

Preparation 10

(R)-3-((S)-1-(3-Chlorophenyl)-1,5-dimethoxypentyl)piperidine

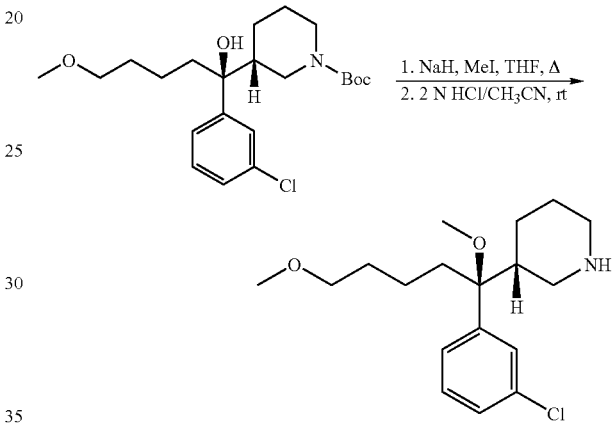

Step 1. (R)-tert-butyl 3-((S)-1-(3-chlorophenyl)-1,5-dimethoxypentyl)piperidine-1-carboxylate To a mixture of (R)-tert-butyl 3-((S)-1-(3-chlorophenyl)-1-hydroxy-5-methoxypentyl)-piperidine-1-carboxylate (0.1874 g, 0.45 mmol, 1.0 equiv) and 60% NaH in oil (0.345 g, 8.6 mmol, 19 equiv) in THF (15 mL) was added iodomethane (1.195 g, 8.4 mmol, 18.5 equiv). The resulting mixture was heated at 70° C. for 16 h and then quenched with water, extracted with EtOAc and dried over Na$_2$SO$_4$. After the solvent was removed, the crude (R)-tert-butyl 3-((S)-1-(3-chlorophenyl)-1,5-dimethoxypentyl)piperidine-1-carboxylate (0.3175 g) was used in the next step without further purification. LC-MS (3 min) t$_R$=2.44 min m/z 450, 448 (M+Na$^+$), 426 (M+H$^+$), 340, 338, 294.

Step 2. (R)-3-((S)-1-(3-chlorophenyl)-1,5-dimethoxypentyl)piperidine

A quarter of the (R)-tert-butyl 3-((S)-1-(3-chlorophenyl)-1,5-dimethoxypentyl)piperidine-1-carboxylate obtained in Step 1 (ca. 75 mg, ca. 0.1 mmol) was dissolved in CH$_3$CN (30 mL) and 2 N HCl (25 mL). The mixture was vigorously stirred at rt for 2 d. The solvents were removed in vacuo to give the HCl salt of (R)-3-((S)-1-(3-chlorophenyl)-1,5-dimethoxypentyl)-piperidine, which was used without further purification. LC-MS (3 min) t$_R$=1.22 min, m/z 328, 326 (M+H$^+$).

(R)-3-((S)-1-(3-chloro-2-fluorophenyl)-1,5-dimethoxypentyl)piperidine was prepared using procedures analogous to those described above, using (R)-tert-butyl 3-((S)-1-(3-chloro-2-fluorophenyl)-1-hydroxy-5-methoxypentyl)piperidine-1-carboxylate in Step 1.

Preparation 11

(1S)-1-(3-chlorophenyl)-2-(2-methoxyethoxy)-1-((3R)-piperidin-3-yl)ethanol

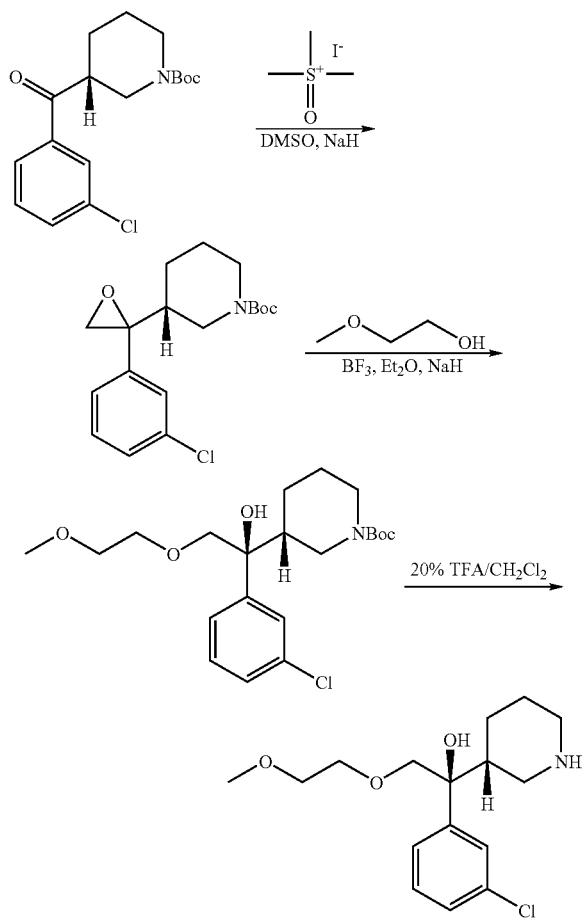

Step 1. (3R)-tert-butyl 3-(2-(3-chlorophenyl)oxiran-2-yl)piperidine-1-carboxylate A flame dried 250 mL round bottom flask was charged with sodium hydride (60% in oil, 1.45 g, 36.2 mmol) and trimethyloxosulfonium iodide (8.05 g, 36.5 mmol). The flask was evacuated and refilled with $N_2$. Dry DMSO (50 mL) was added and the mixture was stirred at rt for 1 h. A portion of this solution (14.5 mL, 10.5 mmol, 1.5 equiv) was added by syringe to a 150 mL round bottom flask which had been charged with (R)-tert-butyl 3-(3-chlorobenzoyl)-piperidine-1-carboxylate (2.27 g, 7 mmol) and THF (30 mL) and placed under $N_2$. The resulting mixture was stirred for 1 h at rt. The reaction mixture was quenched with brine and extracted with EtOAc (3×). The combined organic phase was washed with brine, dried over $Na_2SO_4$, filtered and concentrated in vacuo to give (3R)-tert-butyl 3-(2-(3-chlorophenyl)oxiran-2-yl)piperidine-1-carboxylate as a mixture of two isomers (2.32 g, 6.9 mmol, 99% yield), which was used in the next step without further purification. $^1$H NMR (400 MHz, CDCl$_3$): 1.40 (s, 9H), 1.55-1.72 (m, 3H), 1.85 (m, 1H), 2.01 (m, 1H), 2.35-2.60 (m, 2H), 2.65 (d, 1H), 3.063 (d, 1H), 4.05 (m, 1H), 4.15 (m, 1H), 7.26 (m, 3H), 7.34 (s, 1H); MS (E/Z): 338 (M+H$^+$)

Step 2. (R)-tert-butyl 3-((S)-1-(3-chlorophenyl)-1-hydroxy-2-(2-methoxyethoxy)ethyl)piperidine-1-carboxylate A stirred solution of $BF_3 \cdot Et_2O$ (12.9 mg, 0.0592 mmol) and NaH (22.6 mg, 0.296 mmol) in 2-methoxyethanol (10 mL) was warmed to 55-60° C. and (3R)-tert-butyl 3-(2-(3-chlorophenyl)oxiran-2-yl)piperidine-1-carboxylate (100 mg, 0.296 mmol) was added dropwise. After addition, the reaction mixture was stirred at the same temperature overnight. The reaction mixture was concentrated and the residue was partitioned between $H_2O$ and EtOAc. The organic layer washed with water and brine, dried over $Na_2SO_4$, filtered and concentrated in vacuo. LC-MS analysis of the crude product indicated the presence of two isomers. The crude product was purified by preparative HPLC to give the major isomer (R)-tert-butyl 3-((S)-1-(3-chlorophenyl)-1-hydroxy-2-(2-methoxyethoxy)ethyl)piperidine-1-carboxylate (30 mg, 0.073 mmol); $^1$H NMR (400 MHz, CDCl$_3$): 1.33 (s, 9H), 1.65 (m, 1H), 1.74 (m, 1H), 1.96 (m, 1H), 2.47 (m, 2H), 3.26 (m, 2H), 3.33 (s, 3H), 3.46 (m, 2H), 3.61 (m, 2H), 3.79 (m, 1H), 3.84 (m, 1H), 3.99 (m, 1H), (m, 1H), 7.22 (m, 3H), 7.42 (s, 1H); MS (E/Z): 414 (M+H$^+$)

The minor isomer (R)-tert-butyl 3-((R)-1-(3-chlorophenyl)-1-hydroxy-2-(2-methoxyethoxy)ethyl)piperidine-1-carboxylate was also isolated (25 mg, 0.061 mmol). $^1$H NMR (400 MHz, CDCl$_3$): 1.26 (m, 2H), 1.45 (s, 9H), 1.57 (m, 1H), 1.76 (m, 1H), 2.51 (m, 2H), 3.27 (m, 2H), 3.33 (s, 3H), 3.47 (m, 2H), 3.62 (m, 2H), 3.80 (m, 1H), 3.87 (m, 1H), 4.01 (m, 1H), 4.33 (m, 1H), 7.24 (m, 3H), 7.40 (s, 1H); MS (E/Z): 414 (M+H$^+$)

Step 3. (1S)-1-(3-chlorophenyl)-2-(2-methoxyethoxy)-1-((3R)-piperidin-3-yl)ethanol A solution of (R)-tert-butyl 3-((S)-1-(3-chlorophenyl)-1-hydroxy-2-(2-methoxyethoxy)-ethyl)piperidine-1-carboxylate (30 mg, 0.073 mmol) in 20% TFA/CH$_2$Cl$_2$ (5 mL) was stirred at 0° C. for 30 min. Evaporation of the solvent afforded (1S)-1-(3-chlorophenyl)-2-(2-methoxy-ethoxy)-1-((3R)-piperidin-3-yl)ethanol (30 mg, 0.073 mmol 100%). MS (E/Z): 314 (M+H$^+$).

Preparation 12

(R)-tert-Butyl 3-((R)-(3-ethoxypropoxy)(phenyl)methyl)piperidine-1-carboxylate

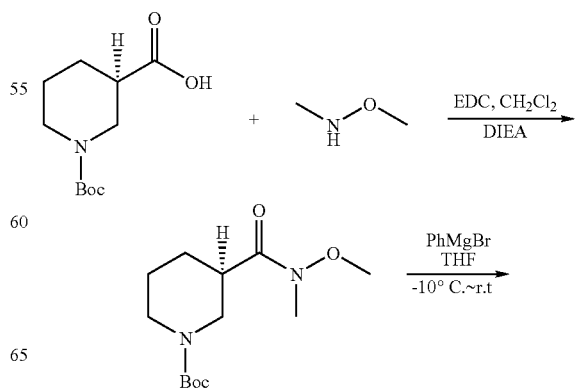

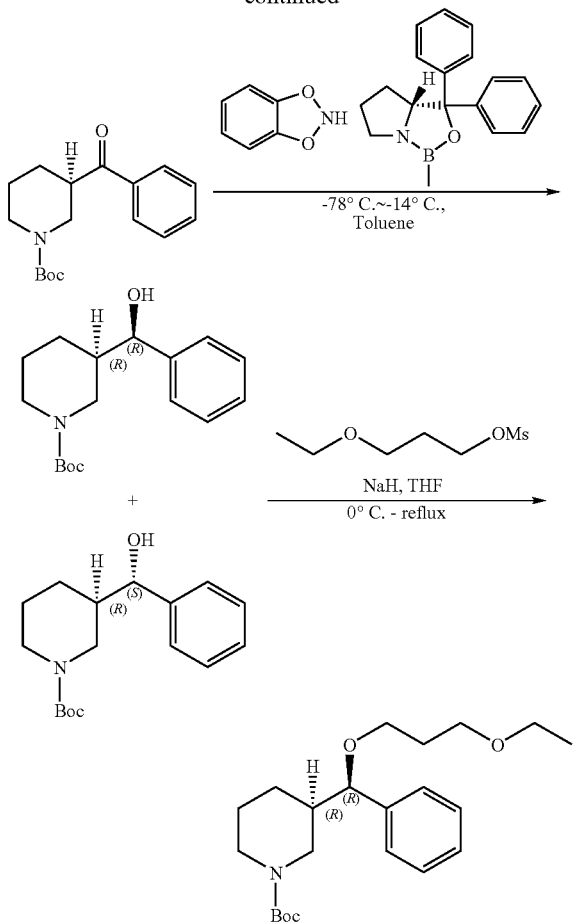

Step 1. (R)-tert-butyl 3-(N-methoxy-N-methylcarbamoyl)piperidine-1-carboxylate (R)-1-(tert-butoxycarbonyl)piperidine-3-carboxylic acid (25 g, 0.11 mol, 1.0 equiv), N,O-dimethylhydroxylamine hydrochloride, (10.5 g, 0.14 mol, 1.25 equiv) and EDC.HCl (26.3 g, 0.14 mol, 1.25 equiv) and diisopropylethylamine (48 mL, 0.28 mol, 2.5 equiv) were dissolved in 400 ml (400 mL) and stirred overnight at rt. The reaction mixture was diluted with EtOAc, washed with 5% aq HCl (2×150 mL), satd aq NaHCO$_3$ (150 mL), brine (100 mL), and dried over Na$_2$SO$_4$. Concentration afforded (R)-tert-butyl 3-(N-methoxy-N-methylcarbamoyl)piperidine-1-carboxylate (24.42 g, 82%) as a clear oil. LC-MS (3 min) t$_R$=1.41 min, m/z 295 (M+Na). $^1$H NMR (CDCl$_3$) □ 4.19-4.00 (m, 2H), 3.77 (m, 3H), 3.12 (s, 3H), 2.79 (m, 2H), 2.64 (m, 1H), 1.89 (m, 1H), 1.71-1.52 (m, 2H), 1.51-1.33 (m, 10H). Chiral HPLC indicated 100% purity. The crude product was used for next step without further purification.

Step 2. (R)-tert-butyl 3-benzoylpiperidine-1-carboxylate (R)-tert-butyl 3-(N-methoxy-N-methylcarbamoyl)piperidine-1-carboxylate (13.6 g, 50 mmol) was dissolved in anhydrous THF (200 mL) and cooled to −10° C. (ice/MeOH bath). Phenylmagnesium bromide solution in THF (100 mL of 1.0 M, 100 mmol, 2 equiv) was added slowly. After 15 min, the reaction mixture was warmed up to rt slowly and stirred for 1 hour. LC-MS showed the reaction was complete. 5% Aq HCl (100 mL) was added slowly to quench the reaction and the mixture was stirred for 20 min. After separation, the aqueous layer was extracted with ether (2×200 mL). The combined organic layers were washed with satd aq NaHCO$_3$ (150 mL), brine (100 mL), and dried over Na$_2$SO$_4$. Concentration afforded crude (R)-tert-butyl 3-benzoylpiperidine-1-carboxylate (16.45 g, 110%) as a clear oil which was used for the next step without further purification. LC-MS (3 min) t$_R$=1.91 min, m/z 302 (M+Na). $^1$H NMR (CDCl$_3$) □ 7.94 (d, 2H), 7.54 (t, 1H), 7.47 (t, 2H), 4.28 (br d, 1H), 4.09 (d, 1H), 3.38 (t, 1H), 2.92 (br t, 1H), 2.72 (t, 1H), 2.01 (d, 1H), 1.79-1.45 (m, 3H) 1.42 (s, 9H). Chiral HPLC indicated 100% purity.

Step 3. (R)-tert-butyl 3-((R)-hydroxy(phenyl)methyl)piperidine-1-carboxylate

A solution of (R)-tert-butyl 3-benzoylpiperidine-1-carboxylate (10.3 g, 35.64 mmol) anhydrous toluene (120 mL) was cooled to −78° C. and (R)-2-methyl-CBS-oxazaborolidine (1.0M in toluene, 17.8 mL, 17.8 mmol, 0.5 equiv) was added slowly. After 5 min, catecholborane (11.4 mL, 107 mmol, 3 equiv) was added slowly. The reaction mixture was then transferred into the freezer (∼14.2° C.) and left overnight. LC-MS (16 min) showed 9:1 ratio of the R to S isomer. The mixture was cooled to 0° C. and water was added dropwise to quench the reaction. The reaction mixture was diluted with ether, washed with 5% aq NaOH (2×150 mL), water (150 mL), 5% aq HCl (100 mL), brine (100 mL), and dried over Na$_2$SO$_4$. After concentration, the crude product was purified by flash chromatography on a 120 g silica gel column eluted with a 4-35% EtOAc in hexanes gradient. The purified product was recrystallized from an ether hexanes mixture to afford (R)-tert-butyl 3-((R)-hydroxy(phenyl)methyl)piperidine-1-carboxylate (4.45 g, 43%) as white solid with the ratio of R/S isomers 23.5:1. LC-MS (3 min) t$_R$=1.70 min; LC-MS (3 min) t$_R$=10.62 min, m/z 314 (M+Na). $^1$H NMR (CDCl$_3$) □ 7.28 (m, 5H), 4.46 (d, 1H), 3.87 (d, 1H), 3.89-3.51 (br s, free exchange 1H), 3.00 (m, 2H), 2.68 (t, 1H), 2.52 (t, 1H), 1.94 (m, 1H), 1.76 (m, 1H), 1.65 (m, 1H), 1.42-1.20 (m, 10H).

Step 4. (R)-tert-Butyl 3-((R)-(3-ethoxypropoxy)(phenyl)methyl)piperidine-1-carboxylate An oven dried flask was charged with (R)-tert-butyl 3-((R) hydroxy(phenyl)methyl)-piperidine-1-carboxylate (3.18 g, 10.9 mmol) and 60% NaH in mineral oil (2.19 g, 54.8, 5 equiv). The flask was purged with N$_2$ gas, cooled to 0° C. and anhydrous THF (100 mL) was added slowly. The mixture was allowed to warm to rt slowly. A solution of 3-ethoxypropyl methanesulfonate (6.0 g, 32.9 mmol, 3 equiv) in anhydrous THF (50 mL) was added. The mixture was heated at reflux for 4 h. LC-MS indicated the reaction completed. The reaction mixture was cooled to 0° C. slowly and water was added dropwise to quench the reaction. After separation, the aqueous layer was extracted with ether three times. The combined organic layers were washed with 5% aq HCl, satd aq NaHCO$_3$, brine, and dried over Na$_2$SO$_4$. After concentration, the crude product was purified by flash chromatography on a 120-g silica gel cartridge eluted with a 0-30% EtOAc in hexanes gradient) to afford (R)-tert-butyl 3-((R)-(3-ethoxypropoxy)(phenyl)methyl)piperidine-1-carboxylate (3.70 g, 90%) as a clear oil. Chiral HPLC indicated 95.5% purity. LC-MS (3 min) t$_R$=2.38 min, m/z 400 (M+Na). $^1$H NMR (CDCl$_3$) □ 7.26 (m, 5H), 4.39 (d, 1H), 3.89 (t, 2H), 3.53-3.40 (m, 4H), 3.38-3.23 (m, 2H), 2.75-2.60 (m, 2H), 1.85-1.47 (m, 4H), 1.45 (s, 9H), 1.40-1.22 (m, 2H), 1.15 (t, 3H), 1.10-0.96 (m, 1H).

Preparation 13

Methyl 2-((R)-(3-chlorophenyl)((R)-piperidin-3-yl)methoxy)ethylcarbamate

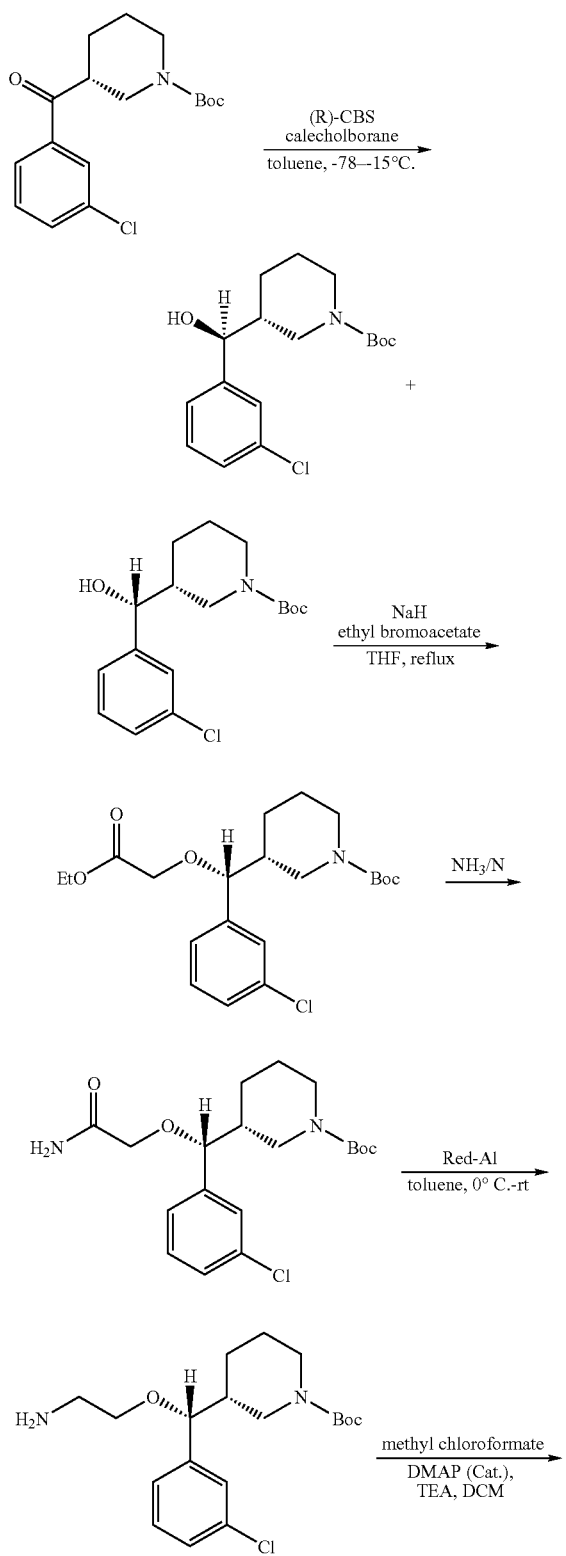

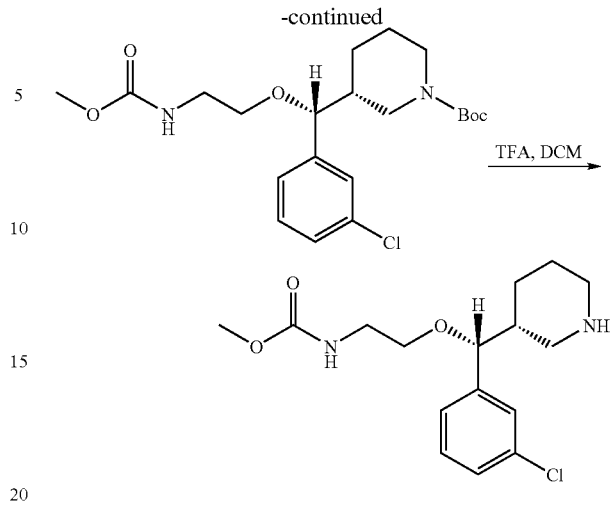

Step 1: (R)-tert-Butyl 3-((R)-(3-chlorophenyl)(hydroxy)methyl)piperidine-1-carboxylate To a solution of (R)-tert-butyl 3-(3-chlorobenzoyl)piperidine-1-carboxylate (5.60 g, 17.29 mmol) and (R)-2-methyl-CBS-oxazaborolidine (1 M in toluene, 9 mL, 9.00 mmol) cooled to −78° C. was added catecholborane (5.6 mL, 54.0 mmol) dropwise. After 20 min, the reaction temperature was allowed to warm to −15° C. and stirred overnight. The reaction was quenched at 0° C. by careful addition of water and diluted with ether. The resulting suspension was filtered through Celite and washed with ether. The filtrate was washed successively with 1 M aq NaOH (3×50 mL), 1 M aq HCl (3×50 mL), satd aq NaHCO$_3$ and brine, and dried over Na$_2$SO$_4$. The solution was filtered, the filtrate was evaporated under vacuum, and the residue was purified by preparative HPLC to afford (R)-tert-butyl 3-((R)-(3-chlorophenyl)(hydroxy)methyl)piperidine-1-carboxylate (2.44 g) and (R)-tert-butyl 3-((S)-(3-chlorophenyl)(hydroxy)methyl)piperidine-1-carboxylate (1.21 g). MS: 348 (M+Na)$^+$.

Step 2: (R)-tert-Butyl 3-((R)-(3-chlorophenyl)(2-ethoxy-2-oxoethoxy)methyl)piperidine-1-carboxylate To a suspension of 60% NaH in oil (960 mg, 24.0 mmol) in anhydrous THF at 0° C. was added a solution of (R)-tert-butyl 3-((R)-(3-chlorophenyl)(2-ethoxy-2-oxoethoxy)methyl)-piperidine-1-carboxylate (1.429 g, 4.40 mmol) in anhydrous THF (10 mL). The reaction mixture was stirred at rt for 30 min and a solution of ethyl bromoacetate (2.204 g, 13.2 mmol) in anhydrous THF (10 mL) was added dropwise. The resulting suspension was heated at reflux for 3 h and cooled to 0° C. again. The same amount of NaH as before was added and stirred for 30 min at rt, followed by addition the same amount of ethyl bromoacetate, and the mixture was heated at reflux overnight. The reaction mixture was cooled to 0° C. and quenched by careful addition of aq NH$_4$Cl. The mixture was extracted with EtOAc (3×). The combined organic phases were washed with brine, dried over Na$_2$SO$_4$, and filtered. The filtrate was evaporated and the residue was purified by flash chromatography on silica gel to afford (R)-tert-butyl 3-((R)-(3-chlorophenyl)(2-ethoxy-2-oxoethoxy)methyl)piperidine-1-carboxylate (1.62 g). MS: 412 (M+H)$^+$.

Step 3: (R)-tert-Butyl 3-((R)-(2-amino-2-oxoethoxy)(3-chlorophenyl)methyl)piperidine-1-carboxylate (R)-tert-Butyl 3-((R)-(3-chlorophenyl)(2-ethoxy-2-oxoethoxy)methyl)piperidine-1-carboxylate (1.50 g, 3.65 mmol)

was dissolved in 7 M $NH_3$ in MeOH, and stirred at rt for 6 h. The mixture was evaporated under reduced pressure to afford the (R)-tert-butyl 3-((R)-(2-amino-2-oxoethoxy)(3-chlorophenyl)methyl)piperidine-1-carboxylate in quantitative yield. MS: 383 $(M+-1)^+$.

Step 4: (R)-tert-Butyl 3-((R)-(2-aminoethoxy)(3-chlorophenyl)methyl)piperidine-1-carboxylate (R)-tert-Butyl 3-((R)-(2-amino-2-oxoethoxy)(3-chlorophenyl)methyl)piperidine-1-carboxylate (1.10 g, 2.60 mmol) was dissolved in anhydrous toluene (30 mL) and cooled to 0° C. Red-Al (65% in toluene, 2.6 mL, 8.64 mmol) was added dropwise. After the addition, the reaction was stirred at rt for 12 h and quenched by adding water slowly. The resulting mixture was filtered through Celite, washing with THF. The filtrate was evaporated under reduced pressure to give crude (R)-tert-butyl 3-((R)-(2-aminoethoxy)(3-chlorophenyl)methyl)piperidine-1-carboxylate (1.05 g), which was used for next step without further purification.

Step 5: (R)-tert-Butyl 3-((R)-(3-chlorophenyl)(2-(methoxycarbonylamino)ethoxy)methyl)piperidine-1-carboxylate To a solution of (R)-tert-butyl 3-((R)-(2-aminoethoxy)(3-chlorophenyl)methyl)piperidine-1-carboxylate (1.05 g, ca. 2.6 mmol), $Et_3N$ (3.96 mL, 2.85 mmol), and DMAP (174 mg, 1.43 mmol) in anhydrous $CH_2Cl_2$ (20 mL) cooled to 0° C. was added a solution of methyl chloroformate (1.35 g, 14.25 mmol) in dichloromethane (20 mL) within 30 min. The reaction was stirred overnight, and evaporated under vacuum. The residue was purified by flash chromatography on silica gel to afford (R)-tert-butyl 3-((R)-(3-chlorophenyl)(2-(methoxycarbonylamino)ethoxy)methyl)piperidine-1-carboxylate (0.65 g). MS: 427 $(M+H)^+$.

Step 6: Methyl 2-((R)-(3-chlorophenyl)((R)-piperidin-3-yl)methoxy)ethylcarbamate To a stirred solution of (R)-tert-butyl 3-((R)-(3-chlorophenyl)(2-(methoxycarbonylamino)-ethoxy)methyl)piperidine-1-carboxylate (91 mg, 0.21 mmol) in $CH_2Cl_2$ (3 mL) at rt was added TFA (0.5 mL). The mixture was stirred until complete removal of the Boc group had occurred. The solvent was removed under vacuum to give methyl 2-((R)-(3-chlorophenyl)((R)-piperidin-3-yl)methoxy)ethylcarbamate as its TFA salt. MS: 327 $(M+H)^+$.

The following compound was prepared using procedures analogous to those described above:
methyl 2-((3-fluorophenyl)(piperidin-3-yl)methoxy)ethylcarbamate using tert-butyl 3-(3-fluorobenzoyl)piperidine-1-carboxylate in Step 1.

Preparation 14

N-(2-((R)-(3-chloro-2-fluorophenyl)((R)-piperidin-3-yl)methoxy)ethyl)acetamide

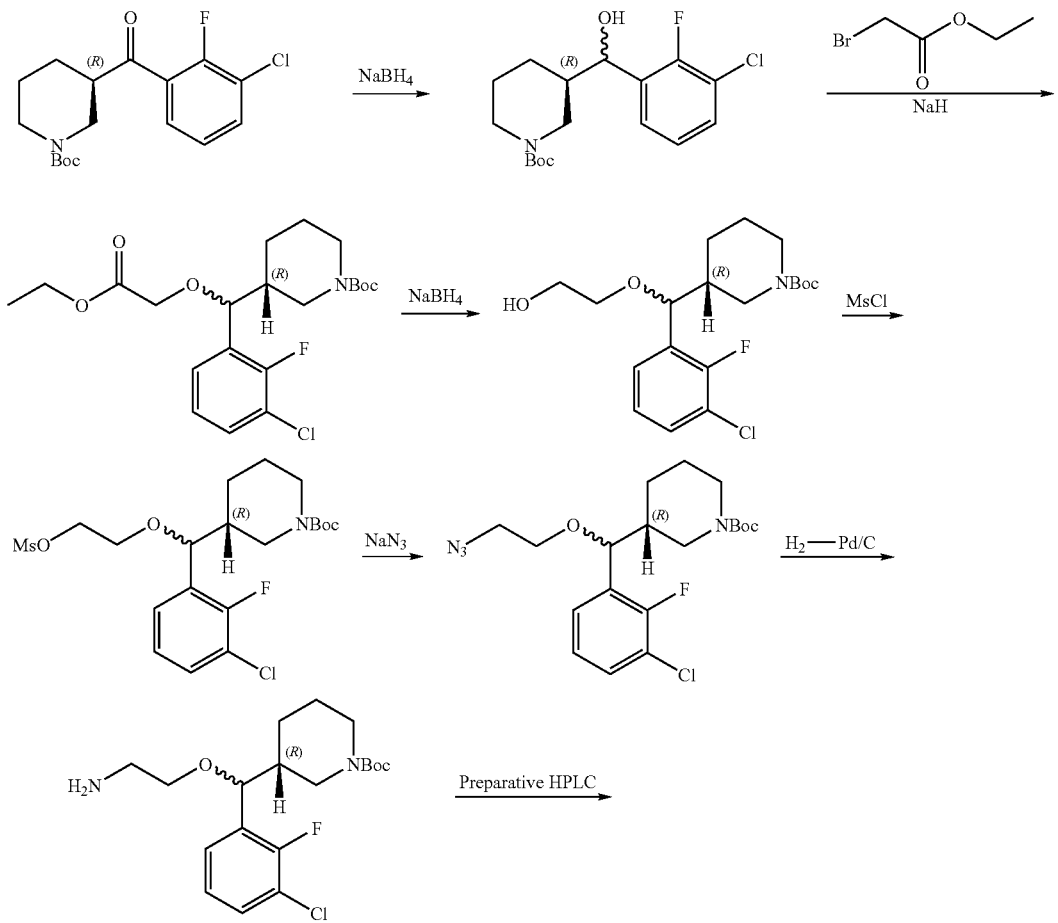

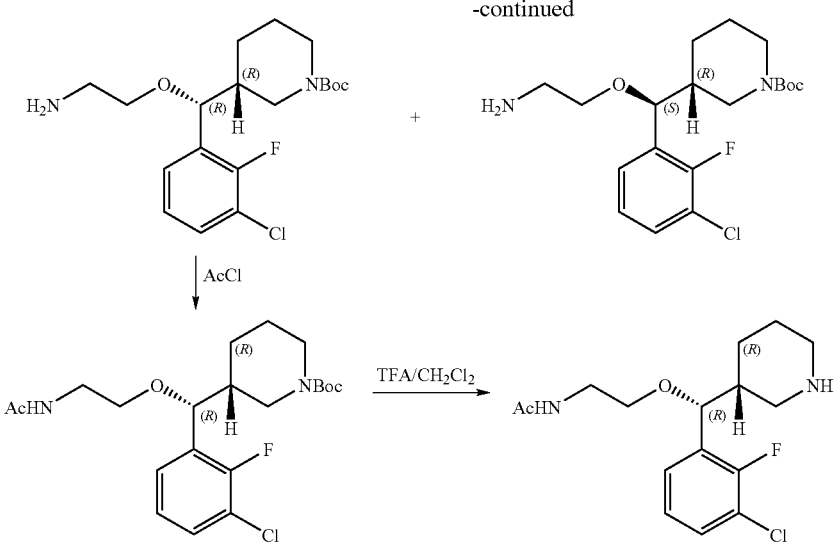

Step 1. (R)-tert-butyl 3-((3-chloro-2-fluorophenyl)(hydroxy)methyl)piperidine-1-carboxylate To a solution of (R)-tert-butyl 3-(3-chloro-2-fluorobenzoyl)piperidine-1-carboxylate (7.75 g, 22.7 mmol) in MeOH (160 mL) was added NaBH$_4$ (6.9 g, 182 mmol) in portions such that the temperature remained below 40° C. After addition, the mixture was stirred at rt for 3 h. TLC showed the start material had disappeared. The solvent was removed in vacuo and the residue was partitioned between water and EtOAc. The organic layer was washed with H$_2$O and brine, dried over Na$_2$SO$_4$ and evaporated to give (R)-tert-butyl 3-((3-chloro-2-fluorophenyl)(hydroxy)methyl)piperidine-1-carboxylate (4.35 g, 56%) which was used in the next step without purification. MS (E/Z): 344 (M+H$^+$).

Step 2. (R)-tert-butyl 3-((3-chloro-2-fluorophenyl)(2-ethoxy-2-oxoethoxy)methyl)piperidine-1-carboxylate To a stirred suspension of NaH (0.608 g, 15.2 mmol) in THF (100 mL) at 0-5° C. was added dropwise a solution of (R)-tert-butyl 3-((3-chloro-2-fluorophenyl)(hydroxy)methyl)-piperidine-1-carboxylate (4.35 g, 12.68 mmol) in THF (30 mL). The reaction mixture was stirred for an additional 1 h at rt. A solution of ethyl bromoacetate (2.52 g, 15.2 mmol) in THF (30 mL) was added dropwise and the mixture was refluxed for 5 h. TLC showed the starting material had disappeared. The reaction mixture was poured into sat'd aq NH$_4$Cl, extracted with EtOAc (3×100 mL), dried over Na$_2$SO$_4$, filtered and concentrated in vacuo. The residue was purified by chromatography on silica gel to afford (R)-tert-butyl 3-((3-chloro-2-fluorophenyl)(2-ethoxy-2-oxoethoxy)methyl)piperidine-1-carboxylate (4.368 g, 80%). $^1$H NMR (400 MHz, CDCl$_3$): 0.861 (m, 2H), 1.25 (m, 6H), 1.38&1.43 (s, 9H), 1.59-2.10 (m, 3H), 2.75 (m, 1H), 3.80 (s, 1H), 3.96 (m, 2H), 4.18 (m, 2H), 4.62 (m, 1H), 7.12 (m, 1H), 7.33 (m, 2H); MS (E/Z): 430 (M+1)

Step 3. (R)-tert-butyl 3-((3-chloro-2-fluorophenyl)(2-hydroxyethoxy)methyl)piperidine-1-carboxylate To a solution of (R)-tert-butyl 3-((3-chloro-2-fluorophenyl)(2-ethoxy-2-oxoethoxy)-methyl)piperidine-1-carboxylate (4.368 g, 10.2 mmol) in MeOH (85 mL) was added NaBH$_4$ (3.18 g, 81.5 mmol) in portions such that the temperature remained below 40° C. After addition, the mixture was stirred at rt for 2~3 h. TLC showed the starting material had disappeared. The solvent was removed in vaczio and the residue was partitioned between water and EtOAc. The organic layer was washed with H$_2$O and brine, dried over Na$_2$SO$_4$ and evaporated to give (R)-tert-butyl 3-((3-chloro-2-fluorophenyl)(2-hydroxyethoxy)methyl)piperidine-1-carboxylate (3.5 g, 89%). $^1$H NMR (400 MHz, CDCl$_3$): 1.18 (m, 1H), 1.38-1.46 (s, 9H), 1.65 (m, 1H), 1.85 (m, 2H), 2.66 (m, 1H), 3.25 (m, 1H), 3.38 (m, 2H), 3.69 (m, 3H), 3.93 (m, 1H), 4.52 (m, 6H); MS (E/Z): 388 (M+1)

Step 4. (R)-tert-butyl 3-((3-chloro-2-fluorophenyl)(2-(methylsulfonyloxy)ethoxy)methyl)-piperidine-1-carboxylate To a solution of (R)-tert-butyl 3-((3-chloro-2-fluorophenyl)(2-hydroxyethoxy)methyl)-piperidine-1-carboxylate (3.5 g, 9 mmol) in dry CH$_2$Cl$_2$ (50 mL) was added Et$_3$N (3.2 g, 4.2 mL, 27 mmol, 4 eq) at 0~−5° C. Then a solution of MsCl (1.23 g, 10.8 mmol, 1.2 eq) in dry CH$_2$Cl$_2$ (20 mL) was added dropwise at the same temperature. After addition, the mixture was allowed to warm to rt gradually. TLC showed the starting material had disappeared. Water (30 mL) was added and the mixture was extracted with CH$_2$Cl$_2$ (3×20 mL). The combined organic layers were washed with 10% aq citric acid, sat'd aq NaHCO$_3$ and brine, then dried over Na$_2$SO$_4$, filtered and concentrated to give 3R-3-[(3-chloro-2-fluoro-phenyl)-(2-methanesulfonyloxy-ethoxy)-methyl]-piperidine-1-carboxylic acid tert-butyl ester (4.13 g, 99%), which was used in the next step without purification. $^1$H NMR (400 MHz, CDCl$_3$): 1.35 (m, 4H), 1.46 (s, 9H), 1.62 (m, 3H), 1.83 (m, 1H), 2.52-2.81 (m, 2H), 3.05 (m, 3H), 3.56 (m, 2H), 3.92 (m, 1H), 4.30 (m, 2H), 4.48 (m, 1H), 7.13 (m, 1H), 7.28 (m, 1H), 7.35 (m, 1H); MS (E/Z): 466 (M+)

Step 5. (R)-tert-butyl 3-((2-azidoethoxy)(3-chloro-2-fluorophenyl)methyl)piperidine-1-carboxylate 3R-3-[(3-chloro-2-fluoro-phenyl)-(2-methanesulfonyloxy-ethoxy)-methyl]-piperidine-1-carboxylic acid tert-butyl ester (4 g, 8.6 mmol) was dissolved in anhydrous DMF (30 mL), solid NaN$_3$ (0.84 g, 12.9 mmol) was added and the reaction mixture was heated at 80° C. overnight. The reaction mixture was cooled to rt and EtOAc (100 mL) was added. The mixture was washed with water (3×30 mL), dried over Na$_2$SO$_4$ and evaporated. The residue was separated on a silica column to give (R)-tert-butyl 3-((2-azidoethoxy)(3-chloro-2-fluorophenyl)methyl)piperidine-1-carboxylate (2.6 g, 73%). ¹H NMR: (400 MHz, CDCl₃): 1.24 (m, 1H), 1.38&1.46 (s, 9H), 1.67 (m, 3H), 1.83 (m, 1H), 2.58-2.81 (m, 2H), 3.32 (m, 2H), 3.45 (m, 2H), 3.92 (m, 1H), 4.20 (m, 1H), 4.50 (m, 1H), 7.13 (t, 1H), 7.34 (m, 2H), 8.02 (s, 1H);

Step 6. (R)-tert-butyl 3-((R)-(2-aminoethoxy)(3-chloro-2-fluorophenyl)methyl)piperidine-1-carboxylate To a solution of (R)-tert-butyl 3-((2-azidoethoxy)(3-chloro-2-fluorophenyl)methyl)-piperidine-1-carboxylate (2.6 g, 6.31 mmol) in EtOAc (50 mL) was added wetted Pd/C (0.1 g) and the mixture was stirred overnight under a hydrogen atmosphere maintained by a balloon. The reaction mixture was filtered through a pad of Celite and the solvent was removed to give (R)-tert-butyl 3-((2-aminoethoxy)(3-chloro-2-fluorophenyl)methyl)piperidine-1-carboxylate which was submitted to reverse phase the preparative HPLC to give (R)-tert-butyl 3-((S)-(2-aminoethoxy)(3-chloro-2-fluorophenyl)methyl)piperidine-1-carboxylate (990 mg, 81%) and (R)-tert-butyl 3-((R)-(2-aminoethoxy)(3-chloro-2-fluorophenyl)methyl)piperidine-1-carboxylate (792 mg, 65%). MS (E/Z): 387 (M+H⁺).

Step 7. (R)-tert-butyl 3-((R)-(2-acetamidoethoxy)(3-chloro-2-fluorophenyl)methyl)piperidine-1-carboxylate To a solution of (R)-tert-butyl 3-((R)-(2-aminoethoxy)(3-chloro-2-fluorophenyl)methyl)-piperidine-1-carboxylate (160 mg, 0.41 mmol) and Et₃N (1 mL) at 0° C. was added acetyl chloride (32.3 mg, 0.41 mmol). The mixture was allowed to warm to rt and stirred overnight. The mixture was concentrated in vacuo to give crude (R)-tert-butyl 3-((R)-(2-acetamidoethoxy)-(3-chloro-2-fluorophenyl)methyl)piperidine-1-carboxylate (95 mg, 54%), which was used in the next step without further purification. ¹H NMR: (400 MHz, CDCl₃): 1.20 (m, 1H), 1.40 (s, 9H), 1.70 (m, 2H), 1.98 (s, 3H), 2.60 (m, 2H), 3.48 (m, 4H), 3.90 (m, 1H), 4.42 (m, 1H), 5.82 (m, 1H), 7.10 (m, 1H), 7.20 (m, 1H), 7.34 (m, 1H); MS (E/Z): 429 (M+1). MS (E/Z): 429 (M+)

Step 8. N-(2-((R)-(3-chloro-2-fluorophenyl)((R)-piperidin-3-yl)methoxy)ethyl)acetamide (R)-tert-butyl 3-((R)-(2-acetamidoethoxy)(3-chloro-2-fluorophenyl)methyl)piperidine-1-carboxylate (95 mg, 1.88 mmol) was dissolved in 20% v/v TFA/CH₂Cl₂ (8 mL) at 0° C., the mixture was allowed to warm to rt for 1 h and then concentrated in vacuo to give N-(2-((R)-(3-chloro-2-fluorophenyl)((R)piperidin-3-yl)methoxy)ethyl)acetamide (63 mg, 87%), which was used without further purification. MS (E/Z): 329 (M+)

Preparation 15

(S)-1-(benzofuran-7-yl)-5-methoxy-1-((R)-piperidin-3-yl)pentan-1-ol

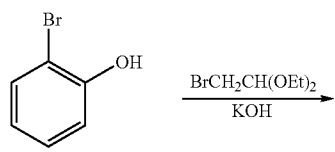

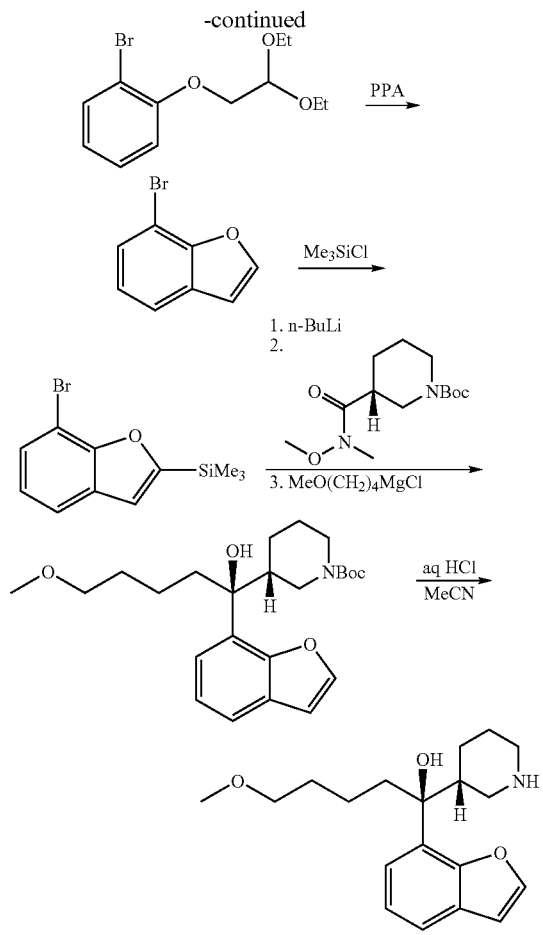

Step 1. 1-(2,2-diethoxyethoxy)-2-bromobenzene

A solution of KOH pellets (85%, 0.68 g, 10.3 mmol) in water (1.5 mL) was added to 2-bromophenol (1 mL, 8.6 mmol). The mixture was diluted with DMSO (20 mL) and bromoacetaldehyde diethyl acetal (1.43 mL, 9.5 mmol) was added. The mixture was heated at 100° C. for 6 h, cooled to rt, diluted with ether (175 mL), washed with water (3×40 mL) and 5% aq NaOH (40 mL), and dried over MgSO₄. Removal of the solvent left 1-(2,2-diethoxyethoxy)-2-bromobenzene (2.62 g, quant) as an oil.

Step 2. 7-bromobenzofuran

A stirred mixture of polyphosphoric acid (~5 g) and chlorobenzene (8 mL) was heated at reflux and a solution of 1-(2,2-diethoxyethoxy)-2-bromobenzene (2.62 g, 9.0 mmol) in chlorobenzene (3 mL) was added dropwise over 10 min. The mixture was heated at reflux for 1.5 h. The mixture was allowed to cool to rt and 1M aq NaOH (20 mL) was added, followed by ether (175 mL). The mixture was washed with water (2×20 mL) and brine (20 mL), and dried over MgSO₄. Evaporation of the solvent left a residue which was purified by a chromatography on a 140-g silica cartridge eluted with hexanes and a 0-10% EtOAc in hexanes gradient. Appropriate fractions were pooled and concentrated to afford 7-bromobenzofuran (0.65 g, 38% from 2-bromophenol) as a clear colorless oil.

Step 3. 7-Bromo-2-(trimethylsilyl)benzofuran

A stirred solution of diisopropylamine (0.65 mL, 4.7 mmol) in THF (15 L) was cooled to 5° C. and n-BuLi (2.5 M in hexanes, 1.9 mL, 4.7 mmol) was added dropwise over 5 min. The mixture was stirred at 5° C. for 15 min and cooled to −70° C. Chlorotrimethylsilane (0.59 mL, 4.7 mmol) was added followed by a solution of 7-bromobenzofuran (0.46 g, 2.35 mmol) in THF (5 mL). The mixture was stirred at −70° C. for 1.5 h and poured into sat'd aq NH₄Cl (80 mL). The mixture was diluted with 5% aq HCl (20 mL) and extracted with ether (2×80 mL). The combined ether extracts were washed with sat'd aq NaHCO₃ (50 mL), dried over MgSO₄ and concentrated to leave crude 7-bromo-2-(trimethylsilyl) benzofuran (0.62 g, 98%) as a yellow oil.

Step 4. (R)-tert-butyl 3-((S)-1-(benzofuran-7-yl)-1-hydroxy-5-methoxypentyl)piperidine-1-carboxylate A stirred solution of 7-bromo-2-(trimethylsilyl)benzofuran (620 mg, 2.3 mmol) in THF (15 mL) was cooled to −70° C. and n-BuLi (2.5 M in hexanes, 0.85 mL, 2.1 mmol) was added dropwise over 2 min. The mixture was stirred at −70° C. for 15 min and a solution of (R)-tert-butyl 3-(N-methoxy-N-methylcarbamoyl)piperidine-1-carboxylate (341 mg, 1.30 mmol) in THF (5 mL) was added dropwise over 2 min. The mixture was stirred at −70° C. for 1 h, poured into satd aq NaHCO₃ (100 mL) and extracted with ether (2×100 mL). The combined ether extracts were washed with brine (40 mL) and dried over MgSO₄. Removal of the solvent afforded crude (R)-tert-butyl 3-((benzofuran-7-yl)carbonyl)piperidine-1-carboxylate (727 mg) as an oil. This material was dissolved in THF (15 mL) and cooled to −70° C. 4-Methoxybutylmagnesium chloride (1.52 M in THF, 2.0 mL, 3.04 mmol) was added dropwise over 2 min. The mixture was stirred at −70° C. for 2 h and poured into sat'd aq NaHCO₃ (100 mL). The mixture was extracted with ether (2×100 mL) and the combined ether extracts were washed with brine (35 mL) and dried over MgSO₄. Removal of the solvent left an oil which was purified by chromatography on a 40-g silica cartridge eluted with a gradient from 0 to 100% EtOAc in hexanes to afford (R)-tert-butyl 3-((S)-1-(benzofuran-7-yl)-1-hydroxy-5-methoxypentyl)piperidine-1-carboxylate (240 mg, 44%) as an oil.

Step 4. (S)-1-(benzofuran-7-yl)-5-methoxy-1-((R)-piperidin-3-yl)pentan-1-ol (R)-tert-butyl 3-((S)-1-(benzofuran-7-yl)-1-hydroxy-5-methoxypentyl)piperidine-1-carboxylate (240 mg, 0.58 mmol) was dissolved in MeCN (20 mL) and 5% aq HCl (10 mL) was added. The mixture was stirred at rt for 1 d and solid K₂CO₃ was added. The mixture was diluted with water (40 mL) and extracted with EtOAc (2×100 mL). The combined organic extracts were washed with brine (25 mL), dried over MgSO₄ and concentrated to leave an oil (150 mg) which was purified by reverse phase preparative HPLC to afford (S)-1-(benzofuran-7-yl)-5-methoxy-1-((R)-piperidin-3-yl)pentan-1-ol (120 mg, 81%) as an oil.

The following piperidines were prepared following procedures analogous to those described above:

(S)-5-methoxy-1-(2-methyl benzofuran-7-yl)-1-((R)-piperidin-3-yl)pentan-1-ol using 7-bromo-2-methylbenzofuran and n-BuLi in Step 4.

(S)-1-(2-isobutylbenzofuran-7-yl)-5-methoxy-1-((R)-piperidin-3-yl)pentan-1-ol using 7-bromo-2-isobutylbenzofuran and n-BuLi in Step 4.

(S)-5-methoxy-1-((R)-piperidin-3-yl)-1-(thiophen-3-yl)pentan-1-ol using 3-bromothiophene and n-BuLi in Step 4.

(S)-5-methoxy-1-((R)-piperidin-3-yl)-1-(pyridin-2-yl)pentan-1-ol from 2-bromopyridine and n-BuLi in Step 4.

(S)-5-methoxy-1-((R)-piperidin-3-yl)-1-(quinolin-8-yl)pentan-1-ol from 8-bromoquinoline and n-BuLi in Step 4.

(S)-1-(1H-indazol-7-yl)-5-methoxy-1-((R)-piperidin-3-yl)pentan-1-ol from 7-bromoindazole and n-BuLi (S)-5-methoxy-1-((R)-piperidin-3-yl)-1-(2-(trimethylsilyl)benzo[b]thiophen-7-yl)pentan-1-ol from 7-bromo-2-(trimethylsilyl)benzothiophene and n-BuLi in Step 4.

(S)-5-methoxy-1-(2-methylbenzofuran-7-yl)-1-((R)-piperidin-3-yl)pentan-1-ol from 7-bromo-2-methylbenzofuran and n-BuLi in Step 4.

(S)-1-(2-fluorobenzofuran-7-yl)-5-methoxy-1-((R)-piperidin-3-yl)pentan-1-ol from 7-bromo-2-fluorobenzofuran and n-BuLi in Step 4.

(S)-1-(5-fluorobenzofuran-7-yl)-5-methoxy-1-((R)-piperidin-3-yl)pentan-1-ol from 7-bromo-5-fluoro-2-(trimethylsilyl)benzofuran and n-BuLi in Step 4.

(S)-1-(2-tert-butylbenzofuran-7-yl)-5-methoxy-1-((R)-piperidin-3-yl)pentan-1-ol from 7-bromo-2-(t-butyl)benzofuran and n-BuLi in Step 4.

(S)-5-methoxy-1-((R)-piperidin-3-yl)-1-(2-(trimethyl silyl)benzo[b]thiophen-4-yl)pentan-1-ol from 4-bromo-2-(trimethylsilyl)benzothiophene and n-BuLi in Step 4.

Preparation 16

(S)-1-(benzo[b]thiophen-2-yl)-5-methoxy-1-((R)-piperidin-3-yl)pentan-1-ol

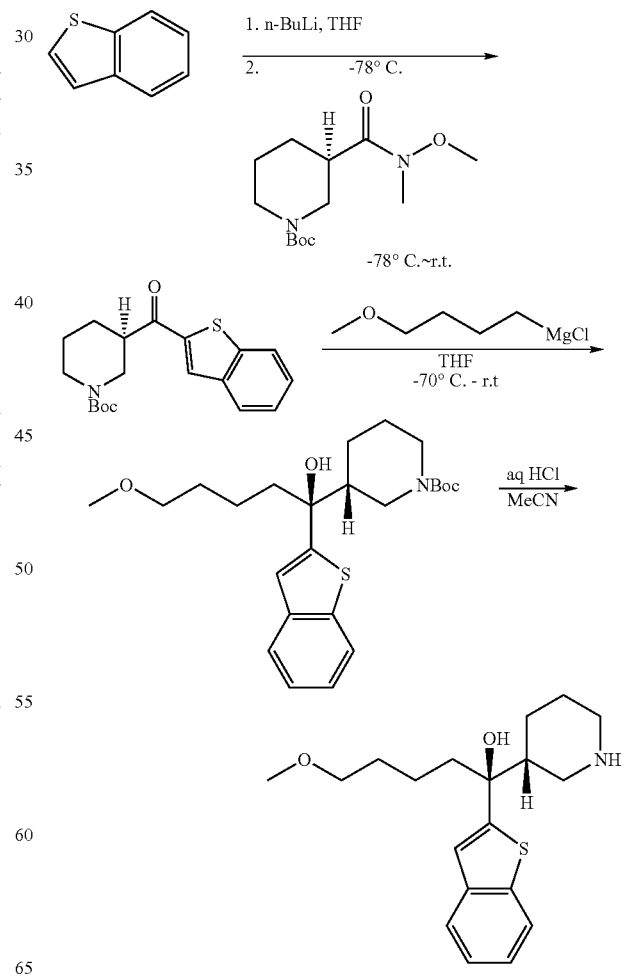

Step 1. (R)-tert-butyl 3-(benzo[b]thiophene-2-carbonyl)piperidine-1-carboxylate

A solution of benzothiophene (117 μL, 1 mmol) in dry THF (4 mL) was cooled to −70° C. A solution of 1.6M n-BuLi in hexanes (950 μL, 1.5 equiv) was added dropwise. After 10 min, a solution of Weinreb amide (282 mg, 1 equiv) in dry THF (2.5 mL) was added dropwise. The mixture was allowed to warm to rt and stirred overnight. Sat'd aq NH₄Cl (30 mL) was added and the mixture was extracted with ether (2×50 mL). The combined ether layers were washed with brine (20 mL) and dried over Na₂SO₄. After concentration, the crude product was purified by chromatography on a 12-g silica cartridge eluted with a gradient from 0 to 15% EtOAc in hexanes to afford (R)-tert-butyl 3-(benzo[b]thiophene-2-carbonyl)piperidine-1-carboxylate (292 mg, 85%).

Step 2. (R)-tert-butyl 3-((S)-1-(benzo[b]thiophen-2-yl)-1-hydroxy-5-methoxypentyl)piperidine-1-carboxylate A solution of (R)-tert-butyl 3-(benzo[b]thiophene-2-carbonyl)piperidine-1-carboxylate (146 mg, 0.423 mmol) in dry THF (5 mL) was cooled to −70° C. A solution of 1.34 M 4-methoxybutylmagnesium chloride in THF (630 μL, 2 equiv) was added slowly. After 10 min, the reaction mixture was allowed to warm up to rt slowly and stirred for another 2 h. Sat'd aq NH₄Cl (20 mL) was added and the mixture was extracted with ether (2×40 mL). The combined ether layers were washed with brine (20 mL) and dried over Na₂SO₄. After concentration, the crude product was purified by chromatography on a 12-g silica cartridge eluted with a gradient from 0 to 35% EtOAc in hexanes to afford (R)-tert-butyl 3-((S)-1-(benzo[b]thiophen-2-yl)-1-hydroxy-5-methoxypentyl)piperidine-1-carboxylate (160.7 mg, 88%).

Step 3. (S)-1-(benzo[b]thiophen-2-yl)-5-methoxy-1-((R)-piperidin-3-yl)pentan-1-ol hydrochloride (R)-tert-butyl 3-((S)-1-(benzo[b]thiophen-2-yl)-1-hydroxy-5-methoxypentyl)piperidine-1-carboxylate (160 mg, 0.37 mmol) was dissolved in 1:1 2 N aq HCl solution/acetonitrile (50 mL). The mixture was stirred overnight at rt and neutralized with 5% aq NaOH. The acetonitrile was removed by evaporation. The aqueous residue was extracted by CH₂Cl₂ (2×40 mL). The combined organic layers were concentrated to afford (S)-1-(benzo[b]thiophen-2-yl)-5-methoxy-1-((R)piperidin-3-yl)pentan-1-ol (102 mg, 83%) which was used without purification.

The following piperidines were prepared using procedures analogous to those described above using the heterocycle and base indicated below in Step 1.

(S)-1-(2,2-difluorobenzo[d][1,3]dioxol-4-yl)-5-methoxy-1-((R)-piperidin-3-yl)pentan-1-ol using 2,2-difluorobenzo[d][1,3]dioxole and s-BuLi in Step 1.

(S)-5-methoxy-1-(1'-methyl-1H-imidazol-2-yl)-1-((R)-piperidin-3-yl)pentan-1-ol using 1-methylimidazole and n-BuLi in Step 1.

1-(5-chloro-1-methyl-1H-imidazol-2-yl)-5-methoxy-1-(piperidin-3-yl)pentan-1-ol using 5-chloro-1-methyl-1H-imidazole and n-BuLi in Step 1.

(S)-5-methoxy-1-((R)-piperidin-3-yl)-1-(thiazol-2-yl)pentan-1-ol using thiazole and n-BuLi in Step 1.

(S)-5-methoxy-1-(5-methylthiazol-2-yl)-1-((R)-piperidin-3-yl)pentan-1-ol using 5-methylthiazole and n-BuLi in Step 1.

4-chloro-2-((R)-(3-methoxypropoxy)((R)-piperidin-3-yl)methyl)pyridine using 4-chloropyridine and n-BuLi/Me₂N(CH₂)₂OLi in Step 1.

Preparation 17

4-bromo-2-(trimethylsilyl)benzothiophene

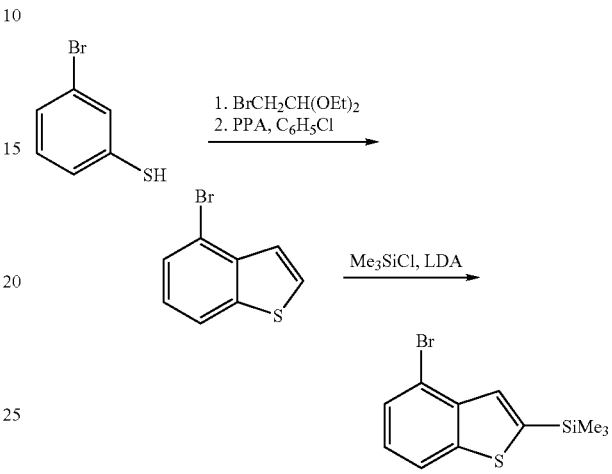

Step 1. (3-bromophenyl)(2,2-diethoxyethyl)sulfane

To a stirred solution of 3-bromothiophenol (5.0 g, 26 mmol) in DMSO (40 mL) was added a solution of KOH pellets (85% by wt, 2.15 g, 32 mmol) in water (4 mL) followed by bromoacetaldehyde diethyl acetal (4.5 mL, 29 mmol). The mixture was stirred at rt for 5 d, diluted with ether (300 mL) and washed with water (3×100 mL). The combined water washes were extracted with ether (100 mL). The combined ether extracts were washed with brine (100 mL), dried over MgSO₄ and concentrated to afford (3-bromophenyl)(2,2-diethoxyethyl)sulfane (8.23 g, 100%) as a colorless oil.

Step 2. 4-bromobenzothiophene

A stirred mixture of (3-bromophenyl)(2,2-diethoxyethyl)sulfane (8.23 g, 26 mmol), polyphosphoric acid (20 mL) and chlorobenzene (30 mL) was heated at 130° C. for 1 h. The mixture was allowed to cool to rt and 1 M aq NaOH (100 mL) was added. The mixture was extracted with ether (2×100 mL). The combined ether extracts were washed with water (25 m) and brine (25 mL) and dried over MgSO₄. Removal of the solvent left an oil (29.55 g) which was chromatographed on a 120-g silica cartridge eluted with hexanes. Fractions containing the desired product were concentrated to afford an oil (3.33 g) which resubmitted to chromatography under the same conditions to afford ~80% pure 4-bromobenzothiophene (1.16 g, 20%).

Step 3. 4-bromo-2-(trimethylsilyl)benzothiophene

A stirred solution of ~80% pure 4-bromobenzothiophene (580 mg, 2.7 mmol) and chlorotrimethylsilane (0.70 mL, 5.4 mmol) in dry THF (10 mL) was cooled to −70° C. and 2 M LDA in 1:1 THF/heptane (1.35 mL, 5.4 mmol) was added dropwise over 2 min. The mixture was stirred at −70° C. for 1.5 h and diluted with ether (80 mL) and 5% aq HCl (20 mL). The organic layer was separated, washed with sat'd aq NaHCO₃ (20 mL) and dried over MgSO₄. Removal of the solvent left 4-bromo-2-(trimethylsilyl)benzothiophene (740 mg, 95%) as an amber oil.

4-Bromo-2-(trimethylsilyl)-benzofuran was made following procedures analogous to those described in Example 90, using 3-bromophenol in Step 1.

Preparation 18

7-bromo-2-methylbenzofuran

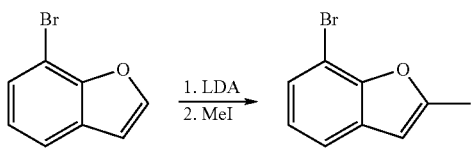

A stirred solution of 7-bromobenzofuran (493 mg, 2.5 mmol) in dry THF (5 mL) was cooled to −70° C. and 2M LDA in 1:1 THF/heptane (1.4 mL, 2.8 mmol) was added dropwise over 2 min. The mixture was stirred at −70° C. for 1 h and methyl iodide (0.19 mL, 3.0 mmol) was added. The mixture was stirred at −70° C. for 3 h and at 0° C. for 1 h. The mixture was poured into 5% aq HCl (60 mL) and extracted with ether (2×50 mL). The combined ether extracts were washed with sat'd aq NaHCO₃ (20 mL) and dried over MgSO₄. Removal of the solvent left an oil (470 mg) which was purified by chromatography on a 40-g silica cartridge eluted with hexanes to afford 7-bromo-2-methylbenzofuran (277 mg, 52%, estimated purity ~80%).

Preparation 19

(S)-1-(2-tert-butyl benzofuran-7-yl)-5-methoxy-1-((R)-piperidin-3-yl)pentan-1-ol

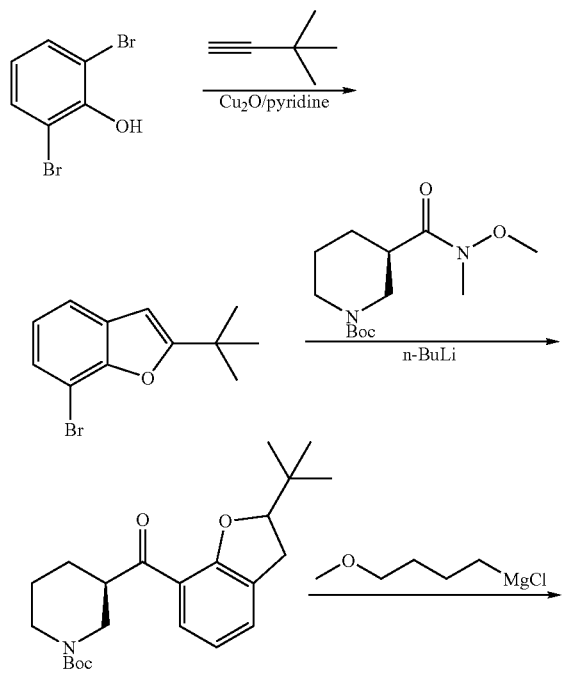

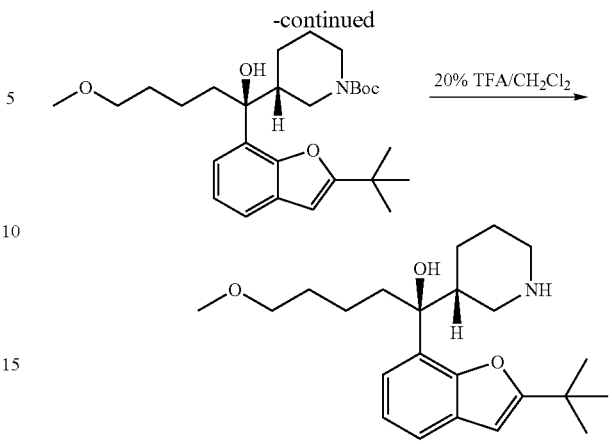

Step 1. 7-bromo-2-tert-butylbenzofuran 3,3-Dimethylbut-1-yne (1.6 g, 20 mmol) was added to a solution of 2,6-dibromophenol (5.0 g, 20 mmol) and Cu₂O (1.7 g, 12 mmol) in dry pyridine (50 mL) under N₂, then the mixture was heated to about 55° C. and stirred overnight. The mixture was filtered and the filtrate was concentrated to give a residue, which was dissolved in EtOAc. This solution was washed with brine and dried over Na₂SO₄. The solvent was removed and the residue was purified by column chromatography to afford 7-bromo-2-tert-butyl-benzofuran (1.3 g, 26%). ¹H NMR (CDCl₃): 1.40 (S, 9H), 6.41 (s, 1H), 7.04 (t, 1H), 7.38 (d, 1H), 7.42 (d, 1H).

Step 2. (R)-tert-butyl 3-(2-tert-butylbenzofuran-7-carbonyl)piperidine-1-carboxylate Under protection of N₂, a solution of 7-bromo-2-tert-butyl-benzofuran (0.5 g, 1.98 mmol) in anhydrous THF (5 mL) was cooled to −78° C. and 2.5 M n-BuLi solution in hexanes (0.87 mL, 2.18 mmol) was added dropwise slowly. The reaction mixture was stirred at −78° C. for 1 h and a solution of (R)-tert-butyl 3-(methoxy(methyl)carbamoyl)piperidine-1-carboxylate (0.65 g, 2.38 mmol) in anhydrous THF (5 mL) was added dropwise slowly. The reaction mixture was warmed to rt and stirred overnight. The mixture was quenched with satd aq NH₄Cl (20 mL) and extracted with EtOAc (3×30 mL). The combined organic extracts were dried over Na₂SO₄. Solvent removal and flash column chromatography afforded (R)-tert-butyl 3-(2-tert-butylbenzofuran-7-carbonyl)piperidine-1-carboxylate (0.41 g, 54%). ¹H NMR (CDCl₃): 7.83 (d, 1H), 7.19 (d, 1H), 7.26 (t, 1H), 6.440 (s, 1H), 4.1 (d, 1H), 3.75 (s, 1H), 2.83 (t, 1H), 2.27 (d, 1H), 1.82 (d, 1H), 1.590 (m, 4H), 1.426 (s, 9H), 1.406 (s, 9H)

Step 3. (R)-tert-butyl 3-((S)-1-(2-tert-butylbenzofuran-7-yl)-1-hydroxy-5-methoxypentyl)piperidine-1-carboxylate A 50 mL three-necked flask was charged with (R)-tert-butyl 3-(2-tert-butylbenzofuran-7-carbonyl)piperidine-1-carboxylate (0.41 g, 1.08 mmol) and anhydrous THF (8 mL). The flask was evacuated and refilled with N₂. The mixture was cooled with dry ice-acetone bath and the Grignard reagent derived from 1-chloro-4-methoxy-butane (5.4 mL, 2M) was added. The reaction mixture was allowed to slowly warm to rt while stirring overnight. The mixture was quenched with satd aq NH₄Cl (20 mL) and extracted with EtOAc (3×20 mL). The combined organic extracts were dried over Na₂SO₄ and concentrated in vacuo to afford (R)tert-butyl 3-((S)-1-(2-tert-butylbenzofuran-7-yl)-1-hydroxy-5-methoxypentyl)piperidine-1-carboxylate (0.5 g, 100%). ¹H NMR:(CDCl$_3$): 1.34 (s, 9H), 1.46 (s, 9H), 1.51 (m, 9H), 2.02 (m, 1H), 2.18 (m, 1H), 2.50 (m, 2)H, 2.67 (t, 1H), 3.23 (m, 5H), 3.99 (s, 1H), 4.43 (s, 1H), 6.35 (s, 1H), 7.16 (t, 1H), 7.23 (d, 1H), 7.39 (dd, 1H), Step 4. (S)-1-(2-tert-butylbenzofuran-7-yl)-5-methoxy-1-((R)-piperidin-3-yl)pentan-1-ol (R)-tert-butyl 3-((S)-1-(2-tert-butylbenzofuran-7-yl)-1-hydroxy-5-methoxypentyl)piperidine-1-carboxylate (250 mg, 0.53 mmol) was dissolved in 20% TFA/CH$_2$Cl$_2$ (4 mL). The reaction mixture was stirred at rt for 1 h. The mixture was quenched with satd aq NaHCO$_3$ (15 mL) and extracted with EtOAc (3×10 mL). The combined organic extracts were dried over Na$_2$SO$_4$. The filtrate was evaporated to give a residue, which was purified by preparative HPLC to afford pure (S)-1-(2-tert-butylbenzofuran-7-yl)-5-methoxy-1-((R)-piperidin-3-yl)pentan-1-ol (185 mg, 94%). $^1$H NMR (CDCl$_3$): 0.95 (s, 1), 1.24 (m, 2H), 1.36 (s, 9H), 1.49 (m, 3H), 1.64 (m, 2H), 2.02 (m, 2H), 2.55 (m, 2H), 2.82 (s, 1H), 3.1 (s, 1H), 3.25 (m, 5H), 3.66 (m, 1H), 6.35 (s, 1H), 7.18 (t, 1H), 7.28 (d, 1H), 7.42 (d, 1H), 8.96 (s, 1H), 9.33 (s, 1H)

The following compounds were prepared using procedures analogous to those described above:

(S)-1-(2-isobutylbenzofuran-7-yl)-5-methoxy-1-((R)-piperidin-3-yl)pentan-1-ol using 4-methylpentyne in place of 3,3-dimethylbut-1-yne in Step 1.

Preparation 20

(S)-1-(2-(cyclopropylmethoxy)-3-fluorophenyl)-5-methoxy-1-((R)-piperidin-3-yl)pentan-1-ol

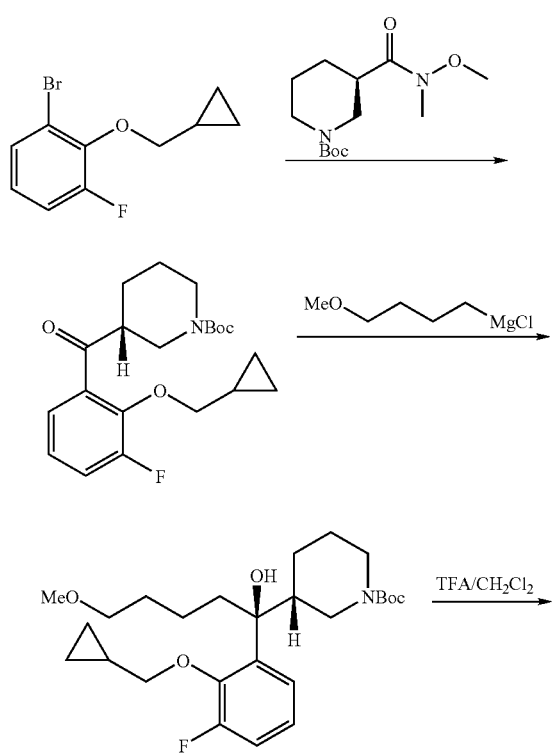

-continued

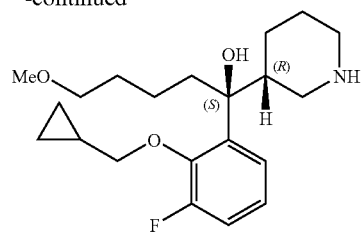

Step 1. (R)-tert-butyl 3-(2-(cyclopropylmethoxy)-3-fluorobenzoyl)piperidine-1-carboxylate A 50 mL three-necked flask was charged with magnesium turning (240 mg, 10 mmol) and a small crystal of iodine. The flash was evacuated and refilled with N$_2$. A portion of a solution of 1-bromo-2-cyclopropylmethyl-3-fluoro-benzene (2.1 g, 8.57 mmol) in dry THF (10 mL) was added dropwise to trigger the reaction. When the color of iodine had disappeared, the residual solution was added dropwise slowly. The mixture was stirred under reflux for 2.5 h and most of magnesium was consumed. The resulting Grignard reagent was used for the next step. To another 100-mL three-necked flask was added (R)-tert-butyl 3-(methoxy(methyl)-carbamoyl)piperidine-1-carboxylate (1.55 g, 5.7 mmol) and THF (15 mL). The flask was evacuated and refilled with N$_2$. The mixture was cooled in a dry ice-acetone bath and the Grignard reagent prepared above (10 mL) was added slowly. The reaction mixture was stirred at −20 to −10° C. for 2.5 h. The mixture was quenched with sat'd aq NH$_4$Cl (20 mL), extracted with EtOAc (3×), and the combined organic layers were dried over Na$_2$SO$_4$. Solvent removal and flash column chromatography, eluting with 5% EtOAc/PE afforded (R)-tert-butyl 3-(2-(cyclopropylmethoxy)-3-fluorobenzoyl)piperidine-1-carboxylate (1.5 g, 70%). $^1$H NMR (400 MHz, CDCl$_3$): 0.27 (m, 2H), 0.57 (m, 2H) 1.20 (m, 1H), 1.43 (s, 9H), 1.60-1.51 (m, 4H), 1.73 (m, 1H), 2.02 (m, 1H), 2.79 (m, 1H), 3.47 (m, 1H), 3.98 (m, 3H), 4.20 (m, 1H), 7.04 (m, 1H), 7.20 (m, 2H). MS (E/Z): 378 (M+H$^+$).

Step 2. (R)-tert-butyl 3-((S)-1-(2-(cyclopropylmethoxy)-3-fluorophenyl)-1-hydroxy-5-methoxypentyl)piperidine-1-carboxylate A flame dried 50 mL three-necked flask was charged with magnesium turnings (380 mg, 15.8 mmol) and a small crystal of iodine in THF (5 mL). The flask was evacuated and refilled with N$_2$. Then a solution of 1-chloro-4-methoxybutane (1.6 g, 13.2 mmol) in THF (10 mL) was added dropwise slowly to the mixture. The reaction mixture was stirred under reflux for 2.5 h and most of the magnesium was consumed. The resulting Grignard reagent was used as follows. To another 100 mL three-necked flask was added (R)-tert-butyl 3-(2-(cyclopropylmethoxy)-3-fluorobenzoyl)piperidine-1-carboxylate (0.5 g, 1.32 mmol) and THF (10 mL). The flask was evacuated and refilled with N$_2$. The mixture was cooled with a dry ice-acetone bath and the Grignard reagent (250 mL) was added. The reaction mixture was allowed to warm slowly to rt while stirring overnight. The mixture was quenched with sat'd aq NH$_4$Cl (10 mL), extracted with EtOAc (3×), and the combined organic layers were dried over Na$_2$SO$_4$ Evaporation of the solvent and purification by flash column chromatography, eluting with 10% EtOAc/PE afforded (R)-tert-butyl 3-((S)-1-(2-(cyclopropylmethoxy)-3-fluorophenyl)-1-hydroxy-5-methoxypentyl)piperidine-1-carboxylate (560 mg, 91%). $^1$H NMR (400 MHz, CDCl$_3$): 0.35 (m, 2H), 0.63 (m, 2H), 1.05 (m, 1H), 1.43 (s, 9H), 1.55-1.20 (m, 9H), 1.85 (m, 1H), 2.55

(m, 1H), 2.67 (m, 1H), 3.27 (s, 3H), 3.33 (m, 2H), 3.85 (m, 1H), 4.05 (m, 2H), 4.25 (m, 1H), 6.97 (m, 3H). MS (E/Z): 466 (M+H+).

Step 3. (S)-1-(2-(cyclopropylmethoxy)-3-fluorophenyl)-5-methoxy-1-((R)piperidin-3-yl)pentan-1-ol A solution of (R)-tert-butyl 3-((S)-1-(2-(cyclopropylmethoxy)-3-fluorophenyl)-1-hydroxy-5-methoxypentyl)piperidine-1-carboxylate (120 mg) in 20% TFA/CH$_2$Cl$_2$ (20 mL) was stirred at 0° C. for 5 min. The solvent was neutralized by addition of sat'd aq NaHCO$_3$, and the mixture was extracted with CH$_2$Cl$_2$ (3×). The combined organic layers were dried over Na$_2$SO$_4$ and evaporated to give the crude product. LC-MS analysis of the crude product indicated the presence of two isomers (10:1). The crude product was purified by reverse phase prep HPLC to afford the major isomer, (S)-1-(2-(cyclopropylmethoxy)-3-fluorophenyl)-5-methoxy-1-((R)-piperidin-3-yl)pentan-1-ol (40 mg, 42%). $^1$H NMR (400 MHz, CD$_4$O): 0.36 (m, 2H), 0.63 (m, 2H), 0.86 (m, 1H), 1.55-1.11 (m, 1H), 1.82 (m, 1H), 2.29 (m, 2H), 2.45 (m, 1H), 2.66 (t, 1H), 2.94 (d, 1H), 3.24 (s, 3H), 3.31 (m, 2H), 3.91 (m, 2H), 6.98 (m, 2H), 726 (m, 1H). MS (E/Z): 366 (M+1). In addition, 2-fluoro-6-((S)-1-hydroxy-5-methoxy-1-((R)-piperidin-3-yl)pentyl)phenol was isolated as a byproduct.

Preparation 21

Piperidines from Weinreb Amides and 2-Bromophenols (S)-5-methoxy-1-(2-(2,2-(dimethyl)propoxy)phenyl)-1-((R)-piperidin-3-yl)pentan-1-ol hydrochloride

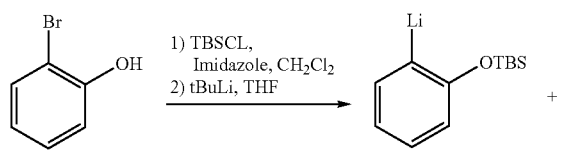

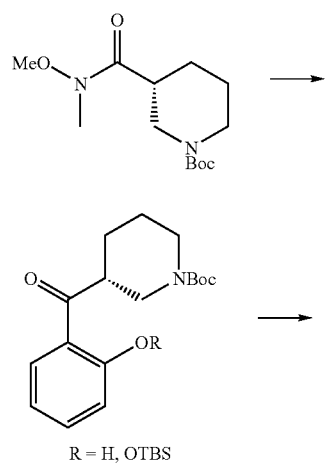

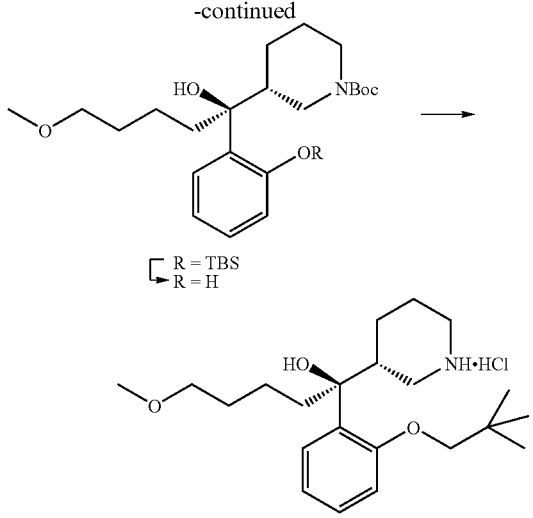

Step 1. Bromo-2-[(tert-butyl)dimethylsiloxy]benzene

A solution of 2-bromophenol (5 mL, 47 mmol), imidazole (8 g, 118 mmol) and tertbutyldimethylsilyl chloride (8.6 g, 57 mmol) in DMF (50 mL) was stirred at rt overnight. The reaction was treated with water (150 mL) and extracted with Et$_2$O (4×25 mL). The organic phase was washed with 50% aq lithium chloride solution twice, dried over MgSO$_4$ and filtered. The solvent was evaporated and the crude product was purified by filtration through silica gel, washing with 1:1 EtOAc/hexanes to afford bromo-2-[(tert-butyl)dimethylsiloxy]benzene (13.4 g, 99%).

Step 2. 2-((S)-1-hydroxy-5-methoxy-1-((R)—N-Boc-piperidin-3-yl)pentyl)[tertbutyldimethylsiloxy]benzene A solution of bromo-2-[(tert-butyl)dimethylsiloxy]benzene (2.1 g, 7.4 mmol) in Et$_2$O (35 mL) was cooled to −78° C. and treated with 1.7 M tert-butyllithium in hexanes (8.6 mL, 15 mmol). The reaction was stirred for 30 min and a solution of (R)-tert-butyl 3-(N-methoxy-N-methylcarbamoyl)piperidine-1-carboxylate (1.0 g, 3.7 mmol) in Et$_2$O was added slowly. The reaction was allowed to stir and warm to rt over a two-hour period. Saturated aq ammonium chloride was added to quench the reaction. The aq phase was extracted with Et$_2$O three times. The combined organic layers were washed with brine and dried over MgSO$_4$. The solvent was removed by evaporation and the crude product was purified by flash chromatography on silica gel eluting with EtOAc/hexanes to give a mixture of (2-tert-butyldimethylsiloxyphenyl)((R)—N-Boc-piperidin-3-yl)methanone and (2-hydroxyphenyl)((R)—N-Boc-piperidin-3-yl)methanone. A −20° C. solution of the crude mixture in tetrahydrofuran was treated with 1.3 M 4-methoxybutylmagnesium chloride in THF (14.9 mL, 19.4 mmol). The reaction was stirred and allowed to warm to rt over a two hour period. The reaction was quenched with ammonium chloride. The aq layer was extracted with Et$_2$O. The combined organic layers were dried over MgSO$_4$ and filtered. The solvent was evaporated and the crude product was purified by flash chromatography on silica gel eluting with EtOAc/hexanes to afford 2-((S)-1-hydroxy-5-methoxy-1-((R)—N-Boc-piperidin-3-yl)pentyl)[tertbutyldimethylsiloxy]benzene (874 mg, 47%) and 2-((S)-1-hydroxy-5-methoxy-1-((R)—N-Boc-piperidin-3-yl)pentyl)phenol (650 mg, 45%).

To a solution of 2-((S)-1-hydroxy-5-methoxy-1-((R)—N-Boc-piperidin-3-yl)pentyl)[tert-butyldimethylsiloxy]benzene (710 mg, 1.40 mmol) in tetrahydrofuran (7 mL) was added 1M tetrabutylammonium fluoride in THF (2.1 mL, 2.1 mmol). The mixture was stirred at rt for one hour. The mixture was diluted with EtOAc (20 mL) and washed with brine twice. The organic layer was dried over sodium sulfate and filtered. The filtrate was evaporated to give a residue, which was purified by flash chromatography on silica gel eluting with EtOAc/hexanes to give 2-((S)-1-hydroxy-5-methoxy-1-((R)—N-Boc-piperidin-3-yl)pentyl)[tertbutyldimethylsiloxy]benzene (450 mg, 81%).

Step 3. ((S)-5-methoxy-1-(2-(2,2-(dimethyl)propoxy)phenyl)-1-((R)-piperidin-3-yl)pentan-1-ol hydrochloride A solution of 2-((S)-1-hydroxy-5-methoxy-1-((R)—N-Boc-piperidin-3-yl)pentyl)phenol (195 mg, 0.500 mmol), 1-bromo-2,2-dimethylpropane (1.0 ml, 7.5 mmol), and cesium carbonate (230 mg, 0.71) in NMP (2 mL) was heated and stirred in a microwave reactor for 20 min at 130° C. After removal of solvent, the mixture was redissolved in methylene chloride and filtered. The filtrate was evaporated to give a residue which was used without any further purification.

A solution of crude (R)-tert-butyl-3-((S)-1-hydroxy-5-methoxy-1-(2-(2,2-(dimethyl)propoxy)phenyl)pentyl)piperidine-1-carboxylate in MeCN (50 mL) was treated with 2M aq hydrochloric acid (50 mL) and stirred at rt overnight. The solvent was evaporated to afford ((S)-5-methoxy-1-(2-(2,2-(dimethyl)propoxy)phenyl)-1-((R)-piperidin-3-yl)pentan-1-ol hydrochloride (122 mg, 67%) as an oil.

The following piperidines were prepared using procedures analogous to those described above, replacing 1-bromo-2,2-dimethylpropane in Step 3 with the alkylating agent indicated and using DMF as solvent at rt in place of NMP at elevated temperature:

| Piperidine | Alkyl halide |
|---|---|
| 1-(2-(cyclopentylmethoxy)phenyl)-5-methoxy-1-((R)-piperidin-3-yl)pentan-1-ol | bromomethylcyclopentane |
| 1-(2-(cyclopentyloxy)phenyl)-5-methoxy-1-((R)-piperidin-3-yl)pentan-1-ol | bromocyclopentane |
| 1-(2-(cyclobutylmethoxy)phenyl)-5-methoxy-1-((R)-piperidin-3-yl)pentan-1-ol | bromomethylcyclobutane |
| 1-(2-(cyclopropylmethoxy)phenyl)-5-methoxy-1-((R)-piperidin-3-yl)pentan-1-ol | bromomethylcyclopropane |
| 1-(2-(2-cyclopropylethoxy)phenyl)-5-methoxy-1-((R)-piperidin-3-yl)pentan-1-ol | (2-bromoethyl)cyclopropane |
| 1-(2-(benzyloxy)phenyl)-5-methoxy-1-((R)-piperidin-3-yl)pentan-1-ol | benzyl bromide |
| 1-(2-(4-fluorobenzyloxy)phenyl)-5-methoxy-1-((R)-piperidin-3-yl)pentan-1-ol | 4-fluorobenzyl bromide |
| 1-(2-(cyclohexylmethoxy)phenyl)-5-methoxy-1-((R)-piperidin-3-yl)pentan-1-ol | bromomethylcyclohexane |

Preparation 22

(3R)-tert-butyl 3-((S)-1-(2-(2-chlorophenyl)phenyl)-1-hydroxy-5-methoxypentyl)piperidine-1-carboxylate

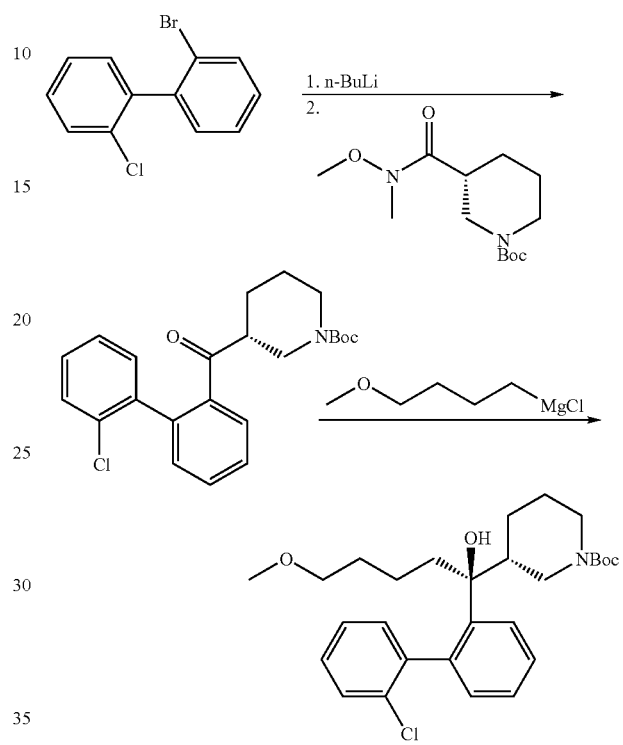

Step 1. (3R)-1-(tert-butoxycarbonyl)-3-((2-(2-chlorophenyl))benzoyl)piperidine

To a solution of 2-bromo-2-chloro-biphenyl (5.34 g, 20 mmol) in anhydrous THF (50 mL) cooled to −78° C. was added dropwise a solution of 1.6 M n-BuLi in hexane (12.5 mL, 20 mmol). The reaction mixture was stirred at −78° C. for 1 h and a solution of (R)-tert-butyl 3-(N-methoxy-N-methylcarbamoyl)-piperidine-1-carboxylate (5.44 g, 20 mmol) in anhydrous THF (50 mL) was added. The mixture was allowed to warm to rt and stirred overnight. The mixture was quenched with satd aq NH₄Cl (100 mL) and extracted with EtOAc (3×75 mL). The combined organic layers were dried over Na₂SO₄ and concentrated to give the crude product, which was purified by flash column chromatography to afford (3R)-1-(tert-butoxycarbonyl)-3-((2-(2-chlorophenyl))benzoyl)piperidine (4.43 g, 55%).

Step 2. (3R)-tert-butyl 3-((S)-1-(2-(2-chlorophenyl)phenyl)-1-hydroxy-5-methoxypentyl)-piperidine-1-carboxylate A 250 mL three-necked flask was charged with magnesium turning (2.88 g, 0.12 mol) and a small crystal of iodine. The flask was evacuated and refilled with N₂. A solution of 1-chloro-4-methoxybutane (15 g, 0.12 mol) in THF (60 ml) was added dropwise to the above mixture. After heating under reflux for 2 h most of magnesium had been consumed and the Grignard solution was cooled to rt. A 250 mL three-necked flask was charged with (3R)-1-(tert-butoxycarbonyl)-3-((2-(2-chlorophenyl))benzoyl)piperidine (4.43 g, 11 mmol) and THF (50 mL), evacuated and refilled with N₂. The mixture was cooled in a dry ice-acetone bath and the Grignard reagent was added dropwise. The mixture was allowed to warm slowly to rt and stirred overnight. The mixture was quenched with satd aq NH$_4$Cl (100 mL) and extracted with EtOAc. The combined organic layers were dried over Na$_2$SO$_4$ and concentrated to give the crude product which was purified by flash column chromatography to afford pure (3R)-tert-butyl 3-((S)-1-(2-(2-chlorophenyl)phenyl)-1-hydroxy-5-methoxypentyl)piperidine-1-carboxylate (2.5 g, 47%).

The following piperidines were prepared using procedures analogous to those described above substituting the bromobiphenyls indicated in Step 1 followed by Boc removal under standard conditions:

| Piperidine | Bromobiphenyl |
| --- | --- |
| 1-(biphenyl-2-yl)-5-methoxy-1-((R)-piperidin-3-yl)pentan-1-ol | 2-bromo-1,1'-biphenyl |
| 5-methoxy-1-((R)-piperidin-3-yl)-1-(2-(pyridin-2-yl)phenyl)pentan-1-ol | 2-(2-bromophenyl)pyridine |
| (S)-5-methoxy-1-(2-(5-methylfuran-2-yl)phenyl)-1-((R)-piperidin-3-yl)pentan-1-ol | 2-(2-bromophenyl)-5-methylfuran |
| (1S)-5-methoxy-1-(2'-methylbiphenyl-2-yl)-1-((R)-piperidin-3-yl)pentan-1-ol | 2-bromo-2'-methylbiphenyl |
| (S)-5-methoxy-1-(3'-methylbiphenyl-2-yl)-1-((R)-piperidin-3-yl)pentan-1-ol | 2-bromo-3'-methylbiphenyl |
| (S)-5-methoxy-1-(4'-methylbiphenyl-2-yl)-1-((R)-piperidin-3-yl)pentan-1-ol | 2-bromo-4'-methylbiphenyl |
| (1S)-1-(2'-fluorobiphenyl-2-yl)-5-methoxy-1-((R)-piperidin-3-yl)pentan-1-ol | 2-bromo-2'-fluorobiphenyl |
| (1S)-1-(3'-fluorobiphenyl-2-yl)-5-methoxy-1-((R)-piperidin-3-yl)pentan-1-ol | 2-bromo-3'-fluorobiphenyl |
| (S)-1-(4'-fluorobiphenyl-2-yl)-5-methoxy-1-((R)-piperidin-3-yl)pentan-1-ol | 2-bromo-4'-fluorobiphenyl |
| (S)-1-(6-fluorobiphenyl-2-yl)-5-methoxy-1-((R)-piperidin-3-yl)pentan-1-ol | 2-bromo-6-fluorobiphenyl |
| (S)-1-(3'-chlorobiphenyl-2-yl)-5-methoxy-1-((R)-piperidin-3-yl)pentan-1-ol | 2-bromo-3'-chlorobiphenyl |
| (S)-1-(4'-chlorobiphenyl-2-yl)-5-methoxy-1-((R)-piperidin-3-yl)pentan-1-ol | 2-bromo-4'-chlorobiphenyl |
| (S)-1-(6-chlorobiphenyl-2-yl)-5-methoxy-1-((R)-piperidin-3-yl)pentan-1-ol | 2-bromo-6-chlorobiphenyl |
| (S)-1-(6-fluoro-3'-methylbiphenyl-2-yl)-5-methoxy-1-((R)-piperidin-3-yl)pentan-1-ol | 2-bromo-6-fluoro-3'-methylbiphenyl |
| (1S)-1-(2'-fluoro-5'-methylbiphenyl-2-yl)-5-methoxy-1-((R)-piperidin-3-yl)pentan-1-ol | 2'-bromo-2-fluoro-5-methylbiphenyl |
| (S)-1-(4-fluoro-3'-methylbiphenyl-2-yl)-5-methoxy-1-((R)-piperidin-3-yl)pentan-1-ol | 2-bromo-4-fluoro-3'-methylbiphenyl |
| (S)-1-(5-fluoro-3'-methylbiphenyl-2-yl)-5-methoxy-1-((R)-piperidin-3-yl)pentan-1-ol | 2-bromo-5-fluoro-3'-methylbiphenyl |
| (S)-1-(3',4'-difluorobiphenyl-2-yl)-5-methoxy-1-((R)-piperidin-3-yl)pentan-1-ol | 2-bromo-3',4'-difluorobiphenyl |
| (1S)-1-(2',3'-difluorobiphenyl-2-yl)-5-methoxy-1-((R)-piperidin-3-yl)pentan-1-ol | 2'-bromo-2,3-difluorobiphenyl |
| (S)-1-(3',6-difluorobiphenyl-2-yl)-5-methoxy-1-((R)-piperidin-3-yl)pentan-1-ol | 2-bromo-3',6-difluorobiphenyl |
| (S)-1-(6-fluoro-3',5'-dimethylbiphenyl-2-yl)-5-methoxy-1-((R)-piperidin-3-yl)pentan-1-ol | 2-bromo-6-fluoro-3',5'-dimethylbiphenyl |
| (1S)-1-(2',6-difluoro-5'-methylbiphenyl-2-yl)-5-methoxy-1-((R)-piperidin-3-yl)pentan-1-ol | 2'-bromo-2,6'-difluoro-5-methylbiphenyl |
| (S)-1-(6-chloro-3'-methylbiphenyl-2-yl)-5-methoxy-1-((R)-piperidin-3-yl)pentan-1-ol | 2-bromo-6-chloro-3'-methylbiphenyl |
| (S)-1-(3'-chloro-6-fluorobiphenyl-2yl)-5-methoxy-1-((R)-piperidin-3-yl)pentan-1-ol | 2-bromo-3'-chloro-6-fluorobiphenyl |
| (S)-1-(6-chloro-3'-fluorobiphenyl-2-yl)-5-methoxy-1-((R)-piperidin-3-yl)pentan-1-ol | 2-bromo-6-chloro-3'-fluorobiphenyl |
| (S)-5-methoxy-1-((R)-piperidin-3-yl)-1-(3'-(trifluoromethyl)biphenyl-2-yl)pentan-1-ol | 2-bromo-3'-(trifluoromethyl)biphenyl |
| (S)-1-(3',6-dichlorobiphenyl-2-yl)-5-methoxy-1-((R)-piperidin-3-yl)pentan-1-ol | 2-bromo-3',6-dichlorobiphenyl |
| (1S)-1-(3'-chloro-2',6-difluorobiphenyl-2-yl)-5-methoxy-1-((R)-piperidin-3-yl)pentan-1-ol | 2'-bromo-3-chloro-2,6'-difluorobiphenyl |
| (S)-1-(5-bromo-3'-methylbiphenyl-2-yl)-5-methoxy-1-((R)-piperidin-3-yl)pentan-1-ol | 5-bromo-2-iodo-3'-methylbiphenyl |

Preparation 24

Methyl (4S)-4-(6-chloro-3'-methylbiphenyl-2-yl)-4-hydroxy-4-(piperidin-3-yl)butylcarbamate

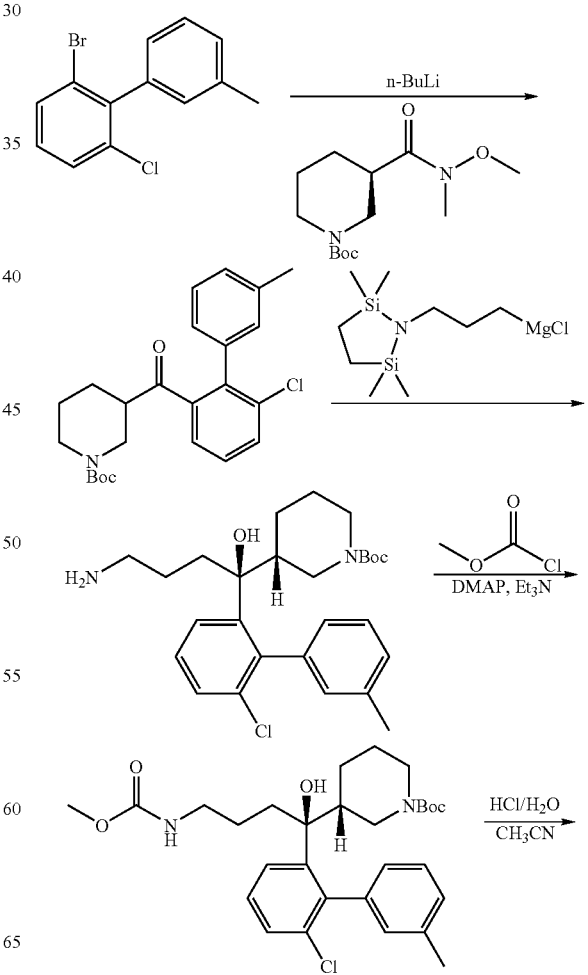

-continued

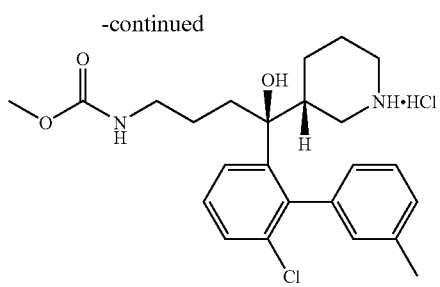

Step 1. (R)-tert-butyl 3-(6-chloro-3'-methylbiphenylcarbonyl)piperidine-1-carboxylate To a solution of 6-bromo-2-fluoro-3'-methylbiphenyl (2 g, 7.14 mmol) in anhydrous THF (30 mL) cooled to −78° C. was added dropwise a solution of 1.6 M of n-BuLi in hexane (4.46 mL). The reaction mixture was stirred at −78° C. for 1 h and a solution of (R)-tert-butyl 3-(methoxy(methyl)carbamoyl)piperidine-1-carboxylate (1.94 g, 7.14 mmol) in anhydrous THF (20 mL) was added. The mixture was allowed to warm to room temperature and stirred overnight. The mixture was quenched with satd aq NH$_4$Cl (40 mL) and extracted with EtOAc (40 mL). The combined organic layers were dried over Na$_2$SO$_4$ and concentrated to give crude product, which was purified by flash column chromatography to afford (R)-tert-butyl 3-(6-chloro-3'-methylbiphenylcarbonyl)piperidine-1-carboxylate (1 g, 34%). $^1$H NMR (400 MHz, CD$_3$OD): 0.80-1.20 (m, 8H), 1.30 (s, 1H), 1.40 (s, 1H), 1.40-1.60 (m, 2H), 2.00-2.18 (s, 1H), 2.30-2.40 (s, 3H), 2.60-2.80 (m, 2H), 3.50-3.80 (m, 2H), 7.00-7.15 (s, 2H), 7.20-7.30 (d, 1H), 7.30-7.40 (t, 2H), 7.39-7.48 (t, 1H), 7.60-7.70 (d, 1H); MS (E/Z): 414 (M+H$^+$)

Step 2. (R)-tert-butyl 3-((S)-4-amino-1-(6-chloro-3'-methylbiphenyl-2-yl)-1-hydroxybutyl)piperidine-1-carboxylate To a solution of (R)-tert-butyl 3-(6-chloro-3'-methylbiphenylcarbonyl)piperidine-1-carboxylate (800 mg, 1.94 mmol) in anhydrous THF (15 mL) cooled to −78° C. was added dropwise a solution of 2 M (3-(2,2,5,5-tetramethyl-1,2,5-azadisilolidin-1-yl)propyl)magnesium chloride in THF (0.968 mL, 1.94 mmol). After addition, the reaction mixture was allowed to warm slowly to room temperature while stirring overnight. The mixture was quenched with satd aq NH$_4$Cl (15 mL) and extracted with CH$_2$Cl$_2$ (3×). The combined organic layers were dried over Na$_2$SO$_4$ and concentrated to give crude (R)-tert-butyl 3-((S)-4-amino-1-(6-chloro-3'-methylbiphenyl-2-yl)-1-hydroxybutyl)piperidine-1-carboxylate (900 mg), which was used in the next step without further purification.

Step 3. (R)-tert-butyl 3-((S)-1-(6-chloro-3'-methylbiphenyl-2-yl)-1-hydroxy-4-(methoxycarbonylamino)butyl)piperidine-1-carboxylate To a solution of (R)-tert-butyl 3-((S)-4-amino-1-(6-chloro-3'-methylbiphenyl-2-yl)-1-hydroxybutyl)piperidine-1-carboxylate (800 mg, 1.69 mmol) in anhydrous CH$_2$Cl$_2$ (15 mL) were added 4-dimethylaminopyridine (1.24 g, 10.17 mmol) and Et$_3$N (2.35 mL, 16.95 mmol). The mixture was cooled with an ice bath and methyl chloroformate (0.65 mL, 8.47 mmol) in CH$_2$Cl$_2$ (5 mL) was added. The reaction mixture was allowed to warm slowly to rt while stirring overnight. The solvent was removed in vacuo and the residue was purified by column chromatography to afford (R)-tert-butyl 3-((S)-1-(6-chloro-3'-methylbiphenyl-2-yl)-1-hydroxy-4-(methoxycarbonylamino)butyl)piperidine-1-carboxylate (700 mg, 78%). $^1$H NMR (400 MHz, CD$_3$OD): 1.00-1.70 (m, 17H), 2.30-2.50 (d, 3H), 2.50-2.70 (s, 1H), 2.90-2.31 (m, 2H), 3.50-3.52 (m, 3H), 3.80-4.20 (m, 2H), 6.0-7.15 (m, 3H), 7.15-7.40 (m, 3H), 7.50-7.70 (m, 1H); MS (E/Z): 531 (M+H$^+$)

Step 4. Methyl (4S)-4-(6-chloro-3'-methylbiphenyl-2-yl)-4-hydroxy-4-(piperidin-3-yl)butylcarbamate To a solution of (R)-tert-butyl 3-((S)-1-(6-chloro-3'-methylbiphenyl-2-yl)-1-hydroxy-4-(methoxycarbonylamino)butyl)piperidine-1-carboxylate (600 mg, 1.13 mg) in CH$_3$CN (18 mL) was added 2N aq HCl (15 mL) and the reaction mixture was vigorously stirred overnight at rt. The solvents were removed in vacuo to give methyl (4S)-4-(6-chloro-3'-methylbiphenyl-2-yl)-4-hydroxy-4-(piperidin-3-yl)butylcarbamate as its hydrochloride salt (500 mg, 95.8%). $^1$H NMR (400 MHz, CD$_3$OD): 1.00-1.20 (m, 1H), 1.30-1.80 (m, 8H), 1.80-2.00 (m, 2H), 2.40-2.50 (d, 3H), 2.75-2.90 (t, 1H), 2.90-3.05 (m, 3H), 3.05-3.12 (t, 1H), 3.20-3.30 (m, 1H), 3.30-3.40 (m, 1H), 3.60-3.70 (d, 4H), 6.90-6.98 (d, 1H), 7.00-7.12 (m, 1H), 7.25-7.50 (m, 4H), 7.75-7.85 (d, 1H); MS (E/Z): 431 (M+H$^+$)

The following piperidines were prepared using procedures analogous to those described above:

N—((S)-4-(6-fluoro-3'-methylbiphenyl-2-yl)-4-hydroxy-4-((R)-piperidin-3-yl)butyl)acetamide using acetyl chloride in place of methyl chloroformate in Step 3.

N—((S)-4-(biphenyl-2-yl)-4-hydroxy-4-((R)-piperidin-3-yl)butyl acetamide using 2-bromobiphenyl in Step 1 and acetyl chloride in place of methyl chloroformate in Step 3.

N—((S)-4-(3'-chloro-6-methylbiphenyl-2-yl)-4-hydroxy-4-((R)-piperidin-3-yl)butyl)acetamide using 6-bromo-2-chloro-3'-methylbiphenyl in Step 1 and acetyl chloride in place of methyl chloroformate in Step 3.

Methyl (S)-4-(6-chloro-3'-methylbiphenyl-2-yl)-4-hydroxy-4-((R)-piperidin-3-yl)butylcarbamate using 6-bromo-2-chloro-3'-methylbiphenyl in Step 1.

N-((4S)-4-(2',6-difluoro-5'-methylbiphenyl-2-yl)-4-hydroxy-4-((R)piperidin-3-yl)butyl)acetamide using 2'-bromo-2,6'-difluoro-5-methylbiphenyl in Step 1 and acetyl chloride in place of methyl chloroformate in Step 3.

Preparation 25

N-(2-((R)-(6-fluoro-3'-methylbiphenyl-2-yl)((R)-piperidin-3-yl)methoxy)ethyl)acetamide

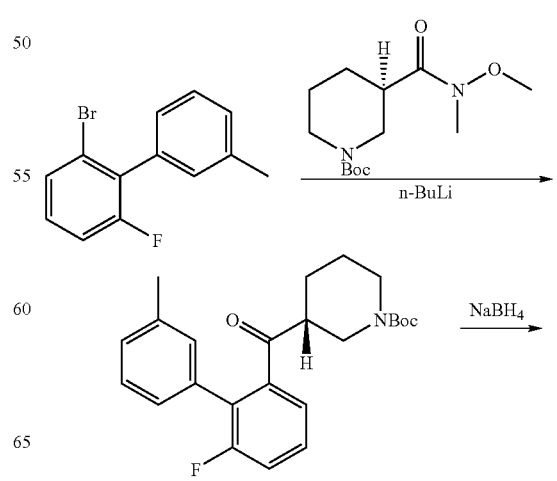

-continued

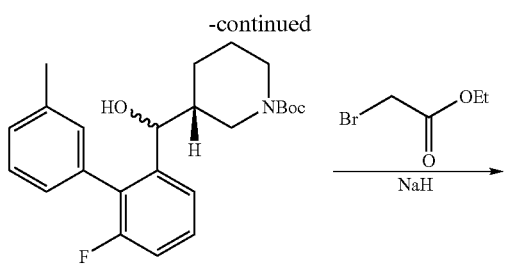

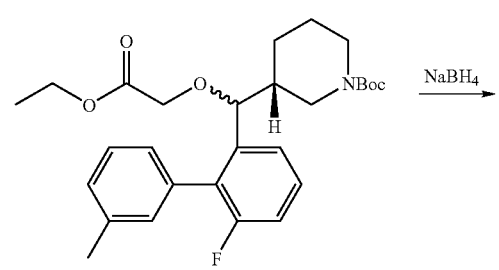

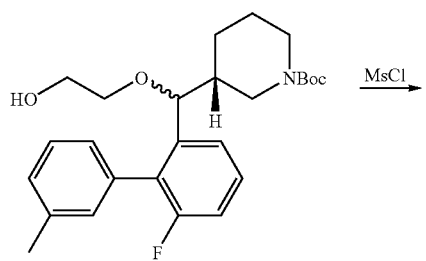

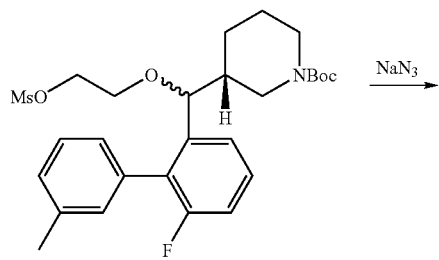

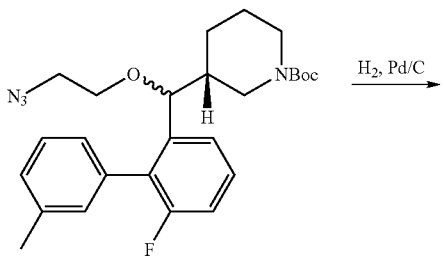

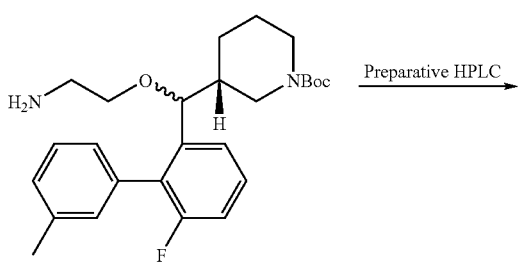

-continued

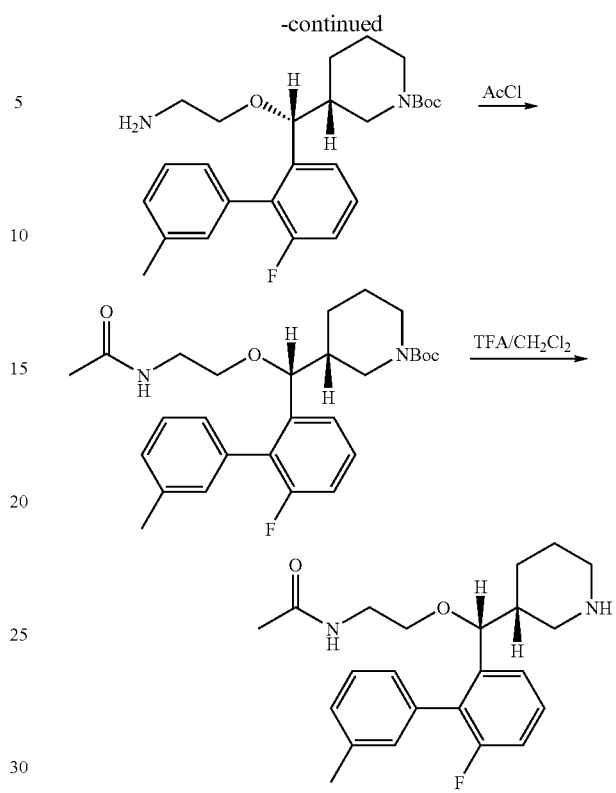

Step 1. (R)-tert-butyl 3-(6-fluoro-3'-methyl biphenyl carbonyl)piperidine-1-carboxylate A stirred solution of 6-bromo-2-fluoro-3'-methyl-biphenyl (7 g, 26.4 mmol) in THF (70 mL) under N₂ was cooled to −78° C. and 2.5 M n-BuLi in hexanes (10.56 mL, 26.4 mmol) was added dropwise slowly. The reaction mixture was stirred at −78° C. for 1 h and a solution of the Weinreb amide (R)-tert-butyl 3-(methoxy(methyl)carbamoyl)piperidine-1-carboxylate (7.18 g, 26.4 mmol) in THF (70 mL) was added dropwise slowly. The reaction mixture warmed to rt and stirred overnight. The mixture was quenched with satd aq NH₄Cl and extracted with EtOAc (3×). The combined organic extracts were dried over Na₂SO₄. Solvent removal and flash column chromatography gave (R)-tert-butyl 3-(6-fluoro-3'-methylbiphenylcarbonyl)piperidine-1-carboxylate (4 g, 40%). ¹H NMR (400 MHz, CDCl₃): 0.89 (m, 1H), 1.39 (s, 9H), 1.55 (m, 1H), 1.73 (m, 1H), 2.03 (m, 1H), 2.40 (s, 3H), 2.81 (m, 1H), 3.09 (m, 1H), 3.25 (m, 1H), 3.80 (m, 2H), 3.95 (m, 2H), 7.09-7.41 (m, 7H).

Step 2. (3R)-tert-butyl 3-((6-fluoro-3'-methylbiphenyl-2-yl)(hydroxy)methyl)piperidine-1-carboxylate To a solution of (R)-tert-butyl 3-(6-fluoro-3'-methylbiphenylcarbonyl)piperidine-1-carboxylate (3.5 g, 6.29 mmol) in MeOH (50 mL) was added NaBH₄ (0.95 g, 25 mmol) in portions at rt. After addition, the mixture was stirred for 2 h. Tlc showed the starting material had disappeared. The solvent was removed in vacuo to leave a residue which was partitioned between water and EtOAc. The organic layer was washed with H₂O and brine, dried over Na₂SO₄ and evaporated to give (3R)-tert-butyl 3-((6-fluoro-3'-methylbiphenyl-2-yl)(hydroxy)methyl)piperidine-1-carboxylate (3.5 g, 100%), which was used in the next step without purification.

Step 3. (3R)-tert-butyl 3-((2-ethoxy-2-oxoethoxy)(6-fluoro-3'-methylbiphenyl-2-yl)methyl)piperidine-1-carboxylate To a suspension of NaH (0.42 g, 17.6 mmol) in THF (50 mL) at 0~5° C. was added dropwise a solution of (3R)-tert-butyl 3-((6-fluoro-3'-methylbiphenyl-2-yl)(hydroxy)methyl) piperidine-1-carboxylate (3.5 g, 8.8 mmol) in THF (30 mL) and the reaction mixture was stirred for 1 h at rt. A solution of ethyl bromoacetate (2.92 g, 17.6 mmol) in THF (30 mL) was added dropwise to the above mixture, and then refluxed for 12 h. Tlc showed the starting material had disappeared. The reaction mixture was poured into satd aq NH$_4$Cl and extracted with EtOAc. The organic layer was dried over Na$_2$SO$_4$, filtered and concentrated in vacuo. The residue was purified by silica gel chromatography to afford (3R)-tert-butyl 3-((2-ethoxy-2-oxoethoxy)(6-fluoro-3'-methylbiphenyl-2-yl)methyl)piperidine-1-carboxylate (1.1 g, 38%). $^1$H NMR (400 MHz, CDCl$_3$): 1.26 (m, 3H), 1.40 (s, 9H), 2.10 (m, 1H), 2.39 (s, 3H), 2.51 (m, 1H), 3.51 (m, 1H), 3.78 (m, 1H), 3.96 (m, 2H), 4.16 (m, 3H), 4.23 (m, 2H), 4.69 (m, 2H), 6.97 (m, 2H), 7.06 (m, 1H), 7.20 (m, 1H), 7.29-7.41 (m, 3H).

Step 4. (3R)-tert-butyl 3-((6-fluoro-3'-methylbiphenyl-2-yl)(2-hydroxyethoxy)methyl)piperidine-1-carboxylate To a solution of (3R)-tert-butyl 3-((2-ethoxy-2-oxoethoxy)(6-fluoro-3'-methylbiphenyl-2-yl)methyl)piperidine-1-carboxylate (1.1 g, 2.3 mmol) in EtOH (20 mL) was added NaBH$_4$ (0.7 g, 18.1 mmol) in portions. After addition, the mixture was stirred at rt overnight. Tlc showed the start material had disappeared. The solvent was removed in vacuo to leave a residue, which was partitioned between water and EtOAc. The organic layer was washed with H$_2$O and brine, dried over Na$_2$SO$_4$, filtered and evaporated to give (3R)-tert-butyl 3-((6-fluoro-3'-methylbiphenyl-2-yl)(2-hydroxyethoxy)methyl)piperidine-1-carboxylate (1 g, 99%) which was used in the next step without purification.

Step 5. (3R)-tert-butyl 3-((6-fluoro-3'-methylbiphenyl-2-yl)(2-(methanesulfonyloxy)ethoxy)methyl)piperidine-1-carboxylate To a solution of (3R)-tert-butyl 3-((6-fluoro-3'-methylbiphenyl-2-yl)(2-hydroxyethoxy)methyl)piperidine-1-carboxylate (1 g, 2.3 mmol) in dry CH$_2$Cl$_2$ (15 mL) was added Et$_3$N (0.9 g, 9.0 mmol) at ca 0 to −5° C. A solution of MsCl (0.5 g, 4.5 mmol) in anhydrous CH$_2$Cl$_2$ (4 mL) was added dropwise at the same temperature. After addition, the mixture was allowed to warm to rt gradually. Tlc showed the starting material had disappeared. Water was added and the aqueous layer was extracted with CH$_2$Cl$_2$. The combined organic extracts were washed with 10% aq citric acid, satd aq NaHCO$_3$ and brine, dried over Na$_2$SO$_4$, filtered and concentrated to give (3R)-tert-butyl 3-((6-fluoro-3'-methylbiphenyl-2-yl)(2-(methanesulfonyloxy)ethoxy)methyl)piperidine-1-carboxylate (1.1 g, yield 94%), which was used in the next step without purification.

Step 6. (3R)-tert-butyl 3-((2-azidoethoxy)(6-fluoro-3'-methylbiphenyl-2-yl)methyl)piperidine-1-carboxylate (3R)-tert-butyl 3-((6-fluoro-3'-methylbiphenyl-2-yl)(2-(methanesulfonyloxy)ethoxy)methyl)piperidine-1-carboxylate (1.1 g, 2 mmol) was dissolved in anhydrous DMF (15 mL), solid NaN$_3$ (280 mg, 4 mmol) was added and the reaction mixture was heated to 80° C. for 5 h. The mixture was cooled to rt and diluted with EtOAc and water. The organic phase was separated, washed with water and dried over MgSO$_4$. Removal of the solvent gave (3R)-tert-butyl 3-((2-azidoethoxy)(6-fluoro-3'-methylbiphenyl-2-yl)methyl)piperidine-1-carboxylate (0.89 g, yield 90%) which was used in the next step without purification.

Step 7. (3R)-tert-butyl 3-((2-aminoethoxy)(6-fluoro-3'-methylbiphenyl-2-yl)methyl)piperidine-1-carboxylate A solution of (3R)-tert-butyl 3-((2-azidoethoxy)(6-fluoro-3'-methylbiphenyl-2-yl)methyl)piperidine-1-carboxylate (0.89 g) in methanol (20 mL) was added to wetted Pd/C (200 mg). After 3 cycles of evacuation and refilling with H$_2$, a balloon of H$_2$ was attached to the vessel and the mixture was stirred overnight. The reaction mixture was filtered through a pad of Celite and the solvent was removed to give the crude amine. Purification by preparative HPLC gave (3R)-tert-butyl 3-((R)-(2-aminoethoxy)(6-fluoro-3'-methylbiphenyl-2-yl)methyl)piperidine-1-carboxylate (220 mg, 26%). $^1$H NMR (400 MHz, CDCl$_3$): 1.10 (m, 2H), 1.43 (s, 9H), 1.49 (m, 2H), 1.89 (m, 1H), 2.10 (m, 1H), 2.39 (s, 3H), 3.16 (m, 2H), 3.51 (m, 2H), 4.15 (m, 1H), 6.97 (m, 3H), 7.10 (m, 1H), 7.30-7.48 (m, 3H).

Step 8. (3R)-tert-butyl 3-((R)-(2-acetamidoethoxy)(6-fluoro-3'-methylbiphenyl-2-yl)methyl)piperidine-1-carboxylate To a solution of (3R)-tert-butyl 3-((R)-(2-aminoethoxy)(6-fluoro-3'-methylbiphenyl-2-yl)methyl)piperidine-1-carboxylate (86 mg, 0.2 mmol) in anhydrous CH$_2$Cl$_2$ (8 mL) was added Et$_3$N (0.5 ml, 20 mmol). The mixture was cooled with an ice bath and acetyl chloride (15 mg, 0.2 mmol) in CH$_2$Cl$_2$ (4 mL) was added. The reaction mixture was stirred at rt for 0.5 h, then washed with water, dried over MgSO$_4$, filtered and concentrated to give (3R)-tert-butyl 3-((R)-(2-acetamidoethoxy)(6-fluoro-3'-methylbiphenyl-2-yl)methyl)piperidine-1-carboxylate (80 mg, 85%), which was used in the next step without purification.

Step 9. N-(2-((R)-(6-fluoro-3'-methylbiphenyl-2-yl)((R)-piperidin-3-yl)methoxy)ethyl)acetamide A solution of (3R)-tert-butyl 3-((R)-(2-acetamidoethoxy)(6-fluoro-3'-methylbiphenyl-2-yl)methyl)piperidine-1-carboxylate (80 mg) in 20% TFA/CH$_2$Cl$_2$ (5 mL) was stirred at 0° C. for 30 min. The solvent was neutralized by adding satd aq NaHCO$_3$ and extracted with CH$_2$Cl$_2$ (3×). The combined organic extracts were dried over Na$_2$SO$_4$ and evaporated to give N-(2-((R)-(6-fluoro-3'-methylbiphenyl-2-yl)((R)-piperidin-3-yl)methoxy)ethyl)acetamide (20 mg, 32%).

The following piperidines were prepared using procedures analogous to those described above:

methyl 2-((R)-(6-fluoro-3'-methylbiphenyl-2-yl)((R)-piperidin-3-yl)methoxy)ethylcarbamate using methyl chloroformate in place of acetyl chloride in Step 8.

3-((R)-(6-fluoro-3'-methylbiphenyl-2-yl)(3-methoxypropoxy)methyl)piperidine using 3-methoxypropyl methanesulfonate in Step 3 and eliminating Steps 4-8.

Preparation 26

N—((R)-4-(6-fluoro-3'-methylbiphenyl-3-yl)-4-((S)-piperidin-3-yl)butyl)acetamide

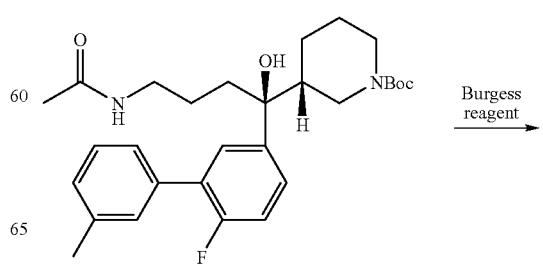

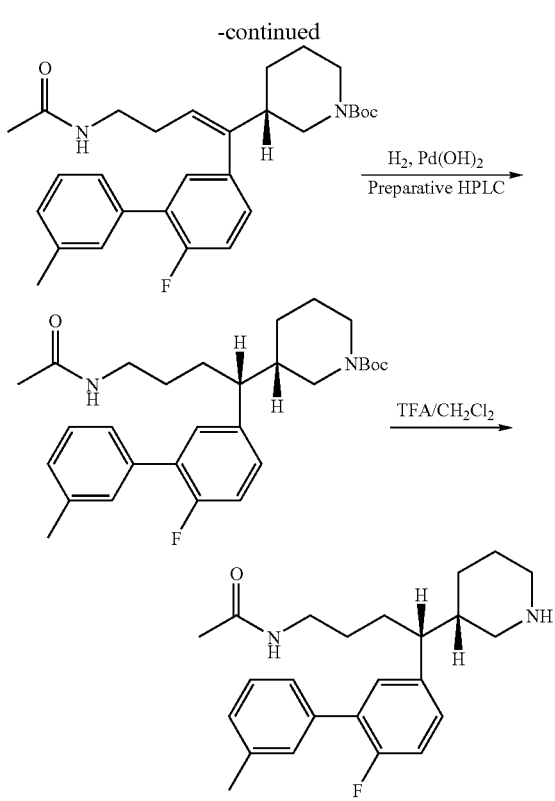

6.97-7.01 (m, 3 H), 3.95-4.18 (m, 1 H), 3.80-3.92 (m, 1 H), 3.03 (m, 2 H), 2.61-2.72 (m, 1 H), 2.42-2.52 (m, 1 H), 2.38 (d, 3 H), 1.90 (s, 3 H), 1.78 (m, 1 H), 1.42-1.65 (m, 4 H), 1.43 (s, 9 H), 1.15-1.31 (m, 3 H), 1.03 (m, 1 H). MS (E/Z): 483 (M+H$^+$)

Step 3. N—((R)-4-(6-fluoro-3'-methylbiphenyl-3-yl)-4-((S)-piperidin-3-yl)butyl)acetamide (S)-tert-butyl 3-((R)-4-acetamido-1-(6-fluoro-3'-methylbiphenyl-3-yl)butyl)piperidine-1-carboxylate (40 mg, 0.083 mmol) was dissolved in a solution of 20% (V/V) TFA/CH$_2$Cl$_2$ (3 mL). The reaction mixture was stirred at rt for 1 h (monitored by HPLC) and a solution of satd aq NaHCO$_3$ was added dropwise to adjust the pH to 7-8. The resulting mixture was extracted with CH$_2$Cl$_2$ (3×5 mL) and the combined extracts were washed with brine, dried over Na$_2$SO$_4$, and concentrated in vacuo to afford N—((R)-4-(6-fluoro-3'-methylbiphenyl-3-yl)-4-((S)piperidin-3-yl)butyl)acetamide (30 mg, 94%). MS (E/Z): 383 (M+H$^+$).

The following compounds were prepared using procedures analogous to those described above:

methyl (R)-4-(6-fluoro-3'-methyl biphenyl-2-yl)-4-((S)-piperidin-3-yl)butylcarbamate starting with methyl (S)-4-(6-fluoro-3'-methylbiphenyl-2-yl)-4-hydroxy-4-((R)-piperidin-3-yl)butylcarbamate.

Preparation 27 a) 6-Bromo-2-fluoro-3'-methylbiphenyl

Step 1. (S)-tert-butyl 3-(4-acetamido-1-(6-fluoro-3'-methylbiphenyl-3-yl)but-1-enyl)piperidine-1-carboxylate To a solution of (R)-tert-butyl 3-((S)-4-acetamido-1-(6-fluoro-3'-methylbiphenyl-3-yl)-1-hydroxybutyl)piperidine-1-carboxylate (380 mg, 0.76 mmol) in anhydrous toluene (8 mL) was added Burgess reagent (352 mg, 1.47 mmol). The reaction mixture was stirred under reflux overnight. The solvent was removed and the residue was partitioned between EtOAc and H$_2$O. The aqueous layer was extracted with EtOAc (3×10 mL). The combined organic extracts were washed with brine, dried over Na$_2$SO$_4$ and filtered. The filtrate was concentrated in vacuo and the residual oil was purified by preparative tlc to afford (S)-tert-butyl 3-(4-acetamido-1-(6-fluoro-3'-methylbiphenyl-3-yl)but-1-enyl)piperidine-1-carboxylate (110 mg, 30% yield). $^1$H NMR (400 MHz, MeOH):7.33-7.39 (m, 2 H), 7.13-7.23 (m, 2 H), 6.95-7.03 (m, 3 H), 5.29-5.33 (m, 1 H), 3.93-4.15 (m, 1 H), 3.78-3.91 (m, 1 H), 3.00-3.04 (m, 2H), 2.40-2.53 (m, 1 H), 2.37 (d, 3 H), 1.89 (s, 3 H), 1.75 (m, 1H), 1.44-1.62 (m, 4 H), 1.41 (s, 9 H), 1.16-1.32 (m, 3H), 1.01 (m, 1 H). MS (E/Z): 481 (M+H$^+$)

Step 2. (S)-tert-butyl 3-((R)-4-acetamido-1-(6-fluoro-3'-methylbiphenyl-3-yl)butyl)piperidine-1-carboxylate To a solution of (S)-tert-butyl 3-(4-acetamido-1-(6-fluoro-3'-methylbiphenyl-3-yl)but-1-enyl)piperidine-1-carboxylate (110 mg, 0.85 mmol) in anhydrous MeOH (3 mL) was added anhydrous Pd(OH)$_2$ (20 mg). The reaction mixture was stirred overnight under a hydrogen atmosphere (monitored by LC-MS) and filtered through a plug of silica. The filtrate was concentrated in vacuo to afford a mixture with two isomers. Purification by preparative HPLC gave (S)-tert-butyl 3-((R)-4-acetamido-1-(6-fluoro-3'-methylbiphenyl-3-yl)butyl)piperidine-1-carboxylate (40 mg, 36% yield). $^1$H NMR (400 MHz, MeOH):7.31-7.37 (m, 2 H), 7.20 (d, 2 H), 7.13 (d, 2 H),

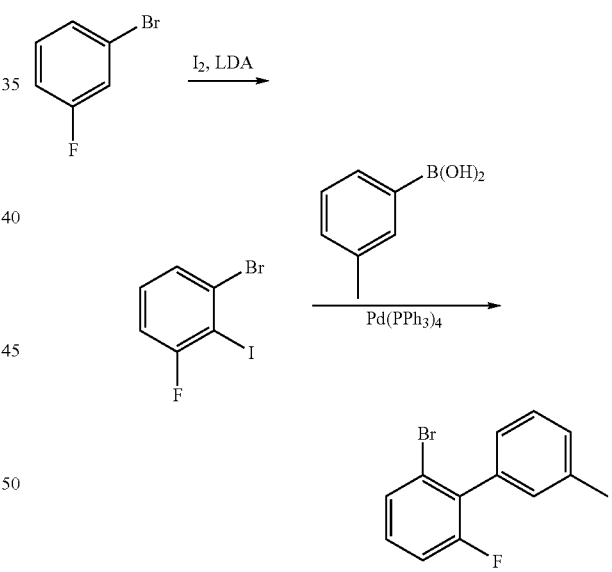

Step 1. 1-Bromo-3-fluoro-2-iodobenzene

To a solution of diisopropylamine (76 mL, 0.4 mol) in dry THF (664 mL) and n-hexane (220 mL) was added 2.5 M n-BuLi (160 mL. 0.4 mol) dropwise at −78° C. during a period of 1 h. The mixture was stirred for 1 h at −78° C. Then a solution of 1-bromo-3-fluoro-benzene (69 g, 0.4 mol) in dry THF (300 mL) at −78° C. was added to the above mixture dropwise. After stirring for an additional 1 h at −78° C., the mixture was added a solution of iodine (101 g, 0.4 mol) in dry THF (400 mL) dropwise at −78° C. The temperature was raised from −78° C. to rt during 2 h. After stirring for 18 h at rt, the mixture was concentrated in vacuo to give crude product (120 g) which was distilled under reduced pressure to afford 1-bromo-3-fluoro-2-iodobenzene (110 g). $^1$H NMR (400 MHz, DMSO): 7.24-7.19 (t, 1H), 7.38-7.32 (m, 1H), 7.55-7.53 (d, 1H).

Step 2. 6-Bromo-2-fluoro-3'-methylbiphenyl

Pd(Ph$_3$P)$_4$ in a 500-mL round-bottom flask under N$_2$ atmosphere was treated sequentially with a solution of 1-bromo-3-fluoro-2-iodo-benzene (30 g, 0.1 mol) in toluene (250 mL), a solution of 2N aq Na$_2$CO$_3$ (200 mL) and 3-methyl phenylboronic acid in ethanol (62 mL). This mixture was heated at reflux under N2 for 12 h, then cooled to rt. The mixture was partitioned between water and EtOAc. The combined organic layers were washed with brine, dried over MgSO$_4$, evaporated and purified by column chromatography to give 6-bromo-2-fluoro-3'-methyl-biphenyl (12 g). $^1$H NMR (400 MHz, CD$_3$OD): 7.03 (m, 2H), 7.48-7.04 (m, 4H), 7.50 (d, 1H).

b) 6-Bromo-2-chloro-3'-methyl-biphenyl

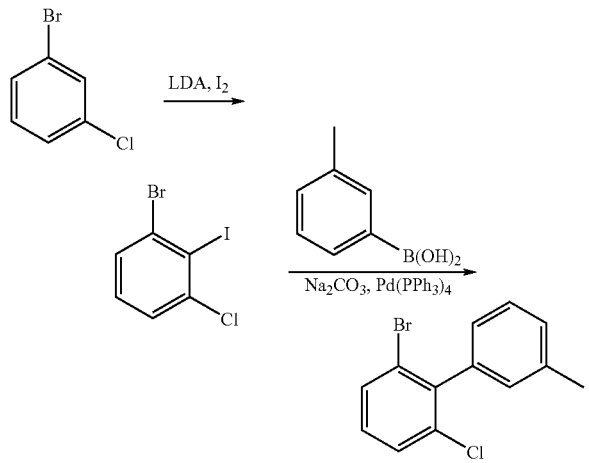

Step 1. 1-bromo-3-chloro-2-iodobenzene

To a solution of diisopropylamine (76 mL, 0.4 mol) in anhydrous THF (664 mL) and n-hexane (220 mL) was added 2.5 M n-BuLi (160 mL, 0.4 mol) dropwise at −78° C. over 1 h. The mixture was stirred for 1 h at −78° C. and a solution of 1-bromo-3-chlorobenzene (76 g, 0.4 mol) in anhydrous THF (300 mL) was added dropwise at −78° C. After stirring for an additional 1 h at the same temperature, a solution of iodine (101 g, 0.4 mol) in anhydrous THF (400 mL) was added dropwise at −78° C. The temperature was raised from −78° C. to room temperature during 2 h. After stirring for 18 h at rt, the mixture was concentrated in vacuo to give the crude product (120 g) which was distilled under reduced pressure to give 1-bromo-3-fluoro-2-iodobenzene (115 g, 91%). $^1$H NMR (400 MHz, CDCl$_3$): 7.12-7.18 (t, 1H), 7.35-7.41 (dd, 1H), 7.49-7.54 (dd, 1H); MS (E/Z): 317 (M+H$^+$)

Step 2. 6-bromo-2-chloro-3'-methyl-biphenyl

A 500-mL round-bottom flask under N$_2$ atmosphere was charged sequentially with Pd(Ph$_3$P)$_4$, 1-bromo-3-fluoro-2-iodobenzene (10 g, 0.032 mol) in toluene (80 mL), 2N aqueous sodium carbonate (55 mL) and 3-methylphenylboronic acid (5.16 g, 0.032 mol) dissolved in ethanol (40 mL). This mixture was heated at reflux under N$_2$ for 12 h and cooled to rt. The mixture was partitioned between water and EtOAc. The combined organic layers were washed with brine, dried over MgSO$_4$, and concentrated. The residue was purified by column chromatography to give 6-bromo-2-chloro-3'-methyl-biphenyl (6 g, 67%). $^1$H NMR (400 MHz, CD$_3$OD): 6.90-7.00 (t, 2H), 7.14-7.24 (m, 2H), 7.26-7.33 (t, 1H), 7.44-7.50 (d, 1H), 7.58-7.62 (d, 1H); MS (E/Z): 281 (M+H$^+$)

The following biaryls were prepared from aryl halides and the boronic acids indicated using the procedures described in Preparations 27a Step 2 and 27b Step 2:

| Biaryl | Aryl halide | Boronic acid |
|---|---|---|
| 2-bromobiphenyl | 2-bromoiodobenzene | phenylboronic acid |
| 2-bromo-2'-methylbiphenyl | 2-bromoiodobenzene | 2-methylphenylboronic acid |
| 2-bromo-3'-methylbiphenyl | 2-bromoiodobenzene | 3-methylphenylboronic acid |
| 2-bromo-4'-methylbiphenyl | 2-bromoiodobenzene | 4-methylphenylboronic acid |
| 2-bromo-2'-fluorobiphenyl | 2-bromoiodobenzene | 2-fluorophenylboronic acid |
| 2-bromo-3'-fluorobiphenyl | 2-bromoiodobenzene | 3-fluorophenylboronic acid |
| 2-bromo-4'-fluorobiphenyl | 2-bromoiodobenzene | 4-fluorophenylboronic acid |
| 2-bromo-2'-chlorobiphenyl | 2-bromoiodobenzene | 2-chlorophenylboronic acid |
| 2-bromo-3'-chlorobiphenyl | 2-bromoiodobenzene | 3-chlorophenylboronic acid |
| 2-bromo-4'-chlorobiphenyl | 2-bromoiodobenzene | 4-chlorophenylboronic acid |
| 2'-bromo-2-fluoro-5-methylbiphenyl | 2-bromoiodobenzene | 2-fluoro-5-methylphenylboronic acid |

-continued

| Biaryl | Aryl halide | Boronic acid |
|---|---|---|
| 2-bromo-3',4'-difluorobiphenyl | 2-bromoiodobenzene | 3,4-difluorophenylboronic acid |
| 2-bromo-3'-(trifluoromethyl)biphenyl | 2-bromoiodobenzene | 3-(trifluoromethyl)phenylboronic acid |
| 2-bromo-6-fluorobiphenyl | 1-bromo-3-fluoro-2-iodobenzene | phenylboronic acid |
| 2-bromo-3'-chloro-6-fluorobiphenyl | 1-bromo-3-fluoro-2-iodobenzene | 3-chlorophenylboronic acid |
| 2-bromo-6-fluoro-3',5'-dimethylbiphenyl | 1-bromo-3-fluoro-2-iodobenzene | 3,5-dimethylphenylboronic acid |
| 2-bromo-3',6-difluorobiphenyl | 1-bromo-3-fluoro-2-iodobenzene | 3-fluorophenylboronic acid |
| 2'-bromo-2,6'-difluoro-5-methylbiphenyl | 1-bromo-3-fluoro-2-iodobenzene | 2-fluoro-5-methylphenylboronic acid |
| 2-bromo-6-chlorobiphenyl | 1-bromo-3-chloro-2-iodobenzene | phenylboronic acid |
| 2-bromo-6-chloro-3'-methylbiphenyl | 1-bromo-3-chloro-2-iodobenzene | 3-methylphenylboronic acid |
| 2-bromo-3',6-dichlorobiphenyl | 1-bromo-3-chloro-2-iodobenzene | 3-chlorophenylboronic acid |
| 2-bromo-6-chloro-3'-fluorobiphenyl | 1-bromo-3-chloro-2-iodobenzene | 3-fluorophenylboronic acid |
| 2-(2-bromophenyl)pyridine | 2-bromopyridine | 2-bromobenzeneboronic acid |
| 2-bromo-5-fluoro-3'-methylbiphenyl | 1-bromo-4-fluoro-2-iodobenzene | 3-methylphenylboronic acid |

Preparation 28

(S)-5-methoxy-1-(2-phenoxyphenyl)-1-((R)-piperidin-3-yl)pentan-1-ol

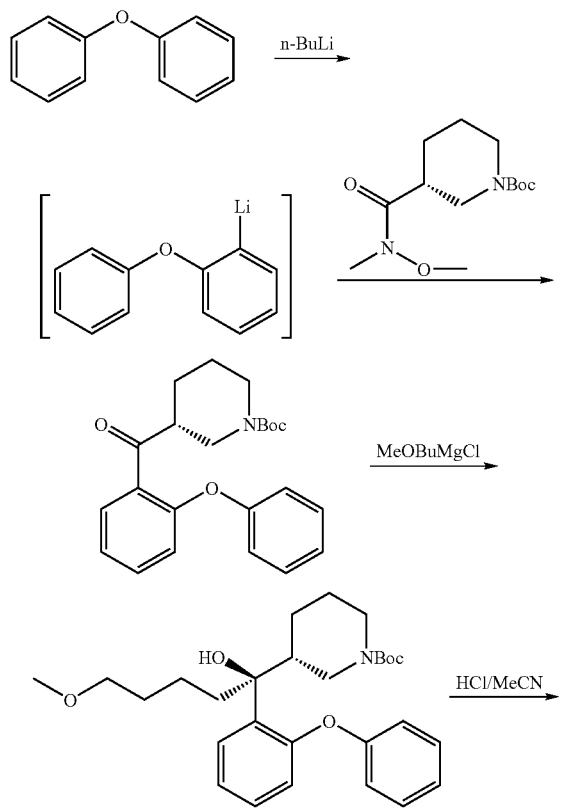

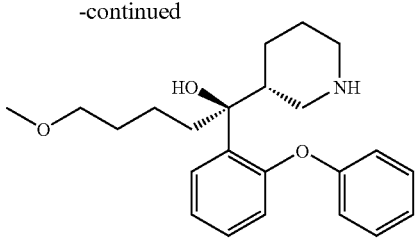

Step 1. 2-(Phenoxy)phenyllithium

To a solution of diphenyl ether (8.60 g, 50.0 mmol) in Et₂O (75 mL) was added n-BuLi (1.6 M in hexane, 32.8 mL, 52.5 mmol). The mixture was refluxed for 48 h, and the resulting solution of 2-(phenoxy)phenyllithium was used in the next step without any further analysis.

Step 2. (3R)-1-(tert-butoxycarbonyl)-3-(2-phenoxybenzoyl)piperidine

To a solution of (R)-tert-butyl 3-(N-methoxy-N-methylcarbamoyl)piperidine-1-carboxylate (4.40 g, 16.2 mmol) in anhydrous THF (18 mL) at −10° C., was added dropwise the solution of 2-phenoxyphenyllithium prepared in Step 1 (80 mL, 32 mmol). The mixture was then warmed to rt, and stirred until no starting material remained (~30 min). The reaction was quenched with 1 N HCl (~30 mL) and extracted with Et₂O (4×10 mL). The combined organic layers were washed with satd aq NaHCO₃ and brine, and dried over Na₂SO₄. The solvent was removed to give (3R)-1-(tert-butoxycarbonyl)-3-(2-phenoxybenzoyl)piperidine (7.44 g, quantitative).

Step 3. (R)-tert-Butyl 3-((S)-1-hydroxy-5-methoxy-1-(2-phenoxyphenyl)pentyl)piperidine-1-carboxylate To a solution of (3R)-1-(tert-butoxycarbonyl)-3-(2-phenoxybenzoyl)piperidine (6.17 g, 16.2 mmol) in THF (30 mL) at −10° C. was added dropwise 2.54 M 4-methoxybutylmagnesium chloride in THF (15 mL, 38 mmol). The resulting solution was warmed to rt slowly, and stirred over night. The

143 reaction was quenched with satd NH₄Cl (10 mL) and extracted with Et₂O (4×10 mL). The combined organic layers were washed with water and brine. The solvent was removed and the residue was purified by flash chromatography to give (R)-tert-butyl 3-((S)-1-hydroxy-5-methoxy-1-(2-phenoxyphenyl)pentyl)piperidine-1-carboxylate (1.97 g, 26% from (R)-tert-butyl 3-(N-methoxy-N-methylcarbamoyl)piperidine-1-carboxylate).

Step 4. (S)-5-Methoxy-1-(2-phenoxyphenyl)-1-((R)-piperidin-3-yl)pentan-1-ol

To a solution of (R)-tert-butyl 3-((S)-1-hydroxy-5-methoxy-1-(2-phenoxyphenyl) pentyl)piperidine-1-carboxylate (1.97 g, 4.19 mmol) in MeCN (100 mL) was added 2 N aq HCl (100 mL) slowly at rt. The resulting solution was stirred at rt until no starting material remained (~16 h), basified to pH=10 with 10 N aq NaOH, and evaporated under reduced pressure to remove MeCN. The aq layer was extracted with CH₂Cl₂ (4×10 mL). The combined organic layers were washed with brine and dried over Na₂SO₄. The solvent was removed in vacuo to afford (S)-5-methoxy-1-(2-phenoxyphenyl)-1-((R)-piperidin-3-yl)pentan-1-ol (1.56 g, quantitative) as a free amine.

The following piperidines were prepared following procedures analogous to those described above:

(S)-1-(2-fluoro-5-(4-fluorophenoxy)phenyl)-5-methoxy-1-((R)-piperidin-3-yl)pentan-1-ol using 4,4'-difluorodiphenyl ether in Step 1.

Preparation 29

(S)-1-(2-(3-Fluorophenoxy)phenyl)-5-methoxy-1-((R)-piperidin-3-yl)pentan-1-ol

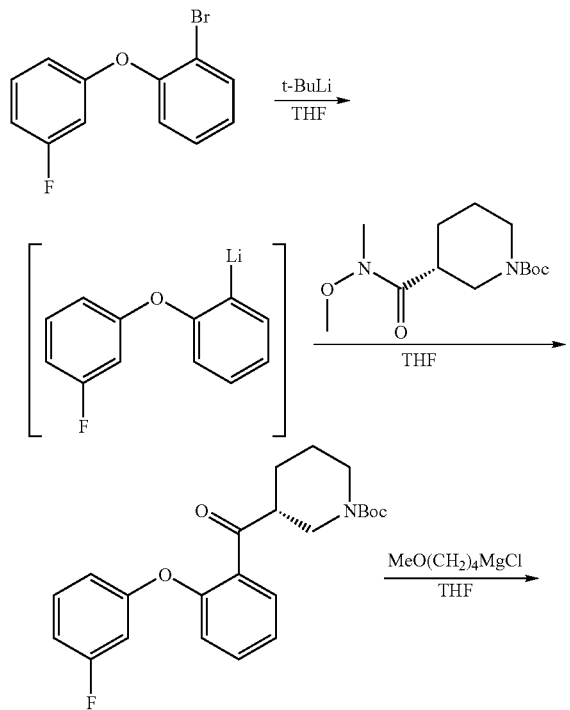

144

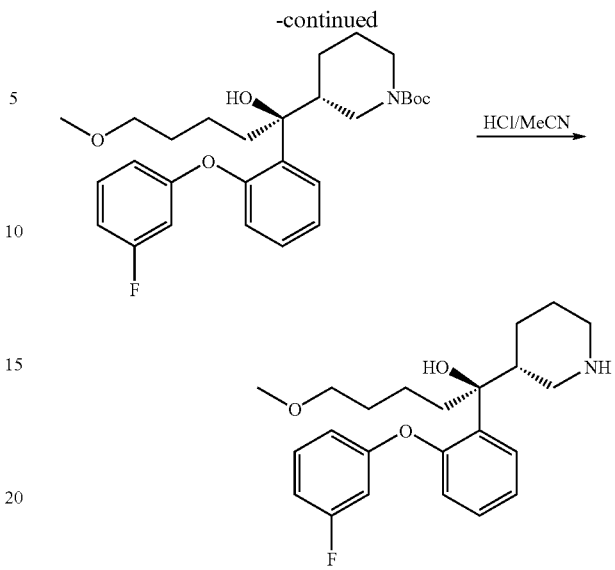

Step 1. 2-(3-Fluorophenoxy)phenyllithium

To a stirred solution of 1-(3-fluorophenoxy)-2-bromobenzene (1.27 g, 4.75 mmol) in THF (10 mL) at −70° C. was added 1.7 M t-BuLi in pentane (5.6 mL, 9.50 mmol) dropwise to keep the temperature below −70° C. The resulting solution was stirred at −70° C. for 30 min, and used for the next step directly.

Step 2. (3R)-1-(tert-butoxycarbonyl)-3-((3-fluorophenoxy)benzoyl)piperidine

To a solution of (R)-tert-butyl 3-(N-methoxy-N-methylcarbamoyl)piperidine-1-carboxylate (0.65 g, 2.37 mmol) in THF (4 mL) at −20° C. was added dropwise the solution of 2-(3-fluorophenoxy)phenyllithium prepared in Step 2 above. After the addition was complete, the resulting solution was allowed to warm to rt slowly, and left at rt for 1 h. The reaction was quenched with 1N HCl (~6 mL), and extracted with Et₂O (4×10 mL). The combined organic layers were washed with satd aq NaHCO₃ and brine, and dried over Na₂SO₄. Removal of the solvent left the crude ketone (1.49 g, quantitative), which was used for next step without further purification.

Step 3. (R)-tert-Butyl 3-((S)-1-(2-(3-fluorophenoxy)phenyl)-1-hydroxy-5-methoxy pentyl)piperidine-1-carboxylate To a solution of (3R)-1-(tert-butoxycarbonyl)-3-((3-fluorophenoxy)benzoyl)piperidine (0.95 g, 2.37 mmol) in THF (3 mL) at −20° C. was added 1.45 M 4-methoxybutyl magnesium chloride in THF (3.3 mL, 4.76 mmol) dropwise. The resulting solution was warmed to rt slowly, and the completion of reaction was confirmed by LC-MS (~20 min). The reaction was quenched with satd aq NH₄Cl (4 mL) and extracted with Et₂O (4×5 mL). The combined organic layers were washed with water and brine, and the solvent was removed in vacuo to give a crude product which was purified by flash column chromatography to afford (R)-tert-butyl 3-((S)-1-(2-(3-fluorophenoxy)phenyl)-1-hydroxy-5-methoxypentyl)piperidine-1-carboxylate (0.50 g, 43%).

Step 4. (S)-1-(2-(3-Fluorophenoxy)phenyl)-5-methoxy-1-((R)-piperidin-3-yl)pentan-1-ol To a solution of (R)-tert-butyl 3-((S)-1-(2-(3-fluorophenoxy)phenyl)-1-hydroxy-5-methoxy pentyl)piperidine-1-carboxylate (0.50 g, 1.03 mmol) in MeCN (60 mL) was added 2 N aq HCl (60 mL) slowly at rt. The resulting solution was stirred at rt overnight, then basified to pH=10 with 10 N aq NaOH. The mixture was evaporated under reduced pressure to remove MeCN. The aq layer was extracted with $CH_2Cl_2$ (4×10 mL), and the combined organic layers were washed with brine and dried over $Na_2SO_4$. The solvent was removed under vacuum to give (S)-1-(2-(3-fluorophenoxy)phenyl)-5-methoxy-1-((R)-piperidin-3-yl)pentan-1-ol (0.40 g, quantitative) as a free amine.

The following piperidines prepared using the above procedures using the halodiphenyl ethers listed below in Step 1.

| Piperidine | Halodiphenyl ether |
| --- | --- |
| (S)-1-(2-(2-ethylphenoxy)phenyl)-5-methoxy-1-((R)-piperidin-3-yl)pentan-1-ol | 1-(2-ethylphenoxy)-2-bromobenzene |
| (S)-1-(2-(4-fluorophenoxy)phenyl)-5-methoxy-1-((R)-piperidin-3-yl)pentan-1-ol | 1-(4-fluorophenoxy)-2-bromobenzene |
| (S)-1-(2-(m-tolyloxy)phenyl)-5-methoxy-1-((R)-piperidin-3-yl)pentan-1-ol | 1-(2-bromophenoxy)-3-methylbenzene |
| (S)-1-(2-(o-tolyloxy)-3-methylphenyl)-5-methoxy-1-((R)-piperidin-3-yl)pentan-1-ol | 2-(o-tolyloxy)-1-bromo-3-methylbenzene |
| (S)-1-(2-(o-tolyloxy)-3,5-difluorophenyl)-5-methoxy-1-((R)-piperidin-3-yl)pentan-1-ol | 2-(o-tolyloxy)-1-bromo-3,5-difluorobenzene |
| (S)-1-(2-(4-fluoro-2-methylphenoxy)phenyl)-5-methoxy-1-((R)-piperidin-3-yl)pentan-1-ol | 1-(4-fluoro-2-methylphenoxy)-2-bromobenzene |
| (S)-1-(2-(5-fluoro-2-methylphenoxy)phenyl)-5-methoxy-1-((R)-piperidin-3-yl)pentan-1-ol | 1-(5-fluoro-2-methylphenoxy)-2-bromobenzene |
| (S)-1-(3,5-difluoro-2-phenoxyphenyl)-5-methoxy-1-((R)-piperidin-3-yl)pentan-1-ol | 2-(o-tolyloxy)-1-bromo-3,5-difluorobenzene |
| (S)-1-(5-fluoro-2-phenoxyphenyl)-5-methoxy-1-((R)-piperidin-3-yl)pentan-1-ol | 2-bromo-4-fluoro-1-phenoxybenzene |
| (S)-1-(3-fluoro-2-(o-tolyloxy)phenyl)-5-methoxy-1-((R)-piperidin-3-yl)pentan-1-ol | 1-bromo-3-fluoro-2-(o-tolyloxy)benzene |
| (S)-5-methoxy-1-(3-methyl-2-(o-tolyloxy)phenyl)-1-((R)-piperidin-3-yl)pentan-1-ol | 1-bromo-3-methyl-2-(o-tolyloxy)benzene |
| (S)-1-(5-fluoro-2-(4-fluorophenoxy)phenyl)-5-methoxy-1-((R)-piperidin-3-yl)pentan-1-ol | 2-bromo-4-fluoro-1-(4-fluorophenoxy)benzene |

The following piperidines were prepared using the above procedures except that in Step 1 Grignard reagents were prepared from the halodiphenyl ethers listed below instead of organolithiums.

| Piperidine | Halodiphenyl ether |
| --- | --- |
| (S)-1-(3-fluoro-2-phenoxyphenyl)-5-methoxy-1-((R)-piperidin-3-yl)pentan-1-ol | 1-chloro-3-fluoro-2-phenoxybenzene |
| (S)-1-(2-(p-tolyloxy)-3-fluorophenyl)-5-methoxy-1-((R)-piperidin-3-yl)pentan-1-ol | 2-(p-tolyloxy)-1-chloro-3-fluorobenzene |

Preparation 30

(R)-tert-butyl 3-((S)-1-(2-(o-tolyloxy)phenyl)-1-hydroxy-5-methoxypentyl)piperidine-1-carboxylate

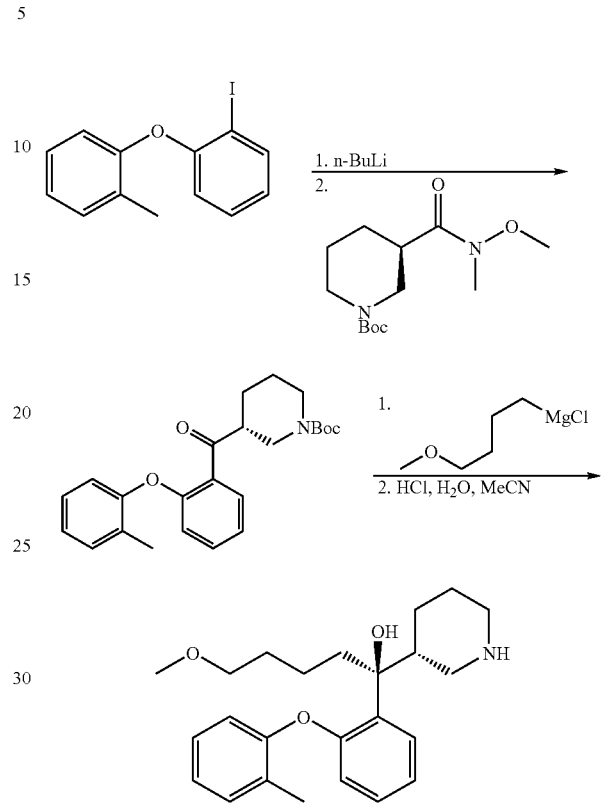

Step 1. (2-(O-tolyloxy)phenyl)((R)-1-(tert-butoxycarbonyl)piperidin-3-yl)methanone To a solution of 1-(o-tolyloxy)-2-iodobenzene (40 g, 0.13 mol) in anhydrous THF (500 mL) cooled to −78° C. was added dropwise 1.6 M n-BuLi in hexanes (52 mL, 0.13 mol). After stirring for 1 h at −78° C., a solution of (R)-tert-butyl 3-(N-methoxy-N-methylcarbamoyl)-piperidine-1-carboxylate (35 g, 0.13 mol) in anhydrous THF (500 mL) was added dropwise. The mixture was allowed to warm to rt and stirred overnight. Saturated aq $NH_4Cl$ (500 mL) was added and the mixture was extracted with EtOAc (3×150 mL). The combined organic layers were dried over $Na_2SO_4$. Solvent removal and flash column chromatography afforded (2-(otolyloxy)phenyl)((R)-1-(tert-butoxycarbonyl)piperidin-3-yl)methanone (23 g, 45%).

Step 2. (R)-tert-butyl 3-((S)-1-(2-(o-tolyloxy)phenyl)-1-hydroxy-5-methoxypentyl)piperidine-1-carboxylate A 500-mL, three-necked flask was charged with magnesium turnings (12 g, 0.5 mol) and a small crystal of iodine. The flask was evacuated and refilled with $N_2$. A solution of 1-chloro-4-methoxybutane (50 g, 0.4 mol) in THF (200 mL) was added dropwise to the mixture. The reaction mixture was stirred at reflux for 2 h and most of magnesium was consumed. The solution of Grignard reagent was cooled to rt.

A 1000 mL, three-necked flask was charged with the (2-(otolyloxy)phenyl)((R)-1-(tert-butoxycarbonyl)piperidin-3-yl)methanone (20 g, 0.05 mol) and THF (250 mL). The flask was evacuated and refilled with $N_2$, the mixture was cooled with a dry ice-acetone bath and the Grignard reagent was added dropwise. The mixture was allowed to warm slowly to rt and stirred overnight. After quenching with satd aq $NH_4Cl$ (500 mL), the mixture was extracted with EtOAc (3×150 mL) and the combined organic layers were dried over $Na_2SO_4$. The solvent was removed and the crude product was purified by flash column chromatography to afford the (R)-tert-butyl 3-((S)-1-(2-(o-tolyloxy)phenyl)-1-hydroxy-5-methoxypentyl)piperidine-1-carboxylate (20 g, 83%).

Step 3. (S)-1-(2-(o-tolyloxy)phenyl)-5-methoxy-1-((R)-piperidin-3-yl)pentan-1-ol The Boc protecting group was removed using 1:1 5% aq HCl/MeCN ar rt.

The following piperidines were prepared from the iododiphenyl ether indicated using procedures analogous to those described above.

| Piperidine | Iododiphenyl ether |
|---|---|
| (S)-1-(2-(2-chlorophenoxy)phenyl)-5-methoxy-1-((R)-piperidin-3-yl)pentan-1-ol | 1-(2-iodophenoxy)-2-chlorobenzene |
| (S)-1-(2-(2-(trifluoromethyl)phenoxy)phenyl)-5-methoxy-1-((R)-piperidin-3-yl)pentan-1-ol | 1-(2-iodophenoxy)-2-(trifluoromethyl)benzene |
| (S)-1-(2-(2-fluorophenoxy)phenyl)-5-methoxy-1-((R)-piperidin-3-yl)pentan-1-ol | 1-(2-iodophenoxy)-2-fluorobenzene |

Preparation 31

1-(3-Fluorophenoxy)-2-bromobenzene

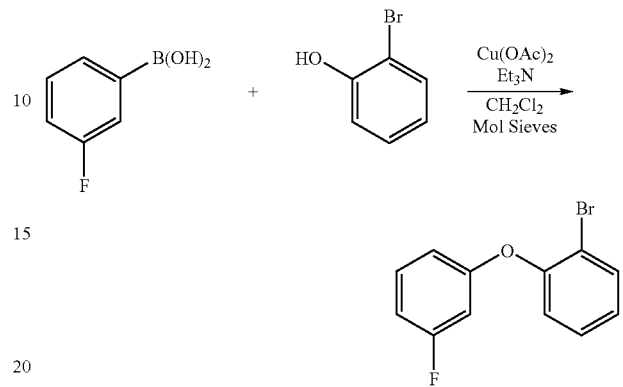

To a stirred solution of 3-fluorophenylboronic acid (2.10 g, 15 mmol), 2-bromophenol (1.77 g, 10 mmol) and $Cu(OAc)_2$ (0.93 g, 5 mmol) in anhydrous $CH_2Cl_2$ (25 mL) was added activated 4 Å molecular sieves (~0.1 g), followed by anhydrous $Et_3N$ (3.5 mL, 25 mmol). The resulting dark green solution was stirred at rt for 48 h. The mixture was evaporated under reduced pressure and the residue was washed several times with $Et_2O$ (~150 mL). The $Et_2O$ solution was washed with satd aq $NH_4Cl$, and 1 N aq HCl. The organic layer was evaporated and the crude product was purified by flash column chromatography to give 1-(3-fluorophenoxy)-2-bromobenzene (1.28 g, 48%) as clear oil.

The following halodiphenyl ethers were prepared following the procedure described above.

| Halodiphenyl ether | Phenol | Boronic Acid |
|---|---|---|
| 1-(2-ethylphenoxy)-2-bromobenzene | 2-bromophenol | 2-ethylphenylboronic acid |
| 1-(4-fluorophenoxy)-2-bromobenzene | 2-bromophenol | 4-fluorophenylboronic acid |
| 1-(2-bromophenoxy)-3-methylbenzene | 2-bromophenol | 3-methylphenylboronic acid |
| 2-(o-tolyloxy)-1-bromo-3-methylbenzene | 2-bromo-6-methylphenol | 2-methylphenylboronic acid |
| 2-(o-tolyloxy)-1-bromo-3,5-difluorobenzene | 2-bromo-4,6-difluorophenol | 2-methylphenylboronic acid |
| 1-(4-fluoro-2-methylphenoxy)-2-bromobenzene | 2-bromophenol | 4-fluoro-2-methylphenylboronic acid |
| 1-(5-fluoro-2-methylphenoxy)-2-bromobenzene | 2-bromophenol | 5-fluoro-2-methylphenylboronic acid |
| 1-chloro-3-fluoro-2-phenoxybenzene | 2-chloro-6-fluorophenol | phenylboronic acid |
| 2-(p-tolyloxy)-1-chloro-3-fluorobenzene | 2-chloro-6-fluorophenol | 4-methylphenylboronic acid |
| 2-bromo-4-fluoro-1-phenoxybenzene | 2-bromo-4-fluorophenol | phenylboronic acid |
| 1-bromo-3-fluoro-2-(o-tolyloxy)benzene | 2-bromo-6-fluorophenol | 2-methylphenylboronic acid |
| 2-bromo-4-fluoro-1-(4-fluorophenoxy)benzene | 2-bromo-4-fluorophenol | 4-fluorophenylboronic acid |

Preparation 32

1-(O-tolyloxy)-2-iodobenzene

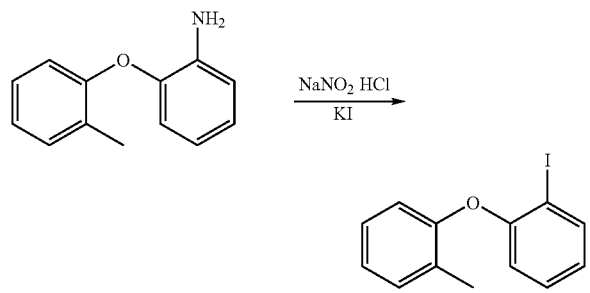

To a solution of 2-(o-tolyloxy)aniline (40 g, 0.2 mol) in 1N aq HCl (400 mL, 0.4 mol, 2 equiv) cooled to 0° C. was added dropwise a solution of NaNO$_2$ (18 g, 0.26 mol, 1.3 equiv) in water (520 ml). The mixture was stirred for 1 h at 0° C. and a solution of KI (83 g, 0.5 mol, 2.5 equiv) in water (500 mL) was added dropwise with vigorous stirring. After 0.5 h the mixture was warmed to 90-100° C. for 1 h, cooled to rt and washed with satd NaHSO$_3$ until the aqueous layer become clear. The mixture was extracted with EtOAc (3×200 mL) and the combined organic layers were washed with aq Na$_2$S$_2$O$_4$ and dried over Na$_2$SO$_4$. After evaporation of the solvent, the solution was passed through a short silica gel column to afford 1-(otolyloxy)-2-iodobenzene (40.0 g, 65%).

Preparation 33

Halodiphenyl Ethers from Phenols and Fluoronitrobenzenes 1-(2-Iodophenoxy)-2-chlorobenzene

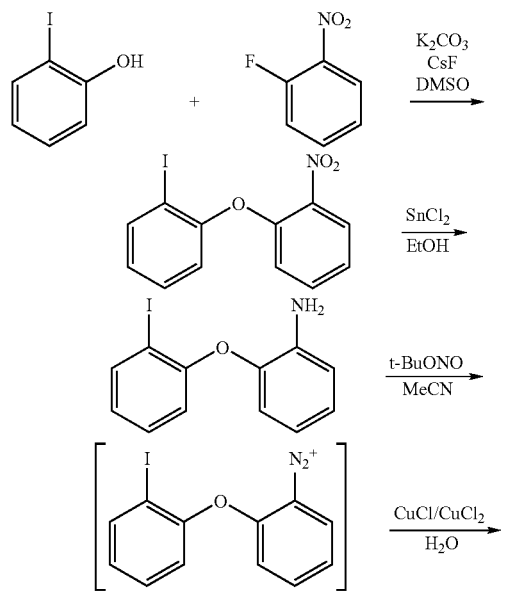

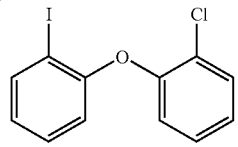

Step 1. 1-(2-Iodophenoxy)-2-nitrobenzene

To a solution of 2-iodophenol (11.82 g, 52.7 mmol) and 1-fluoro-2-nitrobenzene (5.0 g, 35.1 mmol) in DMSO (50 mL was added K$_2$CO$_3$ (14.5 g, 105.3 mmol), followed by CsF (8.0 g, 52.7 mmol). The resulting suspension was stirred at 50° C. until no starting material remained (~5 h), cooled to rt and partitioned between water (50 mL) and CH$_2$Cl$_2$ (50 mL). The water layer was separated and extracted with CH$_2$Cl$_2$ (2×10 mL). The combined organic layers were washed with 1 aq N NaOH (10 mL) and brine, and dried over Na$_2$SO$_4$. Solvent was removed under vacuum to give 1-(2-iodophenoxy)-2-nitrobenzene (11.2 g, 93%) as an oil, which was used for next step without purification.

Step 2. 2-(2-Iodophenoxy)benzenamine

A solution of 1-(2-iodophenoxy)-2-nitrobenzene (9.60 g, 28.1 mmol) and SnCl$_2$.2H$_2$O (13.0 g, 56.0 mmol) in ethanol (25 mL) and water (5 mL) was refluxed until no starting material remained (~1 h). The ethanol was removed in vacuo and the aq layer was basified to pH>10 and extracted with CH$_2$Cl$_2$ (4×10 mL). The combined organic layers were dried over Na$_2$SO$_4$, and the solvent was removed to give a crude 2-(2-Iodophenoxy)benzenamine (8.57 g, 98%), which was used for the next step without purification.

Step 3. 1-(2-Iodophenoxy)-2-chlorobenzene

A solution of crude 2-(2-iodophenoxy)benzenamine (8.57 g, 27.6 mmol) in MeCN (60 mL) was cooled to 0° C. and treated with HBF$_4$ (54 wt % in Et$_2$O, 4.93 mL, 35.9 mmol). The reaction mixture was stirred at 0° C. for 5 min and of t-BuONO (4.10 g, 35.9 mmol) was added dropwise. The resulting mixture was stirred at 0° C. for 10 min, cooled to −20° C., and added to a solution of CuCl (41 g, 414.1 mmol) and CuCl$_2$ (70 g, 414.1 mmol) in water (500 mL) at 0° C. The mixture was stirred vigorously at 25° C. for 2 h, and partitioned between EtOAc and water. The water layer was extracted with EtOAc (3×10 mL) and the combined organic layers were washed with brine, dried over Na$_2$SO$_4$ and concentrated under vacuum. Flash column chromatography gave 1-(2-iodophenoxy)-2-chlorobenzene (5.35 g, 58%).

The following halodiphenyl ethers were prepared following procedures analogous to those described above using the starting materials and reagents indicated:

| Halopdiphenyl ether | Phenol in Step 1 | Halide in Step 3 |
|---|---|---|
| 1-(2-iodophenoxy)-2-(trifluoromethyl)benzene | 2-(trifluoromethyl)phenol | KI |
| 1-(2-iodophenoxy)-2-fluorobenzene | 2-fluorophenol | KI |

Preparation 34

(R)-1-(3-Chloro-2-fluorophenyl)-5-methoxy-1-((R)-morpholin-2-yl)pentan-1-ol

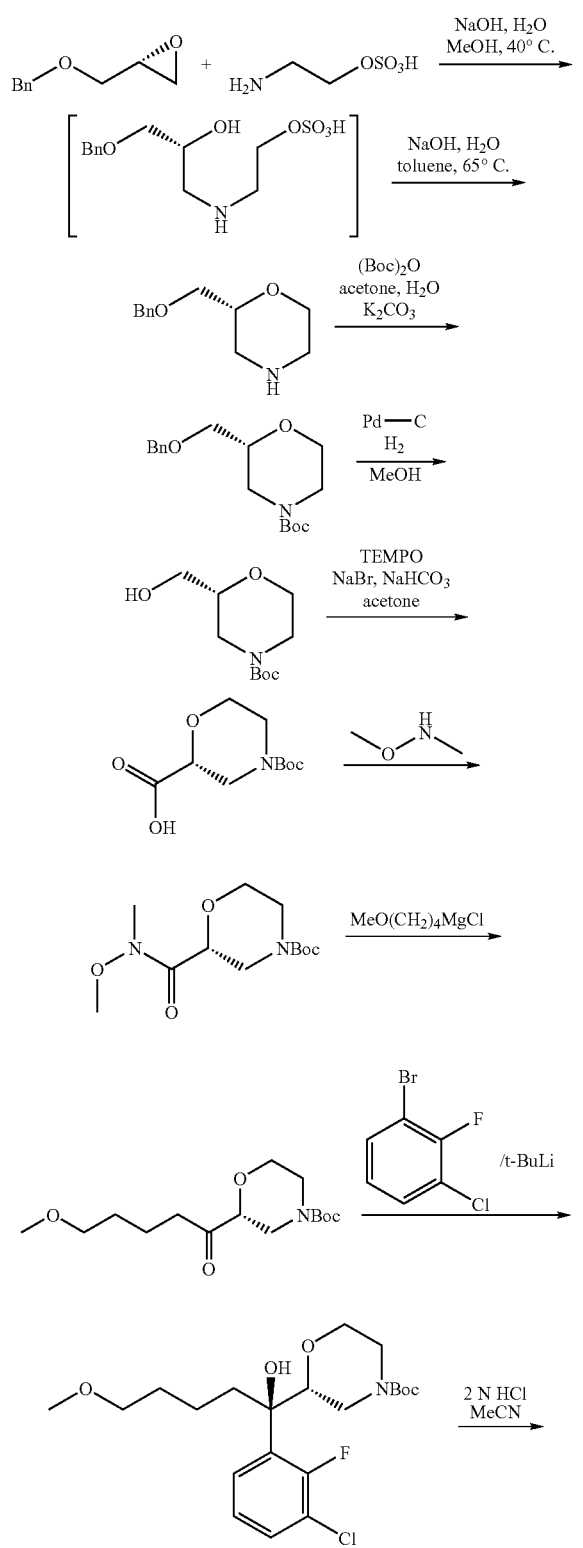

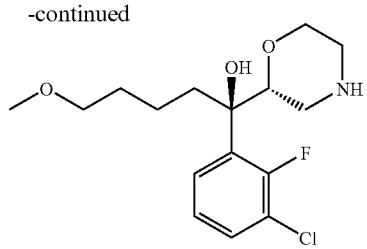

Step 1. (R)-2-(Benzyloxymethyl)morpholine

To a stirred mixture of (R)-2-(benzyloxymethyl)oxirane (10.0 g, 60.9 mmol) and NaOH (19.49 g, 487.2 mmol) in H$_2$O (46 mL) and MeOH (18 mL), there was added 2-aminoethyl hydrogen sulfate (36.8 g, 255.8 mmol) in portions. After addition, the reaction mixture was stirred at 40° C. for 2 h. After cooling, the mixture was treated with NaOH (15.0 g, 375.0 mmol) then toluene (70 mL) and stirred at 65° C. overnight. The mixture was cooled, diluted with toluene (27 mL) and H$_2$O (92 mL). The toluene layer was separated and the aqueous layer was extracted with CH$_2$Cl$_2$ (2×50 mL). The combined organic layers were concentrated to give crude (R)-2-(benzyloxymethyl)morpholine (~14 g), which was used without purification. MS m/z 208 (M+H$^+$).

Step 2. (R)-tert-Butyl 2-(benzyloxymethyl)morpholine-4-carboxylate

To a solution of crude (R)-2-(benzyloxymethyl)morpholine (~14 g) in acetone (100 mL) and H$_2$O (30 mL) at 0° C., was added K$_2$CO$_3$ (25.2 g, 182.7 mmol), followed by (Boc)$_2$O (14.6 g, 67.0 mmol). The resulting solution was warmed to rt, and stirred until no starting material remained (~30 min). Acetone was removed under vacuum and the aqueous solution was extracted with CH$_2$Cl$_2$ (4×10 mL). The combined organic layers were washed with H$_2$O (10 mL) and the solvent was removed. The residue was purified by flash column chromatography to give (R)-tert-butyl 2-(benzyloxymethyl)morpholine-4-carboxylate (8.33 g, 44% over 2 steps). $^1$H NMR (400 MHz, CDCl$_3$): 7.34 (m, 5 H), 4.56 (s, 2 H), 3.88 (d, 2 H), 3.82 (br, 1 H), 3.40 (m, 1 H), 3.48 (m, 3 H), 2.94 (m, 1 H), 2.76 (m, 1 H), 1.44 (s, 9 H); MS m/z 330 (M+Na$^+$).

Step 3. (R)-tert-Butyl 2-(hydroxymethyl)morpholine-4-carboxylate

To a solution of (R)-tert-butyl 2-(benzyloxymethyl)morpholine-4-carboxylate (8.33 g, 27.1 mmol) in EtOH was added Pd—C (wet, 3.6 g), and the resulting mixture was stirred at rt under a H$_2$ balloon overnight. After filtration, the solvent was removed under vacuum and the residue was purified by flash column chromatography to give (R)-tert-butyl 2-(hydroxymethyl)morpholine-4-carboxylate (5.84 g, 99%) as a clear oil. $^1$H NMR (400 MHz, CDCl$_3$): 3.88 (d, 2 H), 3.82 (br, 1 H), 3.64 (d, 1 H), 3.56 (m, 3 H), 2.94 (m, 1 H), 2.76 (m, 1 H), 1.90 (br, 1 H), 1.44 (s, 9 H); MS m/z 218 (M+H$^+$).

Step 4. (R)-4-(tert-Butoxycarbonyl)morpholine-2-carboxylic Acid

Satd aq NaHCO$_3$ (15 mL) was added to a solution of (R)-tert-butyl 2-(hydroxymethyl)-morpholine-4-carboxylate (1.09 g, 5.0 mmol) in acetone (50 mL), stirred and maintained at 0° C. Solid NaBr (0.1 g, 1 mmol) and TEMPO (0.015 g, 0.1 mmol) were added. Trichloroisocyanuric acid (2.32 g, 10.0 mmol) was then added slowly within 20 min at 0° C. After addition the mixture was warmed to rt and stirred overnight. 2-Propanol (3 mL) was added, and the resulting solution was stirred at rt for 30 min, filtered through a pad of Celite, concentrated under vacuum, and treated with satd aq Na$_2$CO$_3$ (15 mL). The aqueous solution was washed with EtOAc (5 mL), acidified with 6 N HCl, and extracted with EtOAc (5×10 mL). These EtOAc extracts were combined, dried over Na$_2$SO$_4$ and concentrated to give (R)-4-(tert-butoxycarbonyl)morpholine-2-carboxylic acid (1.07 g, 92%) as a white solid. $^1$H NMR (400 MHz, CDCl$_3$): 4.20 (br, 1 H), 4.12 (d, 1 H), 4.02 (d, 1 H), 3.84 (m, 1 H), 3.62 (m, 1 H), 3.04 (m, 2 H), 1.44 (s, 9 H); MS m/z 232 (M+H$^+$).

Step 5. (R)-tert-Butyl 2-(methoxy(methyl)carbamoyl)morpholine-4-carboxylate

To a solution of (R)-4-(tert-butoxycarbonyl)morpholine-2-carboxylic acid (1.05 g, 4.54 mmol) in DMF (10 mL) at 0° C. were added N,O-dimethylhydroxylamine hydrochloride (1.36 g, 13.62 mmol), DIEA (3.9 mL, 22.7 mmol), HBTU (1.89 g, 4.99 mmol) and HOBt (0.67 g, 4.99 mmol). The resulting solution was warmed to rt and stirred until no starting material remained (~2 h). The mixture was diluted with H$_2$O (10 mL) and extracted with EtOAc (4×10 mL). The combined organic layers were washed with 1 N aq HCl (10 mL), 1 N aq NaOH (3×10 mL), water (2×10 mL) and brine (10 mL), and dried over Na$_2$SO$_4$. The solvent was removed under vacuum to give (R)-t-butyl 2-(methoxy(methyl)carbamoyl)morpholine-4-carboxylate (1.40 g, quant.), which was used for the next step without further purification; $^1$H NMR (400 MHz, CDCl$_3$) δ: 4.36 (br, 1 H), 4.08 (m, 1 H), 4.00 (d, 1 H), 3.84 (m, 1 H), 3.76 (s, 3 H), 3.58 (m, 1 H), 3.20 (s, 3 H), 3.04 (m, 2 H), 1.44 (s, 9 H); MS m/z 297 (M+Na$^+$).

Step 6. (R)-tert-Butyl 2-(5-methoxypentanoyl)morpholine-4-carboxylate

To a solution of (R)-tert-butyl 2-(methoxy(methyl)carbamoyl)morpholine-4-carboxylate (1.37 g, 5.0 mmol) in THF (10 mL) at −20° C., there was added (4-methoxybutyl)magnesium chloride in THF (1.47 M, 10.2 mL, 15.0 mmol) dropwise such that the temperature remained below −20° C. After addition, the resulting solution was warmed to rt, and quenched with 1 N aq HCl (10 mL). The organic layer was separated, and the aqueous layer was extracted with ether (3×5 mL). The combined organic layers were washed with satd aq NaHCO$_3$ (10 mL) and brine (5 mL), and dried over Na$_2$SO$_4$. The solvent was then removed in vacuo to give (R)-tert-butyl 2-(5-methoxypentanoyl)morpholine-4-carboxylate (1.41 g, 93%), which was used for the next step without purification; MS m/s 324 (M+Na$^+$).

Step 7. (R)-tert-Butyl 2-((R)-1-(3-chloro-2-fluorophenyl)-1-hydroxy-5-methoxypentyl)-morpholine-4-carboxylate To a solution of 1-bromo-3-chloro-2-fluorobenzene (1.42 g, 6.77 mmol) in THF (8 mL) at −70° C., was added t-BuLi in pentane (1.7 M, 7.96 mL, 13.5 mmol) dropwise such that the temperature remained below −70° C. The resulting solution (A) was stirred at the same temperature for another 30 min, and used directly in the next step.

To a solution of (R)-tert-butyl 2-(5-methoxypentanoyl)morpholine-4-carboxylate (0.64 g, 2.12 mmol) in toluene (5 mL) at −20° C., solution A prepared above was added dropwise. The resulting solution was allowed to warm to rt slowly, and kept at same temperature for 1 h. The reaction was quenched with satd aq NH$_4$Cl (8 mL) and extracted with diethyl ether (4×10 mL). The combined organic layers were washed with water and brine, and solvent was removed in vacuo to give a crude product, which was purified by flash column chromatography to afford (R)-tert-butyl 2-((R)-1-(3-chloro-2-fluorophenyl)-1-hydroxy-5-methoxypentyl)morpholine-4-carboxylate (0.40 g, 43%). $^1$H NMR (400 MHz, CDCl$_3$) δ: 7.44 (dd, 1 H), 7.32 (dd, 1 H), 7.04 (dd, 1 H), 4.18 (br, 1 H), 3.80 (m, 3 H), 3.42 (dd, 1 H), 3.24 (st, 5 H), 3.04-2.80 (m, 3 H), 2.04 (m, 1 H), 1.68 (m, 1 H), 1.44 (s, 9 H), 1.30 (m, 3 H), 0.86 (m, 1 H); MS m/z 454 (M+Na$^+$).

Step 8. (R)-1-(3-Chloro-2-fluorophenyl)-5-methoxy-1-((R)-morpholin-2-yl)pentan-1-ol To a solution of (R)-tert-butyl 2-((R)-1-(3-chloro-2-fluorophenyl)-1-hydroxy-5-methoxypentyl)morpholine-4-carboxylate (0.38 g, 0.88 mmol) in MeCN (50 mL), 2 N aq HCl (50 mL) was added slowly at rt. The resulting solution was stirred at rt overnight, basified to pH=10 with 10 N aq NaOH, and evaporated under reduced pressure to remove MeCN. The aqueous layer was extracted with CH$_2$Cl$_2$ (4×5 mL). The combined organic layers were washed with brine and dried over Na$_2$SO$_4$. The solvent was removed in vacuo to give (R)-1-(3-chloro-2-fluorophenyl)-5-methoxy-1-((R)-morpholin-2-yl)pentan-1-ol (0.27 g, 93%) as a free amine. The crude product was used for next step without purification; MS m/z 332 (M+H$^+$).

Preparation 35

(±)-(RS)-1-(3-chlorophenyl)-5-methoxy-1-((RS)-morpholin-2-yl)pentan-1-ol

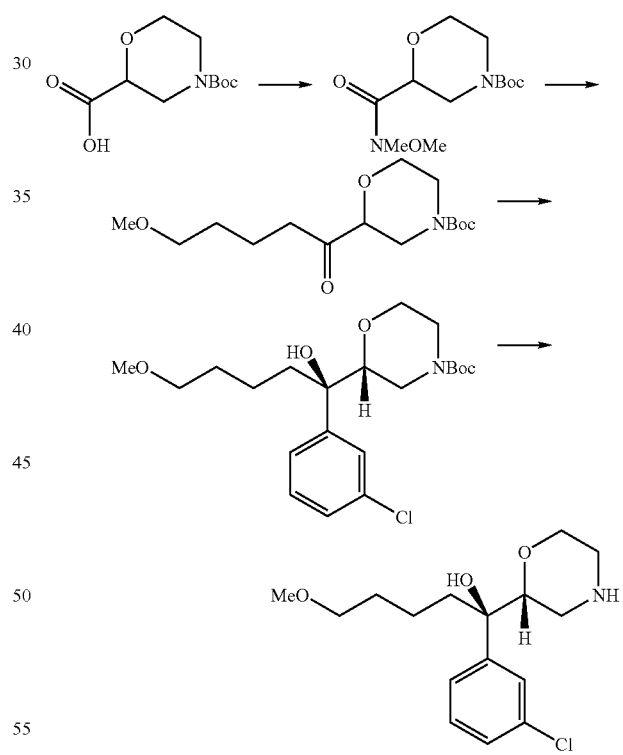

Step 1. (±)-tert-butyl 2-(methoxy(methyl)carbamoyl)morpholine-4-carboxylate

To a stirred solution of (±)-4-(tert-butoxycarbonyl)morpholine-2-carboxylic acid (1.51 g, 6.53 mmol), N,O-dimethylhydroxylamine hydrochloride (0.83 g, 8.49 mmol) and i-Pr$_2$NEt (3.1 mL, 17.6 mmol) in CH$_2$Cl$_2$ (30 mL) was added solid HATU (3.01 g, 7.85 mmol). The mixture was stirred at rt for 3 d, diluted with ether (175 mL), washed with 5% aq HCl (2×50 mL) and satd aq NaHCO$_3$ (50 mL) and dried over MgSO₄. Removal of the solvent left (±)-tert-butyl 2-(methoxy(methyl)carbamoyl)morpholine-4-carboxylate (1.73 g, 96%) as an oil.

Step 2. (±)-tert-butyl 2-(5-methoxypentanoyl)morpholine-4-carboxylate

A stirred solution of (±)-tert-butyl 2-(methoxy(methyl)carbamoyl)morpholine-4-carboxylate (1.73 g, 6.4 mmol) in dry THF (40 mL) was cooled in an ice-salt bath and 1.34 M 4-methoxybutylmagnesium chloride in THF (10 mL, 1.34 mmol) was added dropwise over 3 min. The cooling bath was allowed to expire and the mixture was stirred at rt for 6 h, poured into ice cold 3% aq HCl (100 mL) and extracted with ether (2×100 mL). The combined ether extracts were washed with satd aq NaHCO₃ (35 mL), dried over MgSO₄ and concentrated to afford (±)-tert-butyl 2-(5-methoxypentanoyl)morpholine-4-carboxylate (1.78 g, 93%) as an oil.

Step 3. (±)-(R)-tert-butyl 2-((R)-1-(3-chlorophenyl)-1-hydroxy-5-methoxypentyl)morpholine-4-carboxylate A stirred solution of (±)-tert-butyl 2-(5-methoxypentanoyl)morpholine-4-carboxylate (258 mg, 0.86 mmol) in CH₂CO₂ (5 mL) was cooled to −70 C and 0.5 M 3-chlorophenylmagnesium bromide in THF (4 mL, 2.0 mmol) was added dropwise over 5 min. The cooling bath was allowed to expire. After 1.5 h the mixture had reached rt and was poured into satd aq NaHCO₃ (50 mL). The mixture was extracted with ether (2×50 mL). The combined ether extracts were washed with brine (10 mL), dried over MgSO₄ and concentrated to afford an oil (398 mg). This material was chromatographed on a 12-g silica cartridge eluted with a gradient of 0-100% EtOAc in hexanes to afford (±)-(R)-tert-butyl 2-((R)-1-(3-chlorophenyl)-1-hydroxy-5-methoxypentyl)morpholine-4-carboxylate (274 mg, 76%).

Step 4. (±)-(R)-1-(3-chlorophenyl)-5-methoxy-1-((R)-morpholin-2-yl)pentan-1-ol (±)—(R)-tert-butyl 2-((R)-1-(3-chlorophenyl) 1-hydroxy-5-methoxypentyl)morpholine-4-carboxylate (274 mg, 0.66 mmol) was dissolved in MeCN (10 mL) and 5% aq HCl (5 mL) was added. The mixture was stirred at rt for 2 d. Solid K₂CO₃ (~1 g) was added to the mixture, followed by water (25 mL). The mixture was extracted with ether (2×50 mL). The combined ether extracts were washed with brine (10 mL), dried over MgSO₄ and concentrated to afford a white solid (0.15 g). This material was purified by prep HPLC to afford the TFA salt of (±)-(R)-1-(3-chlorophenyl)-5-methoxy-1-((R)-morpholin-2-yl)pentan-1-ol (163 mg, 55%) as a syrup.

The following morpholines were prepared following procedures analogous to those described above:

(RS)-1-(3-chloro-2-fluorophenyl)-5-methoxy-1-((RS)-morpholin-2-yl)pentan-1-ol-ol using 2-fluoro-3-chlorophenyllithium and THF as solvent in Step 3.

(RS)-1-(benzo[b]thiophen-7-yl)-5-methoxy-1-((RS)-morpholin-2-yl)pentan-1-ol using 7-lithiobenzothiophene, generated from 7-bromobenzothiophene and n-BuLi, and ether as solvent in Step 3.

(R)-1-(3-chloro-2-fluorophenyl)-5-methoxy-1-((R)-morpholin-2-yl)pentan-1-ol using (R)-4-(tert-butoxycarbonyl)morpholine-2-carboxylic acid in Step 1 and 2-fluoro-3-chlorophenyllithium and THF as solvent in Step 3.

Preparation 36

(R)-1-(6-Fluoro-3'-methylbiphenyl-2-yl)-5-methoxy-1-((R)-morpholin-2-yl)pentan-1-ol

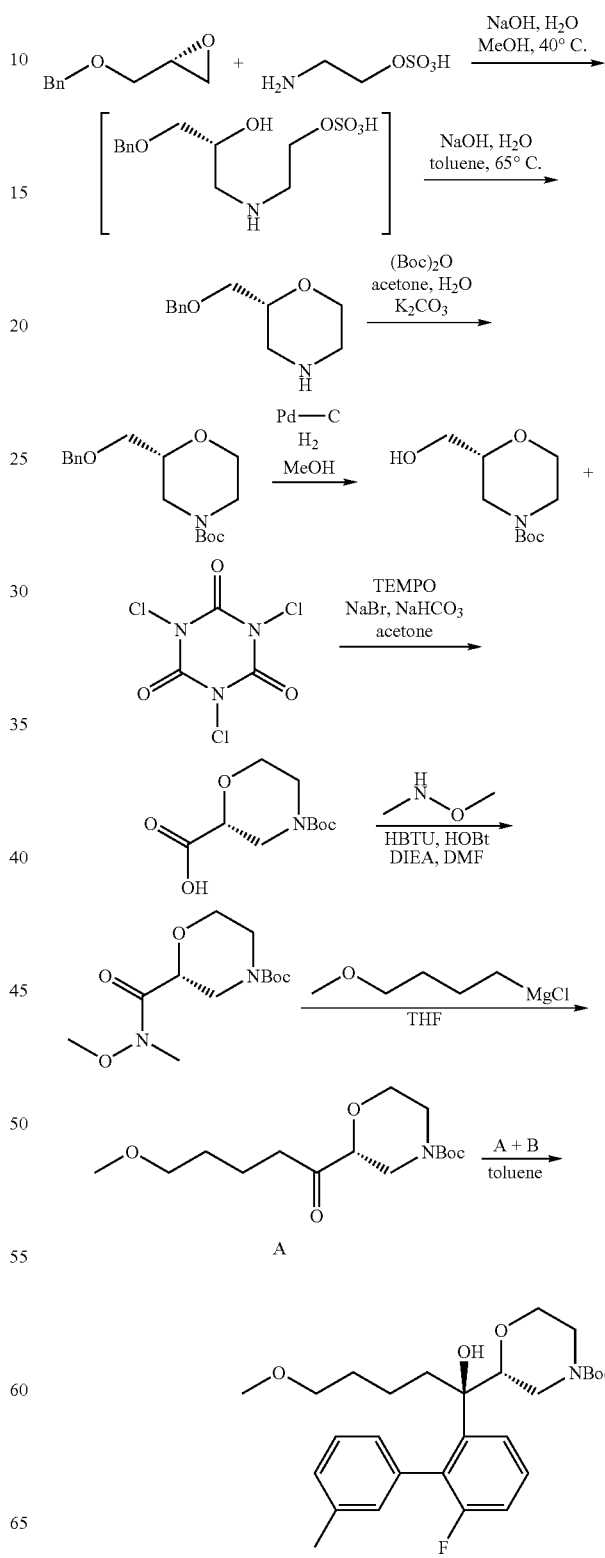

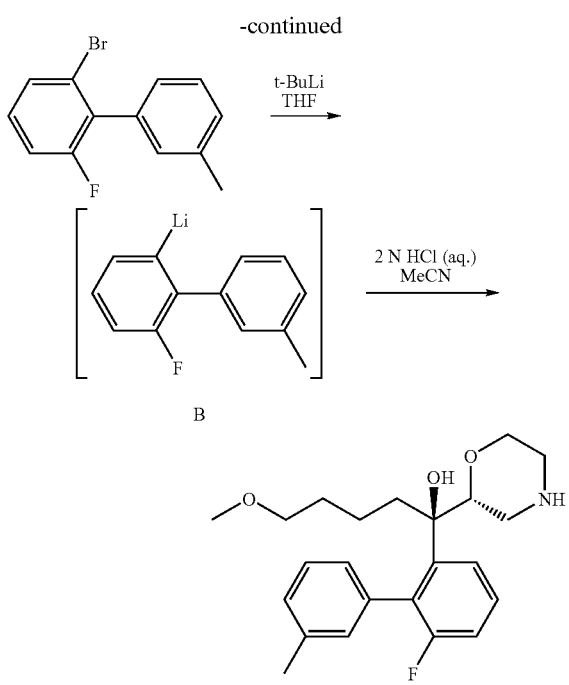

Step 1. (R)-2-(Benzyloxymethyl)morpholine

To a stirred mixture of (R)-2-(benzyloxymethyl)oxirane (10.0 g, 60.9 mmol) and NaOH (19.49 g, 487.2 mmol) in H₂O (46 mL) and MeOH (18 mL), there was added 2-aminoethyl hydrogen sulfate (36.8 g, 255.8 mmol) in portions. After addition was complete, the reaction mixture was stirred at 40° C. for 2 h. After cooling, the mixture was treated with NaOH (15.0 g, 375.0 mmol), followed by toluene (70 mL), and stirred at 65° C. overnight. The mixture was cooled, diluted with toluene (27 mL) and H₂O (92 mL). The toluene layer was separated and the aqueous layer was extracted with CH₂Cl₂ (2×50 mL). The combined organic layers were concentrated to give crude (R)-2-(benzyloxymethyl)morpholine (~14 g), which was used without purification. MS m/z 208 (M+H⁺).

Step 2. (R)-tert-Butyl 2-(benzyloxymethyl)morpholine-4-carboxylate

To a solution of crude (R)-2-(benzyloxymethyl)morpholine (~14 g) in acetone (100 mL) and H₂O (30 mL) at 0° C., there was added K₂CO₃ (25.2 g, 182.7 mmol), followed by (Boc)₂O (14.6 g, 67.0 mmol). The resulting solution was warmed to rt, and stirred until no starting material remained (~30 min). Acetone was removed under vacuum, and the aqueous solution was extracted with CH₂Cl₂ (4×10 mL). The combined organic layers were washed with H₂O (10 mL) and the solvent was removed. The residue was purified by flash column chromatography to give (R)-tert-butyl 2-(benzyloxymethyl)morpholine-4-carboxylate (8.33 g, 44% over 2 steps). ¹H NMR (400 MHz, CDCl₃): 7.34 (m, 5 H), 4.56 (s, 2 H), 3.88 (d, 2 H), 3.82 (br, 1 H), 3.40 (m, 1 H), 3.48 (m, 3 H), 2.94 (m, 1 H), 2.76 (m, 1 H), 1.44 (s, 9 H); MS m/z 330 (M+Na⁺).

Step 3. (R)-tert-Butyl 2-(hydroxymethyl)morpholine-4-carboxylate

To a solution of (R)-tert-butyl 2-(benzyloxymethyl)morpholine-4-carboxylate (8.33 g, 27.1 mmol) in EtOH was added Pd—C (wet, 3.6 g), and the resulting mixture was stirred at rt under a H₂ balloon overnight. After filtration, the solvent was removed under vacuum, and the residue was purified by flash column chromatography to give (R)-tert-butyl 2-(hydroxymethyl)morpholine-4-carboxylate (5.84 g, 99%) as a clear oil. ¹H NMR (400 MHz, CDCl₃): 3.88 (d, 2 H), 3.82 (br, 1 H), 3.64 (d, 1 H), 3.56 (m, 3 H), 2.94 (m, 1 H), 2.76 (m, 1 H), 1.90 (br, 1 H), 1.44 (s, 9 H); MS m/z 218 (M+H⁺).

Step 4. (R)-4-(tert-Butoxycarbonyl)morpholine-2-carboxylic Acid

Satd aq NaHCO₃ (15 mL) was added to a solution of (R)-tert-butyl 2-(hydroxymethyl)-morpholine-4-carboxylate (1.09 g, 5.0 mmol) in acetone (50 mL), stirred and maintained at 0° C. Solid NaBr (0.1 g, 1 mmol) and TEMPO (0.015 g, 0.1 mmol) were added. Trichloroisocyanuric acid (2.32 g, 10.0 mmol) was then added slowly within 20 min at 0° C. After addition, the mixture was warmed to rt and stirred overnight. 2-Propanol (3 mL) was added, and the resulting solution was stirred at rt for 30 min, filtered through a pad of Celite, concentrated under vacuum, and treated with satd aq Na₂CO₃ (15 mL). The aqueous solution was washed with EtOAc (5 mL), acidified with 6 N HCl, and extracted with EtOAc (5×10 mL). The combined organic layers were dried over Na₂SO₄ and the solvent was removed to give (R)-4-(tert-butoxycarbonyl)morpholine-2-carboxylic acid (1.07 g, 92%) as a white solid. ¹H NMR (400 MHz, CDCl₃): 4.20 (br, 1 H), 4.12 (d, 1 H), 4.02 (d, 1 H), 3.84 (m, 1 H), 3.62 (m, 1 H), 3.04 (m, 2 H), 1.44 (s, 9 H); MS m/z 232 (M+H⁺).

Step 5. (R)-tert-Butyl 2-(methoxy(methyl)carbamoyl)morpholine-4-carboxylate

To a solution of (R)-4-(tert-butoxycarbonyl)morpholine-2-carboxylic acid (1.05 g, 4.54 mmol) in DMF (10 mL) at 0° C., was added DIEA (3.9 mL, 22.7 mmol), followed by HBTU (1.89 g, 4.99 mmol) and HOBt (0.67 g, 4.99 mmol). MeONMHMe.HCl (0.48 g, 4.92 mmol) was added and the resulting solution was warmed to rt and stirred until no starting material remained (~2 h). The mixture was diluted with H₂O (10 mL) and extracted with EtOAc (4×10 mL). The combined organic layers were washed with 1 N aq HCl (10 mL), 1 N aq NaOH (3×10 mL), water (2×10 mL) and brine (10 mL), and dried over Na₂SO₄. The solvent was removed under vacuum to give (R)-tert-butyl 2-(methoxy(methyl)carbamoyl)morpholine-4-carboxylate (1.40 g, quant.), which was used without further purification. ¹H NMR (400 MHz, CDCl₃): 4.36 (br, 1 H), 4.08 (m, 1 H), 4.00 (d, 1 H), 3.84 (m, 1 H), 3.76 (s, 3 H), 3.58 (m, 1 H), 3.20 (s, 3 H), 3.04 (m, 2 H), 1.44 (s, 9 H); MS m/z 297 (M+Na⁺).

Step 6. (R)-tert-Butyl 2-(5-methoxypentanoyl)morpholine-4-carboxylate

To a stirred solution of (R)-tert-butyl 2-(methoxy(methyl)carbamoyl)morpholine-4-carboxylate (1.37 g, 5.0 mmol) in THF (10 mL) at −20° C., there was added 1.47 M 4-methoxybutylmagnesium chloride in THF (10.2 mL, 15.0 mmol) dropwise to keep the temperature below −20° C. After addition, the resulting solution was warmed to rt and quenched with 1 N aq HCl (10 mL). The organic layer was separated, and the aqueous layer was extracted with ether (3×5 mL). Combined organic layers were washed with satd aq NaHCO₃ (10 mL) and brine (5 mL) and dried over Na₂SO₄. Removal of the solvent under vacuum gave (R)-tert-butyl 2-(5-methoxypentanoyl)morpholine-4-carboxylate (1.41 g, 93%), which was used without purification. MS m/s 324 (M+Na⁺).

Step 7. (R)-tert-Butyl 2-((R)-1-(6-fluoro-3'-methylbiphenyl-2-yl)-1-hydroxy-5-methoxypentyl)-morpholine-4-carboxylate To a solution of 2-bromo-6-fluoro-3'-methylbiphenyl (1.90 g, 7.17 mmol) in ether (8 mL) at −78° C., there was added t-BuLi in pentane (1.70 M, 8.43 mL, 14.33 mmol) dropwise to keep the temperature below −70° C. The resulting solution was stirred at −78° C.

To a solution of (R)-tert-butyl 2-(5-methoxypentanoyl) morpholine-4-carboxylate (0.68 g, 2.26 mmol) in toluene (8 mL) at −20° C. there was added the above lithium reagent dropwise to keep the solution temperature below −20° C. After addition, the resulting mixture was warmed to rt slowly, and quenched with saturated NH₄Cl (8 mL). The organic layer was separated, and aqueous layer was extracted with ether (3×5 mL). Combined organic layers were washed with water (10 mL), concentrated, and the residue was purified by flash column chromatography to give (R)-tert-butyl 2-((R)-1-(6-fluoro-3'-methylbiphenyl-2-yl)-1-hydroxy-5-methoxypentyl)-morpholine-4-carboxylate (0.48 g, 44%) as a foam. ¹H NMR (400 MHz, CDCl₃): 7.40 (m, 1 H), 7.32 (m, 2 H), 7.20 (d, 1 H), 7.04 (m, 3 H), 3.84 (m, 1 H), 3.78 (m, 2 H), 3.40-3.24 (ms, 7 H), 2.82 (s, 3 H), 1.70-1.20 (m, 5 H), 1.44 (s, 9 H), 0.94 (m, 1 H); MS m/z 510 (M+Na⁺).

Step 8. (R)-1-(6-Fluoro-3'-methylbiphenyl-2-yl)-5-methoxy-1-((R)-morpholin-2-yl)-pentan-1-ol To a solution of (R)-tert-butyl 2-((R)-1-(6-fluoro-3'-methylbiphenyl-2-yl)-1-hydroxy-5-methoxypentyl)morpholine-4-carboxylate (0.46 g, 0.96 mmol) in acetonitrile (50 mL) was added 2 N aq HCl (50 mL). The resulting solution was stirred at rt overnight and basified with 10 N aq NaOH to pH 10. Acetonitrile was removed under vacuum, and the aqueous residue was extracted with CH₂Cl₂ (4×5 mL). The combined organic layers were washed with brine (5 mL), dried over Na₂SO₄, and concentrated to give (R)-1-(6-fluoro-3'-methylbiphenyl-2-yl)-5-methoxy-1-((R)-morpholin-2-yl)pentan-1-ol (0.38, quant.). MS m/z 388 (M+H⁺).

The following morpholines were prepared using procedures analogous to those described above:

(R)-1-(6-chloro-3'-methylbiphenyl-2-yl)-5-methoxy-1-((R)-morpholin-2-yl)pentan-1-ol using 2-bromo-6-chloro-3'-methylbiphenyl in Step 7.

(R)-1-(6-fluoro-3'-(trifluoromethoxy)biphenyl-2-yl)-5-methoxy-1-((R)morpholin-2-yl)pentan-1-ol using 2-bromo-6-fluoro-3'-(trifluoromethoxy)biphenyl in Step 7.

(R)-5-methoxy-1-(3-methoxy-3'-methylbiphenyl-2-yl)-1-((R)-morpholin-2-yl)pentan-1-ol using 2-bromo-3-methoxy-3'-methylbiphenyl in Step 7.

(R)-1-(3'-ethyl-6-fluorobiphenyl-2-yl)-5-methoxy-1-((R)-morpholin-2-yl)pentan-1-ol using 2-bromo-3'-ethyl-6-fluorobiphenyl in Step 7.

(R)-1-(6-fluoro-3'-methoxybiphenyl-2-yl)-5-methoxy-1-((R)-morpholin-2-yl)pentan-1-ol using 2-bromo-6-fluoro-3'-methoxybiphenyl in Step 7.

(R)-1-(3'-chloro-6-fluorobiphenyl-2-yl)-5-methoxy-1-((R)-morpholin-2-yl)pentan-1-ol using 2-bromo-3'-chloro-6-fluorobiphenyl in Step 7.

(R)-1-(3'-cyclopropyl-6-fluorobiphenyl-2-yl)-5-methoxy-1-((R)-morpholin-2-yl)pentan-1-ol using 2-bromo-3'-cyclopropyl-6-fluorobiphenyl in Step 7.

(R)-1-(6-chloro-3'-ethylbiphenyl-2-yl)-5-methoxy-1-((R)-morpholin-2-yl)pentan-1-ol using 2-bromo-6-chloro-3'-ethylbiphenyl in Step 7.

(R)-1-(6-chloro-3',4'-dimethylbiphenyl-2-yl)-5-methoxy-1-((R)-morpholin-2-yl)pentan-1-ol using 2-bromo-6-chloro-3',4'-dimethylbiphenyl in Step 7.

(R)-1-(3'-ethoxy-6-fluorobiphenyl-2-yl)-5-methoxy-1-((R)-morpholin-2-yl)pentan-1-ol using 2-bromo-3'-ethoxy-6-fluorobiphenyl in Step 7.

(R)-1-(6-fluoro-3-methoxy-3'-methylbiphenyl-2-yl)-5-methoxy-1-((R)morpholin-2-yl)pentan-1-ol using 2-bromo-6-fluoro-3-methoxy-3'-methylbiphenyl in Step 7.

(R)-1-(6-chloro-3'-methoxybiphenyl-2-yl)-5-methoxy-1-((R)-morpholin-2-yl)pentan-1-ol using 2-bromo-6-chloro-3'-methoxybiphenyl in Step 7.

(R)-1-(6-fluoro-3'-(methylthio)biphenyl-2-yl)-5-methoxy-1-((R)-morpholin-2-yl)pentan-1-ol using 2'-bromo-6'-fluoro-3-(methylthio)biphenyl in Step 7.

1-(3',6-dichlorobiphenyl-2-yl)-5-methoxy-1-((R)-morpholin-2-yl)pentan-1-ol using 2-bromo-3',6-dichlorobiphenyl in Step 7.

(R)-1-(6-chloro-3'-isopropylbiphenyl-2-yl)-5-methoxy-1-((R)-morpholin-2-yl)pentan-1-ol using 2-bromo-6-chloro-3'-isopropylbiphenyl in Step 7.

(R)-1-(6-chloro-3'-(methylthio)biphenyl-2-yl)-5-methoxy-1-((R)-morpholin-2-yl)pentan-1-ol using (2'-bromo-6'-chlorobiphenyl-3-yl)(methyl)sulfane in Step 7.

(R)-1-(6-fluoro-3'-(trifluoromethyl)biphenyl-2-yl)-5-methoxy-1-((R)morpholin-2-yl)pentan-1-ol using 2-bromo-6-fluoro-3'-(trifluoromethyl)biphenyl in Step 7.

(R)-5-methoxy-1-((R)-morpholin-2-yl)-1-(2-(o-tolyloxy)phenyl)pentan-1-ol using 1-(o-tolyloxy)-2-iodobenzene in Step 7.

The following morpholines were prepared starting in Step 5 with racemic 4-(tert-butoxycarbonyl)morpholine-2-carboxylic acid:

(RS)-5-methoxy-1-((RS)-morpholin-2-yl)-1-(2-(o-tolyloxy)phenyl)pentan-1-ol (RS)-1-(6-chloro-3'-methylbiphenyl-2-yl)-5-methoxy-1-((RS)-morpholin-2-yl)pentan-1-ol.

Preparation 37

(2S)-2-(1-(6-fluoro-3'-methylbiphenyl-2-yl)-5-methoxypentyl)morpholine

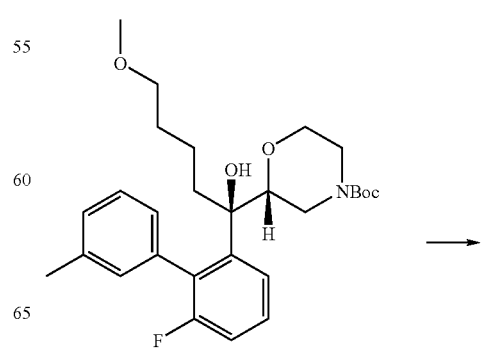

161

-continued

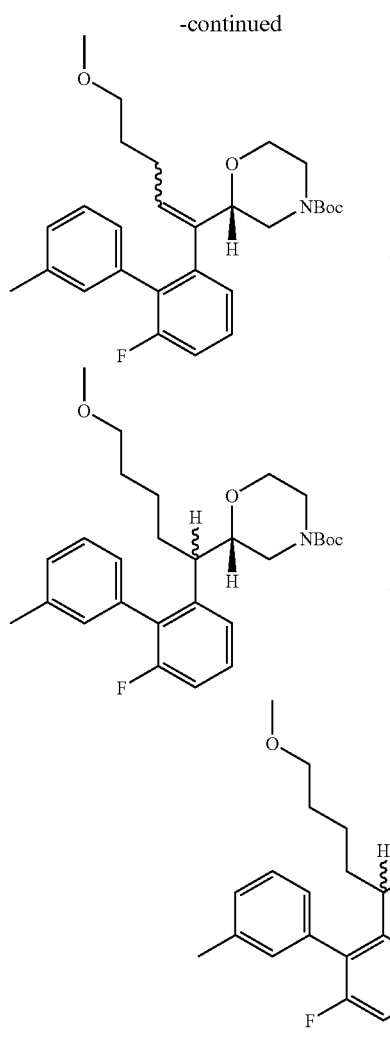

Step 1. (S)-tert-butyl 2-(1-(6-fluoro-3'-methylbiphenyl-2-yl)-5-methoxypent-1-enyl)morpholine-4-carboxylate A mixture of (R)-tert-butyl 2-((R)-1-(6-fluoro-3'-methylbiphenyl-2-yl)-1-hydroxy-5-methoxypentyl)morpholine-4-carboxylate (188 mg, 0.39 mmol) and Burgess' reagent (186 mg, 0.78 mmol) in toluene (3 mL) was heated to reflux under a $N_2$ atmosphere for 2 h, then cooled to rt and diluted with EtOAc, washed with $H_2O$ and brine, dried over $Na_2SO_4$, filtered and evaporated. The residue was purified by flash chromatography to give (S)-tert-butyl 2-(1-(6-fluoro-3'-methylbiphenyl-2-yl)-5-methoxypent-1-enyl)morpholine-4-carboxylate (133 mg, 73%). MS m/z 470 (M+H)$^+$.

Step 2. (2S)-tert-butyl 2-(1-(6-fluoro-3'-methylbiphenyl-2-yl)-5-methoxypentyl)morpholine-4-carboxylate (S)-tert-butyl 2-(1-(6-fluoro-3'-methylbiphenyl-2-yl)-5-methoxypent-1-enyl)morpholine-4-carboxylate (133 mg, 0.28 mmol) was dissolved in methanol and hydrogenated under 50 psi of hydrogen in the presence of 10% Pd(OH)$_2$/C as catalyst for 48 h. The reaction mixture was filtered and evaporated to give (2S)-tert-butyl 2-(1-(6-fluoro-3'-methylbiphenyl-2-yl)-5-methoxypentyl)morpholine-4-carboxylate in nearly quantitative yield. MS m/z 470 (M+H)$^+$.

162

Step 3. (2S)-2-(1-(6-fluoro-3'-methylbiphenyl-2-yl)-5-methoxypentyl)morpholine (2S)-tert-butyl 2-(1-(6-fluoro-3'-methylbiphenyl-2-yl)-5-methoxypentyl)morpholine-4-carboxylate from Step 2 was dissolved in 1 M HCl in MeOH and stirred at 50° C. for 10 min, the solvent was removed under reduced pressure to give (2S)-2-(1-(6-fluoro-3'-methylbiphenyl-2-yl)-5-methoxypentyl)morpholine as its HCl salt in quantitative yield. MS m/z 494 (M+Na)$^+$.

Preparation 38

N-(2-((S)-(6-fluoro-3'-methylbiphenyl-2-yl)((R)-morpholin-2-yl)methoxy)ethyl)acetamide

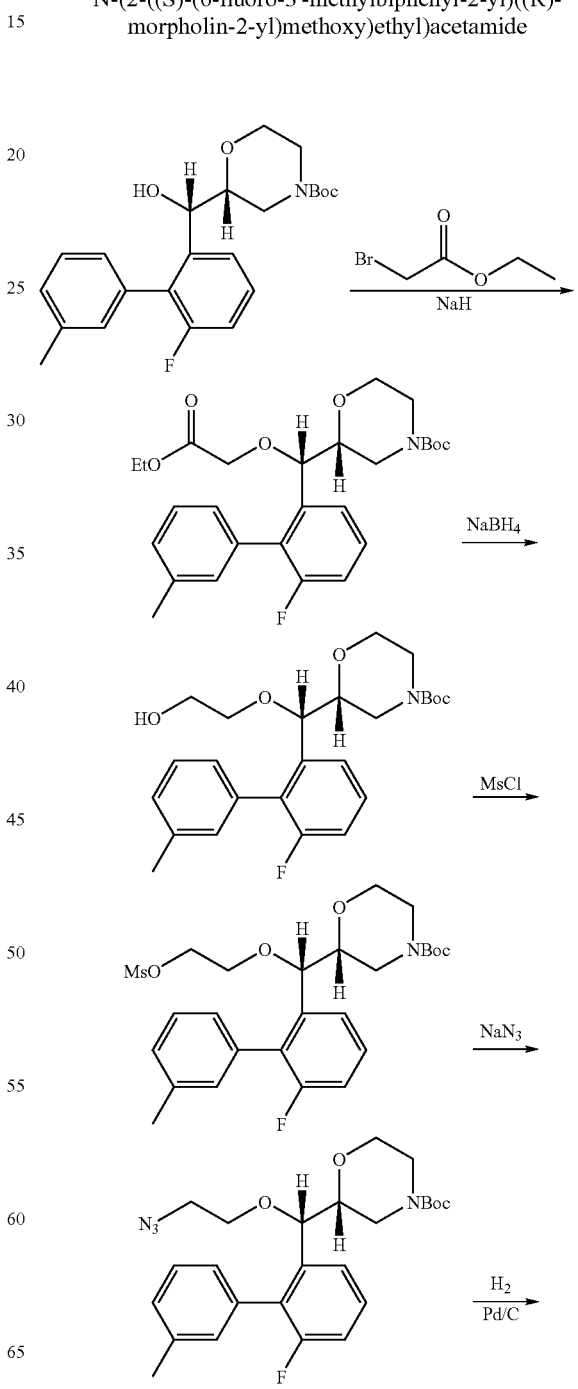

-continued

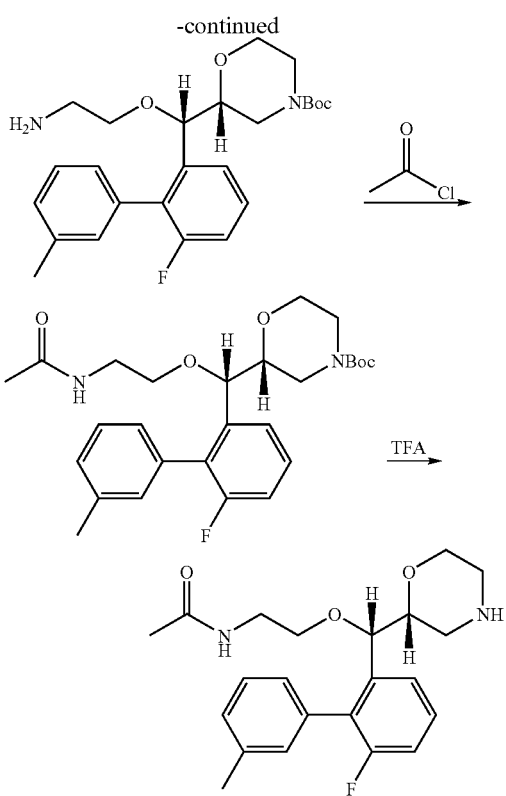

Step 1. (R)-tert-butyl 2-((S)-(2-ethoxy-2-oxoethoxy)(6-fluoro-3'-methylbiphenyl-2-yl)methyl)morpholine-4-carboxylate To a slurry of 60% NaH in oil (0.75 g, 18.7 mmol) in THF (30 mL) was added a solution of (R)-tert-butyl 2-((S)-(6-fluoro-3'-methylbiphenyl-2-yl)(hydroxy)methyl)morpholine-4-carboxylate (2.5 g, 6.23 mmol) in THF (20 mL) dropwise at and then the reaction mixture was stirred for about 1 h at rt. A solution of ethyl 3-bromopropionate (1.55 g, 9.35 mmol) in THF (20 mL) was added dropwise while the temperature was maintained at −15 to −5° C. The mixture was allowed to warm slowly to rt and stirred for ~2 h until the reaction was complete by tlc analysis. The reaction was cooled in an ice bath, quenched with satd aq $NH_4Cl$ (120 mL) and extracted with EtOAc. The combined organic extracts were washed with brine, dried over $NaSO_4$, concentrated and purified by flash chromatography to afford (R)-tert-butyl 2-((S)-(2-ethoxy-2-oxoethoxy)(6-fluoro-3'-methylbiphenyl-2-yl)methyl)morpholine-4-carboxylate (570 mg, 19%). MS (E/Z): 488 (M+H$^+$)

Step 2. (R)-tert-butyl 2-((S)-(6-fluoro-3'-methylbiphenyl-2-yl)(2-hydroxyethoxy)methyl)morpholine-4-carboxylate To a solution of (R)-tert-butyl 2-((S)-(2-ethoxy-2-oxoethoxy)(6-fluoro-3'-methylbiphenyl-2-yl)methyl)morpholine-4-carboxylate (570 mg, 1.17 mmol) in $CH_3OH$ (20 mL) at rt, $NaBH_4$ (355 mg, 9.36 mmol) was added in portions. The mixture was stirred for ~0.5 h at rt and then evaporated. The residue was partitioned between water and EtOAc. The combined organic layers were washed with brine, dried over anhydrous $NaSO_4$ and evaporated to give semi-crude (R)-tert-butyl 2-((S)-(6-fluoro-3'-methylbiphenyl-2-yl)(2-hydroxyethoxy)methyl)morpholine-4-carboxylate (498 mg, 96%), which was used in the next step reaction without further purification. MS (E/Z): 446 (M+H$^+$)

Step 3. (R)-tert-butyl 2-((S)-(6-fluoro-3'-methylbiphenyl-2-yl)(2-(methylsulfonyloxy)ethoxy)methyl)morpholine-4-carboxylate To a solution of (R)-tert-butyl 2-((S)-(6-fluoro-3'-methylbiphenyl-2-yl)(2-hydroxyethoxy)methyl)morpholine-4-carboxylate (498 mg, 1.12 mmol) in dry $CH_2Cl_2$ (15 mL) was added $Et_3N$ (472 mg, 4.68 mmol) at ~0 to −5° C. A solution of MsCl (267 mg, 2.34 mmol) in dry $CH_2Cl_2$ (10 mL) was added dropwise at the same temperature. The mixture was allowed to warm to rt gradually. Tlc showed the stating material had disappeared. Water (10 mL) was added and the aqueous layer was extracted with $CH_2Cl_2$ (3×20 mL). The combined organic layers were washed with 10% aq citric acid, satd aq $NaHCO_3$ and brine, dried over $Na_2SO_4$, filtered and concentrated to afford crude (R)-tert-butyl 2-((S)-(6-fluoro-3'-methylbiphenyl-2-yl)(2-(methylsulfonyloxy)ethoxy)methyl)morpholine-4-carboxylate (554 mg, 95%). which was used in the next step without further purification. MS (E/Z): 524 (M+H$^+$)

Step 4. (R)-tert-butyl 2-((S)-(2-azidoethoxy)(6-fluoro-3'-methylbiphenyl-2-yl)methyl)morpholine-4-carboxylate To a solution of (R)-tert-butyl 2-((S)-(6-fluoro-3'-methylbiphenyl-2-yl)(2-(methylsulfonyloxy)ethoxy)methyl)morpholine-4-carboxylate (554 mg, 1.0 mmol) in anhydrous DMF (18 mL), solid $NaN_3$ (230 mg, 3.51 mmol) was added and the reaction mixture was heated to 70° C. for overnight. The reaction mixture was cooled to rt and diluted with EtOAc (110 mL), and water (30 ml). The organic phase was washed with water (3×30 mL), dried over $Na_2SO_4$ and evaporated to give (R)-tert-butyl 2-((S)-(2-azidoethoxy)(6-fluoro-3'-methylbiphenyl-2-yl)methyl)morpholine-4-carboxylate (423 mg, 90%). MS (E/Z): 471 (M+H$^+$)

Step 5. (R)-tert-butyl 2-((S)-(2-aminoethoxy)(6-fluoro-3'-methylbiphenyl-2-yl)methyl)morpholine-4-carboxylate To a solution of (R)-tert-butyl 2-((S)-(2-azidoethoxy)(6-fluoro-3'-methylbiphenyl-2-yl)methyl)morpholine-4-carboxylate (423 mg, 0.9 mmol) in EtOAc (20 mL) was added wetted Pd/C (42 mg) and the mixture was hydrogenated overnight using a balloon of hydrogen. The mixture was filtered through a pad of Celite and the solvent was removed to give (R)-tert-butyl 2-((S)-(2-aminoethoxy)(6-fluoro-3'-methylbiphenyl-2-yl)methyl)morpholine-4-carboxylate (430 mg, 100%). MS (E/Z): 445 (M+H$^+$)

Step 6. (R)-tert-butyl 2-((S)-(2-acetamidoethoxy)(6-fluoro-3'-methylbiphenyl-2-yl)methyl)morpholine-4-carboxylate To a round-bottom flask were added (R)-tert-butyl 2-((S)-(2-aminoethoxy)(6-fluoro-3'-methylbiphenyl-2-yl)methyl)morpholine-4-carboxylate (280 mg, 0.63 mmol), triethylamine (0.19 mL, 1.89 mmol) and anhydrous $CH_2Cl_2$ (15 mL). The mixture was cooled in an ice bath and a solution of acetyl chloride (49.2 mg, 0.045 mL, 0.63 mmol) was added. The reaction mixture was allowed to warm slowly to rt and stirred until the reaction was complete (ca 1~2 h). The solvent was removed by evaporation, and the residue was purified by preparative tlc to give (R)-tert-butyl 2-((S)-(2-acetamidoethoxy)(6-fluoro-3'-methylbiphenyl-2-yl)methyl)morpholine-4-carboxylate (202 mg, 66%). $^1$H NMR (300 MHz, CDCl$_3$): δ=1.45 (s, 9 H), 1.93 (s, 3 H), 2.38 (s, 3 H), 2.87~3.2 (m, 6 H), 3.32~3.92 (m, 5 H), 4.28 (d, 1 H), 7.01~7.25 (m, 3 H), 7.28~7.37 (m, 4 H), 9.41-9.54 (s, 1 H). MS (E/Z): 487 (M+H$^+$)

Step 7. N-(2-((S)-(6-fluoro-3'-methylbiphenyl-2-yl)((R)-morpholin-2-yl)methoxy)ethyl)acetamide (R)-tert-butyl 2-((S)-(2-acetamidoethoxy)(6-fluoro-3'-methylbiphenyl-2-yl)methyl)morpholine-4-carboxylate (202 mg, 0.42 mmol) was dissolved in 20% TFA in $CH_2Cl_2$ (8 mL) and stirred for about 1 h at rt. The mixture was neutralized with satd aq NaHCO$_3$ and the product was extracted with CH$_2$Cl$_2$. The combined organic layers were washed with brine, dried over Na$_2$SO$_4$ and concentrated to give N-(2-((S)-(6-fluoro-3'-methylbiphenyl-2-yl)((R)-morpholin-2-yl)methoxy)ethyl)acetamide (130 mg, 82%). $^1$H NMR (300 MHz, CDCl$_3$): δ=1.98 (s, 3 H), 2.39 (s, 3 H), 2.90~3.3 (m, 6 H), 3.31~3.41 (m, 2 H), 3.6~4.0 (m, 3 H), 4.33 (d, 1 H), 6.56~6.57 (s, 1 H), 6.97~7.14 (m, 3 H), 7.27~7.40 (m, 4 H), 9.40~9.55 (s, 1H). MS (E/Z): 387 (M+H$^+$).

The following compounds were prepared using procedures analogous to those described above:

methyl 2-((S)-(6-fluoro-3'-methylbiphenyl-2-yl)((R)-morpholin-2-yl)methoxy)ethylcarbamate using methyl chloroformate in place of acetyl chloride in Step 6.

EXAMPLE 1 methyl 2-((R)-((R)-1-((2S,3S)-5-(butylamino)-1-cyclohexyl-3-hydroxy-5-oxopentan-2-ylcarbamoyl)piperidin-3-yl)(3-chlorophenyl)methoxy)ethylcarbamate Step 1. tert-Butyl (2S,3S)-5-(butylamino)-1-cyclohexyl-3-hydroxy-5-oxopentan-2-ylcarbamate To a stirred solution of Boc-cyclohexylstatine (345 mg, 11.1 mmol), n-butylamine (0.22 mL, 2.2 mmol) and DIEA (0.39 mmol, 2.2 mmol) in CH$_2$Cl$_2$ (10 mL) was added solid HATU (630 mg, 1.65 mmol). The mixture was stirred at rt for 18 h, diluted with ether (90 mL), washed with 5 aq HCl (20 mL), satd aq NaHCO$_3$ (20 mL) and brine (20 mL) and dried over MgSO$_4$. Removal of the solvent left tert-butyl (2S,3S)-5-(butylamino)-1-cyclohexyl-3-hydroxy-5-oxopentan-2-ylcarbamate (394 mg, 97%) as a white solid which was used without purification.

Step 2. (3S,4S)-4-Amino-N-butyl-5-cyclohexyl-3-hydroxypentanamide tert-butyl (2S,3S)-5-(butylamino)-1-cyclohexyl-3-hydroxy-5-oxopentan-2-ylcarbamate (394 mg, 1.1 mmol) was dissolved in 4M HCl in dioxane (5 mL, 200 mmol and stirred at rt for 4 h. Removal of the solvent left a sticky solid (344 mg). This material was taken up in 10% aq K2CO3 (20 mL) and extracted with CH2Cl2 (4×30 mL). The combined

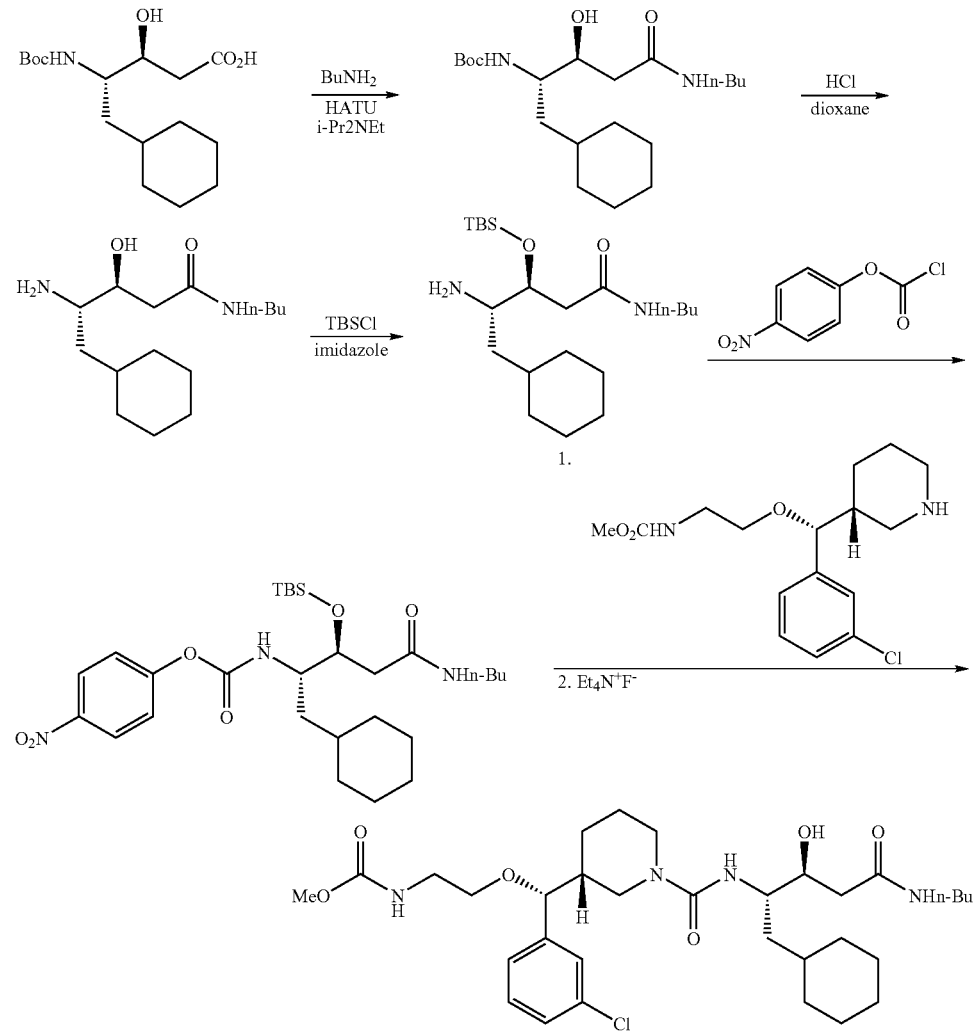

CH2Cl2 extracts were dried over MgSO4 and concentrated to afford (3S,4S)-4-Amino-N-butyl-5-cyclohexyl-3-hydroxypentanamide (279 mg, 97%).

Step 3. (3S,4S)-4-Amino-N-butyl-3-(tert-butyldimethylsilyloxy)-5-cyclohexylpentanamide A solution of the HCl salt of (3S,4S)-4-amino-N-butyl-5-cyclohexyl-3-hydroxypentanamide (279 mg, 1.03 mmol), TBSCl (311 mg, 2.06 mmol) and imidazole (281 mg, 4.12 mmol) in dry DMF (2 mL) was stirred at rt for 2 d. The mixture was diluted with EtOAc (90 mL), washed with 1:1 water/brine (3×20 mL), dried over $Na_2SO_4$ and concentrated to leave crude (3S,4S)-4-amino-N-butyl-3-(tertbutyldimethylsilyloxy)-5-cyclohexylpentanamide (311 mg, 78%) as a yellow syrup.

Step 4. 4-Nitrophenyl (2S,3S)-5-(butylamino)-3-(tert-butyldimethylsilyloxy)-1-cyclohexyl-5-oxopentan-2-ylcarbamate To a stirred solution of crude (3S,4S)-4-amino-N-butyl-3-(tertbutyldimethylsilyloxy)-5-cyclohexylpentanamide (311 mg, 0.81 mmol) in MeCN were added powdered NaHCO3 (203 mg, 2.43 mmol) and p-nitrophenyl chloroformate (244 mg, 1.21 mmol) and the mixture was stirred overnight at rt. The mixture was concentrated under reduced pressure. The residue was taken up in 1:1 EtOAc/Et2O (90 mL), washed with water (20 mL) and brine (20 mL), dried over $MgSO_4$ and concentrated to leave an orange oil. This material was chromatographed on a 40-g silica cartridge eluted with a 0 to 100% ethyl acetate in hexanes gradient to afford 4-nitrophenyl (2S,3S)-5-(butylamino)-3-(tert-butyldimethylsilyloxy)-1-cyclohexyl-5-oxopentan-2-ylcarbamate (39 mg, 8%).

Step 5. Methyl 2-((R)-((R)-1-((2S,3S)-5-(butylamino)-1-cyclohexyl-3-hydroxy-5-oxopentan-2-ylcarbamoyl)piperidin-3-yl)(3-chlorophenyl)methoxy)ethylcarbamate A solution of methyl 2-((R)-(3-chlorophenyl)((R)-piperidin-3-yl)methoxy)ethylcarbamate (40 mg, 0.12 mmol) and DIEA (0.10 mL, 0.55 mmol) in $CH_2Cl_2$ (1 mL) was added to 4-nitrophenyl (2S,3S)-5-(butylamino)-3-(tert-butyldimethylsilyloxy)-1-cyclohexyl-5-oxopentan-2-ylcarbamate (39 mg, 0.07 mmol). The mixture was stirred at rt for 3 h, diluted with ether (100 mL), washed with 5% aq HCl (20 mL) and 1 M aq NaOH (20 mL) and dried over $MgSO_4$. Removal of the solvent left an oil (43 mg) which was dissolved in MeCN (2 mL) and treated with $Et_4N^+F^-$ (25 mg, 0.18 mmol). The solution was stirred at rt for 3 h and submitted directly to preparative HPLC to afford Methyl 2-((R)-((R)-1-((2S,3S)-5-(butylamino)-1-cyclohexyl-3-hydroxy-5-oxopentan-2-ylcarbamoyl)piperidin-3-yl)(3-chlorophenyl)methoxy)ethylcarbamate (30 mg, 38%) as an oil. $^1$H NMR ($CD_3OD$) 0.92 (t, 3H), 1.0-1.9 (22H), 2.26 (m, 1H), 2.35 (m, 1H), 2.92 (m, 2H), 3.17 (m, 2H), 3.23 (m, 2H), 3.30 (2H), 3.61 (s, 3H), 3.80 (br d, 1H), 3.88 (br d, 1H), 3.94 (m, 1H), 4.03 (d, 1H), 4.15 (br d, 1H), 7.21 (d, 1H), 7.34 (3H); LC-MS (16 min) $t_R$=9.89 min, m/z=623. It is noted that although the compound described in this example was the only compound prepared, the other compounds of the invention described herein could be prepared in accordance with the methods taught herein.

EXAMPLE 2

In Vitro Activity Studies—$IC_{50}$ for Renin

The compounds of the invention are believed to have enzyme-inhibiting properties. In particular, they inhibit the action of the natural enzyme renin. The latter passes from the kidneys into the blood where it effects the cleavage of angiotensinogen, releasing the decapeptide angiotensin I which is then cleaved in the blood, lungs, the kidneys and other organs by angiotensin converting enzyme to form the octapeptide angiotensin II. The octapeptide increases blood pressure both directly by binding to its receptor, causing arterial vasoconstriction, and indirectly by liberating from the adrenal glands the sodium-ion-retaining hormone aldosterone, accompanied by an increase in extracellular fluid volume. That increase can be attributed to the action of angiotensin II. Inhibitors of the enzymatic activity of renin bring about a reduction in the formation of angiotensin I. As a result a smaller amount of angiotensin II is produced. The reduced concentration of that active peptide hormone is the direct cause of the hypotensive effect of renin inhibitors.

The action of renin inhibitors in vitro is demonstrated experimentally by means of a test which measures the increase in fluorescence of an internally quenched peptide substrate. The sequence of this peptide corresponds to the sequence of human angiotensinogen. The following test protocol is used: All reactions are carried out in a flat bottom white opaque microtiter plate. A 4 µL aliquot of 400 µM renin substrate (DABCYL-γ-Abu-Ile-His-Pro-Phe-His-Leu-Val-Ile-His-Thr-EDANS) in 192 µL assay buffer (50 mM BES, 150 mM NaCl, 0.25 mg/mL bovine serum albumin, pH7.0) is added to 4 µL of test compound in DMSO at various concentrations ranging from 10 µM to 1 nM final concentrations. Next, 100 µL of trypsin-activated recombinant human renin (final enzyme concentration of 0.2-2 nM) in assay buffer is added, and the solution is mixed by pipetting. The increase in fluorescence at 495 nm (excitation at 340 nm) is measured for 60-360 min at rt using a Perkin-Elmer Fusion microplate reader. The slope of a linear portion of the plot of fluorescence increase as a function of time is then determined, and the rate is used for calculating percent inhibition in relation to uninhibited control. The percent inhibition values are plotted as a function of inhibitor concentration, and the $IC_{50}$ is determined from a fit of this data to a four parameter equation. The $IC_{50}$ is defined as the concentration of a particular inhibitor that reduces the formation of product by 50% relative to a control sample containing no inhibitor. (Wang G. T. et al. *Anal. Biochem.* 1993, 210, 351; Nakamura, N. et al. *J. Biochem.* (*Toko*) 1991, 109, 741; Murakaini, K. et al. *Anal Biochem.* 1981, 110, 232).

EXAMPLE 3

In Vitro Activity Studies—$IC_{50}$ for Renin

All reactions are carried out in a low volume, black, 384 well microtiter plate (greiner bio-one). Compounds are diluted in 100% DMSO, and a 100 nL aliquot of each compound concentration is stamped into the plate using a Hummingbird (Genomic Solutions). 5 µL of 600 µM renin (trypsin-activated recombinant human renin) is then added to the plate, followed by 5 µL of 2 µM substrate (Arg-Glu-Lys (5-FAM)-Ile-His-Pro-Phe-His-Leu-Val-Ile-His-Thr-Lys(5,6-TAMRA)-Arg-$CONH_2$). Both renin and substrate are made up in buffer containing 50 mM HEPES, 125 mM NaCl, 0.1% CHAPS, with the pH adjusted to 7.4. After 2 hours of reaction at room temperature, the plates are read on a Viewlux (PerkinElmer) with an excitation/emission of 485/530 nm, and using a 505 nm cutoff filter. The percent inhibition values are plotted as a function of inhibitor concentration, and the $IC_{50}$ is determined from a fit of this data to a four parameter equation. The $IC_{50}$ is defined as the concentration of a particular inhibitor that reduces the formation of product by 50% relative to a control sample containing no inhibitor.

EXAMPLE 4

IC$_{50}$ Values of the Disclosed Compounds for Renin

The IC$_{50}$ value of the disclosed compound of Example 1 for renin was determined according to the protocol described in Example 2. The value obtained was 113 nM. Generally, in these in vitro systems of Examples 2 and 3, the compounds of the invention are believed to exhibit inhibition activity at minimum concentrations of from approximately $5 \times 10^{-5}$ M to approximately $10^{-12}$ M. Preferred compounds of the invention would be expected to exhibit inhibition activity at minimum concentrations of from approximately $10^{-8}$ M to approximately $10^{-12}$ M. (Wang G. T. et al. *Anal. Biochem.* 1993, 210, 351; Nakamura, N. et al., *J. Biochem. (Tokyo)* 1991, 109, 741; Murakami, K. et al. *Anal Biochem.* 1981, 110, 232).

EXAMPLE 5

In Vitro Activity of the Disclosed Compounds in Human Plasma

The action of renin inhibitors in vitro in human plasma is demonstrated experimentally by the decrease in plasma renin activity (PRA) levels observed in the presence of the compounds. Incubations mixtures contain in the final volume of 250 μL 95.5 mM N,N-bis(2-hydroxyethyl)-2-aminoethanesulfonic acid, pH 7.0, 8 mM EDTA, 0.1 mM neomycin sulfate, 1 mg/ml sodium azide, 1 mM phenylmethanesulfonyl fluoride, 2% DMSO and 87.3% of pooled mixed-gender human plasma stabilized with EDTA. For plasma batches with low PRA (less than 1 ng/ml/hr) ~2 pM of recombinant human renin is added to achieve PRA of 3-4 ng/ml/hr. The cleavage of endogenous angiotensinogen in plasma is carried out at 37° C. for 90 min and the product angiotensin I is measured by competitive radioimmunoassay using DiaSorin PRA kit. Uninhibited incubations containing 2% DMSO and fully inhibited controls with 2 μM of isovaleryl-Phe-Nle-Sta-AlaSta-OH are used for deriving percent of inhibition for each concentration of inhibitors and fitting dose-response data into a four parametric model from which IC$_{50}$ values, defined as concentrations of inhibitors at which 50% inhibition occurs, is determined.

EXAMPLE 6

Efficacy of the Disclosed Inhibitors in a Transgenic Rat Model

The efficacy of the renin inhibitors is also evaluated in vivo in double transgenic rats engineered to express human renin and human angiotensinogen (Bohlender J, Fukamizu A, Lippoldt A, Nomura T, Dietz R, Menard J, Murakami K, Luft F C, Ganten D. High human renin hypertension in transgenic rats. *Hypertension* 1997, 29, 428-434).

Experiments are conducted in 5-10 week-old double transgenic rats (dTGRs). The model has been described in detail earlier. Briefly, the human renin construct are used to generate transgenic animals (hRen) made up the entire genomic human renin gene (10 exons and 9 introns), with 3.0 kB of the 5'-promoter region and 1.2 kB of 3' additional sequences. The human angiotensinogen construct made up the entire human angiotensinogen gene (5 exons and 4 introns), with 1.3 kB of 5'-flanking and 2.4 kB of 3'-flanking sequences are used to generate rats producing human angiotensinogen (hAogen). The hRen and hAogen rats are rederived using embryo transfer from breeding pairs obtained under license from Ascencion Gmbh (Germany). The hAogen and hRen are then crossed to produce the double transgenic dTGR) off-spring. The dTGr rats are maintained on irradiated rodent chow (5VO2, Purina Mills Inc) and normal water. Radio telemetry transmitters (TA11PAC40, Data Sciences International) are surgically implanted at 5-6 weeks of age. The telemetry system provides 24-h recordings of systolic, mean, diastolic arterial pressure (SAP, MAP, DAP, respectively) and heart rate (HR). Prior to dosing, baseline hemodynamic measures are obtained for 24 hours. Rats are then dosed orally with vehicle or drug and monitored up to 48 hours post-dose.

While this invention has been particularly shown and described with references to preferred embodiments thereof, it will be understood by those skilled in the art that various changes in form and details may be made therein without departing from the scope of the invention encompassed by the appended claims.

What is claimed is:

1. A compound selected from the group consisting of:

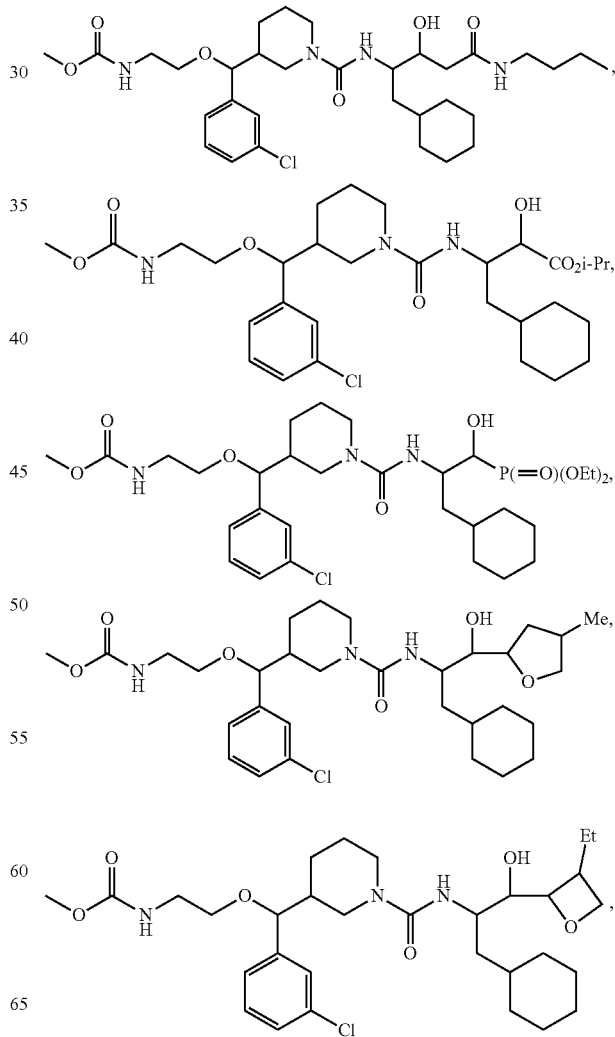

-continued
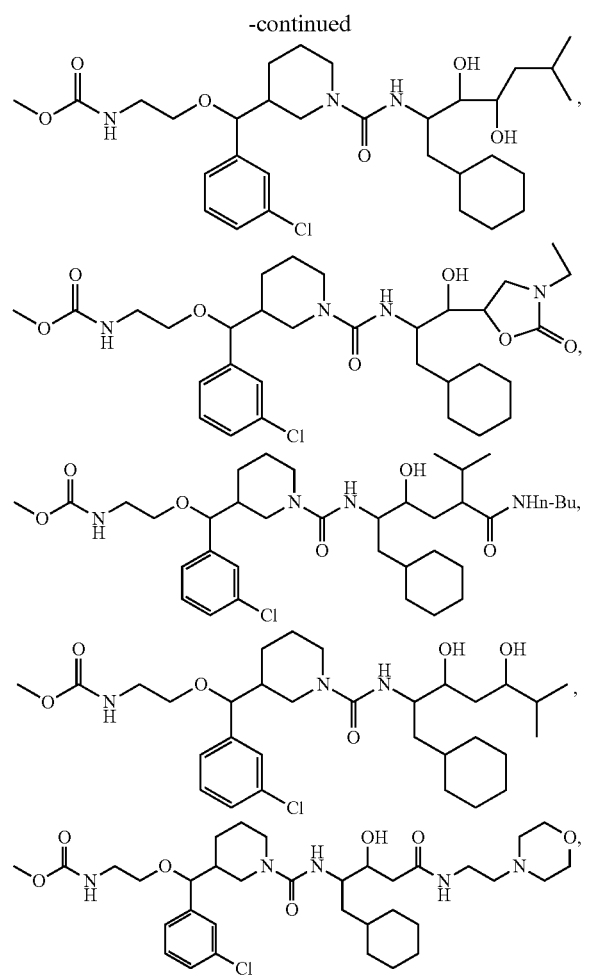
-continued
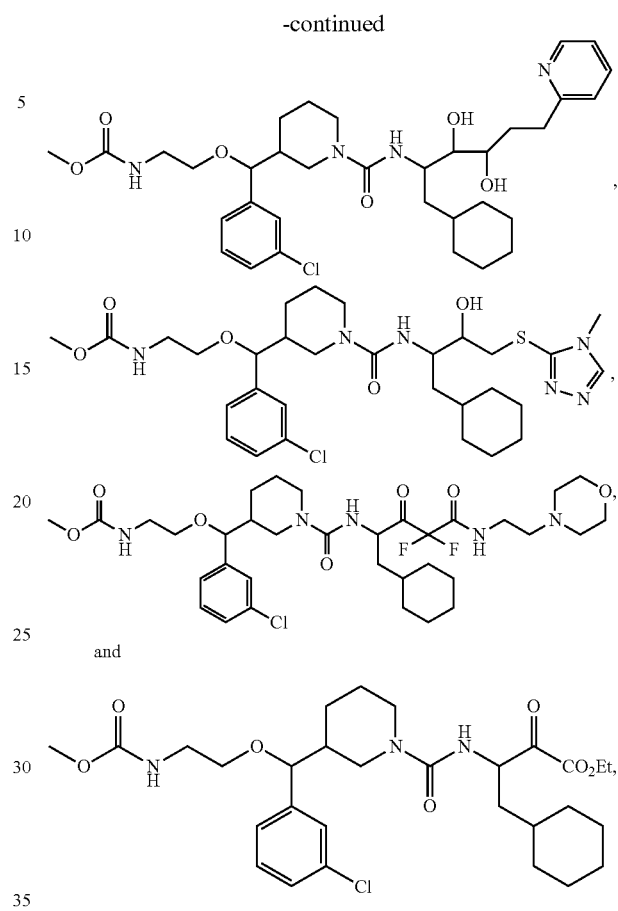
or an enantiomer, diastereomer or salt thereof.
2. A compound selected from the group consisting of:
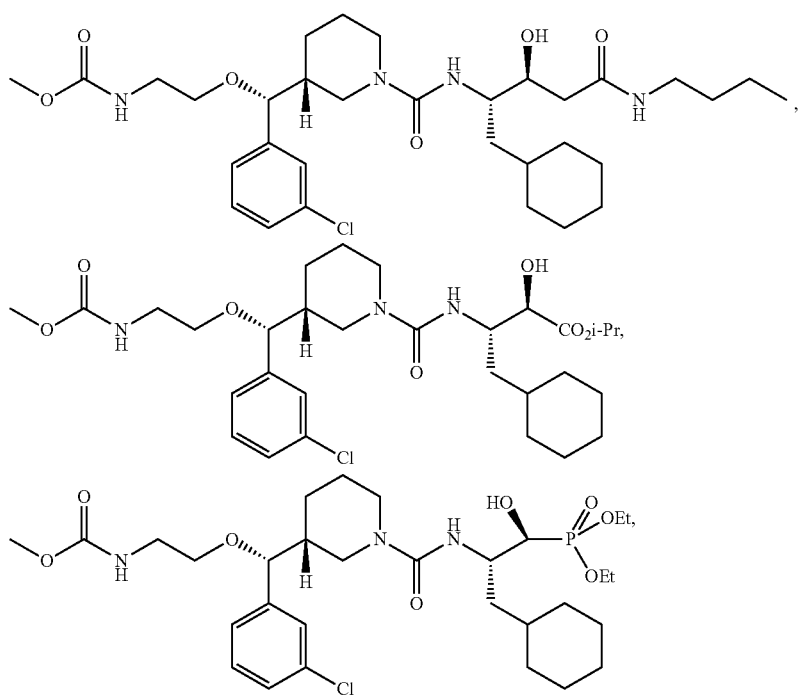

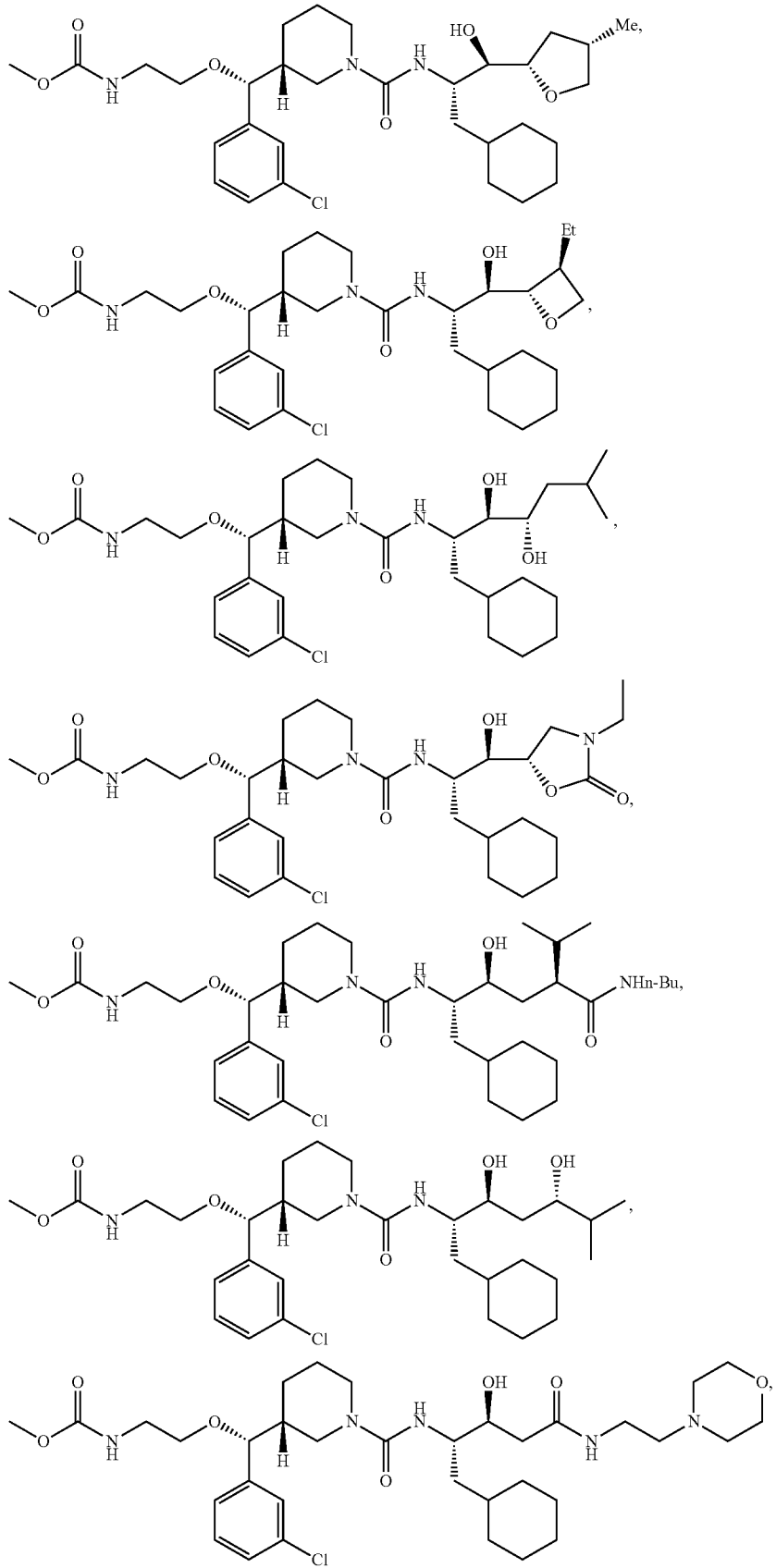

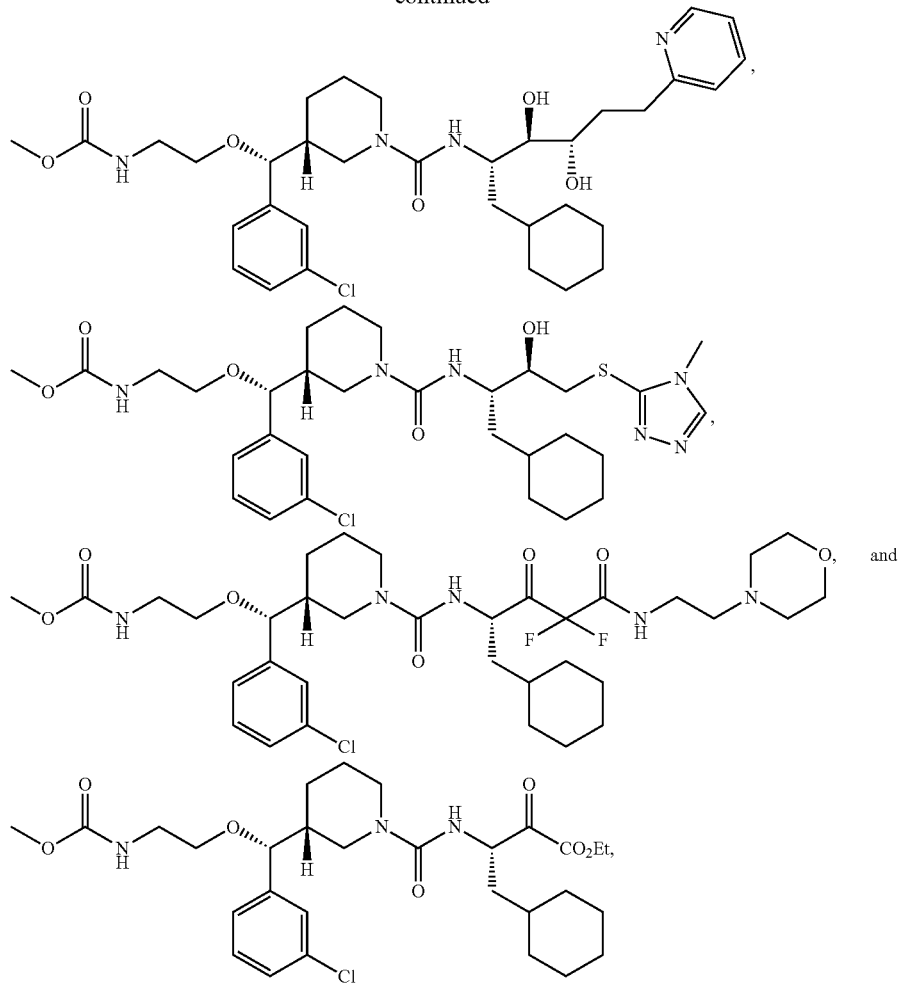

or an enantiomer, diastereomer or salt thereof.

3. A pharmaceutical composition comprising a compound of claim 1 or enantiomer, diastereomer, or salt thereof and a pharmaceutically acceptable carrier or excipient.

4. A pharmaceutical composition comprising a compound of claim 2, or enantiomer, diastereomer, or salt thereof and a pharmaceutically acceptable carrier or excipient.

* * * * *